(12) United States Patent
Capone et al.

(10) Patent No.: US 11,773,139 B2
(45) Date of Patent: Oct. 3, 2023

(54) EPSTEIN-BARR VIRUS ANTIGEN CONSTRUCTS

(71) Applicant: GLAXOSMITHKLINE BIOLOGICALS SA, Rixensart (BE)

(72) Inventors: Stefania Capone, Rome (IT); Antonella Folgori, Rome (IT); Armin Lahm, Rome (IT); Benjamin Wizel, Rockville, MD (US)

(73) Assignee: GlaxoSmithKline Biologicals SA, Rixensart (BE)

( * ) Notice: Subject to any disclaimer, the term of this patent is extended or adjusted under 35 U.S.C. 154(b) by 447 days.

(21) Appl. No.: 16/770,963

(22) PCT Filed: Dec. 14, 2018

(86) PCT No.: PCT/IB2018/060101
§ 371 (c)(1),
(2) Date: Jun. 9, 2020

(87) PCT Pub. No.: WO2019/123169
PCT Pub. Date: Jun. 27, 2019

(65) Prior Publication Data
US 2021/0198321 A1    Jul. 1, 2021

Related U.S. Application Data

(60) Provisional application No. 62/608,038, filed on Dec. 20, 2017.

(51) Int. Cl.
| | | |
|---|---|---|
| *C07K 14/005* | (2006.01) | |
| *A61K 39/245* | (2006.01) | |
| *C12N 7/00* | (2006.01) | |
| *A61K 39/00* | (2006.01) | |

(52) U.S. Cl.
CPC .......... *C07K 14/005* (2013.01); *A61K 39/245* (2013.01); *C12N 7/00* (2013.01); *A61K 2039/70* (2013.01); *C12N 2710/16222* (2013.01); *C12N 2710/16234* (2013.01); *C12N 2710/16271* (2013.01)

(58) Field of Classification Search
CPC .......... C07K 14/005; C07K 2319/00; A61K 39/245; A61K 2039/70; A61K 2039/5258; A61K 2039/545; A61K 2039/57; A61K 39/12; C12N 7/00; C12N 2710/16222; C12N 2710/16234; C12N 2710/16271; C12N 2710/10343; C12N 2710/16034; C12N 2710/24143; C12N 15/86; A61P 31/20; A61P 31/22; A61P 35/00

See application file for complete search history.

(56) References Cited

U.S. PATENT DOCUMENTS

| | | | |
|---|---|---|---|
| 5,716,845 A | 2/1998 | Sugden | |
| 2009/0130134 A1 | 5/2009 | Pancre | |
| 2009/0202584 A1 | 8/2009 | Thomson et al. | |
| 2009/0305324 A1 | 12/2009 | Kuzushima | |
| 2009/0324630 A1* | 12/2009 | Jensen | A61K 39/12 435/325 |
| 2014/0004081 A1* | 1/2014 | Cobbold | A61K 39/145 424/134.1 |
| 2020/0276295 A1* | 9/2020 | Ogembo | C07K 16/085 |
| 2020/0330587 A1* | 10/2020 | Kanekiyo | C07K 14/195 |

FOREIGN PATENT DOCUMENTS

| | | |
|---|---|---|
| DE | 4427117 C1 | 10/1995 |
| JP | 2016523888 A | 8/2016 |
| JP | 2017523139 A | 8/2017 |
| WO | 2007/065215 A1 | 6/2007 |
| WO | 2007/097820 A2 | 8/2007 |
| WO | 2014/059489 A1 | 4/2014 |
| WO | 2015001361 A1 | 1/2015 |
| WO | 2015189425 A1 | 12/2015 |
| WO | 2016198621 A1 | 12/2016 |

OTHER PUBLICATIONS

Roy S., et al. Simian adenovirus 34, complete genome. GenBank: FJ025905.1. Dep. Mar. 8, 2012. (Year: 2012).*
Duraiswamy, et al., "Therapeutic LMP1 polyeptiope vaccine for EBV-associated Hodgkin disease and nasopharyngeal carcinoma." Blood, American Society of Hematology; 2003; pp. 3150-3156; 101(8).
Hui, et al., "Phase I Trial of Recombinant Modified Vaccinia Ankara Encoding Epstein-Barr Viral Tumor Antigens in Nasopharyngeal Carcinoma Patients." Cancer Research; 2013; pp. 1676-1688; vol. 73(6).
Khanna, et al., "Localization of Epstein-Barr Virus Cytotoxic T Cell Epitopes using Recombinant Vaccinia: Implications for Vaccine Development" The Journal of Experimental Medicine; 1992; pp. 169-176; vol. 176(1).
Smith, et al., "Functional Reversion of Antigen-Specific CD8+ T Cells from Patients with Hodgkin Lymphoma following In Vitro Stimulation with Recombinant Polyepitope." The Journal of Immunology; 2006; pp. 4897-4906; vol. 177(7).

(Continued)

*Primary Examiner* — Rachel B Gill
(74) *Attorney, Agent, or Firm* — Romit Majumdar

(57) ABSTRACT

The invention provides Epstein-Barr Virus antigen polynucleotides, polypeptides and vectors; as well as immunogenic compositions comprising the same. It includes the use of Epstein-Barr Virus antigen constructs to produce vaccines for treating and preventing Epstein-Barr Virus infections and Epstein-Barr Virus-associated diseases, such as multiple sclerosis, rheumatoid arthritis and systemic lupus erythematosus.

18 Claims, 11 Drawing Sheets
Specification includes a Sequence Listing.

(56) References Cited

OTHER PUBLICATIONS

Smith, et al., "Effective Treatment of Metastatic Forms of Esptein-Barr Virus-Associated Nasopharyngeal Carcinoma with a Novel Adenovirus-Based Adoptive Immunotherapy." Cancer Research; 2012; pp. 1116-1125; vol. 72(5).

* cited by examiner

A) EBV-Latent construct

B) EBV-Latent+Lytic construct

A) CalHV3-Latent construct

B) CalHV3-Latent+Lytic construct

C) Genetic adjuvanted CalHV3-Latent+Lytic construct

A) T-cell responses to EBV constructs in mice

B) T-cell responses to CalHV3 constructs in mice

A) Cumulative response to EBV-LLy antigens

B) Responses to single EBV-LLy antigens

SEQUENCE LISTING

<160> NUMBER OF SEQ ID NOS: 54

<210> SEQ ID NO 1
<211> LENGTH: 386
<212> TYPE: PRT
<213> ORGANISM: Human herpesvirus 4

<400> SEQUENCE: 1

```
Met Glu His Asp Leu Glu Arg Gly Pro Pro Gly Pro Arg Arg Pro Pro
1               5                   10                  15

Arg Gly Pro Pro Leu Ser Ser Ser Leu Gly Leu Ala Leu Leu Leu Leu
            20                  25                  30

Leu Leu Ala Leu Leu Phe Trp Leu Tyr Ile Val Met Ser Asp Trp Thr
        35                  40                  45

Gly Gly Ala Leu Leu Val Leu Tyr Ser Phe Ala Leu Met Leu Ile Ile
    50                  55                  60

Ile Ile Leu Ile Ile Phe Ile Phe Arg Arg Asp Leu Leu Cys Pro Leu
65                  70                  75                  80

Gly Ala Leu Cys Ile Leu Leu Leu Met Ile Thr Leu Leu Leu Ile Ala
                85                  90                  95

Leu Trp Asn Leu His Gly Gln Ala Leu Phe Leu Gly Ile Val Leu Phe
            100                 105                 110

Ile Phe Gly Cys Leu Leu Val Leu Gly Ile Trp Ile Tyr Leu Leu Glu
        115                 120                 125

Met Leu Trp Arg Leu Gly Ala Thr Ile Trp Gln Leu Leu Ala Phe Phe
    130                 135                 140

Leu Ala Phe Phe Leu Asp Leu Ile Leu Leu Ile Ile Ala Leu Tyr Leu
145                 150                 155                 160

Gln Gln Asn Trp Trp Thr Leu Leu Val Asp Leu Leu Trp Leu Leu Leu
                165                 170                 175

Phe Leu Ala Ile Leu Ile Trp Met Tyr Tyr His Gly Gln Arg His Ser
            180                 185                 190

Asp Glu His His His Asp Asp Ser Leu Pro His Pro Gln Gln Ala Thr
        195                 200                 205

Asp Asp Ser Gly His Glu Ser Asp Ser Asn Ser Asn Glu Gly Arg His
    210                 215                 220

His Leu Leu Val Ser Gly Ala Gly Asp Gly Pro Pro Leu Cys Ser Gln
225                 230                 235                 240

Asn Leu Gly Ala Pro Gly Gly Gly Pro Asp Asn Gly Pro Gln Asp Pro
                245                 250                 255

Asp Asn Thr Asp Asp Asn Gly Pro Gln Asp Pro Asp Asn Thr Asp Asp
            260                 265                 270

Asn Gly Pro His Asp Pro Leu Pro Gln Asp Pro Asp Asn Thr Asp Asp
        275                 280                 285
```

```
Asn Gly Pro Gln Asp Pro Asn Thr Asp Asp Asn Gly Pro His Asp
        290                 295                 300

Pro Leu Pro His Ser Pro Ser Asp Ser Ala Gly Asn Asp Gly Pro
305                 310                 315                 320

Pro Gln Leu Thr Glu Glu Val Glu Asn Lys Gly Gly Asp Gln Gly Pro
            325                 330                 335

Pro Leu Met Thr Asp Gly Gly Gly His Ser His Asp Ser Gly His
            340                 345                 350

Gly Gly Gly Asp Pro His Leu Pro Thr Leu Leu Gly Ser Ser Gly
        355                 360                 365

Ser Gly Gly Asp Asp Asp Pro His Gly Pro Val Gln Leu Ser Tyr
        370                 375                 380

Tyr Asp
385

<210> SEQ ID NO 2
<211> LENGTH: 62
<212> TYPE: PRT
<213> ORGANISM: Human herpesvirus 4

<400> SEQUENCE: 2

Met Ser Asp Trp Thr Gly Gly Ala Leu Leu Val Leu Tyr Ser Phe Ala
1               5                   10                  15

Leu Met Leu Ile Ile Ile Leu Ile Ile Phe Ile Phe Arg Arg Asp
                20                  25                  30

Leu Leu Cys Pro Leu Gly Ala Leu Cys Ile Leu Leu Leu Met Ile Thr
            35                  40                  45

Leu Leu Leu Ile Ala Leu Trp Asn Leu His Gly Gln Ala Leu
        50                  55                  60

<210> SEQ ID NO 3
<211> LENGTH: 85
<212> TYPE: PRT
<213> ORGANISM: Human herpesvirus 4

<400> SEQUENCE: 3

Phe Leu Gly Ile Val Leu Phe Ile Phe Gly Cys Leu Leu Val Leu Gly
1               5                   10                  15

Ile Trp Ile Tyr Leu Leu Glu Met Leu Trp Arg Leu Gly Ala Thr Ile
                20                  25                  30

Trp Gln Leu Leu Ala Phe Phe Leu Ala Phe Phe Leu Asp Leu Ile Leu
            35                  40                  45

Leu Ile Ile Ala Leu Tyr Leu Gln Gln Asn Trp Trp Thr Leu Leu Val
        50                  55                  60

Asp Leu Leu Trp Leu Leu Phe Leu Ala Ile Leu Ile Trp Met Tyr
65                  70                  75                  80

Tyr His Gly Gln Arg
                85

<210> SEQ ID NO 4
<211> LENGTH: 40
<212> TYPE: PRT
<213> ORGANISM: Human herpesvirus 4

<400> SEQUENCE: 4

His Ser Asp Glu His His His Asp Asp Ser Leu Pro His Pro Gln Gln
1               5                   10                  15
```

```
Ala Thr Asp Asp Ser Gly His Glu Asp Ser Asn Ser Asn Glu Gly
            20                  25                  30

Arg His His Leu Leu Val Ser Gly
            35                  40

<210> SEQ ID NO 5
<211> LENGTH: 114
<212> TYPE: PRT
<213> ORGANISM: Human herpesvirus 4

<400> SEQUENCE: 5

Asn Gly Pro His Asp Pro Leu Pro Gln Asp Pro Asp Asn Thr Asp Asp
1               5                   10                  15

Asn Gly Pro Gln Asp Pro Asp Asn Thr Asp Asp Asn Gly Pro His Asp
            20                  25                  30

Pro Leu Pro His Ser Pro Ser Asp Ser Ala Gly Asn Asp Gly Gly Pro
            35                  40                  45

Pro Gln Leu Thr Glu Glu Val Glu Asn Lys Gly Gly Asp Gln Gly Pro
        50                  55                  60

Pro Leu Met Thr Asp Gly Gly Gly His Ser His Asp Ser Gly His Gly
65                  70                  75                  80

Gly Gly Asp Pro His Leu Pro Thr Leu Leu Leu Gly Ser Ser Gly
                85                  90                  95

Ser Gly Gly Asp Asp Asp Pro His Gly Pro Val Gln Leu Ser Tyr
            100                 105                 110

Tyr Asp

<210> SEQ ID NO 6
<211> LENGTH: 497
<212> TYPE: PRT
<213> ORGANISM: Human herpesvirus 4

<400> SEQUENCE: 6

Met Gly Ser Leu Glu Met Val Pro Met Gly Ala Gly Pro Pro Ser Pro
1               5                   10                  15

Gly Gly Asp Pro Asp Gly Tyr Asp Gly Gly Asn Asn Ser Gln Tyr Pro
            20                  25                  30

Ser Ala Ser Gly Ser Ser Gly Asn Thr Pro Thr Pro Pro Asn Asp Glu
        35                  40                  45

Glu Arg Glu Ser Asn Glu Glu Pro Pro Pro Tyr Glu Asp Pro Tyr
        50                  55                  60

Trp Gly Asn Gly Asp Arg His Ser Asp Tyr Gln Pro Leu Gly Thr Gln
65                  70                  75                  80

Asp Gln Ser Leu Tyr Leu Gly Leu Gln His Asp Gly Asn Asp Gly Leu
                85                  90                  95

Pro Pro Pro Pro Tyr Ser Pro Arg Asp Asp Ser Ser Gln His Ile Tyr
            100                 105                 110

Glu Glu Ala Gly Arg Gly Ser Met Asn Pro Val Cys Leu Pro Val Ile
        115                 120                 125

Val Ala Pro Tyr Leu Phe Trp Leu Ala Ala Ile Ala Ala Ser Cys Phe
130                 135                 140

Thr Ala Ser Val Ser Thr Val Val Thr Ala Thr Gly Leu Ala Leu Ser
145                 150                 155                 160

Leu Leu Leu Leu Ala Ala Val Ala Ser Ser Tyr Ala Ala Ala Gln Arg
                165                 170                 175

Lys Leu Leu Thr Pro Val Thr Val Leu Thr Ala Val Val Thr Phe Phe
```

```
                        180                 185                 190
Ala Ile Cys Leu Thr Trp Arg Ile Glu Asp Pro Pro Phe Asn Ser Leu
                195                 200                 205

Leu Phe Ala Leu Leu Ala Ala Ala Gly Gly Leu Gln Gly Ile Tyr Val
    210                 215                 220

Leu Val Met Leu Val Leu Ile Leu Ala Tyr Arg Arg Arg Trp Arg
225                 230                 235                 240

Arg Leu Thr Val Cys Gly Gly Ile Met Phe Leu Ala Cys Val Leu Val
                245                 250                 255

Leu Ile Val Asp Ala Val Leu Gln Leu Ser Pro Leu Leu Gly Ala Val
                260                 265                 270

Thr Val Val Ser Met Thr Leu Leu Leu Ala Phe Val Leu Trp Leu
                275                 280                 285

Ser Ser Pro Gly Gly Leu Gly Thr Leu Gly Ala Ala Leu Leu Thr Leu
                290                 295                 300

Ala Ala Ala Leu Ala Leu Leu Ala Ser Leu Ile Leu Gly Thr Leu Asn
305                 310                 315                 320

Leu Thr Thr Met Phe Leu Leu Met Leu Leu Trp Thr Leu Val Val Leu
                325                 330                 335

Leu Ile Cys Ser Ser Cys Ser Ser Cys Pro Leu Ser Lys Ile Leu Leu
                340                 345                 350

Ala Arg Leu Phe Leu Tyr Ala Leu Ala Leu Leu Leu Ala Ser Ala
                355                 360                 365

Leu Ile Ala Gly Gly Ser Ile Leu Gln Thr Asn Phe Lys Ser Leu Ser
                370                 375                 380

Ser Thr Glu Phe Ile Pro Asn Leu Phe Cys Met Leu Leu Ile Val
385                 390                 395                 400

Ala Gly Ile Leu Phe Ile Leu Ala Ile Leu Thr Glu Trp Gly Ser Gly
                405                 410                 415

Asn Arg Thr Tyr Gly Pro Val Phe Met Cys Leu Gly Gly Leu Leu Thr
                420                 425                 430

Met Val Ala Gly Ala Val Trp Leu Thr Val Met Ser Asn Thr Leu Leu
                435                 440                 445

Ser Ala Trp Ile Leu Thr Ala Gly Phe Leu Ile Phe Leu Ile Gly Phe
    450                 455                 460

Ala Leu Phe Gly Val Ile Arg Cys Cys Arg Tyr Cys Cys Tyr Tyr Cys
465                 470                 475                 480

Leu Thr Leu Glu Ser Glu Glu Arg Pro Pro Thr Pro Tyr Arg Asn Thr
                485                 490                 495

Val

<210> SEQ ID NO 7
<211> LENGTH: 71
<212> TYPE: PRT
<213> ORGANISM: Human herpesvirus 4

<400> SEQUENCE: 7

Met Asn Pro Val Cys Leu Pro Val Ile Val Ala Pro Tyr Leu Phe Trp
1               5                   10                  15

Leu Ala Ala Ile Ala Ala Ser Cys Phe Thr Ala Ser Val Ser Thr Val
                20                  25                  30

Val Thr Ala Thr Gly Leu Ala Leu Ser Leu Leu Leu Ala Ala Val
                35                  40                  45

Ala Ser Ser Tyr Ala Ala Ala Gln Arg Lys Leu Leu Thr Pro Val Thr
```

```
                   50                  55                  60

Val Leu Thr Ala Val Thr
 65                  70

<210> SEQ ID NO 8
<211> LENGTH: 94
<212> TYPE: PRT
<213> ORGANISM: Human herpesvirus 4

<400> SEQUENCE: 8

Phe Phe Ala Ile Cys Leu Thr Trp Arg Ile Glu Asp Pro Pro Phe Asn
  1               5                  10                  15

Ser Leu Leu Phe Ala Leu Leu Ala Ala Gly Gly Leu Gln Gly Ile
                 20                  25                  30

Tyr Val Leu Val Met Leu Val Leu Ile Leu Ala Tyr Arg Arg Arg
                 35                  40                  45

Trp Arg Arg Leu Thr Val Cys Gly Gly Ile Met Phe Leu Ala Cys Val
                 50                  55                  60

Leu Val Leu Ile Val Asp Ala Val Leu Gln Leu Ser Pro Leu Leu Gly
 65                  70                  75                  80

Ala Val Thr Val Val Ser Met Thr Leu Leu Leu Ala Phe
                 85                  90

<210> SEQ ID NO 9
<211> LENGTH: 115
<212> TYPE: PRT
<213> ORGANISM: Human herpesvirus 4

<400> SEQUENCE: 9

Val Leu Trp Leu Ser Ser Pro Gly Gly Leu Gly Thr Leu Gly Ala Ala
  1               5                  10                  15

Leu Leu Thr Leu Ala Ala Ala Leu Ala Leu Leu Ala Ser Leu Ile Leu
                 20                  25                  30

Gly Thr Leu Asn Leu Thr Thr Met Phe Leu Leu Met Leu Leu Trp Thr
                 35                  40                  45

Leu Val Val Leu Leu Ile Cys Ser Ser Cys Ser Ser Cys Pro Leu Ser
                 50                  55                  60

Lys Ile Leu Leu Ala Arg Leu Phe Leu Tyr Ala Leu Ala Leu Leu Leu
 65                  70                  75                  80

Leu Ala Ser Ala Leu Ile Ala Gly Gly Ser Ile Leu Gln Thr Asn Phe
                 85                  90                  95

Lys Ser Leu Ser Ser Thr Glu Phe Ile Pro Asn Leu Phe Cys Met Leu
                100                 105                 110

Leu Leu Ile
       115

<210> SEQ ID NO 10
<211> LENGTH: 98
<212> TYPE: PRT
<213> ORGANISM: Human herpesvirus 4

<400> SEQUENCE: 10

Val Ala Gly Ile Leu Phe Ile Leu Ala Ile Leu Thr Glu Trp Gly Ser
  1               5                  10                  15

Gly Asn Arg Thr Tyr Gly Pro Val Phe Met Cys Leu Gly Gly Leu Leu
                 20                  25                  30

Thr Met Val Ala Gly Ala Val Trp Leu Thr Val Met Ser Asn Thr Leu
                 35                  40                  45
```

Leu Ser Ala Trp Ile Leu Thr Ala Gly Phe Leu Ile Phe Leu Ile Gly
            50                  55                  60

Phe Ala Leu Phe Gly Val Ile Arg Cys Cys Arg Tyr Cys Cys Tyr Tyr
 65                  70                  75                  80

Cys Leu Thr Leu Glu Ser Glu Glu Arg Pro Pro Thr Pro Tyr Arg Asn
                85                  90                  95

Thr Val

<210> SEQ ID NO 11
<211> LENGTH: 641
<212> TYPE: PRT
<213> ORGANISM: Human herpesvirus 4

<400> SEQUENCE: 11

Met Ser Asp Glu Gly Pro Gly Thr Gly Pro Gly Asn Gly Leu Gly Glu
 1                   5                  10                  15

Lys Gly Asp Thr Ser Gly Pro Glu Gly Ser Gly Gly Ser Gly Pro Gln
                20                  25                  30

Arg Arg Gly Gly Asp Asn His Gly Arg Gly Arg Gly Arg Gly Arg Gly
            35                  40                  45

Arg Gly Gly Arg Pro Gly Ala Pro Gly Gly Ser Gly Ser Gly Pro
 50                  55                  60

Arg His Arg Asp Gly Val Arg Arg Pro Gln Lys Arg Pro Ser Cys Ile
 65                  70                  75                  80

Gly Cys Lys Gly Thr His Gly Gly Thr Gly Ala Gly Ala Gly Ala Gly
                85                  90                  95

Gly Ala Gly Ala Gly Gly Ala Gly Ala Gly Gly Ala Gly Ala Gly Gly
            100                 105                 110

Gly Gly Ala Gly Gly Ala Gly Gly Ala Gly Gly Ala Gly Ala Gly Gly
            115                 120                 125

Gly Ala Gly Ala Gly Gly Ala Gly Ala Gly Gly Ala Gly Gly Ala Gly
            130                 135                 140

Gly Gly Ala Gly Ala Gly Gly Ala Gly Gly Ala Gly Ala Gly Ala Gly
145                 150                 155                 160

Gly Gly Ala Gly Gly Ala Gly Gly Ala Gly Gly Ala Gly Gly Ala Gly
                165                 170                 175

Ala Gly Gly Gly Ala Gly Gly Ala Gly Ala Gly Gly Ala Gly Gly Gly
            180                 185                 190

Ala Gly Gly Ala Gly Ala Gly Gly Ala Gly Ala Gly Gly Gly Ala Gly
            195                 200                 205

Gly Ala Gly Gly Ala Gly Ala Gly Gly Ala Gly Ala Gly Gly Gly Ala
            210                 215                 220

Gly Gly Ala Gly Gly Ala Gly Ala Gly Gly Ala Gly Ala Gly Gly Ala
225                 230                 235                 240

Gly Ala Gly Gly Ala Gly Ala Gly Gly Ala Gly Gly Ala Gly Ala Gly
                245                 250                 255

Gly Ala Gly Gly Ala Gly Ala Gly Gly Ala Gly Gly Ala Gly Ala Gly
            260                 265                 270

Gly Gly Ala Gly Gly Ala Gly Ala Gly Gly Ala Gly Gly Ala Gly Ala
            275                 280                 285

Ala Gly Gly Ala Gly Gly Ala Gly Ala Gly Gly Ala Gly Gly Ala Gly
            290                 295                 300

Ala Gly Gly Ala Gly Gly Ala Gly Ala Gly Gly Ala Gly Gly Ala Gly
305                 310                 315                 320

Gly Ala Gly Ala Gly Gly Gly Arg Gly Arg Gly Ser Gly Gly
            325                 330                 335

Arg Gly Arg Gly Gly Ser Gly Gly Arg Gly Gly Ser Gly Gly
            340                 345                 350

Arg Arg Gly Arg Gly Arg Glu Arg Ala Arg Gly Gly Ser Arg Glu Arg
            355                 360                 365

Ala Arg Gly Arg Gly Arg Gly Arg Gly Glu Lys Arg Pro Arg Ser Pro
            370                 375                 380

Ser Ser Gln Ser Ser Ser Gly Ser Pro Pro Arg Arg Pro Pro Pro
385                 390                 395                 400

Gly Arg Arg Pro Phe Phe His Pro Val Gly Ala Asp Tyr Phe Glu
            405                 410                 415

Tyr His Gln Glu Gly Gly Pro Asp Gly Glu Pro Asp Val Pro Pro Gly
            420                 425                 430

Ala Ile Glu Gln Gly Pro Ala Asp Asp Pro Gly Glu Gly Pro Ser Thr
            435                 440                 445

Gly Pro Arg Gly Gln Gly Asp Gly Gly Arg Arg Lys Lys Gly Gly Trp
            450                 455                 460

Phe Gly Lys His Arg Gly Gln Gly Gly Ser Asn Pro Lys Phe Glu Asn
465                 470                 475                 480

Ile Ala Glu Gly Leu Arg Ala Leu Leu Ala Arg Ser His Val Glu Arg
            485                 490                 495

Thr Thr Asp Glu Gly Thr Trp Val Ala Gly Val Phe Val Tyr Gly Gly
            500                 505                 510

Ser Lys Thr Ser Leu Tyr Asn Leu Arg Arg Gly Thr Ala Leu Ala Ile
            515                 520                 525

Pro Gln Cys Arg Leu Thr Pro Leu Ser Arg Leu Pro Phe Gly Met Ala
            530                 535                 540

Pro Gly Pro Gly Pro Gln Pro Gly Pro Leu Arg Glu Ser Ile Val Cys
545                 550                 555                 560

Tyr Phe Met Val Phe Leu Gln Thr His Ile Phe Ala Glu Val Leu Lys
            565                 570                 575

Asp Ala Ile Lys Asp Leu Val Met Thr Lys Pro Ala Pro Thr Cys Asn
            580                 585                 590

Ile Arg Val Thr Val Cys Ser Phe Asp Asp Gly Val Asp Leu Pro Pro
            595                 600                 605

Trp Phe Pro Pro Met Val Glu Gly Ala Ala Ala Glu Gly Asp Asp Gly
            610                 615                 620

Asp Asp Gly Asp Glu Gly Gly Asp Gly Asp Glu Glu Gly Gln
625                 630                 635                 640

Glu

<210> SEQ ID NO 12
<211> LENGTH: 86
<212> TYPE: PRT
<213> ORGANISM: Human herpesvirus 4

<400> SEQUENCE: 12

Met Ser Asp Glu Gly Pro Gly Thr Gly Pro Gly Asn Gly Leu Gly Glu
1               5                   10                  15

Lys Gly Asp Thr Ser Gly Pro Glu Gly Ser Gly Gly Ser Gly Pro Gln
            20                  25                  30

Arg Arg Gly Gly Asp Asn His Gly Arg Gly Arg Gly Arg Gly Arg Gly
            35                  40                  45

```
Arg Gly Gly Gly Arg Pro Gly Ala Pro Gly Gly Ser Gly Ser Gly Pro
         50                  55                  60

Arg His Arg Asp Gly Val Arg Pro Gln Lys Arg Pro Ser Cys Ile
 65                  70                  75                  80

Gly Cys Lys Gly Thr His
                 85

<210> SEQ ID NO 13
<211> LENGTH: 944
<212> TYPE: PRT
<213> ORGANISM: Human herpesvirus 4

<400> SEQUENCE: 13

Met Asp Lys Asp Arg Pro Gly Pro Pro Ala Leu Asp Asp Asn Met Glu
 1               5                  10                  15

Glu Glu Val Pro Ser Thr Ser Val Val Gln Glu Gln Val Ser Ala Gly
                 20                  25                  30

Asp Trp Glu Asn Val Leu Ile Glu Leu Ser Asp Ser Ser Ser Glu Lys
             35                  40                  45

Glu Ala Glu Asp Ala His Leu Glu Pro Ala Gln Lys Gly Thr Lys Arg
         50                  55                  60

Lys Arg Val Asp His Asp Ala Gly Gly Ser Ala Pro Ala Arg Pro Met
 65                  70                  75                  80

Leu Pro Pro Gln Pro Asp Leu Pro Gly Arg Glu Ala Ile Leu Arg Arg
                 85                  90                  95

Phe Pro Leu Asp Leu Arg Thr Leu Leu Gln Ala Ile Gly Ala Ala Ala
                100                 105                 110

Thr Arg Ile Asp Thr Arg Ala Ile Asp Gln Phe Phe Gly Ser Gln Ile
            115                 120                 125

Ser Asn Thr Glu Met Tyr Ile Met Tyr Ala Met Ala Ile Arg Gln Ala
130                 135                 140

Ile Arg Asp Arg Arg Arg Asn Pro Ala Ser Arg Arg Asp Gln Ala Lys
145                 150                 155                 160

Trp Arg Leu Gln Thr Leu Ala Ala Gly Trp Pro Met Gly Tyr Gln Ala
                165                 170                 175

Tyr Ser Ser Trp Met Tyr Ser Tyr Thr Asp His Gln Thr Thr Pro Thr
            180                 185                 190

Phe Val His Leu Gln Ala Thr Leu Gly Cys Thr Gly Gly Arg Arg Cys
        195                 200                 205

His Val Thr Phe Ser Ala Gly Thr Phe Lys Leu Pro Arg Cys Thr Pro
    210                 215                 220

Gly Asp Arg Gln Trp Leu Tyr Val Gln Ser Ser Val Gly Asn Ile Val
225                 230                 235                 240

Gln Ser Cys Asn Pro Arg Tyr Ser Ile Phe Phe Asp Tyr Met Ala Ile
                245                 250                 255

His Arg Ser Leu Thr Lys Ile Trp Glu Glu Val Leu Thr Pro Asp Gln
            260                 265                 270

Arg Val Ser Phe Met Glu Phe Leu Gly Phe Leu Gln Arg Thr Asp Leu
        275                 280                 285

Ser Tyr Ile Lys Ser Phe Val Ser Asp Ala Leu Gly Thr Ser Ile
    290                 295                 300

Gln Thr Pro Trp Ile Asp Asp Asn Pro Ser Thr Glu Thr Ala Gln Ala
305                 310                 315                 320

Trp Asn Ala Gly Phe Leu Arg Gly Arg Ala Tyr Gly Ile Asp Leu Leu
```

```
                     325                 330                 335
Arg Thr Glu Gly Glu His Val Glu Gly Ala Thr Gly Glu Thr Arg Glu
            340                 345                 350
Glu Ser Glu Asp Thr Glu Ser Asp Gly Asp Glu Asp Leu Pro Cys
            355                 360                 365
Ile Val Ser Arg Gly Gly Pro Lys Val Lys Arg Pro Ile Phe Ile
370                 375                 380
Arg Arg Leu His Arg Leu Leu Met Arg Ala Gly Lys Arg Thr Glu
385                 390                 395                 400
Gln Gly Lys Glu Val Leu Glu Lys Ala Arg Gly Ser Thr Tyr Gly Thr
            405                 410                 415
Pro Arg Pro Pro Val Pro Lys Pro Arg Pro Glu Val Pro Gln Ser Asp
            420                 425                 430
Glu Thr Ala Thr Ser His Gly Ser Ala Gln Val Pro Glu Pro Pro Thr
            435                 440                 445
Ile His Leu Ala Ala Gln Gly Met Ala Tyr Pro Leu His Glu Gln His
            450                 455                 460
Gly Met Ala Pro Cys Pro Val Ala Gln Ala Pro Pro Thr Pro Leu Pro
465                 470                 475                 480
Pro Val Ser Pro Gly Asp Gln Leu Pro Gly Val Phe Ser Asp Gly Arg
            485                 490                 495
Val Ala Cys Ala Pro Val Pro Ala Pro Ala Gly Pro Ile Val Arg Pro
            500                 505                 510
Trp Glu Pro Ser Leu Thr Gln Ala Ala Gly Gln Ala Phe Ala Pro Val
            515                 520                 525
Arg Pro Gln His Met Pro Val Glu Pro Val Pro Val Pro Thr Val Ala
            530                 535                 540
Leu Glu Arg Pro Val Tyr Pro Lys Pro Val Arg Pro Ala Pro Pro Lys
545                 550                 555                 560
Ile Ala Met Gln Gly Pro Gly Glu Thr Ser Gly Ile Arg Arg Ala Arg
            565                 570                 575
Glu Arg Trp Arg Pro Ala Pro Trp Thr Pro Asn Pro Pro Arg Ser Pro
            580                 585                 590
Ser Gln Met Ser Val Arg Asp Arg Leu Ala Arg Leu Arg Ala Glu Ala
            595                 600                 605
Gln Val Lys Gln Ala Ser Val Glu Val Gln Pro Pro Gln Leu Thr Gln
            610                 615                 620
Val Ser Pro Gln Gln Pro Met Glu Gly Pro Leu Val Pro Glu Gln Gln
625                 630                 635                 640
Met Phe Pro Gly Ala Pro Phe Ser Gln Val Ala Asp Val Val Arg Ala
            645                 650                 655
Pro Gly Val Pro Ala Met Gln Pro Gln Tyr Phe Asp Leu Pro Leu Ile
            660                 665                 670
Gln Pro Ile Ser Gln Gly Ala Pro Val Ala Pro Leu Arg Ala Ser Met
            675                 680                 685
Gly Pro Val Pro Pro Val Pro Ala Thr Gln Pro Gln Tyr Phe Asp Ile
            690                 695                 700
Pro Leu Thr Glu Pro Ile Asn Gln Gly Ala Ser Ala Ala His Phe Leu
705                 710                 715                 720
Pro Gln Gln Pro Met Glu Gly Pro Leu Val Pro Glu Gln Trp Met Phe
            725                 730                 735
Pro Gly Ala Ala Leu Ser Gln Ser Val Arg Pro Gly Val Ala Gln Ser
            740                 745                 750
```

```
Gln Tyr Phe Asp Leu Pro Leu Thr Gln Pro Ile Asn His Gly Ala Pro
            755                 760                 765

Ala Ala His Phe Leu His Gln Pro Pro Met Glu Gly Pro Trp Val Pro
770                 775                 780

Glu Gln Trp Met Phe Gln Gly Ala Pro Ser Gln Gly Thr Asp Val
785                 790                 795                 800

Val Gln His Gln Leu Asp Ala Leu Gly Tyr Thr Leu His Gly Leu Asn
                805                 810                 815

His Pro Gly Val Pro Val Ser Pro Ala Val Asn Gln Tyr His Leu Ser
                820                 825                 830

Gln Ala Ala Phe Gly Leu Pro Ile Asp Glu Asp Glu Ser Gly Glu Gly
                835                 840                 845

Ser Asp Thr Ser Glu Pro Cys Glu Ala Leu Asp Leu Ser Ile His Gly
                850                 855                 860

Arg Pro Cys Pro Gln Ala Pro Glu Trp Pro Val Gln Glu Glu Gly Gly
865                 870                 875                 880

Gln Asp Ala Thr Glu Val Leu Asp Leu Ser Ile His Gly Arg Pro Arg
                885                 890                 895

Pro Arg Thr Pro Glu Trp Pro Val Gln Gly Glu Gly Gly Gln Asn Val
                900                 905                 910

Thr Gly Pro Glu Thr Arg Arg Val Val Val Ser Ala Val Val His Met
                915                 920                 925

Cys Gln Asp Asp Glu Phe Pro Asp Leu Gln Asp Pro Pro Asp Glu Ala
                930                 935                 940

<210> SEQ ID NO 14
<211> LENGTH: 66
<212> TYPE: PRT
<213> ORGANISM: Human herpesvirus 4

<400> SEQUENCE: 14

Ile Arg Asp Arg Arg Asn Pro Ala Ser Arg Arg Asp Gln Ala Lys
1               5                   10                  15

Trp Arg Leu Gln Thr Leu Ala Ala Gly Trp Pro Met Gly Tyr Gln Ala
                20                  25                  30

Tyr Ser Ser Trp Met Tyr Ser Tyr Thr Asp His Gln Thr Thr Pro Thr
                35                  40                  45

Phe Val His Leu Gln Ala Thr Leu Gly Cys Thr Gly Gly Arg Arg Cys
            50                  55                  60

His Val
65

<210> SEQ ID NO 15
<211> LENGTH: 55
<212> TYPE: PRT
<213> ORGANISM: Human herpesvirus 4

<400> SEQUENCE: 15

Thr Phe Ser Ala Gly Thr Phe Lys Leu Pro Arg Cys Thr Pro Gly Asp
1               5                   10                  15

Arg Gln Trp Leu Tyr Val Gln Ser Ser Val Gly Asn Ile Val Gln Ser
                20                  25                  30

Cys Asn Pro Arg Tyr Ser Ile Phe Phe Asp Tyr Met Ala Ile His Arg
            35                  40                  45

Ser Leu Thr Lys Ile Trp Glu
            50                  55
```

```
<210> SEQ ID NO 16
<211> LENGTH: 88
<212> TYPE: PRT
<213> ORGANISM: Human herpesvirus 4

<400> SEQUENCE: 16

Trp Ile Asp Asp Asn Pro Ser Thr Glu Thr Ala Gln Ala Trp Asn Ala
1               5                   10                  15

Gly Phe Leu Arg Gly Arg Ala Tyr Gly Ile Asp Leu Leu Arg Thr Glu
            20                  25                  30

Gly Glu His Val Glu Gly Ala Thr Gly Glu Thr Arg Glu Glu Ser Glu
        35                  40                  45

Asp Thr Glu Ser Asp Gly Asp Asp Glu Asp Leu Pro Cys Ile Val Ser
    50                  55                  60

Arg Gly Gly Pro Lys Val Lys Arg Pro Pro Ile Phe Ile Arg Arg Leu
65                  70                  75                  80

His Arg Leu Leu Leu Met Arg Ala
                85

<210> SEQ ID NO 17
<211> LENGTH: 25
<212> TYPE: PRT
<213> ORGANISM: Human herpesvirus 4

<400> SEQUENCE: 17

Gly Lys Arg Thr Glu Gln Gly Lys Glu Val Leu Glu Lys Ala Arg Gly
1               5                   10                  15

Ser Thr Tyr Gly Thr Pro Arg Pro Pro
            20                  25

<210> SEQ ID NO 18
<211> LENGTH: 40
<212> TYPE: PRT
<213> ORGANISM: Human herpesvirus 4

<400> SEQUENCE: 18

Ala Gln Val Pro Glu Pro Pro Thr Ile His Leu Ala Ala Gln Gly Met
1               5                   10                  15

Ala Tyr Pro Leu His Glu Gln His Gly Met Ala Pro Cys Pro Val Ala
            20                  25                  30

Gln Ala Pro Pro Thr Pro Leu Pro
        35                  40

<210> SEQ ID NO 19
<211> LENGTH: 62
<212> TYPE: PRT
<213> ORGANISM: Human herpesvirus 4

<400> SEQUENCE: 19

Gly Arg Val Ala Cys Ala Pro Val Pro Ala Pro Ala Gly Pro Ile Val
1               5                   10                  15

Arg Pro Trp Glu Pro Ser Leu Thr Gln Ala Ala Gly Gln Ala Phe Ala
            20                  25                  30

Pro Val Arg Pro Gln His Met Pro Val Glu Pro Val Pro Val Pro Thr
        35                  40                  45

Val Ala Leu Glu Arg Pro Val Tyr Pro Lys Pro Val Arg Pro
    50                  55                  60
```

-continued

```
<210> SEQ ID NO 20
<211> LENGTH: 51
<212> TYPE: PRT
<213> ORGANISM: Human herpesvirus 4

<400> SEQUENCE: 20

Arg Pro Ala Pro Trp Thr Pro Asn Pro Arg Ser Pro Ser Gln Met
1               5                   10                  15

Ser Val Arg Asp Arg Leu Ala Arg Leu Arg Ala Glu Ala Gln Val Lys
            20                  25                  30

Gln Ala Ser Val Glu Val Gln Pro Pro Gln Leu Thr Gln Val Ser Pro
        35                  40                  45

Gln Gln Pro
    50

<210> SEQ ID NO 21
<211> LENGTH: 245
<212> TYPE: PRT
<213> ORGANISM: Human herpesvirus 4

<400> SEQUENCE: 21

Met Met Asp Pro Asn Ser Thr Ser Glu Asp Val Lys Phe Thr Pro Asp
1               5                   10                  15

Pro Tyr Gln Val Pro Phe Val Gln Ala Phe Asp Gln Ala Thr Arg Val
            20                  25                  30

Tyr Gln Asp Leu Gly Gly Pro Ser Gln Ala Pro Leu Pro Cys Val Leu
        35                  40                  45

Trp Pro Val Leu Pro Glu Pro Leu Pro Gln Gly Gln Leu Thr Ala Tyr
    50                  55                  60

His Val Ser Thr Ala Pro Thr Gly Ser Trp Phe Ser Ala Pro Gln Pro
65                  70                  75                  80

Ala Pro Glu Asn Ala Tyr Gln Ala Tyr Ala Ala Pro Gln Leu Phe Pro
                85                  90                  95

Val Ser Asp Ile Thr Gln Asn Gln Gln Thr Asn Gln Ala Gly Gly Glu
            100                 105                 110

Ala Pro Gln Pro Gly Asp Asn Ser Thr Val Gln Thr Ala Ala Ala Val
        115                 120                 125

Val Phe Ala Cys Pro Gly Ala Asn Gln Gly Gln Gln Leu Ala Asp Ile
    130                 135                 140

Gly Val Pro Gln Pro Ala Pro Val Ala Ala Pro Ala Arg Arg Thr Arg
145                 150                 155                 160

Lys Pro Gln Gln Pro Glu Ser Leu Glu Glu Cys Asp Ser Glu Leu Glu
                165                 170                 175

Ile Lys Arg Tyr Lys Asn Arg Val Ala Ser Arg Lys Cys Arg Ala Lys
            180                 185                 190

Phe Lys Gln Leu Leu Gln His Tyr Arg Glu Val Ala Ala Ala Lys Ser
        195                 200                 205

Ser Glu Asn Asp Arg Leu Arg Leu Leu Lys Gln Met Cys Pro Ser
    210                 215                 220

Leu Asp Val Asp Ser Ile Ile Pro Arg Thr Pro Asp Val Leu His Glu
225                 230                 235                 240

Asp Leu Leu Asn Phe
                245

<210> SEQ ID NO 22
<211> LENGTH: 66
<212> TYPE: PRT
```

<213> ORGANISM: Human herpesvirus 4

<400> SEQUENCE: 22

Asp Leu Gly Gly Pro Ser Gln Ala Pro Leu Pro Cys Val Leu Trp Pro
1               5                   10                  15

Val Leu Pro Glu Pro Leu Pro Gln Gly Gln Leu Thr Ala Tyr His Val
            20                  25                  30

Ser Thr Ala Pro Thr Gly Ser Trp Phe Ser Ala Pro Gln Pro Ala Pro
        35                  40                  45

Glu Asn Ala Tyr Gln Ala Tyr Ala Ala Pro Gln Leu Phe Pro Val Ser
    50                  55                  60

Asp Ile
65

<210> SEQ ID NO 23
<211> LENGTH: 51
<212> TYPE: PRT
<213> ORGANISM: Human herpesvirus 4

<400> SEQUENCE: 23

Arg Lys Pro Gln Gln Pro Glu Ser Leu Glu Glu Cys Asp Ser Glu Leu
1               5                   10                  15

Glu Ile Lys Arg Tyr Lys Asn Arg Val Ala Ser Arg Lys Cys Arg Ala
            20                  25                  30

Lys Phe Lys Gln Leu Leu Gln His Tyr Arg Glu Val Ala Ala Ala Lys
        35                  40                  45

Ser Ser Glu
    50

<210> SEQ ID NO 24
<211> LENGTH: 1153
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Met Arg Pro Ala Pro Trp Thr Pro Asn Pro Arg Ser Pro Ser Gln
1               5                   10                  15

Met Ser Val Arg Asp Arg Leu Ala Arg Leu Arg Ala Glu Ala Gln Val
            20                  25                  30

Lys Gln Ala Ser Val Glu Val Gln Pro Pro Gln Leu Thr Gln Val Ser
        35                  40                  45

Pro Gln Gln Pro Val Ala Gly Ile Leu Phe Ile Leu Ala Ile Leu Thr
    50                  55                  60

Glu Trp Gly Ser Gly Asn Arg Thr Tyr Gly Pro Val Phe Met Cys Leu
65              70                  75                  80

Gly Gly Leu Leu Thr Met Val Ala Gly Ala Val Trp Leu Thr Val Met
            85                  90                  95

Ser Asn Thr Leu Leu Ser Ala Trp Ile Leu Thr Ala Gly Phe Leu Ile
            100                 105                 110

Phe Leu Ile Gly Phe Ala Leu Phe Gly Val Ile Arg Cys Cys Arg Tyr
        115                 120                 125

Cys Cys Tyr Tyr Cys Leu Thr Leu Glu Ser Glu Glu Arg Pro Pro Thr
    130                 135                 140

Pro Tyr Arg Asn Thr Val Ile Arg Asp Arg Arg Arg Asn Pro Ala Ser

-continued

```
            145                 150                 155                 160
Arg Arg Asp Gln Ala Lys Trp Arg Leu Gln Thr Leu Ala Ala Gly Trp
                    165                 170                 175
Pro Met Gly Tyr Gln Ala Tyr Ser Ser Trp Met Tyr Ser Tyr Thr Asp
                180                 185                 190
His Gln Thr Thr Pro Thr Phe Val His Leu Gln Ala Thr Leu Gly Cys
            195                 200                 205
Thr Gly Gly Arg Arg Cys His Val Phe Leu Gly Ile Val Leu Phe Ile
        210                 215                 220
Phe Gly Cys Leu Leu Val Leu Gly Ile Trp Ile Tyr Leu Leu Glu Met
225                 230                 235                 240
Leu Trp Arg Leu Gly Ala Thr Ile Trp Gln Leu Leu Ala Phe Phe Leu
                245                 250                 255
Ala Phe Phe Leu Asp Leu Ile Leu Ile Ile Ala Leu Tyr Leu Gln
                260                 265                 270
Gln Asn Trp Trp Thr Leu Leu Val Asp Leu Leu Trp Leu Leu Leu Phe
            275                 280                 285
Leu Ala Ile Leu Ile Trp Met Tyr Tyr His Gly Gln Arg Gly Arg Val
        290                 295                 300
Ala Cys Ala Pro Val Pro Ala Pro Ala Gly Pro Ile Val Arg Pro Trp
305                 310                 315                 320
Glu Pro Ser Leu Thr Gln Ala Ala Gly Gln Ala Phe Ala Pro Val Arg
                325                 330                 335
Pro Gln His Met Pro Val Glu Pro Val Pro Val Pro Thr Val Ala Leu
                340                 345                 350
Glu Arg Pro Val Tyr Pro Lys Pro Val Arg Pro Val Leu Trp Leu Ser
            355                 360                 365
Ser Pro Gly Gly Leu Gly Thr Leu Gly Ala Ala Leu Leu Thr Leu Ala
        370                 375                 380
Ala Ala Leu Ala Leu Leu Ala Ser Leu Ile Leu Gly Thr Leu Asn Leu
385                 390                 395                 400
Thr Thr Met Phe Leu Leu Met Leu Leu Trp Thr Leu Val Val Leu Leu
                405                 410                 415
Ile Cys Ser Ser Cys Ser Ser Cys Pro Leu Ser Lys Ile Leu Leu Ala
                420                 425                 430
Arg Leu Phe Leu Tyr Ala Leu Ala Leu Leu Leu Ala Ser Ala Leu
            435                 440                 445
Ile Ala Gly Gly Ser Ile Leu Gln Thr Asn Phe Lys Ser Leu Ser Ser
        450                 455                 460
Thr Glu Phe Ile Pro Asn Leu Phe Cys Met Leu Leu Ile His Ser
465                 470                 475                 480
Asp Glu His His His Asp Asp Ser Leu Pro His Pro Gln Gln Ala Thr
                485                 490                 495
Asp Asp Ser Gly His Glu Ser Asp Ser Asn Ser Asn Glu Gly Arg His
            500                 505                 510
His Leu Leu Val Ser Gly Ala Gln Val Pro Glu Pro Thr Ile His
        515                 520                 525
Leu Ala Ala Gln Gly Met Ala Tyr Pro Leu His Glu Gln His Gly Met
530                 535                 540
Ala Pro Cys Pro Val Ala Gln Ala Pro Pro Thr Pro Leu Pro Phe Phe
545                 550                 555                 560
Ala Ile Cys Leu Thr Trp Arg Ile Glu Asp Pro Pro Phe Asn Ser Leu
                565                 570                 575
```

```
Leu Phe Ala Leu Leu Ala Ala Ala Gly Gly Leu Gln Gly Ile Tyr Val
                580                 585                 590
Leu Val Met Leu Val Leu Leu Ile Leu Ala Tyr Arg Arg Arg Trp Arg
            595                 600                 605
Arg Leu Thr Val Cys Gly Gly Ile Met Phe Leu Ala Cys Val Leu Val
        610                 615                 620
Leu Ile Val Asp Ala Val Leu Gln Leu Ser Pro Leu Leu Gly Ala Val
625                 630                 635                 640
Thr Val Val Ser Met Thr Leu Leu Leu Ala Phe Asn Gly Pro His
                645                 650                 655
Asp Pro Leu Pro Gln Asp Pro Asn Thr Asp Asn Gly Pro Gln
                660                 665                 670
Asp Pro Asp Asn Thr Asp Asn Gly Pro His Asp Pro Leu Pro His
            675                 680                 685
Ser Pro Ser Asp Ser Ala Gly Asn Asp Gly Gly Pro Pro Gln Leu Thr
        690                 695                 700
Glu Glu Val Glu Asn Lys Gly Gly Asp Gln Gly Pro Pro Leu Met Thr
705                 710                 715                 720
Asp Gly Gly Gly Gly His Ser His Asp Ser Gly His Gly Gly Asp
                725                 730                 735
Pro His Leu Pro Thr Leu Leu Leu Gly Ser Ser Gly Ser Gly Gly Asp
                740                 745                 750
Asp Asp Asp Pro His Gly Pro Val Gln Leu Ser Tyr Tyr Asp Gly Lys
        755                 760                 765
Arg Thr Glu Gln Gly Lys Glu Val Leu Glu Lys Ala Arg Gly Ser Thr
        770                 775                 780
Tyr Gly Thr Pro Arg Pro Pro Met Ser Asp Trp Thr Gly Gly Ala Leu
785                 790                 795                 800
Leu Val Leu Tyr Ser Phe Ala Leu Met Leu Ile Ile Ile Leu Ile
                805                 810                 815
Ile Phe Ile Phe Arg Arg Asp Leu Leu Cys Pro Leu Gly Ala Leu Cys
                820                 825                 830
Ile Leu Leu Leu Met Ile Thr Leu Leu Leu Ile Ala Leu Trp Asn Leu
                835                 840                 845
His Gly Gln Ala Leu Met Ser Asp Glu Gly Pro Gly Thr Gly Pro Gly
850                 855                 860
Asn Gly Leu Gly Glu Lys Gly Asp Thr Ser Gly Pro Glu Gly Ser Gly
865                 870                 875                 880
Gly Ser Gly Pro Gln Arg Arg Gly Gly Asp Asn His Gly Arg Gly Arg
                885                 890                 895
Gly Arg Gly Arg Gly Arg Gly Gly Arg Pro Gly Ala Pro Gly Gly
                900                 905                 910
Ser Gly Ser Gly Pro Arg His Arg Asp Gly Val Arg Arg Pro Gln Lys
        915                 920                 925
Arg Pro Ser Cys Ile Gly Cys Lys Gly Thr His Trp Ile Asp Asp Asn
        930                 935                 940
Pro Ser Thr Glu Thr Ala Gln Ala Trp Asn Ala Gly Phe Leu Arg Gly
945                 950                 955                 960
Arg Ala Tyr Gly Ile Asp Leu Leu Arg Thr Glu Gly Glu His Val Glu
                965                 970                 975
Gly Ala Thr Gly Glu Thr Arg Glu Glu Ser Glu Asp Thr Glu Ser Asp
                980                 985                 990
```

| | | | | | | | | | | | |
|---|---|---|---|---|---|---|---|---|---|---|---|
| Gly | Asp | Asp | Glu | Asp | Leu | Pro | Cys | Ile | Val | Ser | Arg | Gly | Gly | Pro | Lys |
| | | 995 | | | | 1000 | | | | 1005 | |
| Val | Lys | Arg | Pro | Pro | Ile | Phe | Ile | Arg | Arg | Leu | His | Arg | Leu | Leu |
| | 1010 | | | | 1015 | | | | 1020 | | |
| Leu | Met | Arg | Ala | Met | Asn | Pro | Val | Cys | Leu | Pro | Val | Ile | Val | Ala |
| | 1025 | | | | 1030 | | | | 1035 | | |
| Pro | Tyr | Leu | Phe | Trp | Leu | Ala | Ala | Ile | Ala | Ala | Ser | Cys | Phe | Thr |
| | 1040 | | | | 1045 | | | | 1050 | | |
| Ala | Ser | Val | Ser | Thr | Val | Val | Thr | Ala | Thr | Gly | Leu | Ala | Leu | Ser |
| | 1055 | | | | 1060 | | | | 1065 | | |
| Leu | Leu | Leu | Leu | Ala | Ala | Val | Ala | Ser | Ser | Tyr | Ala | Ala | Ala | Gln |
| | 1070 | | | | 1075 | | | | 1080 | | |
| Arg | Lys | Leu | Leu | Thr | Pro | Val | Thr | Val | Leu | Thr | Ala | Val | Val | Thr |
| | 1085 | | | | 1090 | | | | 1095 | | |
| Thr | Phe | Ser | Ala | Gly | Thr | Phe | Lys | Leu | Pro | Arg | Cys | Thr | Pro | Gly |
| | 1100 | | | | 1105 | | | | 1110 | | |
| Asp | Arg | Gln | Trp | Leu | Tyr | Val | Gln | Ser | Ser | Val | Gly | Asn | Ile | Val |
| | 1115 | | | | 1120 | | | | 1125 | | |
| Gln | Ser | Cys | Asn | Pro | Arg | Tyr | Ser | Ile | Phe | Phe | Asp | Tyr | Met | Ala |
| | 1130 | | | | 1135 | | | | 1140 | | |
| Ile | His | Arg | Ser | Leu | Thr | Lys | Ile | Trp | Glu |
| | 1145 | | | | 1150 | |

<210> SEQ ID NO 25
<211> LENGTH: 3459
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 25

```
atgagacctg ctccctggac acctaatcct cccaggtccc ccagccagat gagcgtgaga      60
gacagactgg ctaggctgag agccgaggct caggtcaagc aggccagcgt cgaggtgcaa     120
cccccctcagc tcacccaggt gtcccccccag cagcctgtgg ccggcattct gttcattctg     180
gccattctga ccgagtgggg aagcggcaac agaacctacg ccctgtcttc catgtgcctc     240
ggaggactgc tgacaatggt ggctggcgcc gtgtggctca ccgtcatgtc caacaccctg     300
ctcagcgcct ggattctgac cgccggattc ctgatctttc tgatcggatt cgctctcttt     360
ggcgtcatca ggtgttgcag gtactgttgc tactactgcc tgaccctcga gagcgaggaa     420
agacccccca cccccctacag gaatacagtg attagggaca aaggaggaa tcctgcctcc     480
aggagagacc aggccaaatg gagactccaa acactcgccg ctggatggcc catgggctac     540
caggcctata gctcctggat gtacagctac accgaccatc agacaacacc caccttcgtg     600
catctgcagg ctacactggg ctgcaccgga ggcagaaggt gtcacgtgtt ctgggaatc     660
gtgctgttca tctttggatg cctgctcgtg ctgggcatct ggatttatct cctggagatg     720
ctctggagac tcggcgctac aatttggcag ctgctcgcct tttttctggc cttcttctg     780
gacctgatcc tcctgatcat cgccctgtac ctccaacaga actggtggac cctcctggtg     840
gatctgctgt ggctcctcct cttcctggcc atcctgatct ggatgtacta ccatggccag     900
agaggaaggg tcgcttgcgc tcctgtccct gctcctgctg ccccatcgt gaggccttgg     960
gagccttccc tcacacaggc cgccggccag gcctttgctc ccgtgaggcc ccagcacatg    1020
```

```
cctgtggaac ccgtgcccgt ccccacagtg gctctggaaa ggcctgtgta ccccaagccc    1080
gtgagacctg tcctctggct cagcagccct ggaggactcg gaacactcgg agccgctctc    1140
ctgacactgg ccgctgctct ggctctgctg gctagcctga tcctgggaac cctcaacctc    1200
accaccatgt ttctcctcat gctcctgtgg accctcgtgg tgctgctcat ctgttccagc    1260
tgctccagct gcccctgag caagatcctg ctggccaggc tgttcctgta cgccctcgcc    1320
ctcctgctgc tggctagcgc cctgatcgct ggcggaagca tcctccagac caatttcaag    1380
agcctctcct ccaccgagtt catccccaac ctgttctgta tgttactgct gatccatagc    1440
gacgagcacc atcatgacga ctccctgccc catcctcagc aggccacaga cgactccggc    1500
cacgagagcg acagcaatag caatgagggc aggcaccatc tgctcgtgtc cggagctcaa    1560
gtccccgagc ctcccaccat ccatctcgcc gcccagggaa tggcttaccc cctccacgag    1620
cagcacggca tggccccttg tccgtcgct caagcccccc ctacacctct gccctttttc    1680
gccatttgtc tgacctggag aatcgaggac ccccccttca acagcctgct gttcgccctg    1740
ctcgccgccg ctggcggcct ccagggcatt tacgtcctcg tgatgctggt gctgctgatc    1800
ctcgcttaca ggagaagatg gaggagactg acagtgtgcg gcggcatcat gtttctcgcc    1860
tgcgtcctgg tcctgatcgt ggacgccgtc ctgcaactca gcccctcct gggagctgtg    1920 acagtggtct ccatgaccct gctgctgctg gccttcaacg accccacga tcctctgccc    1980 caagatcctg acaataccga cgataacggc ccccaagacc ccgataacac cgacgacaat    2040
ggccctcacg accctctgcc ccatagcct tccgatagcg ctggcaacga tggcggccct    2100
cctcagctga cagaggaggt ggaaaataag ggcggcgatc agggaccccc cctgatgaca    2160
gatggcggag gaggacacag ccatgatagc ggacatggcg gaggcgatcc ccatctgcct    2220
accctcctcc tgggcagctc cggttctgga ggcgacgatg atgaccctca cggccctgtg    2280
cagctctcct actacgacgg caaaaggacc gaacaaggaa agaggtcct ggagaaggcc    2340 aggggcagca catacggaac ccccaggcct cccatgtccg attggaccgg aggagccctg    2400
ctggtcctct acagcttcgc cctgatgctg atcattatca tcctgatcat ctttatcttc    2460
agaagggacc tgctgtgccc ctcggcgcc ctgtgcatcc tgctgctcat gatcacactc    2520
ctcctgatcg ccctctggaa cctgcacgga caagccctga tgtccgatga gggacctgga    2580
acaggacccg gaaacggact gggcgagaag ggagatacaa gcggcccga aggcagcggc    2640 ggaagcggac cccaaagaag gggcggcgac aaccacggaa gaggaagagg caggggcaga    2700
ggcagaggag gaggaagacc tggagccct ggcggttctg gaagcggacc caggcacagg    2760
gacggagtga ggaggcctca aaaaagaccc agctgcatcg gctgcaaggg aacccactgg    2820
attgatgata cccctccac agagaccgct caggcctgga cgccggctt cctgaggga    2880 agagcctatg gcatcgatct gctgaggacc gagggcgaac acgtggaggg agccaccgga    2940
gagacaaggg aggaaagcga agacacagaa agcgatggcg acgacgaaga cctgccctgc    3000
attgtgtcca ggggcggacc caaggtgaag aggcccccta tctttatcag aaggctccat    3060
agactgctcc tgatgagggc catgaaccct gtgtgcctgc ccgtgatcgt ggcccccatc    3120
ctcttttggc tggccgccat tgccgctagc tgcttcaccg cctccgtgtc cacagtggtg    3180
acagccaccg gcctcgccct gagcctgctg ctcctcgctg ccgtggcctc cagctacgcc    3240
gctgctcaaa gaaagctcct gacccctgtc accgtcctga cagccgtcgt gaccaccttt    3300
tccgctggca cctcaagct gcctaggtgc acacctggcg acaggcagtg gctctacgtg    3360
cagagctccg tgggcaatat tgtgcagagc tgcaatccca ggtacagcat ttttttcgac    3420
```
tacatggcca tccataggtc cctcaccaag atctgggag         3459

<210> SEQ ID NO 26
<211> LENGTH: 1270
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 26

```
Met Arg Pro Ala Pro Trp Thr Pro Asn Pro Arg Ser Pro Ser Gln
1               5                   10                  15

Met Ser Val Arg Asp Arg Leu Ala Arg Leu Arg Ala Glu Ala Gln Val
            20                  25                  30

Lys Gln Ala Ser Val Glu Val Gln Pro Pro Gln Leu Thr Gln Val Ser
        35                  40                  45

Pro Gln Gln Pro Val Ala Gly Ile Leu Phe Ile Leu Ala Ile Leu Thr
    50                  55                  60

Glu Trp Gly Ser Gly Asn Arg Thr Tyr Gly Pro Val Phe Met Cys Leu
65                  70                  75                  80

Gly Gly Leu Leu Thr Met Val Ala Gly Ala Val Trp Leu Thr Val Met
                85                  90                  95

Ser Asn Thr Leu Leu Ser Ala Trp Ile Leu Thr Ala Gly Phe Leu Ile
            100                 105                 110

Phe Leu Ile Gly Phe Ala Leu Phe Gly Val Ile Arg Cys Cys Arg Tyr
        115                 120                 125

Cys Cys Tyr Tyr Cys Leu Thr Leu Glu Ser Glu Glu Arg Pro Pro Thr
    130                 135                 140

Pro Tyr Arg Asn Thr Val Arg Lys Pro Gln Gln Pro Glu Ser Leu Glu
145                 150                 155                 160

Glu Cys Asp Ser Glu Leu Glu Ile Lys Arg Tyr Lys Asn Arg Val Ala
                165                 170                 175

Ser Arg Lys Cys Arg Ala Lys Phe Lys Gln Leu Leu Gln His Tyr Arg
            180                 185                 190

Glu Val Ala Ala Ala Lys Ser Ser Glu Ile Arg Asp Arg Arg Arg Asn
        195                 200                 205

Pro Ala Ser Arg Arg Asp Gln Ala Lys Trp Arg Leu Gln Thr Leu Ala
    210                 215                 220

Ala Gly Trp Pro Met Gly Tyr Gln Ala Tyr Ser Ser Trp Met Tyr Ser
225                 230                 235                 240

Tyr Thr Asp His Gln Thr Thr Pro Thr Phe Val His Leu Gln Ala Thr
                245                 250                 255

Leu Gly Cys Thr Gly Gly Arg Arg Cys His Val Phe Leu Gly Ile Val
            260                 265                 270

Leu Phe Ile Phe Gly Cys Leu Leu Val Leu Gly Ile Trp Ile Tyr Leu
        275                 280                 285

Leu Glu Met Leu Trp Arg Leu Gly Ala Thr Ile Trp Gln Leu Leu Ala
    290                 295                 300

Phe Phe Leu Ala Phe Phe Leu Asp Leu Ile Leu Ile Ile Ala Leu
305                 310                 315                 320

Tyr Leu Gln Gln Asn Trp Trp Thr Leu Leu Val Asp Leu Leu Trp Leu
                325                 330                 335

Leu Leu Phe Leu Ala Ile Leu Ile Trp Met Tyr Tyr His Gly Gln Arg
```

-continued

```
            340                 345                 350
Gly Arg Val Ala Cys Ala Pro Val Pro Ala Pro Ala Gly Pro Ile Val
            355                 360                 365
Arg Pro Trp Glu Pro Ser Leu Thr Gln Ala Ala Gly Gln Ala Phe Ala
            370                 375                 380
Pro Val Arg Pro Gln His Met Pro Val Glu Pro Val Pro Val Pro Thr
385                 390                 395                 400
Val Ala Leu Glu Arg Pro Val Tyr Pro Lys Pro Val Arg Pro Val Leu
            405                 410                 415
Trp Leu Ser Ser Pro Gly Gly Leu Gly Thr Leu Gly Ala Ala Leu Leu
            420                 425                 430
Thr Leu Ala Ala Ala Leu Ala Leu Leu Ala Ser Leu Ile Leu Gly Thr
            435                 440                 445
Leu Asn Leu Thr Thr Met Phe Leu Leu Met Leu Leu Trp Thr Leu Val
            450                 455                 460
Val Leu Leu Ile Cys Ser Ser Cys Ser Ser Cys Pro Leu Ser Lys Ile
465                 470                 475                 480
Leu Leu Ala Arg Leu Phe Leu Tyr Ala Leu Ala Leu Leu Leu Leu Ala
            485                 490                 495
Ser Ala Leu Ile Ala Gly Gly Ser Ile Leu Gln Thr Asn Phe Lys Ser
            500                 505                 510
Leu Ser Ser Thr Glu Phe Ile Pro Asn Leu Phe Cys Met Leu Leu Leu
            515                 520                 525
Ile His Ser Asp Glu His His Asp Asp Ser Leu Pro His Pro Gln
            530                 535                 540
Gln Ala Thr Asp Asp Ser Gly His Glu Ser Asp Ser Asn Ser Asn Glu
545                 550                 555                 560
Gly Arg His His Leu Leu Val Ser Gly Ala Gln Val Pro Glu Pro Pro
            565                 570                 575
Thr Ile His Leu Ala Ala Gln Gly Met Ala Tyr Pro Leu His Glu Gln
            580                 585                 590
His Gly Met Ala Pro Cys Pro Val Ala Gln Ala Pro Pro Thr Pro Leu
            595                 600                 605
Pro Phe Phe Ala Ile Cys Leu Thr Trp Arg Ile Glu Asp Pro Pro Phe
            610                 615                 620
Asn Ser Leu Leu Phe Ala Leu Leu Ala Ala Gly Gly Leu Gln Gly
625                 630                 635                 640
Ile Tyr Val Leu Val Met Leu Val Leu Leu Ile Leu Ala Tyr Arg Arg
            645                 650                 655
Arg Trp Arg Arg Leu Thr Val Cys Gly Gly Ile Met Phe Leu Ala Cys
            660                 665                 670
Val Leu Val Leu Ile Val Asp Ala Val Leu Gln Leu Ser Pro Leu Leu
            675                 680                 685
Gly Ala Val Thr Val Val Ser Met Thr Leu Leu Leu Ala Phe Asn
            690                 695                 700
Gly Pro His Asp Pro Leu Pro Gln Asp Pro Asp Asn Thr Asp Asp Asn
705                 710                 715                 720
Gly Pro Gln Asp Pro Asp Asn Thr Asp Asn Gly Pro His Asp Pro
            725                 730                 735
Leu Pro His Ser Pro Ser Asp Ser Ala Gly Asn Asp Gly Pro Pro
            740                 745                 750
Gln Leu Thr Glu Glu Val Glu Asn Lys Gly Gly Asp Gln Gly Pro Pro
            755                 760                 765
```

-continued

```
Leu Met Thr Asp Gly Gly Gly His Ser His Asp Ser Gly His Gly
770                 775                 780
Gly Gly Asp Pro His Leu Pro Thr Leu Leu Leu Gly Ser Ser Gly Ser
785                 790                 795                 800
Gly Gly Asp Asp Asp Pro His Gly Pro Val Gln Leu Ser Tyr Tyr
            805                 810                 815
Asp Gly Lys Arg Thr Glu Gln Gly Lys Glu Val Leu Glu Lys Ala Arg
                820                 825                 830
Gly Ser Thr Tyr Gly Thr Pro Arg Pro Pro Met Ser Asp Trp Thr Gly
        835                 840                 845
Gly Ala Leu Leu Val Leu Tyr Ser Phe Ala Leu Met Leu Ile Ile Ile
        850                 855                 860
Ile Leu Ile Ile Phe Ile Phe Arg Arg Asp Leu Leu Cys Pro Leu Gly
865                 870                 875                 880
Ala Leu Cys Ile Leu Leu Leu Met Ile Thr Leu Leu Leu Ile Ala Leu
                885                 890                 895
Trp Asn Leu His Gly Gln Ala Leu Met Ser Asp Glu Gly Pro Gly Thr
                900                 905                 910
Gly Pro Gly Asn Gly Leu Gly Glu Lys Gly Asp Thr Ser Gly Pro Glu
        915                 920                 925
Gly Ser Gly Gly Ser Gly Pro Gln Arg Arg Gly Gly Asp Asn His Gly
    930                 935                 940
Arg Gly Arg Gly Arg Gly Arg Gly Arg Gly Gly Arg Pro Gly Ala
945                 950                 955                 960
Pro Gly Gly Ser Gly Ser Gly Pro Arg His Arg Asp Gly Val Arg Arg
                965                 970                 975
Pro Gln Lys Arg Pro Ser Cys Ile Gly Cys Lys Gly Thr His Trp Ile
            980                 985                 990
Asp Asp Asn Pro Ser Thr Glu Thr Ala Gln Ala Trp Asn Ala Gly Phe
                995                 1000                1005
Leu Arg Gly Arg Ala Tyr Gly Ile Asp Leu Leu Arg Thr Glu Gly
    1010                1015                1020
Glu His Val Glu Gly Ala Thr Gly Glu Thr Arg Glu Glu Ser Glu
    1025                1030                1035
Asp Thr Glu Ser Asp Gly Asp Asp Glu Asp Leu Pro Cys Ile Val
    1040                1045                1050
Ser Arg Gly Gly Pro Lys Val Lys Arg Pro Pro Ile Phe Ile Arg
    1055                1060                1065
Arg Leu His Arg Leu Leu Leu Met Arg Ala Met Asn Pro Val Cys
    1070                1075                1080
Leu Pro Val Ile Val Ala Pro Tyr Leu Phe Trp Leu Ala Ala Ile
    1085                1090                1095
Ala Ala Ser Cys Phe Thr Ala Ser Val Ser Thr Val Val Thr Ala
    1100                1105                1110
Thr Gly Leu Ala Leu Ser Leu Leu Leu Leu Ala Ala Val Ala Ser
    1115                1120                1125
Ser Tyr Ala Ala Ala Gln Arg Lys Leu Leu Thr Pro Val Thr Val
    1130                1135                1140
Leu Thr Ala Val Val Thr Thr Phe Ser Ala Gly Thr Phe Lys Leu
    1145                1150                1155
Pro Arg Cys Thr Pro Gly Asp Arg Gln Trp Leu Tyr Val Gln Ser
    1160                1165                1170
```

| | | | | | | | | | | |
|---|---|---|---|---|---|---|---|---|---|---|
|Ser|Val|Gly|Asn|Ile|Val|Gln|Ser|Cys|Asn|Pro|Arg|Tyr|Ser|Ile|
| |1175| | | |1180| | | | |1185| | | | |

Phe Phe Asp Tyr Met Ala Ile His Arg Ser Leu Thr Lys Ile Trp
    1190            1195                1200

Glu Asp Leu Gly Gly Pro Ser Gln Ala Pro Leu Pro Cys Val Leu
    1205            1210                1215

Trp Pro Val Leu Pro Glu Pro Leu Pro Gln Gly Gln Leu Thr Ala
    1220            1225                1230

Tyr His Val Ser Thr Ala Pro Thr Gly Ser Trp Phe Ser Ala Pro
    1235            1240                1245

Gln Pro Ala Pro Glu Asn Ala Tyr Gln Ala Tyr Ala Ala Pro Gln
    1250            1255                1260

Leu Phe Pro Val Ser Asp Ile
    1265            1270

<210> SEQ ID NO 27
<211> LENGTH: 3810
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 27

```
atgagacctg ctccctggac acctaatcct cccaggtccc ccagccagat gagcgtgaga    60
gacagactgg ctaggctgag agccgaggct caggtcaagc aggccagcgt cgaggtgcaa   120 cccccctcagc tcacccaggt gtccccccag cagcctgtgg ccggcattct gttcattctg   180
gccattctga ccgagtgggg aagcggcaac agaacctacg ccctgtcttc atgtgcctc    240 ggaggactgc tgacaatggt ggctggcgcc gtgtggctca ccgtcatgtc caacaccctg   300
ctcagcgcct ggattctgac cgccggattc ctgatctttc tgatcggatt cgctctcttt   360
ggcgtcatca ggtgttgcag gtactgttgc tactactgcc tgaccctcga gagcgaggaa   420 agaccccccca cccccctacag gaatacagtg aggaaaccctc agcagcccga gagcctcgag   480
gagtgcgata gcgagctgga gattaaaagg tataagaata gggtggcctc caggaagtgt   540
agggctaaat caaacagct cctgcaacac tatagggaag tggccgccgc caagtccagc   600
gagattaggg acagaaggag gaatcctgcc tccaggagag accaggccaa atggagactc   660
caaacactcg ccgctggatg gcccatgggc taccaggcct atagctcctg gatgtacagc   720
tacaccgacc atcagacaac acccacccttc gtgcatctgc aggctacact gggctgcacc   780
ggaggcagaa ggtgtcacgt gtttctggga atcgtgctgt tcatctttgg atgcctgctc   840
gtgctgggca tctggattta tctcctggag atgctctgga gactcggcgc tacaatttgg   900
cagctgctcg cctttttctct ggccttcttt ctggacctga tcctcctgat catcgccctg   960
tacctccaac agaactggtg gacccctcctg gtggatctgc tgtggctcct cctcttcctg  1020
gccatcctga tctggatgta ctaccatggc cagagaggaa gggtcgcttg cgctcctgtc  1080
cctgctcctg ctggccccat cgtgaggcct ggagagcctt ccctcacaca ggccgccggc  1140 caggccttg ctcccgtgag gccccagcac atgcctgtgg aacccgtgcc cgtccccaca  1200
gtggctctgg aaaggcctgt gtacccccaag cccgtgagac ctgtcctctg gctcagcagc  1260
cctggaggac tcgaaacact cggagccgct tcctgacac tggccgctgc tctggctctg  1320
ctggctagcc tgatcctggg aaccctcaac ctcaccacca tgtttctcct catgctcctg  1380
```

```
tggaccctcg tggtgctgct catctgttcc agctgctcca gctgcccct  gagcaagatc   1440 ctgctggcca ggctgttcct gtacgccctc gccctcctgc tgctggctag cgccctgatc   1500
gctggcggaa gcatcctcca gaccaatttc aagagcctct cctccaccga gttcatcccc   1560
aacctgttct gtatgttact gctgatccat agcgacgagc accatcatga cgactccctg   1620
ccccatcctc agcaggccac agacgactcc ggccacgaga gcgacagcaa tagcaatgag   1680
ggcaggcacc atctgctcgt gtccggagct caagtcccg  agcctccac  catccatctc   1740 gccgcccagg gaatggctta ccccctccac gagcagcacg gcatggcccc ttgtcccgtc   1800
gctcaagccc cccctacacc tctgcccttt ttcgccattt gtctgacctg gagaatcgag   1860
gaccccccct tcaacagcct gctgttcgcc ctgctcgccg ccgctggcgg cctccagggc   1920
atttacgtcc tcgtgatgct ggtgctgctg atcctcgctt acaggagaag atggaggaga   1980
ctgacagtgt gcggcggcat catgtttctc gcctgcgtcc tggtcctgat cgtggacgcc   2040
gtcctgcaac tcagccccct cctgggagct gtgacagtgg tctccatgac cctgctgctg   2100
ctggccttca acggaccca  cgatcctctg ccccaagatc ctgacaatac cgacgataac   2160
ggcccccaag accccgataa caccgacgac aatggccctc acgaccctct gccccatagc   2220
ccttccgata gcgctggcaa cgatggcggc cctcctcagc tgacagagga ggtggaaaat   2280
aagggcggcg atcagggacc ccccctgatg acagatggcg gaggaggaca cagccatgat   2340
agcggacatg gcggaggcga tccccatctg cctaccctcc tcctgggcag ctccggttct   2400
ggaggcgacg atgatgaccc tcacggcct  gtgcagctct cctactacga cggcaaaagg   2460
accgaacaag gaaaagaggt cctggagaag gccaggggca gcacatacgg aaccccagg   2520 cctcccatgt ccgattggac cggaggagcc ctgctggtcc tctacagctt cgccctgatg   2580
ctgatcatta tcatcctgat catctttatc ttcagaaggg acctgctgtg ccctctcggc   2640
gccctgtgca tcctgctgct catgatcaca ctcctcctga tcgccctctg gaacctgcac   2700
ggacaagccc tgatgtccga tgagggacct ggaacaggac ccggaaacgg actgggcgag   2760
aagggagata caagcggccc cgaaggcagc ggcggaagcg gaccccaaag aagggggcgg   2820
gacaaccacg gaagaggaag aggcaggggc agaggcagag gaggaggaag acctggagcc   2880
cctggcggtt ctggaagcgg acccaggcac agggacggag tgaggaggcc tcaaaaaaga   2940
cccagctgca tcggctgcaa gggaaccac  tggattgatg ataacccctc cacagagacc   3000
gctcaggcct ggaacgccgg cttcctgagg ggaagagcct atggcatcga tctgctgagg   3060
accgagggcg aacacgtgga gggagccacc ggagagacaa gggaggaaag cgaagacaca   3120
gaaagcgatg gcgacgacga agacctgccc tgcattgtgt ccaggggcgg acccaaggtg   3180
aagaggcccc ctatctttat cagaaggctc catagactgc tcctgatgag ggccatgaac   3240
cctgtgtgcc tgcccgtgat cgtggccccc tacctctttt ggctggccgc cattgccgct   3300
agctgcttca ccgcctccgt gtccacagtg gtgacagcca ccggcctcgc cctgagcctg   3360
ctgctcctcg ctgccgtggc ctccagctac gccgctgctc aaagaaagct cctgaccctt   3420
gtcaccgtcc tgacagccgt cgtgaccacc tttttccgctg gcaccttcaa gctgcctagg   3480
tgcacacctg gcgacaggca gtggctctac gtgcagagct ccgtgggcaa tattgtgcag   3540
agctgcaatc ccaggtacag catttttttc gactacatgg ccatccatag gtccctcacc   3600
aagatctggg aggatctggg aggcccttcc caggctcctc tgcccgtgcgt gctgtggcct   3660 gtgctgcctag agcctctgcc ccaaggccag ctgcagcct  atcacgtgtc caccgctcct   3720
acaggttctt ggttcagcgc tccccagccc gctcccgaaa acgcttacca ggcttacgcc   3780
``` gcccccagc tgttccccgt ctccgacatc 3810

<210> SEQ ID NO 28
<211> LENGTH: 355
<212> TYPE: PRT
<213> ORGANISM: Callitrichine gammaherpesvirus 3

<400> SEQUENCE: 28

```
Met Ala Pro Arg Arg Leu Ser Gly Pro Pro Trp Leu Thr Val Leu
1               5                   10                  15

Leu Leu Leu Ser Thr Leu Ser Val Ala Ala Leu Leu Ile Leu Phe Leu
                20                  25                  30

Ile Phe Ser Ala Gly Ala Thr Ile Ser Thr Glu Ala Ser Leu Leu Val
            35                  40                  45

Leu Leu Leu Leu Phe Val Thr Leu Leu Pro Leu Ser Ser Asn
50                  55                  60

Gly Leu Gln Leu Pro Ala Ala Leu Ile Leu Ile Gln Cys Phe Leu Leu
65                  70                  75                  80

Ala Ala Asp Tyr Leu Ala Tyr Leu Ile Leu Pro Thr Ile Ser Glu Asp
                85                  90                  95

Phe Leu Ile Leu Ile Ala Ile Leu Val Ile Val Ile Leu Val Gly Thr
            100                 105                 110

Ile Thr Thr Leu Val Gly Ala Ile Gly Gly Ile Arg Ala Arg Arg Ser
115                 120                 125

Phe Leu Phe Ile Cys Ile Phe Phe Leu Phe Leu Ser Leu Phe Leu Thr
            130                 135                 140

Ile Leu Ala Leu Leu Leu Gly Phe Ser Trp Leu Leu Leu Val Ala Ile
145                 150                 155                 160

Leu Phe Trp Val Leu Trp Leu Val Ile Leu Ile Leu Leu Leu Leu Val
                165                 170                 175

Tyr Pro Ile Pro His His Pro Leu Pro Thr Ser Leu Arg Phe Arg Met
            180                 185                 190

Lys Gln Arg Val Ser Ser Asp Pro Thr Gly Ser Asp Arg Ser Pro Gln
        195                 200                 205

Gly Ser His Asn Ser Leu Asn Ser Pro Asp Glu Glu Asp Pro Lys Asp
        210                 215                 220

Asp Thr Lys Gln Pro Leu Cys Asn Met Thr Gln Gly Gly Pro Val
225                 230                 235                 240

Asn Gly Gln Leu Leu Gly Gln His Ala Gln Cys Pro Pro His Tyr Pro
                245                 250                 255

Cys Cys His Ile Gln His Pro Asp Gly Glu Asp Ser Asp Gly Asp Asp
            260                 265                 270

Gly Lys Ser Trp Gly Asp Ala Gly Glu Glu Asp Asn Gly Pro Asn Asp
        275                 280                 285

Pro Asn Thr Asn Asn Gly Asn Glu Gly Gly Glu Gly Asp Asp Tyr Lys
        290                 295                 300

Ser Trp Arg Lys Pro Glu Glu Glu Asp Asn Gly Pro Asn Asp Pro Asn
305                 310                 315                 320

Thr Asn Asn Arg Ile Glu Asp Gly Asp Gly Asp Gly Lys Ser Trp
                325                 330                 335

Arg Asn Pro Glu Glu Glu Asp Asn Arg Lys Gln Asp Arg Leu Gly Thr
            340                 345                 350

Lys Pro Phe
    355
```

<210> SEQ ID NO 29
<211> LENGTH: 93
<212> TYPE: PRT
<213> ORGANISM: Callitrichine gammaherpesvirus 3

<400> SEQUENCE: 29

Met Ala Pro Arg Arg Leu Ser Gly Pro Pro Trp Leu Thr Val Leu
1               5                   10                  15

Leu Leu Leu Ser Thr Leu Ser Val Ala Ala Leu Leu Ile Leu Phe Leu
            20                  25                  30

Ile Phe Ser Ala Gly Ala Thr Ile Ser Thr Glu Ala Ser Leu Leu Val
        35                  40                  45

Leu Leu Leu Leu Phe Val Thr Leu Leu Leu Pro Leu Leu Ser Ser Asn
50                  55                  60

Gly Leu Gln Leu Pro Ala Ala Leu Ile Leu Ile Gln Cys Phe Leu Leu
65                  70                  75                  80

Ala Ala Asp Tyr Leu Ala Tyr Leu Ile Leu Pro Thr Ile
                85                  90

<210> SEQ ID NO 30
<211> LENGTH: 198
<212> TYPE: PRT
<213> ORGANISM: Callitrichine gammaherpesvirus 3

<400> SEQUENCE: 30

Ser Glu Asp Phe Leu Ile Leu Ile Ala Ile Leu Val Ile Val Ile Leu
1               5                   10                  15

Val Gly Thr Ile Thr Thr Leu Val Gly Ala Ile Gly Gly Ile Arg Ala
            20                  25                  30

Arg Arg Ser Phe Leu Phe Ile Cys Ile Phe Phe Leu Phe Leu Ser Leu
        35                  40                  45

Phe Leu Thr Ile Leu Ala Leu Leu Leu Gly Phe Ser Trp Leu Leu Leu
50                  55                  60

Val Ala Ile Leu Phe Trp Val Leu Trp Leu Val Ile Leu Ile Leu Leu
65                  70                  75                  80

Leu Leu Val Tyr Pro Ile Pro His His Pro Leu Pro Thr Ser Leu Arg
                85                  90                  95

Phe Arg Met Lys Gln Arg Val Ser Ser Asp Pro Thr Gly Ser Asp Arg
            100                 105                 110

Ser Pro Gln Gly Ser His Asn Ser Leu Asn Ser Pro Asp Glu Glu Asp
        115                 120                 125

Pro Lys Asp Asp Thr Lys Gln Pro Leu Cys Asn Met Thr Gln Gly Gly
130                 135                 140

Pro Pro Val Asn Gly Gln Leu Leu Gly Gln His Ala Gln Cys Pro Pro
145                 150                 155                 160

His Tyr Pro Cys Cys His Ile Gln His Pro Asp Gly Glu Asp Ser Asp
                165                 170                 175

Gly Asp Asp Gly Lys Ser Trp Gly Asp Ala Gly Glu Glu Asp Asn Gly
            180                 185                 190

Pro Asn Asp Pro Asn Thr
        195

<210> SEQ ID NO 31
<211> LENGTH: 64
<212> TYPE: PRT
<213> ORGANISM: Callitrichine gammaherpesvirus 3

```
<400> SEQUENCE: 31

Asn Asn Gly Asn Glu Gly Glu Gly Asp Asp Tyr Lys Ser Trp Arg
1               5                   10                  15

Lys Pro Glu Glu Asp Asn Gly Pro Asn Asp Pro Asn Thr Asn Asn
            20                  25                  30

Arg Ile Glu Asp Gly Asp Gly Asp Asp Gly Lys Ser Trp Arg Asn Pro
        35                  40                  45

Glu Glu Glu Asp Asn Arg Lys Gln Asp Arg Leu Gly Thr Lys Pro Phe
        50                  55                  60

<210> SEQ ID NO 32
<211> LENGTH: 413
<212> TYPE: PRT
<213> ORGANISM: Callitrichine gammaherpesvirus 3

<400> SEQUENCE: 32

Met Ala Gly His Trp Tyr Glu Ser Val Ile Pro Gly Leu Phe Leu Cys
1               5                   10                  15

Pro Leu Ile Leu Pro Ser Leu Phe Trp Ile Cys Ser Leu Leu Thr Phe
            20                  25                  30

Leu Val Gly His Gly Ala Asn Ile Val Ser Ala Val Leu Phe Leu Val
        35                  40                  45

Leu Ala Trp Cys Leu Leu Ile Ala Asn Trp Asn Val Thr Arg Glu Asp
    50                  55                  60

Phe Val Ser Gly Arg Arg Ser Ser Met Ser Ser Leu Ser Val Ala Ala
65                  70                  75                  80

Ser Thr Ala Thr Ala Met Phe Ala Ser Phe Leu Thr Leu Ser Phe Asp
            85                  90                  95

Gly Leu Gly Leu Leu Phe Gly Thr Ala Leu Val Ile Gln Thr Ile
        100                 105                 110

Tyr Val Leu Tyr Leu Val Val Met Glu Ile Thr Val Trp Ile Met Met
        115                 120                 125

Phe Arg Tyr Leu His Phe Trp Ile Thr Leu Leu Phe Leu Leu Ser Pro
    130                 135                 140

Ile Ile Leu Ser Val Ala Cys Leu Ile Ile Gln Ser Ser Ala Leu Leu
145                 150                 155                 160

Ile Glu Ala Val Val Thr Thr Ile Thr Val Leu Ala Ile Phe Leu
            165                 170                 175

Trp Leu Pro Pro Gln Gly Ala Glu Ala Asp Leu Gly Thr Ala Leu Leu
        180                 185                 190

Ile Leu Asn Thr Ala Leu Cys Leu Val Val Leu Ile Leu Thr Ala Ile
        195                 200                 205

Pro Thr Asp Ala Gln Ile Leu Thr Val Phe Cys Leu Phe Cys Gln Trp
    210                 215                 220

Thr Leu Phe Ile Cys Leu Gly Ile Arg Met Ile Cys Asn Trp Arg Gly
225                 230                 235                 240

Lys Leu Thr Arg Ile Ile Cys Leu Lys Phe Cys Leu Tyr Gly Leu Ile
            245                 250                 255

Ser Ala Ser Leu Ser Phe Gly Trp Tyr Ala Phe Leu Lys Glu Val Thr
        260                 265                 270

Leu Pro Thr Thr Ala Thr Val Asp Pro Arg Gln Leu Pro Leu Phe Leu
    275                 280                 285

Phe Ile Leu Ser Ser Val Leu Val Ile Leu Ala Ile Met Met Glu Phe
        290                 295                 300
```

```
Gln Thr Ser Ser Leu Phe Ala Ala Leu Phe Val Ile Ile Ala Gly
305                 310                 315                 320

Met Leu Cys Val Thr Val Gly Val Ile Phe Leu Ala Gly Val Lys
            325                 330                 335

Pro Leu Leu Ser Gly Met Ile Cys Ala Ser Gly Ile Thr Met Leu Val
        340                 345                 350

Leu Gly Val Val Leu Leu Val Val Cys Thr Arg Ala Ser Thr Arg Glu
            355                 360                 365

Ser Ile Tyr Glu Asp Leu Arg Tyr Pro Thr Arg Asp Ala Asn Gly Glu
    370                 375                 380

Tyr Glu Asn Val Gly Tyr Pro Pro Arg Asp Gly Asp Ala Pro His Arg
385                 390                 395                 400

Leu Gly Glu Pro Val Tyr Asp Asp Val Glu Gln Ala Thr
            405                 410
```

<210> SEQ ID NO 33
<211> LENGTH: 210
<212> TYPE: PRT
<213> ORGANISM: Callitrichine gammaherpesvirus 3

<400> SEQUENCE: 33

```
Met Ala Gly His Trp Tyr Glu Ser Val Ile Pro Gly Leu Phe Leu Cys
1               5                   10                  15

Pro Leu Ile Leu Pro Ser Leu Phe Trp Ile Cys Ser Leu Leu Thr Phe
            20                  25                  30

Leu Val Gly His Gly Ala Asn Ile Val Ser Ala Val Leu Phe Leu Val
        35                  40                  45

Leu Ala Trp Cys Leu Leu Ile Ala Asn Trp Asn Val Thr Arg Glu Asp
    50                  55                  60

Phe Val Ser Gly Arg Arg Ser Ser Met Ser Ser Leu Ser Val Ala Ala
65                  70                  75                  80

Ser Thr Ala Thr Ala Met Phe Ala Ser Phe Leu Thr Leu Ser Phe Asp
                85                  90                  95

Gly Leu Gly Leu Leu Leu Phe Gly Thr Ala Leu Val Ile Gln Thr Ile
            100                 105                 110

Tyr Val Leu Tyr Leu Val Val Met Glu Ile Thr Val Trp Ile Met Met
        115                 120                 125

Phe Arg Tyr Leu His Phe Trp Ile Thr Leu Leu Phe Leu Leu Ser Pro
    130                 135                 140

Ile Ile Leu Ser Val Ala Cys Leu Ile Ile Gln Ser Ser Ala Leu Leu
145                 150                 155                 160

Ile Glu Ala Val Val Val Thr Thr Ile Thr Val Leu Ala Ile Phe Leu
                165                 170                 175

Trp Leu Pro Pro Gln Gly Ala Glu Ala Asp Leu Gly Thr Ala Leu Leu
            180                 185                 190

Ile Leu Asn Thr Ala Leu Cys Leu Val Val Leu Ile Leu Thr Ala Ile
        195                 200                 205

Pro Thr
    210
```

<210> SEQ ID NO 34
<211> LENGTH: 153
<212> TYPE: PRT
<213> ORGANISM: Callitrichine gammaherpesvirus 3

<400> SEQUENCE: 34

```
Asp Ala Gln Ile Leu Thr Val Phe Cys Leu Phe Cys Gln Trp Thr Leu
1               5                   10                  15

Phe Ile Cys Leu Gly Ile Arg Met Ile Cys Asn Trp Arg Gly Lys Leu
            20                  25                  30

Thr Arg Ile Ile Cys Leu Lys Phe Cys Leu Tyr Gly Leu Ile Ser Ala
            35                  40                  45

Ser Leu Ser Phe Gly Trp Tyr Ala Phe Leu Lys Glu Val Thr Leu Pro
50                  55                  60

Thr Thr Ala Thr Val Asp Pro Arg Gln Leu Pro Leu Phe Leu Phe Ile
65                  70                  75                  80

Leu Ser Ser Val Leu Val Ile Leu Ala Ile Met Met Glu Phe Gln Thr
                85                  90                  95

Ser Ser Ser Leu Phe Ala Ala Leu Phe Val Ile Ile Ala Gly Met Leu
            100                 105                 110

Cys Val Thr Val Gly Val Ile Phe Leu Leu Ala Gly Val Lys Pro Leu
            115                 120                 125

Leu Ser Gly Met Ile Cys Ala Ser Gly Ile Thr Met Leu Val Leu Gly
        130                 135                 140

Val Val Leu Leu Val Val Cys Thr Arg
145                 150

<210> SEQ ID NO 35
<211> LENGTH: 50
<212> TYPE: PRT
<213> ORGANISM: Callitrichine gammaherpesvirus 3

<400> SEQUENCE: 35

Ala Ser Thr Arg Glu Ser Ile Tyr Glu Asp Leu Arg Tyr Pro Thr Arg
1               5                   10                  15

Asp Ala Asn Gly Glu Tyr Glu Asn Val Gly Tyr Pro Pro Arg Asp Gly
            20                  25                  30

Asp Ala Pro His Arg Leu Gly Glu Pro Val Tyr Asp Asp Val Glu Gln
            35                  40                  45

Ala Thr
    50

<210> SEQ ID NO 36
<211> LENGTH: 327
<212> TYPE: PRT
<213> ORGANISM: Callitrichine gammaherpesvirus 3

<400> SEQUENCE: 36

Met Pro Arg Gly Arg Ser Thr Gly Arg Lys Gly Arg Asp Thr Glu Lys
1               5                   10                  15

Glu Arg Ser Arg Ser Pro Leu Arg Ala Pro Gly G

```
Pro Pro Ser Arg Ser Pro Ser Pro Gln Pro Thr Val Ser Glu Gln Ser
        115                 120                 125

Gln Gln Ser Pro Arg Gln Ser Pro Gln Gly Thr Ser Gln Gly Ser
    130                 135                 140

Thr Arg Pro Gln Val Pro Gly Gly Ala Thr Thr Arg Lys Arg Gly Gly
145                 150                 155                 160

Val Arg Gly Gln Pro Ala Lys Cys His Gly Lys Tyr Thr Thr Thr Ala
                165                 170                 175

Glu Gly Leu Thr Ala Leu Leu Asn Arg Arg His Ser Pro Arg Thr Ser
                180                 185                 190

Asn Glu Gly Arg Trp Met Asn Gly Val Met Ala Val Asn Leu Ser Lys
                195                 200                 205

Trp Pro Leu Tyr Ser Leu Arg Arg Ala Leu Ala Leu Ala Ala Asn Glu
        210                 215                 220

Val Arg Ile Ser Pro Leu Phe Arg Leu Pro Tyr Gly Ser Ala Phe Gly
225                 230                 235                 240

Pro Gly Pro Gln Pro Gly Pro Ile Leu Glu Ser Ser Thr Trp Gly Phe
                245                 250                 255

Leu Val Phe Thr Gln Thr Ser Leu Phe Ala Asp Asp Ile Ala Asp Ala
            260                 265                 270

Ile Arg Asp Tyr Cys Thr Thr His Pro Gly Pro Thr Arg Asn Thr Gln
        275                 280                 285

Val Val Leu Met Asn Phe Glu Gly Ser Gly Val Pro Leu Pro Met Phe
    290                 295                 300

Phe Pro Pro Gly Glu Thr Glu Glu Gln Arg Glu Gly Asp Arg Ala
305                 310                 315                 320

Ser Asp Ser Asp Glu Ser Glu
                325

<210> SEQ ID NO 37
<211> LENGTH: 51
<212> TYPE: PRT
<213> ORGANISM: Callitrichine gammaherpesvirus 3

<400> SEQUENCE: 37

Met Pro Arg Gly Arg Ser Thr Gly Arg Lys Gly Arg Asp Thr Glu Lys
1               5                   10                  15

Glu Arg Ser Arg Ser Pro Leu Arg Ala Pro Gly Gly Ser Asp Gly Pro
            20                  25                  30

Ser Thr Arg Ala Gly Cys Gly Ala Gly Pro Cys Gln Leu Ser Ser Pro
        35                  40                  45

Ile Ala Gly
    50

<210> SEQ ID NO 38
<211> LENGTH: 119
<212> TYPE: PRT
<213> ORGANISM: Callitrichine gammaherpesvirus 3

<400> SEQUENCE: 38

Ser Pro Ser Pro Cys His His Arg Asp Glu Pro Pro Ser Arg Ser Pro
1               5                   10                  15

Ser Pro Gln Pro Thr Val Ser Glu Gln Ser Gln Gln Ser Pro Arg Gln
            20                  25                  30

Gln Ser Pro Gln Gly Thr Ser Gln Gly Ser Thr Arg Pro Gln Val Pro
        35                  40                  45
```

```
Gly Gly Ala Thr Thr Arg Lys Arg Gly Gly Val Arg Gly Gln Pro Ala
        50                  55                  60

Lys Cys His Gly Lys Tyr Thr Thr Ala Glu Gly Leu Thr Ala Leu
 65                  70                  75                  80

Leu Asn Arg Arg His Ser Pro Arg Thr Ser Asn Glu Gly Arg Trp Met
                    85                  90                  95

Asn Gly Val Met Ala Val Asn Leu Ser Lys Trp Pro Leu Tyr Ser Leu
                100                 105                 110

Arg Arg Ala Leu Ala Leu Ala
                115
```

<210> SEQ ID NO 39
<211> LENGTH: 106
<212> TYPE: PRT
<213> ORGANISM: Callitrichine gammaherpesvirus 3

<400> SEQUENCE: 39

```
Ala Asn Glu Val Arg Ile Ser Pro Leu Phe Arg Leu Pro Tyr Gly Ser
 1               5                  10                  15

Ala Phe Gly Pro Gly Pro Gln Pro Gly Pro Ile Leu Glu Ser Ser Thr
                20                  25                  30

Trp Gly Phe Leu Val Phe Thr Gln Thr Ser Leu Phe Ala Asp Asp Ile
                35                  40                  45

Ala Asp Ala Ile Arg Asp Tyr Cys Thr Thr His Pro Gly Pro Thr Arg
        50                  55                  60

Asn Thr Gln Val Val Leu Met Asn Phe Glu Gly Ser Gly Val Pro Leu
 65                  70                  75                  80

Pro Met Phe Phe Pro Pro Gly Glu Glu Thr Glu Glu Gln Arg Glu Gly
                85                  90                  95

Asp Arg Ala Ser Asp Ser Asp Glu Ser Glu
                100                 105
```

<210> SEQ ID NO 40
<211> LENGTH: 252
<212> TYPE: PRT
<213> ORGANISM: Callitrichine gammaherpesvirus 3

<400> SEQUENCE: 40

```

```
Asn Asn Asp Glu His Ala Ile Ser Ala Ser His His Ala Ser Asp Gly
145                 150                 155                 160

Ser Val Asn Gln Gln Lys Glu Asn Gln Pro Gln Thr Leu Glu Glu Cys
                165                 170                 175

Lys Thr Asp Gln Glu Arg Lys Arg Tyr Arg Asn Arg Leu Ala Ser Arg
            180                 185                 190

Arg Cys Arg Ala Lys Phe Arg Asn Gln Leu Glu His Phe Arg Thr Val
        195                 200                 205

Ala Ala Ala Lys Thr Glu Gly Asn Asn Arg Leu Arg Val Leu Ile Arg
    210                 215                 220

Gln Met Cys Pro Thr Leu Asp Val Glu Ser Ile Val Pro Ser Thr Ser
225                 230                 235                 240

Ala Gly Tyr His Glu Pro Leu Asn His Leu Thr His
                245                 250

<210> SEQ ID NO 41
<211> LENGTH: 146
<212> TYPE: PRT
<213> ORGANISM: Callitrichine gammaherpesvirus 3

<400> SEQUENCE: 41

Met Asp Leu Asp Gly Thr Gly Gly Gly Glu Gly Tyr Ser Gln Met Val
1               5                   10                  15

Pro Ile Ala Thr Ala Pro Gly Ser Gly His Ala Ala Thr Tyr Gln Asp
            20                  25                  30

Leu Gln Ala Ala Pro Tyr Ile Ile Trp Pro Leu Gln Thr Asp Cys Gln
        35                  40                  45

Pro Val Ala Thr Thr Phe Ala Ser Pro Gly Gln Ile Gln Trp Tyr Thr
    50                  55                  60

Ser Ala Val Pro Gln Pro Thr Glu His Cys Ser Gln Phe Thr Asn Ala
65                  70                  75                  80

Pro Thr Val Asn Gln Gln Gln Pro Ile Ser Gln Pro Gln Pro Glu Asn
                85                  90                  95

Pro Pro Ala Phe Thr Phe Thr Gln Pro Ala Ser Ile Ile Pro Gly Val
            100                 105                 110

Ile Ser Ala Ser Asn Leu Asn Val Ser Ala Ser Pro Ile Ile Pro Ser
        115                 120                 125

Asp His Val Leu Pro Ile Ile Thr Ser Val Thr Ser Leu Ala Gln Pro
    130                 135                 140

Asn Asn
145

<210> SEQ ID NO 42
<211> LENGTH: 106
<212> TYPE: PRT
<213> ORGANISM: Callitrichine gammaherpesvirus 3

<400> SEQUENCE: 42

Asp Glu His Ala Ile Ser Ala Ser His His Ala Ser Asp Gly Ser Val
1               5                   10                  15

Asn Gln Gln Lys Glu Asn Gln Pro Gln Thr Leu Glu Glu Cys Lys Thr
            20                  25                  30

Asp Gln Glu Arg Lys Arg Tyr Arg Asn Arg Leu Ala Ser Arg Arg Cys
        35                  40                  45

Arg Ala Lys Phe Arg Asn Gln Leu Glu His Phe Arg Thr Val Ala Ala
    50                  55                  60
```

Ala Lys Thr Glu Glu Asn Asn Arg Leu Arg Val Leu Ile Arg Gln Met
65                  70                  75                  80

Cys Pro Thr Leu Asp Val Glu Ser Ile Val Pro Ser Thr Ser Ala Gly
                85                  90                  95

Tyr His Glu Pro Leu Asn His Leu Thr His
            100                 105

<210> SEQ ID NO 43
<211> LENGTH: 216
<212> TYPE: PRT
<213> ORGANISM: Callithrix jacchus

<400> SEQUENCE: 43

Met Asp Asp Gln Arg Asp Leu Ile Ser Asn Asn Glu Gln Leu Pro Met
1               5                   10                  15

Leu Gly Gln Arg Pro Gly Ala Pro Glu Ser Lys Cys Ser Arg Gly Ala
            20                  25                  30

Val Tyr Thr Val Phe Ser Ile Leu Val Ala Leu Leu Ala Gly Gln
        35                  40                  45

Ala Thr Thr Ala Tyr Phe Leu Tyr Gln Gln Gln Gly Arg Leu Asp Lys
50                  55                  60

Leu Thr Val Thr Ser Gln Asn Leu Gln Leu Glu Asn Leu Arg Met Lys
65                  70                  75                  80

Leu Pro Lys Pro Ala Lys Pro Leu Ser Gln Met Arg Met Ala Thr Pro
            85                  90                  95

Leu Leu Met Gln Ala Leu Pro Met Ala Gly Leu Pro Gln Lys Pro Met
            100                 105                 110

Gln Asn Ala Thr Lys His Gly Asn Met Thr Glu Asp His Val Met His
            115                 120                 125

Leu Leu Leu Asn Ala Asp Pro Leu Lys Val Tyr Pro Pro Leu Lys Gly
130                 135                 140

Ser Leu Ser Glu Asn Leu Lys His Leu Lys Asn Thr Met Glu Thr Met
145                 150                 155                 160

Asp Trp Lys Val Phe Glu Ser Trp Leu His His Trp Leu Leu Phe Glu
                165                 170                 175

Met Ser Lys His Ser Leu Glu Gln Lys Pro Thr Glu Ala Pro Pro Lys
            180                 185                 190

Glu Ser Leu Glu Leu Glu Asp Pro Ser Ser Gly Leu Gly Val Thr Lys
            195                 200                 205

Gln Asp Leu Gly Pro Val Ala Met
    210                 215

<210> SEQ ID NO 44
<211> LENGTH: 1045
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Met Ser Glu Asp Phe Leu Ile Leu Ile Ala Ile Leu Val Ile Val Ile
1               5                   10                  15

Leu Val Gly Thr Ile Thr Thr Leu Val Gly Ala Ile Gly Gly Ile Arg
            20                  25                  30

Ala Arg Arg Ser Phe Leu Phe Ile Cys Ile Phe Phe Leu Phe Leu Ser

```
                35                  40                  45
Leu Phe Leu Thr Ile Leu Ala Leu Leu Gly Phe Ser Trp Leu Leu
 50                  55                  60

Leu Val Ala Ile Leu Phe Trp Val Leu Trp Leu Val Ile Leu Ile Leu
 65                  70                  75                  80

Leu Leu Leu Val Tyr Pro Ile Pro His His Pro Leu Pro Thr Ser Leu
                 85                  90                  95

Arg Phe Arg Met Lys Gln Arg Val Ser Ser Asp Pro Thr Gly Ser Asp
                100                 105                 110

Arg Ser Pro Gln Gly Ser His Asn Ser Leu Asn Ser Pro Asp Glu Glu
            115                 120                 125

Asp Pro Lys Asp Asp Thr Lys Gln Pro Leu Cys Asn Met Thr Gln Gly
        130                 135                 140

Gly Pro Pro Val Asn Gly Gln Leu Leu Gly His Ala Gln Cys Pro
145                 150                 155                 160

Pro His Tyr Pro Cys Cys His Ile Gln His Pro Asp Gly Glu Asp Ser
                165                 170                 175

Asp Gly Asp Asp Gly Lys Ser Trp Gly Asp Ala Gly Glu Glu Asp Asn
                180                 185                 190

Gly Pro Asn Asp Pro Asn Thr Ala Ser Thr Arg Glu Ser Ile Tyr Glu
            195                 200                 205

Asp Leu Arg Tyr Pro Thr Arg Asp Ala Asn Gly Glu Tyr Glu Asn Val
        210                 215                 220

Gly Tyr Pro Pro Arg Asp Gly Asp Ala Pro His Arg Leu Gly Glu Pro
225                 230                 235                 240

Val Tyr Asp Asp Val Glu Gln Ala Thr Ala Asn Glu Val Arg Ile Ser
                245                 250                 255

Pro Leu Phe Arg Leu Pro Tyr Gly Ser Ala Phe Gly Pro Gly Pro Gln
                260                 265                 270

Pro Gly Pro Ile Leu Glu Ser Ser Thr Trp Gly Phe Leu Val Phe Thr
            275                 280                 285

Gln Thr Ser Leu Phe Ala Asp Asp Ile Ala Asp Ala Ile Arg Asp Tyr
        290                 295                 300

Cys Thr Thr His Pro Gly Pro Thr Arg Asn Thr Gln Val Val Leu Met
305                 310                 315                 320

Asn Phe Glu Gly Ser Gly Val Pro Leu Pro Met Phe Pro Pro Gly
                325                 330                 335

Glu Glu Thr Glu Glu Gln Arg Glu Gly Asp Arg Ala Ser Asp Ser Asp
            340                 345                 350

Glu Ser Glu Asp Ala Gln Ile Leu Thr Val Phe Cys Leu Phe Cys Gln
        355                 360                 365

Trp Thr Leu Phe Ile Cys Leu Gly Ile Arg Met Ile Cys Asn Trp Arg
        370                 375                 380

Gly Lys Leu Thr Arg Ile Ile Cys Leu Lys Phe Cys Leu Tyr Gly Leu
385                 390                 395                 400

Ile Ser Ala Ser Leu Ser Phe Gly Trp Tyr Ala Phe Leu Lys Glu Val
                405                 410                 415

Thr Leu Pro Thr Thr Ala Thr Val Asp Pro Arg Gln Leu Pro Leu Phe
            420                 425                 430

Leu Phe Ile Leu Ser Ser Val Leu Val Ile Leu Ala Ile Met Met Glu
        435                 440                 445

Phe Gln Thr Ser Ser Ser Leu Phe Ala Ala Leu Phe Val Ile Ile Ala
        450                 455                 460
```

```
Gly Met Leu Cys Val Thr Val Gly Val Ile Phe Leu Leu Ala Gly Val
465                 470                 475                 480

Lys Pro Leu Leu Ser Gly Met Ile Cys Ala Ser Gly Ile Thr Met Leu
                    485                 490                 495

Val Leu Gly Val Val Leu Leu Val Cys Thr Arg Ser Pro Ser Pro
                500                 505                 510

Cys His His Arg Asp Glu Pro Ser Arg Ser Pro Ser Pro Gln Pro
            515                 520                 525

Thr Val Ser Glu Gln Ser Gln Gln Ser Pro Arg Gln Gln Ser Pro Gln
530                 535                 540

Gly Thr Ser Gln Gly Ser Thr Arg Pro Gln Val Pro Gly Gly Ala Thr
545                 550                 555                 560

Thr Arg Lys Arg Gly Gly Val Arg Gly Gln Pro Ala Lys Cys His Gly
                565                 570                 575

Lys Tyr Thr Thr Thr Ala Glu Gly Leu Thr Ala Leu Leu Asn Arg Arg
                580                 585                 590

His Ser Pro Arg Thr Ser Asn Glu Gly Arg Trp Met Asn Gly Val Met
            595                 600                 605

Ala Val Asn Leu Ser Lys Trp Pro Leu Tyr Ser Leu Arg Arg Ala Leu
610                 615                 620

Ala Leu Ala Met Ala Pro Arg Arg Leu Ser Gly Pro Pro Trp Leu
625                 630                 635                 640

Thr Val Leu Leu Leu Leu Ser Thr Leu Ser Val Ala Ala Leu Leu Ile
                645                 650                 655

Leu Phe Leu Ile Phe Ser Ala Gly Ala Thr Ile Ser Thr Glu Ala Ser
                660                 665                 670

Leu Leu Val Leu Leu Leu Phe Val Thr Leu Leu Leu Pro Leu Leu
                675                 680                 685

Ser Ser Asn Gly Leu Gln Leu Pro Ala Ala Leu Ile Leu Ile Gln Cys
690                 695                 700

Phe Leu Leu Ala Ala Asp Tyr Leu Ala Tyr Leu Ile Leu Pro Thr Ile
705                 710                 715                 720

Met Pro Arg Gly Arg Ser Thr Gly Arg Lys Gly Arg Asp Thr Glu Lys
                725                 730                 735

Glu Arg Ser Arg Ser Pro Leu Arg Ala Pro Gly Gly Ser Asp Gly Pro
                740                 745                 750

Ser Thr Arg Ala Gly Cys Gly Ala Gly Pro Cys Gln Leu Ser Ser Pro
                755                 760                 765

Ile Ala Gly Asn Asn Gly Asn Glu Gly Gly Glu Gly Asp Asp Tyr Lys
                770                 775                 780

Ser Trp Arg Lys Pro Glu Glu Glu Asp Asn Gly Pro Asn Asp Pro Asn
785                 790                 795                 800

Thr Asn Asn Arg Ile Glu Asp Gly Asp Gly Asp Asp Gly Lys Ser Trp
                805                 810                 815

Arg Asn Pro Glu Glu Glu Asp Asn Arg Lys Gln Asp Arg Leu Gly Thr
                820                 825                 830

Lys Pro Phe Met Ala Gly His Trp Tyr Glu Ser Val Ile Pro Gly Leu
                835                 840                 845

Phe Leu Cys Pro Leu Ile Leu Pro Ser Leu Phe Trp Ile Cys Ser Leu
                850                 855                 860

Leu Thr Phe Leu Val Gly His Gly Ala Asn Ile Val Ser Ala Val Leu
865                 870                 875                 880
```

Phe Leu Val Leu Ala Trp Cys Leu Leu Ile Ala Asn Trp Asn Val Thr
                885                 890                 895

Arg Glu Asp Phe Val Ser Gly Arg Arg Ser Ser Met Ser Ser Leu Ser
            900                 905                 910

Val Ala Ala Ser Thr Ala Thr Ala Met Phe Ala Ser Phe Leu Thr Leu
            915                 920                 925

Ser Phe Asp Gly Leu Gly Leu Leu Phe Gly Thr Ala Leu Val Ile
        930                 935                 940

Gln Thr Ile Tyr Val Leu Tyr Leu Val Val Met Glu Ile Thr Val Trp
945                 950                 955                 960

Ile Met Met Phe Arg Tyr Leu His Phe Trp Ile Thr Leu Leu Phe Leu
                965                 970                 975

Leu Ser Pro Ile Ile Leu Ser Val Ala Cys Leu Ile Ile Gln Ser Ser
            980                 985                 990

Ala Leu Leu Ile Glu Ala Val Val  Val Thr Thr Ile Thr  Val Leu Ala
            995                 1000                1005

Ile Phe  Leu Trp Leu Pro Pro  Gln Gly Ala Glu Ala  Asp Leu Gly
    1010                1015                1020

Thr Ala  Leu Leu Ile Leu Asn  Thr Ala Leu Cys Leu  Val Val Leu
    1025                1030                1035

Ile Leu  Thr Ala Ile Pro Thr
    1040                1045

<210> SEQ ID NO 45
<211> LENGTH: 3135
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 45
atgtccgagg actttctgat tctgatcgcc atcctggtga tcgtgattct cgtgggcaca        60
atcacaaccc tggtgggcgc catcggcggc attagggcca ggaggagctt cctcttcatt       120
tgcatcttct tcctgttcct ctccctcttc ctgacaatcc tcgccctgct gctgggcttc       180
agctggctcc tgctggtggc catcctgttc tgggtgctct ggctggtcat cctcattctg       240
ctgctgctgg tgtaccctat tcctcaccac cccctgccca cctccctcag gtttagaatg       300
aagcagaggg tgagcagcga ccccacaggt tctgacagaa gccctcaggg cagccataat       360
agcctgaact ccccgatga ggaggacccc aaggatgaca ccaagcaacc tctgtgcaac       420
atgacccagg gcggacctcc cgtcaatgga cagctcctcg acaacatgc tcaatgcccc       480 cctcactatc cctgctgcca tattcagcat cccgacggag aggattccga tggagacgat       540
ggcaagtcct gggcgatgc cggagaggaa gacaatggcc ctaacgaccc taacaccgcc       600
agcaccagag agtccattta cgaggacctc agataccca aagggacgc caatggcgag       660 tatgagaacg tgggataccc ccctagggac ggagatgccc ctcataggct cggagagcct       720
gtgtatgacg atgtggagca agccaccgct aacgaggtga aatctcccc tctgttcaga       780 ctgccctacg gaagcgcttt cggacctggc ccccagcctg gacccattct ggagagctcc       840
acatggggct ttctggtctc cacacagacc tccctgttcg ccgacgacat tgccgacgct       900
attagggact actgcacaac ccaccctggc cccacaagga cacccaggt ggtcctcatg       960 aacttcgagg gcagcggagt gcccctgcct atgtttttc ccctggaga ggagacagaa      1020

```
gagcagagag agggcgatag agctagcgac tccgacgagt ccgaagacgc tcagatcctg    1080
accgtgttct gcctgttttg ccagtggaca ctctttatct gcctgggaat caggatgatc    1140
tgtaactgga ggggcaaact caccaggatc atctgcctga agttctgcct ctacggactg    1200
atttccgcct ccctgtcctt cggctggtac gcttttctga aggaagtgac cctccccacc    1260
acagccaccg ttgatcctag caactcccc ctgttcctct tcatcctgag ctccgtgctg     1320
gtgattctcg ccatcatgat ggagtttcaa acatcctcca gcctcttcgc tgctctgttc    1380
gtgattatcg ccggaatgct gtgcgtcaca gtgggcgtga ttttctgct ggctggcgtc     1440
aagcctctcc tgagcggcat gatctgcgcc tccggcatca caatgctcgt gctcggcgtc    1500
gtgctgctgg tggtgtgcac cagaagcccc agcccttgtc atcacaggga tgaaccccc    1560
tccagaagcc ccagccctca acccaccgtc tccgagcagt cccagcagtc cccaggcag    1620
cagagccctc aaggcacatc ccagggttct acaagacctc aggtgcctgg aggcgccacc    1680
accagaaaaa gaggcggcgt gagaggccaa cctgccaagt gtcacggcaa gtacaccaca    1740
accgccgagg gactgaccgc tctcctgaat aggaggcaca gccccaggac atccaacgag    1800
ggcaggtgga tgaatggagt catggctgtg aacctctcca aatggcccct gtacagcctg    1860
aggagagccc tggccctcgc catggctcct agaaggaggc tctccggccc tccctggctg    1920
acagtgctgc tgctgctgtc cacactgagc gtggccgccc tgctgattct cttcctgatt    1980
ttcagcgccg cgccaccat tagcacagaa gccagcctgc tggtcctgct cctgctgttt    2040
gtgaccctgc tgctgcctct cctgtcctcc aacggactcc agctccctgc cgccctgatt    2100
ctgatccagt gtttcctcct ggccgctgat tatctcgcct acctgattct gcctaccatt    2160
atgcccaggg gcagaagcac aggaaggaag ggcagggaca cagagaaaga gaggagcaga    2220
tcccctctca gagctcctgg cggttctgat ggacccagca caagggctgg ctgtggagcc    2280
ggaccctgtc agctgagcag ccccatcgcc ggaaacaacg gcaatgaagg cggcgagggc    2340
gacgactaca agagctggag gaagcccgag aagaggaca acggcccaa tgaccccaat     2400
accaacaaca ggattgagga tggagacggc gacgacggaa atcctggag gaatcctgag    2460
gaggaggata acagaaagca ggacaggctg ggcaccaagc ctttcatggc cggccactgg    2520
tatgagagcg tgattcccgg cctgttcctc tgcccctga tcctcccttc cctgttctgg    2580
atttgctccc tgctgacctt cctggtgggc cacggagcca atattgtgag cgccgtcctg    2640
ttcctcgtgc tggcttggtg tctcctcatt gccaactgga acgtgacaag agaggacttc    2700
gtgtccggca ggagaagctc catgagcagc ctgtccgtgg ccgcttccac cgccacagcc    2760
atgttcgcca gcttcctcac cctgagcttt gatggcctgg gctgctgct gtttggcacc    2820
gccctggtga tccagacaat ttacgtgctg tatctggtgg tcatggagat caccgtgtgg    2880
atcatgatgt ttaggtatct ccactttgg atcaccctgc tgttcctgct gagccccatt    2940
attctctccg tcgcctgtct catcatccaa tcctccgccc tgctgatcga ggctgtggtc    3000
gtcaccacca tcacagtcct ggccattttt ctgtggctcc tcctcaagg cgctgaggcc    3060
gatctcggca ccgccctgct gattctgaat accgccctgt gcctggtcgt gctgatcctg    3120
accgctatcc ctaca                                                    3135
```

<210> SEQ ID NO 46
<211> LENGTH: 1270
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 46

```
Met Arg Pro Ala Pro Trp Thr Pro Asn Pro Arg Ser Pro Ser Gln
1               5                   10                  15

Met Ser Val Arg Asp Arg Leu Ala Arg Leu Arg Ala Glu Ala Gln Val
            20                  25                  30

Lys Gln Ala Ser Val Glu Val Gln Pro Pro Gln Leu Thr Gln Val Ser
        35                  40                  45

Pro Gln Gln Pro Val Ala Gly Ile Leu Phe Ile Leu Ala Ile Leu Thr
    50                  55                  60

Glu Trp Gly Ser Gly Asn Arg Thr Tyr Gly Pro Val Phe Met Cys Leu
65                  70                  75                  80

Gly Gly Leu Leu Thr Met Val Ala Gly Ala Val Trp Leu Thr Val Met
                85                  90                  95

Ser Asn Thr Leu Leu Ser Ala Trp Ile Leu Thr Ala Gly Phe Leu Ile
            100                 105                 110

Phe Leu Ile Gly Phe Ala Leu Phe Gly Val Ile Arg Cys Cys Arg Tyr
        115                 120                 125

Cys Cys Tyr Tyr Cys Leu Thr Leu Glu Ser Glu Arg Pro Pro Thr
    130                 135                 140

Pro Tyr Arg Asn Thr Val Arg Lys Pro Gln Gln Pro Glu Ser Leu Glu
145                 150                 155                 160

Glu Cys Asp Ser Glu Leu Glu Ile Lys Arg Tyr Lys Asn Arg Val Ala
                165                 170                 175

Ser Arg Lys Cys Arg Ala Lys Phe Lys Gln Leu Leu Gln His Tyr Arg
            180                 185                 190

Glu Val Ala Ala Lys Ser Ser Glu Ile Arg Asp Arg Arg Asn
        195                 200                 205

Pro Ala Ser Arg Arg Asp Gln Ala Lys Trp Arg Leu Gln Thr Leu Ala
    210                 215                 220

Ala Gly Trp Pro Met Gly Tyr Gln Ala Tyr Ser Ser Trp Met Tyr Ser
225                 230                 235                 240

Tyr Thr Asp His Gln Thr Thr Pro Thr Phe Val His Leu Gln Ala Thr
                245                 250                 255

Leu Gly Cys Thr Gly Gly Arg Arg Cys His Val Phe Leu Gly Ile Val
            260                 265                 270

Leu Phe Ile Phe Gly Cys Leu Leu Val Leu Gly Ile Trp Ile Tyr Leu
        275                 280                 285

Leu Glu Met Leu Trp Arg Leu Gly Ala Thr Ile Trp Gln Leu Leu Ala
    290                 295                 300

Phe Phe Leu Ala Phe Leu Asp Leu Ile Leu Ile Ile Ala Leu
305                 310                 315                 320

Tyr Leu Gln Gln Asn Trp Trp Thr Leu Leu Val Asp Leu Leu Trp Leu
                325                 330                 335

Leu Leu Phe Leu Ala Ile Leu Ile Trp Met Tyr Tyr His Gly Gln Arg
            340                 345                 350

Gly Arg Val Ala Cys Ala Pro Val Pro Ala Pro Gly Pro Ile Val
        355                 360                 365

Arg Pro Trp Glu Pro Ser Leu Thr Gln Ala Ala Gly Gln Ala Phe Ala
    370                 375                 380

Pro Val Arg Pro Gln His Met Pro Val Glu Pro Val Pro Thr
385                 390                 395                 400
```

```
Val Ala Leu Glu Arg Pro Val Tyr Pro Lys Pro Val Arg Pro Val Leu
                405             410             415

Trp Leu Ser Ser Pro Gly Gly Leu Gly Thr Leu Gly Ala Ala Leu Leu
            420             425             430

Thr Leu Ala Ala Ala Leu Ala Leu Leu Ala Ser Leu Ile Leu Gly Thr
        435             440             445

Leu Asn Leu Thr Thr Met Phe Leu Leu Met Leu Leu Trp Thr Leu Val
    450             455             460

Val Leu Leu Ile Cys Ser Ser Cys Ser Cys Pro Leu Ser Lys Ile
465             470             475             480

Leu Leu Ala Arg Leu Phe Leu Tyr Ala Leu Ala Leu Leu Leu Leu Ala
            485             490             495

Ser Ala Leu Ile Ala Gly Gly Ser Ile Leu Gln Thr Asn Phe Lys Ser
            500             505             510

Leu Ser Ser Thr Glu Phe Ile Pro Asn Leu Phe Cys Met Leu Leu Leu
        515             520             525

Ile His Ser Asp Glu His His His Asp Asp Ser Leu Pro His Pro Gln
        530             535             540

Gln Ala Thr Asp Asp Ser Gly His Glu Ser Asp Ser Asn Ser Asn Glu
545             550             555             560

Gly Arg His His Leu Leu Val Ser Gly Ala Gln Val Pro Glu Pro Pro
                565             570             575

Thr Ile His Leu Ala Ala Gln Gly Met Ala Tyr Pro Leu His Glu Gln
            580             585             590

His Gly Met Ala Pro Cys Pro Val Ala Gln Ala Pro Pro Thr Pro Leu
            595             600             605

Pro Phe Phe Ala Ile Cys Leu Thr Trp Arg Ile Glu Asp Pro Pro Phe
        610             615             620

Asn Ser Leu Leu Phe Ala Leu Leu Ala Ala Gly Gly Leu Gln Gly
625             630             635             640

Ile Tyr Val Leu Val Met Leu Val Leu Leu Ile Leu Ala Tyr Arg Arg
                645             650             655

Arg Trp Arg Arg Leu Thr Val Cys Gly Gly Ile Met Phe Leu Ala Cys
            660             665             670

Val Leu Val Leu Ile Val Asp Ala Val Leu Gln Leu Ser Pro Leu Leu
            675             680             685

Gly Ala Val Thr Val Val Ser Met Thr Leu Leu Leu Ala Phe Asn
        690             695             700

Gly Pro His Asp Pro Leu Pro Gln Asp Pro Asp Asn Thr Asp Asp Asn
705             710             715             720

Gly Pro Gln Asp Pro Asp Asn Thr Asp Asn Gly Pro His Asp Pro
            725             730             735

Leu Pro His Ser Pro Ser Asp Ser Ala Gly Asn Asp Gly Pro Pro
            740             745             750

Gln Leu Thr Glu Glu Val Glu Asn Lys Gly Gly Asp Gln Gly Pro Pro
        755             760             765

Leu Met Thr Asp Gly Gly Gly His Ser His Asp Ser Gly His Gly
    770             775             780

Gly Gly Asp Pro His Leu Pro Thr Leu Leu Gly Ser Ser Gly Ser
785             790             795             800

Gly Gly Asp Asp Asp Pro His Gly Pro Val Gln Leu Ser Tyr Tyr
            805             810             815
```

-continued

```
Asp Gly Lys Arg Thr Glu Gln Gly Lys Glu Val Leu Glu Lys Ala Arg
            820                 825                 830

Gly Ser Thr Tyr Gly Thr Pro Arg Pro Pro Met Ser Asp Trp Thr Gly
        835                 840                 845

Gly Ala Leu Leu Val Leu Tyr Ser Phe Ala Leu Met Leu Ile Ile Ile
    850                 855                 860

Ile Leu Ile Ile Phe Ile Phe Arg Arg Asp Leu Leu Cys Pro Leu Gly
865                 870                 875                 880

Ala Leu Cys Ile Leu Leu Leu Met Ile Thr Leu Leu Leu Ile Ala Leu
                885                 890                 895

Trp Asn Leu His Gly Gln Ala Leu Met Ser Asp Glu Gly Pro Gly Thr
            900                 905                 910

Gly Pro Gly Asn Gly Leu Gly Glu Lys Gly Asp Thr Ser Gly Pro Glu
        915                 920                 925

Gly Ser Gly Gly Ser Gly Pro Gln Arg Arg Gly Gly Asp Asn His Gly
    930                 935                 940

Arg Gly Arg Gly Arg Gly Arg Gly Gly Arg Pro Gly Ala
945                 950                 955                 960

Pro Gly Gly Ser Gly Ser Gly Pro Arg His Arg Asp Gly Val Arg Arg
        965                 970                 975

Pro Gln Lys Arg Pro Ser Cys Ile Gly Cys Lys Gly Thr His Trp Ile
            980                 985                 990

Asp Asp Asn Pro Ser Thr Glu Thr Ala Gln Ala Trp Asn Ala Gly Phe
            995                 1000                1005

Leu Arg Gly Arg Ala Tyr Gly Ile Asp Leu Leu Arg Thr Glu Gly
    1010                1015                1020

Glu His Val Glu Gly Ala Thr Gly Glu Thr Arg Glu Glu Ser Glu
    1025                1030                1035

Asp Thr Glu Ser Asp Gly Asp Asp Glu Asp Leu Pro Cys Ile Val
    1040                1045                1050

Ser Arg Gly Gly Pro Lys Val Lys Arg Pro Pro Ile Phe Ile Arg
    1055                1060                1065

Arg Leu His Arg Leu Leu Leu Met Arg Ala Met Asn Pro Val Cys
    1070                1075                1080

Leu Pro Val Ile Val Ala Pro Tyr Leu Phe Trp Leu Ala Ala Ile
    1085                1090                1095

Ala Ala Ser Cys Phe Thr Ala Ser Val Ser Thr Val Val Thr Ala
    1100                1105                1110

Thr Gly Leu Ala Leu Ser Leu Leu Leu Ala Ala Val Ala Ser
    1115                1120                1125

Ser Tyr Ala Ala Ala Gln Arg Lys Leu Leu Thr Pro Val Thr Val
    1130                1135                1140

Leu Thr Ala Val Val Thr Thr Phe Ser Ala Gly Thr Phe Lys Leu
    1145                1150                1155

Pro Arg Cys Thr Pro Gly Asp Arg Gln Trp Leu Tyr Val Gln Ser
    1160                1165                1170

Ser Val Gly Asn Ile Val Gln Ser Cys Asn Pro Arg Tyr Ser Ile
    1175                1180                1185

Phe Phe Asp Tyr Met Ala Ile His Arg Ser Leu Thr Lys Ile Trp
    1190                1195                1200

Glu Asp Leu Gly Gly Pro Ser Gln Ala Pro Leu Pro Cys Val Leu
    1205                1210                1215

Trp Pro Val Leu Pro Glu Pro Leu Pro Gln Gly Gln Leu Thr Ala
```

```
                1220                1225                1230

Tyr His Val Ser Thr Ala Pro Thr Gly Ser Trp Phe Ser Ala Pro
    1235                1240                1245

Gln Pro Ala Pro Glu Asn Ala Tyr Gln Ala Tyr Ala Ala Pro Gln
    1250                1255                1260

Leu Phe Pro Val Ser Asp Ile
    1265                1270

<210> SEQ ID NO 47
<211> LENGTH: 3810
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 47
atgagacctg ctccctggac acctaatcct cccaggtccc ccagccagat gagcgtgaga      60
gacagactgg ctaggctgag agccgaggct caggtcaagc aggccagcgt cgaggtgcaa     120
ccccctcagc tcacccaggt gtcccccag  cagcctgtgg ccggcattct gttcattctg     180
gccattctga ccgagtgggg aagcggcaac agaacctacg ccctgtcttc catgtgcctc     240
ggaggactgc tgacaatggt ggctggcgcc gtgtggctca ccgtcatgtc caacaccctg     300
ctcagcgcct ggattctgac cgccggattc ctgatctttc tgatcggatt cgctctcttt     360
ggcgtcatca ggtgttgcag gtactgttgc tactactgcc tgaccctcga gagcgaggaa     420
agacccccca cccctacag  gaatacagtg aggaaacctc agcagcccga gagcctcgag     480
gagtgcgata cgagctgga  gattaaaagg tataagaata gggtggcctc caggaagtgt     540
agggctaaat tcaaacagct cctgcaacac tatagggaag tggccgccgc caagtccagc     600
gagattaggg acagaaggag gaatcctgcc tccaggagag accaggccaa atggagactc     660
caaacactcg ccgctggatg gcccatgggc taccaggcct atagctcctg gatgtacagc     720
tacaccgacc atcagacaac acccaccttc gtgcatctgc aggctacact gggctgcacc     780
ggaggcagaa ggtgtcacgt gtttctggga atcgtgctgt tcatctttgg atgcctgctc     840
gtgctgggca tctggattta tctcctggag atgctctgga gactcggcgc tacaatttgg     900
cagctgctcg ccttttttct ggccttcttt ctggacctga tcctcctgat catcgccctg     960
tacctccaac agaactggtg gaccctcctg gtggatctgc tgtggctcct cctcttcctg    1020
gccatcctga tctggatgta ctaccatggc cagagaggaa gggtcgcttg cgctcctgtc    1080
cctgctcctg ctggccccat cgtgaggcct gggagcctt  ccctcacaca ggccgccggc    1140
caggcctttg ctcccgtgag gccccagcac atgcctgtgg aacccgtgcc cgtcccaca     1200 gtggctctgg aaaggcctgt gtaccccaag cccgtgagac ctgtcctctg gctcagcagc    1260
cctggaggac tcgaaacact cggagccgct ccctgacac  tggccgctgc tctggctctg    1320
ctggctagcc tgatcctggg aaccctcaac ctcaccacca tgtttctcct catgctcctg    1380
tggaccctcg tggtgctgct catctgttcc agctgctcca gctgccccct gagcaagatc    1440
ctgctggcca gctgttcct  gtacgccctc gccctcctgc tgctggctag cgccctgatc    1500
gctggcggaa gcatcctcca gaccaatttc aagagcctct cctccaccga gttcatcccc    1560
aacctgttct gtatgttact gctgatccat agcgacgagc accatcatga cgactccctg    1620 cccatcctc  agcaggccac agacgactcc ggccacgaga gcgacagcaa tagcaatgag    1680
```

| | |
|---|---|
| ggcaggcacc atctgctcgt gtccggagct caagtcccog agcctcccac catccatctc | 1740 |
| gccgcccagg gaatggctta ccccctccac gagcagcacg gcatggcccc ttgtcccgtc | 1800 |
| gctcaagccc ccctacacc tctgcccttt ttcgccattt gtctgacctg gagaatcgag | 1860 |
| gaccccccct tcaacagcct gctgttcgcc ctgctcgccg ccgctggcgg cctccagggc | 1920 |
| atttacgtcc tcgtgatgct ggtgctgctg atcctcgctt acaggagaag atggaggaga | 1980 |
| ctgacagtgt gcggcggcat catgtttctc gcctgcgtcc tggtcctgat cgtggacgcc | 2040 |
| gtcctgcaac tcagcccct cctgggagct gtgacagtgg tctccatgac cctgctgctg | 2100 |
| ctggccttca acggaccca cgatcctctg cccaagatc ctgacaatac cgacgataac | 2160 |
| ggcccccaag accccgataa caccgacgac aatggccctc acgaccctct gccccatagc | 2220 |
| ccttccgata cgctggcaa cgatggcggc cctcctcagc tgacagagga ggtgaaaat | 2280 |
| aagggcggcg atcagggacc cccctgatg acagatggcg aggaggaca cagccatgat | 2340 |
| agcggacatg gcggaggcga tcccatctg cctaccctcc tcctgggcag ctccggttct | 2400 |
| ggaggcgacg atgatgaccc tcacggccct gtgcagctct cctactacga cggcaaaagg | 2460 |
| accgaacaag gaaaagaggt cctggagaag gccaggggca gcacatacgg aaccccagg | 2520 |
| cctcccatgt ccgattggac cggaggagcc ctgctggtcc tctacagctt cgccctgatg | 2580 |
| ctgatcatta tcatcctgat catctttatc ttcagaaggg acctgctgtg ccctctcggc | 2640 |
| gccctgtgca tcctgctgct catgatcaca ctcctcctga tcgccctctg gaacctgcac | 2700 |
| ggacaagccc tgatgtccga tgagggacct ggaacaggac ccggaaacgg actgggcgag | 2760 |
| aaggagata caagcggccc cgaaggcagc ggcggaagcg accccaaag aaggggcggc | 2820 |
| gacaaccacg gaagaggaag aggcagggc agaggcagag gaggaggaag acctggagcc | 2880 |
| cctggcggtt ctggaagcgg acccaggcac agggacggag tgaggaggcc tcaaaaaaga | 2940 |
| cccagctgca tcggctgcaa gggaacccac tggattgatg ataacccctc cacagagacc | 3000 |
| gctcaggcct ggaacgccgg cttcctgagg ggaagagcct atggcatcga tctgctgagg | 3060 |
| accgagggcg aacacgtgga gggagccacc ggagagacaa gggaggaaag cgaagacaca | 3120 |
| gaaagcgatg cgacgacga agacctgccc tgcattgtgt ccaggggcgg acccaaggtg | 3180 |
| aagaggcccc ctatctttat cagaaggctc catagactgc tcctgatgag ggccatgaac | 3240 |
| cctgtgtgcc tgcccgtgat cgtggcccc tacctcttt ggctggccgc cattgccgct | 3300 |
| agctgcttca ccgcctccgt gtccacagtg gtgacagcca ccggcctcgc cctgagcctg | 3360 |
| ctgctcctcg ctgccgtggc ctccagctac gccgctgctc aaagaaagct cctgaccct | 3420 |
| gtcaccgtcc tgacagccgt cgtgaccacc ttttccgctg gcaccttcaa gctgcctagg | 3480 |
| tgcacacctg gcgacaggca gtggctctac gtgcagagct ccgtgggcaa tattgtgcag | 3540 |
| agctgcaatc ccaggtacag catttttttc gactacatgg ccatccatag gtccctcacc | 3600 |
| aagatctggg aggatctggg aggccccttcc caggctcctc tgccctgcgt gctgtggcct | 3660 |
| gtgctgcctg agcctctgcc ccaaggccag ctgacagcct atcacgtgtc caccgctcct | 3720 |
| acaggttctt ggttcagcgc tccccagccc gctcccgaaa acgcttacca ggcttacgcc | 3780 |
| gcccccagc tgttcccgt ctccgacatc | 3810 |

<210> SEQ ID NO 48
<211> LENGTH: 1512
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 48

```
Met Asp Asp Gln Arg Asp Leu Ile Ser Asn Asn Glu Gln Leu Pro Met
1               5                   10                  15

Leu Gly Gln Arg Pro Gly Ala Pro Glu Ser Lys Cys Ser Arg Gly Ala
            20                  25                  30

Val Tyr Thr Val Phe Ser Ile Leu Val Ala Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ser Gln Asn Leu Gln Leu Glu Asn Leu Arg Met Lys
65                  70                  75                  80

Leu Pro Lys Pro Ala Lys Pro Leu Ser Gln Met Arg Met Ala Thr Pro
                85                  90                  95

Leu Leu Met Gln Ala Leu Pro Met Ala Gly Leu Pro Gln Lys Pro Met
            100                 105                 110

Gln Asn Ala Thr Lys His Gly Asn Met Thr Glu Asp His Val Met His
        115                 120                 125

Leu Leu Leu Asn Ala Asp Pro Leu Lys Val Tyr Pro Pro Leu Lys Gly
    130                 135                 140

Ser Leu Ser Glu Asn Leu Lys His Leu Lys Asn Thr Met Glu Thr Met
145                 150                 155                 160

Asp Trp Lys Val Phe Glu Ser Trp Leu His His Trp Leu Leu Phe Glu
                165                 170                 175

Met Ser Lys His Ser Leu Glu Gln Lys Pro Thr Glu Ala Pro Pro Lys
            180                 185                 190

Glu Ser Leu Glu Leu Glu Asp Pro Ser Ser Gly Leu Gly Val Thr Lys
        195                 200                 205

Gln Asp Leu Gly Pro Val Ala Met Ser Glu Asp Phe Leu Ile Leu Ile
    210                 215                 220

Ala Ile Leu Val Ile Val Ile Leu Val Gly Thr Ile Thr Thr Leu Val
225                 230                 235                 240

Gly Ala Ile Gly Gly Ile Arg Ala Arg Arg Ser Phe Leu Phe Ile Cys
                245                 250                 255

Ile Phe Phe Leu Phe Leu Ser Leu Phe Leu Thr Ile Leu Ala Leu Leu
            260                 265                 270

Leu Gly Phe Ser Trp Leu Leu Leu Val Ala Ile Leu Phe Trp Val Leu
        275                 280                 285

Trp Leu Val Ile Leu Ile Leu Leu Leu Val Tyr Pro Ile Pro His
    290                 295                 300

His Pro Leu Pro Thr Ser Leu Arg Phe Arg Met Lys Gln Arg Val Ser
305                 310                 315                 320

Ser Asp Pro Thr Gly Ser Asp Arg Ser Pro Gln Gly Ser His Asn Ser
                325                 330                 335

Leu Asn Ser Pro Asp Glu Glu Asp Pro Lys Asp Thr Lys Gln Pro
            340                 345                 350

Leu Cys Asn Met Thr Gln Gly Gly Pro Pro Val Asn Gly Gln Leu Leu
        355                 360                 365

Gly Gln His Ala Gln Cys Pro Pro His Tyr Pro Cys Cys His Ile Gln
    370                 375                 380

His Pro Asp Gly Glu Asp Ser Asp Gly Asp Gly Lys Ser Trp Gly
385                 390                 395                 400
```

```
Asp Ala Gly Glu Glu Asp Asn Gly Pro Asn Asp Pro Asn Thr Ala Ser
                405                 410                 415
Thr Arg Glu Ser Ile Tyr Glu Asp Leu Arg Tyr Pro Thr Arg Asp Ala
                420                 425                 430
Asn Gly Glu Tyr Glu Asn Val Gly Tyr Pro Pro Arg Asp Gly Asp Ala
                435                 440                 445
Pro His Arg Leu Gly Glu Pro Val Tyr Asp Val Glu Gln Ala Thr
450                 455                 460
Ala Asn Glu Val Arg Ile Ser Pro Leu Phe Arg Leu Pro Tyr Gly Ser
465                 470                 475                 480
Ala Phe Gly Pro Gly Pro Gln Pro Gly Pro Ile Leu Glu Ser Ser Thr
                485                 490                 495
Trp Gly Phe Leu Val Phe Thr Gln Thr Ser Leu Phe Ala Asp Asp Ile
                500                 505                 510
Ala Asp Ala Ile Arg Asp Tyr Cys Thr Thr His Pro Gly Pro Thr Arg
                515                 520                 525
Asn Thr Gln Val Val Leu Met Asn Phe Glu Gly Ser Gly Val Pro Leu
                530                 535                 540
Pro Met Phe Phe Pro Pro Gly Glu Thr Glu Glu Gln Arg Glu Gly
545                 550                 555                 560
Asp Arg Ala Ser Asp Ser Asp Glu Ser Glu Asp Ala Gln Ile Leu Thr
                565                 570                 575
Val Phe Cys Leu Phe Cys Gln Trp Thr Leu Phe Ile Cys Leu Gly Ile
                580                 585                 590
Arg Met Ile Cys Asn Trp Arg Gly Lys Leu Thr Arg Ile Ile Cys Leu
                595                 600                 605
Lys Phe Cys Leu Tyr Gly Leu Ile Ser Ala Ser Leu Ser Phe Gly Trp
                610                 615                 620
Tyr Ala Phe Leu Lys Glu Val Thr Leu Pro Thr Thr Ala Thr Val Asp
625                 630                 635                 640
Pro Arg Gln Leu Pro Leu Phe Leu Phe Ile Leu Ser Ser Val Leu Val
                645                 650                 655
Ile Leu Ala Ile Met Met Glu Phe Gln Thr Ser Ser Ser Leu Phe Ala
                660                 665                 670
Ala Leu Phe Val Ile Ile Ala Gly Met Leu Cys Val Thr Val Gly Val
                675                 680                 685
Ile Phe Leu Leu Ala Gly Val Lys Pro Leu Leu Ser Gly Met Ile Cys
                690                 695                 700
Ala Ser Gly Ile Thr Met Leu Val Leu Gly Val Val Leu Leu Val Val
705                 710                 715                 720
Cys Thr Arg Asp Glu His Ala Ile Ser Ala Ser His His Ala Ser Asp
                725                 730                 735
Gly Ser Val Asn Gln Gln Lys Glu Asn Gln Pro Gln Thr Leu Glu Glu
                740                 745                 750
Cys Lys Thr Asp Gln Glu Arg Lys Arg Tyr Arg Asn Arg Leu Ala Ser
                755                 760                 765
Arg Arg Cys Arg Ala Lys Phe Arg Asn Gln Leu Glu His Phe Arg Thr
                770                 775                 780
Val Ala Ala Ala Lys Thr Glu Glu Asn Asn Arg Leu Arg Val Leu Ile
785                 790                 795                 800
Arg Gln Met Cys Pro Thr Leu Asp Val Glu Ser Ile Val Pro Ser Thr
                805                 810                 815
```

```
Ser Ala Gly Tyr His Glu Pro Leu Asn His Leu Thr His Ser Pro Ser
            820                 825                 830

Pro Cys His His Arg Asp Glu Pro Pro Ser Arg Ser Pro Ser Pro Gln
            835                 840                 845

Pro Thr Val Ser Glu Gln Ser Gln Gln Ser Pro Arg Gln Gln Ser Pro
            850                 855                 860

Gln Gly Thr Ser Gln Gly Ser Thr Arg Pro Gln Val Pro Gly Gly Ala
865                 870                 875                 880

Thr Thr Arg Lys Arg Gly Val Arg Gly Gln Pro Ala Lys Cys His
                885                 890                 895

Gly Lys Tyr Thr Thr Thr Ala Glu Gly Leu Thr Ala Leu Leu Asn Arg
                900                 905                 910

Arg His Ser Pro Arg Thr Ser Asn Glu Gly Arg Trp Met Asn Gly Val
            915                 920                 925

Met Ala Val Asn Leu Ser Lys Trp Pro Leu Tyr Ser Leu Arg Arg Ala
            930                 935                 940

Leu Ala Leu Ala Met Ala Pro Arg Arg Leu Ser Gly Pro Pro Trp
945                 950                 955                 960

Leu Thr Val Leu Leu Leu Ser Thr Leu Ser Val Ala Ala Leu Leu
                965                 970                 975

Ile Leu Phe Leu Ile Phe Ser Ala Gly Ala Thr Ile Ser Thr Glu Ala
            980                 985                 990

Ser Leu Leu Val Leu Leu Leu Phe Val Thr Leu Leu Leu Pro Leu
            995                1000                1005

Leu Ser Ser Asn Gly Leu Gln Leu Pro Ala Ala Leu Ile Leu Ile
    1010                1015                1020

Gln Cys Phe Leu Leu Ala Ala Asp Tyr Leu Ala Tyr Leu Ile Leu
    1025                1030                1035

Pro Thr Ile Met Pro Arg Gly Arg Ser Thr Gly Arg Lys Gly Arg
    1040                1045                1050

Asp Thr Glu Lys Glu Arg Ser Arg Ser Pro Leu Arg Ala Pro Gly
    1055                1060                1065

Gly Ser Asp Gly Pro Ser Thr Arg Ala Gly Cys Gly Ala Gly Pro
    1070                1075                1080

Cys Gln Leu Ser Ser Pro Ile Ala Gly Asn Asn Gly Asn Glu Gly
    1085                1090                1095

Gly Glu Gly Asp Asp Tyr Lys Ser Trp Arg Lys Pro Glu Glu Glu
    1100                1105                1110

Asp Asn Gly Pro Asn Asp Pro Asn Thr Asn Asn Arg Ile Glu Asp
    1115                1120                1125

Gly Asp Gly Asp Asp Gly Lys Ser Trp Arg Asn Pro Glu Glu Glu
    1130                1135                1140

Asp Asn Arg Lys Gln Asp Arg Leu Gly Thr Lys Pro Phe Met Asp
    1145                1150                1155

Leu Asp Gly Thr Gly Gly Gly Glu Gly Tyr Ser Gln Met Val Pro
    1160                1165                1170

Ile Ala Thr Ala Pro Gly Ser Gly His Ala Ala Thr Tyr Gln Asp
    1175                1180                1185

Leu Gln Ala Ala Pro Tyr Ile Ile Trp Pro Leu Gln Thr Asp Cys
    1190                1195                1200

Gln Pro Val Ala Thr Thr Phe Ala Ser Pro Gly Gln Ile Gln Trp
    1205                1210                1215

Tyr Thr Ser Ala Val Pro Gln Pro Thr Glu His Cys Ser Gln Phe
```

| | | | | | | | | | | |
|---|---|---|---|---|---|---|---|---|---|---|
| | | 1220 | | | 1225 | | | 1230 | | |
| Thr | Asn | Ala | Pro | Thr | Val | Asn | Gln | Gln | Pro | Ile | Ser | Gln | Pro |
| | 1235 | | | | 1240 | | | | 1245 | |

Thr Asn Ala Pro Thr Val Asn Gln Gln Pro Ile Ser Gln Pro
    1235                    1240                    1245

Gln Pro Glu Asn Pro Pro Ala Phe Thr Phe Thr Gln Pro Ala Ser
 1250                     1255                    1260

Ile Ile Pro Gly Val Ile Ser Ala Ser Asn Leu Asn Val Ser Ala
 1265                     1270                    1275

Ser Pro Ile Ile Pro Ser Asp His Val Leu Pro Ile Ile Thr Ser
 1280                     1285                    1290

Val Thr Ser Leu Ala Gln Pro Asn Asn Met Ala Gly His Trp Tyr
 1295                     1300                    1305

Glu Ser Val Ile Pro Gly Leu Phe Leu Cys Pro Leu Ile Leu Pro
 1310                     1315                    1320

Ser Leu Phe Trp Ile Cys Ser Leu Leu Thr Phe Leu Val Gly His
 1325                     1330                    1335

Gly Ala Asn Ile Val Ser Ala Val Leu Phe Leu Val Leu Ala Trp
 1340                     1345                    1350

Cys Leu Leu Ile Ala Asn Trp Asn Val Thr Arg Glu Asp Phe Val
 1355                     1360                    1365

Ser Gly Arg Arg Ser Ser Met Ser Ser Leu Ser Val Ala Ala Ser
 1370                     1375                    1380

Thr Ala Thr Ala Met Phe Ala Ser Phe Leu Thr Leu Ser Phe Asp
 1385                     1390                    1395

Gly Leu Gly Leu Leu Leu Phe Gly Thr Ala Leu Val Ile Gln Thr
 1400                     1405                    1410

Ile Tyr Val Leu Tyr Leu Val Val Met Glu Ile Thr Val Trp Ile
 1415                     1420                    1425

Met Met Phe Arg Tyr Leu His Phe Trp Ile Thr Leu Leu Phe Leu
 1430                     1435                    1440

Leu Ser Pro Ile Ile Leu Ser Val Ala Cys Leu Ile Ile Gln Ser
 1445                     1450                    1455

Ser Ala Leu Leu Ile Glu Ala Val Val Val Thr Thr Ile Thr Val
 1460                     1465                    1470

Leu Ala Ile Phe Leu Trp Leu Pro Pro Gln Gly Ala Glu Ala Asp
 1475                     1480                    1485

Leu Gly Thr Ala Leu Leu Ile Leu Asn Thr Ala Leu Cys Leu Val
 1490                     1495                    1500

Val Leu Ile Leu Thr Ala Ile Pro Thr
 1505                     1510

<210> SEQ ID NO 49
<211> LENGTH: 4536
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 49
atggacgacc agcgggacct gatcagcaac aacgagcagc tgcccatgct gggccagagg     60
cctggcgccc ctgagagcaa gtgtagcaga ggcgccgtgt acaccgtgtt cagcatcctg    120
gtggccctgc tgctggccgg acaggccacc accgcctact ttctgtatca gcagcaggga    180
cggctggaca agctgaccgt gaccagccag aacctgcagc tggaaaacct gcggatgaag    240

```
ctgcccaagc cgccaagcc cctgagccag atgagaatgg ccaccccct gctgatgcag      300 gccctgccta tggccggcct gccccagaaa cccatgcaga acgccaccaa gcacggcaac     360
atgaccgagg accacgtgat gcatctgctg ctgaacgccg accccctgaa ggtgtacccc     420
ccactgaagg gcagcctgag cgagaacctg aagcacctga gaacaccat ggaaaccatg      480 gactggaagg tgttcgagag ctggctgcac cactggctgc tgttcgagat gagcaagcac     540
agcctggaac agaagcccac cgaggcccct cccaaagaga gcctggaact ggaagatccc     600
agcagcggcc tgggcgtgac caagcaggat ctgggccccg tggctatgtc cgaggacttt     660
ctgattctga tcgccatcct ggtgatcgtg attctcgtgg gcacaatcac aaccctggtg     720
ggcgccatcg gcggcattag ggccaggagg agcttcctct tcatttgcat cttcttcctg     780
ttcctctccc tcttcctgac aatcctcgcc ctgctgctgg gcttcagctg gctcctgctg     840
gtggccatcc tgttctgggt gctctggctg gtcatcctca ttctgctgct gctggtgtac     900
cctattcctc accaccccct gcccacctcc ctcaggttta gaatgaagca gagggtgagc     960
agcgacccca caggttctga cagaagccct cagggcagcc ataatagcct gaactccccc    1020
gatgaggagg accccaagga tgacaccaag caacctctgt gcaacatgac ccagggcgga    1080
cctcccgtca atggacagct cctcggacaa catgctcaat gcccccctca ctatccctgc    1140
tgccatattc agcatcccga cggagaggat tccgatggag acgatggcaa gtcctggggc    1200
gatgccggag aggaagacaa tggccctaac gaccctaaca ccgccagcac cagagagtcc    1260
atttacgagg acctcagata ccccacaagg gacgccaatg gcgagtatga aacgtggga     1320 taccccccta gggacggaga tgcccctcat aggctcggag agcctgtgta tgacgatgtg    1380
gagcaagcca ccgctaacga ggtgagaatc tcccctctgt tcagactgcc ctacggaagc    1440
gctttcggac ctggcccca gcctggaccc attctggaga gctccacatg gggctttctg    1500
gtcttcacac agacctccct gttcgccgac gacattgccg acgctattag ggactactgc    1560
acaacccacc ctggccccac aaggaacacc caggtggtcc tcatgaactt cgagggcagc    1620
ggagtgcccc tgcctatgtt ttttccccct ggagaggaga cagaagagca gagagagggc    1680
gatagagcta gcgactccga cgagtccgaa gacgctcaga tcctgaccgt gttctgcctg    1740
ttttgccagt ggacactctt tatctgcctg ggaatcagga tgatctgtaa ctggagggc    1800 aaactcacca ggatcatctg cctgaagttc tgcctctacg gactgatttc cgcctccctg    1860
tccttcggct ggtacgcttt tctgaaggaa gtgaccctcc ccaccacagc caccgttgat    1920
cctaggcaac tccccctgtt cctcttcatc ctgagctccg tgctggtgat tctcgccatc    1980
atgatggagt ttcaaacatc ctccagcctc ttcgctgctc tgttcgtgat tatcgccgga    2040
atgctgtgcg tcacagtggg cgtgattttt ctgctggctg gcgtcaagcc tctcctgagc    2100
ggcatgatct gcgcctccgg catcacaatg ctcgtgctcg gcgtcgtgct gctggtggtg    2160
tgcaccagag atgagcacgc tatttccgcc agccaccatg ctagcgatgg ctccgtgaat    2220
cagcagaagg aaaatcagcc ccagaccctg aggaatgca agacagatca ggagaggaag      2280
aggtacagga acaggctggc ctccaggagg tgtagagcta agttcaggaa ccagctggaa    2340
cattttagga cagtcgccgc tgctaagaca gaggagaaca acaggctcag ggtgctcatc    2400
aggcagatgt gtcctacact ggacgtggaa tccatcgtcc cctccacctc cgccggctac    2460
cacgagcctc tgaatcacct gacccacagc cccagccctt gtcatcacag ggatgaaccc    2520
ccctccagaa gccccagccc tcaacccacc gtctccgagc agtcccagca gtcccccagg    2580
cagcagagcc ctcaaggcac atcccagggt tctacaagac ctcaggtgcc tggaggcgcc    2640
```

-continued

```
accaccagaa aaagaggcgg cgtgagaggc caacctgcca agtgtcacgg caagtacacc    2700
acaaccgccg agggactgac cgctctcctg aataggaggc acagcccag gacatccaac     2760 gagggcaggt ggatgaatgg agtcatggct gtgaacctct ccaaatggcc cctgtacagc    2820
ctgaggagag ccctggccct cgccatggct cctagaagga ggctctccgg ccctccctgg    2880
ctgacagtgc tgctgctgct gtccacactg agcgtggccg ccctgctgat tctcttcctg    2940
attttcagcg ccggcgccac cattagcaca gaagccagcc tgctggtcct gctcctgctg    3000
tttgtgaccc tgctgctgcc tctcctgtcc tccaacggac tccagctccc tgccgccctg    3060
attctgatcc agtgtttcct cctggccgct gattatctcg cctacctgat tctgcctacc    3120
attatgccca ggggcagaag cacaggaagg aagggcaggg acacagagaa agagaggagc    3180
agatcccctc tcagagctcc tggcggttct gatggaccca gcacaaggc tggctgtgga     3240 gccggaccct gtcagctgag cagccccatc gccggaaaca acggcaatga aggcggcgag    3300
ggcgacgact acaagagctg gaggaagccc gaggaagagg acaacggccc caatgacccc    3360
aataccaaca acaggattga ggatggagac ggcgacgacg gaaaatcctg gaggaatcct    3420
gaggaggagg ataacagaaa gcaggacagg ctgggcacca agcctttcat ggacctcgac    3480
ggaaccggcg gaggcgaggg ctacagccag atggtcccta tcgccaccgc ccccggaagc    3540
ggccacgccg ctacctatca ggatctccag gccgcccctt acatcatctg gcctctccag    3600
accgattgcc agcctgtggc taccaccttc gcctcccccg gacagatcca gtggtataca    3660
agcgccgtcc cccagcccac agagcattgc tcccagtttta caaacgctcc caccgtcaac    3720
cagcagcagc ctattagcca accccagccc gaaaatcccc ctgctttcac ctttacccag    3780
cccgcttcca tcattcccgg cgtcattagc gcctccaacc tgaacgtgag cgcttcccct    3840
atcatcccta gcgaccatgt cctccccatc attacctccg tgaccagcct cgcccaacct    3900
aataacatgg ccggccactg gtatgagagc gtgattcccg gcctgttcct ctgcccctg     3960 atcctcccctt ccctgttctg gatttgctcc ctgctgacct tcctggtggg ccacggagcc    4020
aatattgtga gcgccgtcct gttcctcgtg ctggcttggt gtctcctcat tgccaactgg    4080
aacgtgacaa gagaggactt cgtgtccggc aggagaagct ccatgagcag cctgtccgtg    4140
gccgcttcca ccgccacagc catgttcgcc agcttcctca ccctgagctt tgatggcctg    4200
ggcctgctgc tgtttggcac cgccctggtg atccagacaa tttacgtgct gtatctggtg    4260
gtcatggaga tcaccgtgtg gatcatgatg tttaggtatc tccacttttg gatcaccctg    4320
ctgttcctgc tgagccccat tattctctcc gtcgcctgtc tcatcatcca atcctccgcc    4380
ctgctgatcg aggctgtggt cgtcaccacc atcacagtcc tggccatttt tctgtggctc    4440
cctcctcaag gcgctgaggc cgatctcggc accgccctgc tgattctgaa taccgccctg    4500
tgcctggtcg tgctgatcct gaccgctatc cctaca                              4536
```

<210> SEQ ID NO 50
<211> LENGTH: 44035
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (15712)..(15712)
<223> OTHER INFORMATION: a, c, t, g, unknown or other

```
<400> SEQUENCE: 50
catcatcaat aatataccttt attttggatt gaagccaata tgataatgag atgggcggcg      60
cggggcgggg cgcggggcgg gaggcgggtt tgggggcggg ccggcgggcg gggcggtgtg     120
gcggaagtgg actttgtaag tgtggcggat gtgacttgct agtgccgggc gcggtaaaag     180
tgacgttttc cgtgcgcgac aacgccccg ggaagtgaca ttttccccgc ggttttttacc     240
ggatgttgta gtgaatttgg gcgtaaccaa gtaagatttg gccatttcg cgggaaaact     300
gaaacgggga agtgaaatct gattaatttt gcgttagtca taccgcgtaa tatttgtcta     360
gggccgaggg actttggccg attacgtgga ggactcgccc aggtgttttt tgaggtgaat     420
ttccgcgttc cgggtcaaag tctgcgtttt attattatag gatatcccat tgcatacgtt     480
gtatccatat cataatatgt acatttatat tggctcatgt ccaacattac cgccatgttg     540
acattgatta ttgactagtt attaatagta atcaattacg gggtcattag ttcatagccc     600
atatatggag ttccgcgtta cataacttac ggtaaatggc ccgcctggct gaccgcccaa     660
cgacccccgc ccattgacgt caataatgac gtatgttccc atagtaacgc caatagggac     720
tttccattga cgtcaatggg tggagtattt acggtaaact gcccacttgg cagtacatca     780
agtgtatcat atgccaagta cgccccctat tgacgtcaat gacggtaaat ggcccgcctg     840
gcattatgcc cagtacatga ccttatggga cttcctact tggcagtaca tctacgtatt     900
agtcatcgct attaccatgg tgatgcggtt ttggcagtac atcaatgggc gtggatagcg     960
gtttgactca cggggattc caagtctcca ccccattgac gtcaatggga gtttgttttg    1020
gcaccaaaat caacgggact ttccaaaatg tcgtaacaac tccgcccat tgacgcaaat    1080
gggcggtagg cgtgtacggt gggaggtcta tataagcaga gctctcccta tcagtgatag    1140
agatctcct atcagtgata gagatcgtcg acgagctcgt ttagtgaacc gtcagatcgc    1200
ctggagacgc catccacgct gttttgacct ccatagaaga caccgggacc gatccagcct    1260
ccgcggccgg gaacggtgca ttggaacgcg gattccccgt gccaagagtg agatcttccg    1320
tttatctagg taccagatat cgccaccatg agacctgctc cctggacacc taatcctccc    1380
aggtccccca gccagatgag cgtgagagac agactggcta ggctgagagc cgaggctcag    1440
gtcaagcagg ccagcgtcga ggtgcaaccc cctcagctca cccaggtgtc cccccagcag    1500
cctgtggccg gcattctgtt cattctggcc attctgaccg agtgggaag cggcaacaga    1560
acctacggcc ctgtcttcat gtgcctcgga ggactgctga caatggtggc tggcgccgtg    1620
tggctcaccg tcatgtccaa caccctgctc agcgcctgga ttctgaccgc cggattcctg    1680
atctttctga tcggattcgc tctctttggc gtcatcaggt gttgcaggta ctgttgctac    1740
tactgcctga ccctcgagag cgaggaaaga cccccaccc cctacaggaa tacagtgatt    1800
agggacagaa ggaggaatcc tgcctccagg agagaccagg ccaaatggag actccaaaca    1860
ctcgccgctg gatggcccat gggctaccag gcctatagct cctggatgta cagctacacc    1920
gaccatcaga caacacccac cttcgtgcat ctgcaggcta cactgggctg caccggaggc    1980
agaaggtgtc acgtgtttct gggaatcgtg ctgttcatct ttggatgcct gctcgtgctg    2040
ggcatctgga tttatctcct ggagatgctc tggagactcg gcgctacaat ttggcagctg    2100
ctcgcctttt ttctggcctt cttctggac ctgatcctcc tgatcatcgc cctgtacctc    2160
caacagaact ggtggaccct cctggtggat ctgctgtggc tcctcctctt cctggccatc    2220
ctgatctgga tgtactacca tggccagaga ggaagggtcg cttgcgctcc tgtccctgct    2280
cctgctggcc ccatcgtgag gccttgggag ccttccctca cacaggccgc cggccaggcc    2340
```

```
tttgctcccg tgaggcccca gcacatgcct gtggaacccg tgcccgtccc cacagtggct    2400
ctggaaaggc ctgtgtaccc caagcccgtg agacctgtcc tctggctcag cagccctgga    2460
ggactcggaa cactcggagc cgctctcctg acactggccg ctgctctggc tctgctggct    2520
agcctgatcc tgggaaccct caacctcacc accatgtttc tcctcatgct cctgtggacc    2580
ctcgtggtgc tgctcatctg ttccagctgc tccagctgcc ccctgagcaa gatcctgctg    2640
gccaggctgt tcctgtacgc cctcgccctc tgctgctggg ctagcgccct gatcgctggc    2700
ggaagcatcc tccagaccaa tttcaagagc ctctcctcca ccgagttcat ccccaacctg    2760
ttctgtatgt tactgctgat ccatagcgac gagcaccatc atgacgactc cctgccccat    2820
cctcagcagg ccacagacga ctccggccac gagagcgaca gcaatagcaa tgagggcagg    2880
caccatctgc tcgtgtccgg agctcaagtc cccgagcctc ccaccatcca tctcgccgcc    2940
cagggaatgg cttaccccct ccacgagcag cacggcatgg cccctcgtcc cgtcgctcaa    3000 gccccccta cacctctgcc cttttttcgcc atttgtctga cctggagaat cgaggacccc    3060
cccttcaaca gcctgctgtt cgccctgctc gccgccgctg gcggcctcca gggcatttac    3120
gtcctcgtga tgctggtgct gctgatcctc gcttacagga aagatggag gagactgaca    3180 gtgtgcggcg gcatcatgtt tctcgcctgc gtcctggtcc tgatcgtgga cgccgtcctg    3240
caactcagcc ccctcctggg agctgtgaca gtggtctcca tgaccctgct gctgctggcc    3300
ttcaacggac cccacgatcc tctgccccaa gatcctgaca ataccgacga taacggcccc    3360
caagaccccg ataacaccga cgacaatggc cctcacgacc ctctgcccca tagcccttcc    3420
gatagcgctg gcaacgatgg cggccctcct cagctgacag aggaggtgga aaataagggc    3480
ggcgatcagg gaccccccct gatgacagat ggcggaggag gacacagcca tgatagcgga    3540
catggcggag gcgatcccca tctgcctacc ctcctcctgg gcagctccgg ttctggaggc    3600
gacgatgatg accctcacgg ccctgtgcag ctctccctact acgacggcaa aaggaccgaa    3660
caaggaaaag aggtcctgga aaggccagg ggcagcacat acggaacccc caggcctccc    3720
atgtccgatt ggaccggagg agccctgctg gtcctctaca gcttcgccct gatgctgatc    3780
attatcatcc tgatcatctt tatcttcaga agggacctgc tgtgccctct cggcgccctg    3840
tgcatcctgc tgctcatgat cacactcctc ctgatcgccc tctggaacct gcacggacaa    3900
gccctgatgt ccgatgaggg acctggaaca ggacccggaa acggactggg cgagaaggga    3960
gatacaagcg gccccgaagg cagcggcgga agcggacccc aaagaagggg cggcgacaac    4020
cacggaagag gaagaggcag gggcagaggc agaggaggag gaagacctgg agccctggc    4080 ggttctggaa gcggacccag gcacagggac ggagtgagga ggcctcaaaa aagacccagc    4140
tgcatcggct gcaagggaac ccactggatt gatgataacc cctccacaga gaccgctcag    4200
gcctggaacg ccggcttcct gaggggaaga gcctatggca tcgatctgct gaggaccgag    4260
ggcgaacacg tggagggagc caccggagag acaagggagg aaagcgaaga cacagaaagc    4320
gatggcgacg acgaagacct gccctgcatt gtgtccaggg gcggacccaa ggtgaagagg    4380
ccccctatct ttatcagaag gctccataga ctgctcctga tgagggccat gaaccctgtg    4440
tgcctgcccg tgatcgtggc ccctactctc tttggctgg ccgccattgc cgctagctgc    4500
ttcaccgcct ccgtgtccac agtggtgaca gccaccggcc tcgcctgag cctgctgctc    4560 ctcgctgccg tggcctccag ctacgccgct gctcaaagaa agctcctgac ccctgtcacc    4620
gtcctgacag ccgtcgtgac caccttttcc gctggcacct tcaagctgcc taggtgcaca    4680
```

```
cctggcgaca ggcagtggct ctacgtgcag agctccgtgg gcaatattgt gcagagctgc    4740
aatcccaggt acagcatttt tttcgactac atggccatcc ataggtccct caccaagatc    4800
tgggagtgat gatgagcggc cgcgatctgc tgtgccttct agttgccagc catctgttgt    4860
ttgcccctcc cccgtgcctt ccttgaccct ggaaggtgcc actcccactg tccttttccta   4920 ataaaatgag gaaattgcat cgcattgtct gagtaggtgt cattctattc tggggggtgg    4980
ggtggggcag gacagcaagg gggaggattg gaagacaat agcaggcatg ctggggatgc     5040
ggtgggctct atggccgatc agcgatcgct gaggtgggtg agtgggcgtg gcctggggtg    5100
gtcatgaaaa tatataagtt gggggtctta gggtctcttt atttgtgttg cagagaccgc    5160
cggagccatg agcgggagca gcagcagcag cagtagcagc agcgccttgg atggcagcat    5220
cgtgagccct tatttgacga cgcggatgcc ccactgggcc ggggtgcgtc agaatgtgat    5280
gggctccagc atcgacggcc gacccgtcct gcccgcaaat tccgccacgc tgacctatgc    5340
gaccgtcgcg gggacgccgt tggacgccac cgccgccgcc gccgccaccg cagccgcctc    5400
ggccgtgcgc agcctggcca cggactttgc attcctggga ccactggcga caggggctac    5460
ttctcgggcc gctgctgccg ccgttcgcga tgacaagctg accgccctgc tggcgcagtt    5520
ggatgcgctt actcgggaac tgggtgacct ttctcagcag gtcatggccc tgcgccagca    5580
ggtctcctcc ctgcaagctg gcgggaatgc ttctcccaca aatgccgttt aagataaata    5640
aaaccagact ctgtttggat taagaaaag tagcaagtgc attgctctct ttatttcata    5700
attttccgcg cgcgatagge cctagaccag cgttctcggt cgttgagggt gcggtgtatc    5760
ttctccagga cgtggtagag gtggctctgg acgttgagat acatgggcat gagcccgtcc    5820 cggggggtgga ggtagcacca ctgcagagct tcatgctccg gggtggtgtt gtagatgatc    5880
cagtcgtagc aggagcgctg gcatggtgc ctaaaaatgt ccttcagcag caggccgatg     5940
gccaggggga ggcccttggt gtaagtgttt acaaaacggt taagttggga agggtgcatt    6000
cggggagaga tgatgtgcat cttggactgt attttttagat tggcgatgtt ccgcccaga    6060 tcccttctgg gattcatgtt gtgcaggacc accagtacag tgtatccggt gcacttgggg    6120
aatttgtcat gcagcttaga gggaaaagcg tggaagaact tggagacgcc tttgtggcct    6180
cccagatttt ccatgcattc gtccatgatg atggcaatgg gcccgcggga ggcagcttgg    6240
gcaaagatat ttctggggtc gctgacgtcg tagttgtgtt ccaggtgag gtcgtcatag      6300 gccatttttta caaagcgcgg gcggagggtg cccgactggg ggatgatggt cccctctggc   6360
cctggggcgt agttcccctc gcagatctgc atttcccagg ccttaatctc ggaggggga    6420 atcatatcca cctgcggggc gatgaagaaa acggtttccg gagccgggga gattaactgg    6480
gatgagagca ggtttctaag cagctgtgat tttccacaac cggtgggccc ataaataaca    6540
cctataaccg gttgcagctg gtagtttaga gagctgcagc tgccgtcgtc ccggaggagg    6600
ggggccacct cgttgagcat gtccctgacg cgcatgttct ccccgaccag atccgccaga    6660
aggcgctcgc cgcccaggga cagcagctct tgcaaggaag caaagttttt cagcggcttg    6720
aggccgtccg ccgtgggcat gttttttcagg gtctggctca gcagctccag gcggtcccag    6780
agctcggtga cgtgctctac ggcatctcta tccagcatat ctcctcgttt cgcgggttgg    6840
ggcgactttc gctgtagggc accaagcggt ggtcgtccag cggggccaga gtcatgtcct    6900
tccatgggcg cagggtcctc gtcagggtgg tctgggtcac ggtgaagggg tgcgctccgg    6960
gctgagcgct tgccaaggtg cgcttgaggc tggttctgct ggtgctgaag cgctgccggt    7020
cttcgccctg cgcgtcggcc aggtagcatt tgaccatggt gtcatagtcc agcccctccg    7080
```

```
cggcgtgtcc cttggcgcgc agcttgccct tggaggtggc gccgcacgag gggcagagca   7140
ggctcttgag cgcgtagagc ttgggggcga ggaagaccga ttcggggag taggcgtccg    7200 cgccgcagac cccgcacacg gtctcgcact ccaccagcca ggtgagctcg ggcgcgccg    7260 ggtcaaaaac caggtttccc ccatgctttt tgatgcgttt cttacctcgg gtctccatga   7320
ggtggtgtcc ccgctcggtg acgaagaggc tgtccgtgtc tccgtagacc gacttgaggg   7380
gtcttttctc caggggggtc cctcggtctt cctcgtagag gaactcggac cactctgaga   7440
cgaaggcccg cgtccaggcc aggacgaagg aggctatgtg ggaggggtag cggtcgttgt   7500
ccactagggg gtccaccttc tccaaggtgt gaagacacat gtcgccttcc tcggcgtcca   7560
ggaaggtgat tggcttgtag gtgtaggcca cgtgaccggg ggttcctgac ggggggtat    7620 aaaaggggt gggggcgcgc tcgtcgtcac tctcttccgc atcgctgtct gcagggcca    7680 gctgctgggg tgagtattcc ctctcgaagg cgggcatgac ctccgcgctg aggttgtcag   7740
tttccaaaaa cgaggaggat ttgatgttca cctgtcccga ggtgatacct ttgagggtac   7800
ccgcgtccat ctggtcagaa aacacgatct ttttattgtc cagcttggtg gcgaacgacc   7860
cgtagagggc gttggagagc agcttggcga tggagcgcag ggtctggttc ttgtccctgt   7920
cggcgcgctc cttggccgcg atgttgagct gcacgtactc gcgcgcgacg cagcgccact   7980
cggggaagac ggtggtgcgc tcgtcgggca ccaggcgcac gcgccagccg cggttgtgca   8040
gggtgaccag gtccacgctg gtggcgacct cgccgcgcag gcgctcgttg gtccagcaga   8100 gacgccgcc cttgcgcgag cagaaggggg cagggggtc gagctgggtc tcgtccgggg    8160
ggtccgcgtc cacggtgaaa accccggggc gcaggcgcgc gtcgaagtag tctatcttgc   8220
aaccttgcat gtccagcgcc tgctgccagt cgcgggcggc gagcgcgcgc tcgtaggggt   8280
tgagcggcgg gccccagggc atgggtggg tgagtgcgga ggcgtacatg ccgcagatgt    8340
catagacgta gaggggctcc cgcaggaccc cgatgtaggt ggggtagcag cggccgccgc   8400
ggatgctggc gcgcacgtag tcatacagct cgtgcgaggg ggcgaggagg tcggggccca   8460
ggttggtgcg ggcggggcgc tccgcgcgga agacgatctg cctgaagatg gcatgcgagt   8520
tggaagagat ggtgggcgc tggaagacgt tgaagctggc gtcctgcagg ccgacggcgt    8580
cgcgcacgaa ggaggcgtag gagtcgcgca gcttgtgtac cagctcggcg gtgacctgca   8640
cgtcgagcgc gcagtagtcg agggtctcgc ggatgatgtc atatttagcc tgcccccttct  8700 ttttccacag ctcgcggttg aggacaaact cttcgcggtc tttccagtac tcttggatcg   8760
ggaaaccgtc cggttccgaa cggtaagagc ctagcatgta gaactggttg acggcctggt   8820
aggcgcagca gcccttctcc acggggaggg cgtaggcctg cgcggccttg cggagcgagg   8880
tgtgggtcag ggcgaaggtg tccctgacca tgactttgag gtactggtgc ttgaagtcgg   8940
agtcgtcgca gccgccccgc tcccagagcg agaagtcggt gcgcttcttg gagcgggggt   9000
tgggcagagc gaaggtgaca tcgttgaaga ggattttgcc cgcgcgggc atgaagttgc     9060 gggtgatgcg gaagggcccc ggcacttcag agcggttgtt gatgacctgg gcggcgagca   9120
cgatctcgtc gaagccgttg atgttgtggc ccacgatgta gagttccagg aagcggggcc   9180
ggccctttac ggtgggcagc ttctttagct cttcgtaggt gagctcctcg ggcgaggcga   9240
ggccgtgctc ggccagggcc cagtccgcga ggtgcgggtt gtctctgagg aaggacttcc   9300
agaggtcgcg ggccaggagg gtctgcaggc ggtctctgaa ggtcctgaac tggcggccca   9360
cggccatttt ttcgggggtg atgcagtaga aggtgagggg gtcttgctgc cagcggtccc   9420
```

```
agtcgagctg cagggcgagg tcgcgcgcgg cggtgaccag gcgctcgtcg cccccgaatt      9480
tcatgaccag catgaagggc acgagctgct ttccgaaggc ccccatccaa gtgtaggtct      9540
ctacatcgta ggtgacaaag aggcgctccg tgcgaggatg cgagccgatc gggaagaact      9600
ggatctcccg ccaccagttg gaggagtggc tgttgatgtg gtggaagtag aagtcccgtc      9660
gccgggccga acactcgtgc tggcttttgt aaaagcgagc gcagtactgg cagcgctgca      9720
cgggctgtac ctcatgcacg agatgcacct ttcgcccgcg cacgaggaag ccaggggaa       9780
atctgagccc cccgcctggc tcgcggcatg gctggttctc ttctactttg gatgcgtgtc      9840
cgtctccgtc tggctcctcg aggggtgtta cggtggagcg gaccaccacg ccgcgcgagc      9900
cgcaggtcca gatatcggcg cgcggcggtc ggagtttgat gacgacatcg cgcagctggg      9960
agctgtccat ggtctggagc tcccgcgcg cggcaggtc agccgggagt tcttgcaggt        10020
tcacctcgca gagtcgggcc agggcgcggg gcaggtctag gtggtacctg atctctaggg      10080
gcgtgttggt ggcggcgtcg atggcttgca ggagcccgca gccccggggg gcgacgacgg      10140
tgccccgcgg ggtggtggtg gtggtggcgg tgcagctcag aagcggtgcc gcgggcgggc      10200
ccccggaggt agggggggct ccggtcccgc gggcaggggc ggcagcggca cgtcggcgtg      10260
gagcgcgggc aggagttggt gctgtgcccg gaggttgctg gcgaaggcga cgacgcggcg      10320
gttgatctcc tggatctggc gcctctgcgt gaagacgacg ggcccggtga gcttgaacct      10380
gaaagagagt tcgacagaat caatctcggt gtcattgacc gcggcctggc gcaggatctc      10440
ctgcacgtct cccgagttgt cttggtaggc gatctcggcc atgaactgct cgatctcttc      10500
ctcctggagg tctccgcgtc cggcgcgttc cacggtggcc gccaggtcgt tggagatgcg      10560
ccccatgagc tgcgagaagg cgttgagtcc gccctcgttc cagactcggc tgtagaccac      10620
gcccccctgg tcatcgcggg cgcgcatgac cacctgcgcg aggttgagct ccacgtgccg      10680
cgcgaagacg gcgtagttgc gcagacgctg gaagaggtag ttgagggtgg tggcggtgtg      10740
ctcggccacg aagaagttca tgacccagcg gcgcaacgtg gattcgttga tgtcccccaa      10800
ggcctccagc cgttccatgg cctcgtagaa gtccacggcg aagttgaaaa actgggagtt      10860
gcgcgccgac acggtcaact cctcctccag aagacggatg agctcggcga cggtgtcgcg      10920
cacctcgcgc tcgaaggcta tggggatctc ttcctccgct agcatcacca cctcctcctc      10980
ttcctcctct tctggcactt ccatgatggc ttcctcctct tcgggggtg gcggcggcgg       11040
cggtggggga gggggcgctc tgcgccggcg gcggcgcacc gggaggcggt ccacgaagcg      11100
cgcgatcatc tccccgcggc ggcggcgcat ggtctcggtg acggcgcggc cgttctcccg      11160
ggggcgcagt tggaagacgc cgccggacat ctggtgctgg ggcgggtggc cgtgaggcag      11220
cgagacggcg ctgacgatgc atctcaacaa ttgctgcgta ggtacgccgc cgagggacct      11280
gagggagtcc atatccaccg gatccgaaaa cctttcgagg aaggcgtcta accagtcgca      11340
gtcgcaaggt aggctgagca ccgtggcggg cggcgggggg tgggggagt gtctggcgga       11400
ggtgctgctg atgatgtaat tgaagtaggc ggacttgaca cggcggatgg tcgacaggag      11460
caccatgtcc ttgggtccgg cctgctggat gcggaggcgg tcggctatgc cccaggcttc      11520
gttctggcat cggcgcaggt ccttgtagta gtcttgcatg agcctttcca ccggcacctc      11580
ttctccttcc tcttctgctt cttccatgtc tgcttcggcc ctggggcggc gccgcgcccc      11640
cctgccccca atgcgcgtga ccccgaaccc cctgagcggt tggagcaggg ccaggtcggc      11700
gacgacgcgc tcgccagga tggcctgctg cacctgcgtg agggtggttt ggaagtcatc       11760
caagtccacg aagcggtggt aggcgcccgt gttgatggtg taggtgcagt tggccatgac      11820
```

```
ggaccagttg acggtctggt ggcccggttg cgacatctcg gtgtacctga gtcgcgagta    11880
ggcgcgggag tcgaagacgt agtcgttgca agtccgcacc aggtactggt agcccaccag    11940
gaagtgcggc ggcggctggc ggtagagggg ccagcgcagg gtggcggggg ctccgggggc    12000
caggtcttcc agcatgaggc ggtggtaggc gtagatgtac ctggacatcc aggtgatacc    12060
cgcggcggtg gtggaggcgc gcgggaagtc gcgcacccgg ttccagatgt tgcgcagggg    12120
cagaaagtgc tccatggtag gcgtgctctg tccagtcaga cgcgcgcagt cgttgatact    12180
ctagaccagg gaaaacgaaa gccggtcagc gggcactctt ccgtggtctg gtgaatagat    12240
cgcaagggta tcatggcgga gggcctcggt tcgagccccg ggtccgggcc ggacggtccg    12300
ccatgatcca cgcggttacc gcccgcgtgt cgaacccagg tgtgcgacgt cagacaacgg    12360
tggagtgttc cttttggcgt ttttctggcc gggcgccggc gccgcgtaag agactaagcc    12420
gcgaaagcga aagcagtaag tggctcgctc cccgtagccg gagggatcct tgctaagggt    12480
tgcgttgcgg cgaaccccgg ttcgaatccc gtactcgggc cggccggacc cgcggctaag    12540
gtgttggatt ggcctccccc tcgtataaag accccgcttg cggattgact ccggacacgg    12600
ggacgagccc ctttattttt tgctttcccc agatgcatcc ggtgctgcgg cagatgcgcc    12660
ccccgcccca gcagcagcaa caacaccagc aagagcggca gcaacagcag cgggagtcat    12720
gcagggcccc ctcacccacc ctcggcgggc cggccacctc ggcgtccgcg gccgtgtctg    12780
gcgcctgcgg cggcggcggg gggccggctg acgaccccga ggagcccccg cggcgcaggg    12840
ccagacacta cctggacctg gaggaggcg agggcctggc gcggctgggg gcgccgtctc    12900
ccgagcgcca cccgcgggtg cagctgaagc gcgactcgcg cgaggcgtac gtgcctcggc    12960
agaacctgtt cagggaccgc gcgggcgagg agcccgagga gatgcgggac aggaggttca    13020
gcgcagggcg ggagctgcgg caggggctga accgcgagcg gctgctgcgc gaggaggact    13080
ttgagcccga cgcgcggacg gggatcagcc ccgcgcgcgc gcacgtggcg gccgccgacc    13140
tggtgacggc gtacgagcag acggtgaacc aggagatcaa cttccaaaag agtttcaaca    13200
accacgtgcg cacgctggtg gcgcgcgagg aggtgaccat cgggctgatg cacctgtggg    13260
actttgtaag cgcgctggtg cagaacccca acagcaagcc tctgacggcg cagctgttcc    13320
tgatagtgca gcacagcagg gacaacgagg cgtttaggga cgcgctgctg aacatcaccg    13380
agcccgaggg tcgtggctg ctggacctga ttaacatcct gcagagcata gtggtgcagg    13440
agcgcagcct gagcctggcc gacaaggtgg cggccatcaa ctactcgatg ctgagcctgg    13500
gcaagttta cgcgcgcaag atctaccaga cgccgtacgt gcccatagac aaggaggtga    13560
agatcgacgg ttttttacatg cgcatggcgc tgaaggtgct caccctgagc gacgacctgg    13620
gcgtgtaccg caacgagcgc atccacaagg ccgtgagcgt gagccggcgg cgcgagctga    13680
gcgaccgcga gctgatgcac agcctgcagc gggcgctggc gggcgccggc agcggcgaca    13740
gggaggcgga gtcctacttc gatgcggggg cggacctgcg ctgggcgccc agccggcggg    13800
ccctggaggc cgcggggtc cgcgaggact atgacgagga cggcgaggag gatgaggagt    13860
acagagctaga ggagggcgag tacctggact aaaaccgcggg tggtgtttcc ggtagatgca    13920
agacccgaac gtggtggacc cggcgctgcg ggcggctctg cagagccagc cgtccggcct    13980
taactcctca gacgactggc gacaggtcat ggaccgcatc atgtcgctga cggcgcgtaa    14040
cccggacgcg ttccggcagc agccgcaggc caacaggctc tccgccatcc tggaggcggt    14100
ggtgcctgcg cgctcgaacc ccacgcacga gaaggtgctg gccatagtga acgcgctggc    14160
```

```
cgagaacagg gccatccgcc cggacgaggc cgggctggtg tacgacgcgc tgctgcagcg   14220
cgtggcccgc tacaacagcg gcaacgtgca gaccaacctg gaccggctgg tggggggacgt   14280 gcgcgaggcg gtggcgcagc gcgagcgcgc ggatcggcag ggcaacctgg gctccatggt   14340
ggcgctgaat gccttcctga gcacgcagcc ggccaacgtg ccgcgggggc aggaagacta   14400
caccaacttt gtgagcgcgc tgcggctgat ggtgaccgag acccccaga gcgaggtgta   14460 ccagtcgggc ccggactact tcttccagac cagcagacag ggcctgcaga cggtgaacct   14520
gagccaggct ttcaagaacc tgcgggggct gtggggcgtg aaggcgccca ccggcgaccg   14580
ggcgacggtg tccagcctgc tgacgcccaa ctcgcgcctg ctgctgctgc tgatcgcgcc   14640
gttcacggac agcggcagcg tgtcccggga cacctacctg gggcacctgc tgaccctgta   14700
ccgcgaggcc atcgggcagg cgcaggtgga cgagcacacc ttccaggaga tcaccagcgt   14760
gagccgcgcg ctggggcagg aggacacgag cagcctggag gcgactctga actacctgct   14820
gaccaaccgg cggcagaaga ttccctcgct gcacagcctg acctccgagg aggagcgcat   14880
cttgcgctac gtgcagcaga gcgtgagcct gaacctgatg cgcgacgggg tgacgcccag   14940
cgtggcgctg gacatgaccg cgcgcaacat ggaaccgggc atgtacgccg cgcaccggcc   15000
ttacatcaac cgcctgatgg actacctgca tcgcgcggcg gccgtgaacc ccgagtactt   15060
taccaacgcc atcctgaacc cgcactggct cccgccgccc gggttctaca gcggggggctt   15120 cgaggtcccg gagaccaacg atggcttcct gtgggacgac atggacgaca cgtgttctc   15180 cccgcggccg caggcgctgg cggaagcgtc cctgctgcgt cccaagaagg aggaggagga   15240
ggaggcgagt cgccgccgcg gcagcagcgg cgtggcttct ctgtccgagc tggggggcggc   15300 agccgccgcg cgccccgggt ccctgggcgg cagcccctttt ccgagcctgg tgggggtctct   15360 gcacagcgag cgcaccaccc gccctcggct gctgggcgag gacgagtacc tgaataactc   15420
cctgctgcag ccggtgcggg agaaaaacct gcctcccgcc ttccccaaca cgggatagga   15480
gagcctggtg gacaagatga gcagatggaa gacctatgcg caggagcaca gggacgcgcc   15540 tgccgctccgg ccgcccacgc ggcgccagcg ccacgaccgg cagcggggc tggtgtggga   15600 tgacgaggac tccgcggacg atagcagcgt gctggacctg ggagggggagcg gcaacccgtt   15660 cgcgcacctg cgcccccgcc tggggaggat gttttaaaaa aaaaaaaaaa angcaagaag   15720
catgatgcaa aaattaaata aaactcacca aggccatggc gaccgagcgt tggtttcttg   15780
tgttcccttc agtatgcggc gcgcggcgat gtaccaggag ggacctcctc cctcttacga   15840
gagcgtggtg ggcgcggcgg cggcggcgcc ctcttctccc tttgcgtcgc agctgctgga   15900
gccgccgtac gtgcctccgc gctacctgcg gcctacgggg gggagaaaca gcatccgtta   15960
ctcggagctg gcgcccctgt tcgacaccac ccgggtgtac ctggtggaca acaagtcggc   16020
ggacgtggcc tccctgaact accagaacga ccacagcaat ttttttgacca cggtcatcca   16080 gaacaatgac tacagcccga gcgaggccag cacccagacc atcaatctgg atgaccggtc   16140
gcactggggc ggcgacctga aaaccatcct gcacaccaac atgcccaacg tgaacgagtt   16200
catgttcacc aataagttca aggcgcgggt gatggtgtcg cgctcgcaca ccaaggaaga   16260
ccgggtggga ctgaagtacg agtgggtgga gttcgagctg ccagagggca actactccga   16320
gaccatgacc attgacctga tgaacaacgc gatcgtggag cactatctga aagtgggcag   16380
gcagaacggg gtcctggaga gcgacatcgg ggtcaagttc gacaccagga acttccgcct   16440
ggggctggac ccgtgaccg ggctggttat gcccgggtg tacaccaacg aggccttcca   16500
tcccgacatc atcctgctgc ccggctgcgg ggtggacttc acttacagcc gcctgagcaa   16560
```

```
cctcctgggc atccgcaagc ggcagcccct tccaggagggc ttcaggatca cctacgagga   16620
cctggagggg ggcaacatcc ccgcgctcct cgatgtggag gcctaccagg atagcttgaa   16680
ggaaaatgag gcgggacagg aggataccgc ccccgccgcc tccgccgccg ccgagcaggg   16740
cgaggatgct gctgacaccg cggccgcgga cggggcagag gccgaccccg ctatggtggt   16800
ggaggctccc gagcaggagg aggacatgaa tgacagtgcg gtgcgcggag acaccttcgt   16860
cacccggggg gaggaaaagc aagcggaggc cgaggccgcg gccgaggaaa agcaactggc   16920
ggcagcagcg gcggcggcgg cgttggccgc ggcggaggct gagtctgagg ggaccaagcc   16980
cgccaaggag cccgtgatta gcccctgac cgaagatagc aagaagcgca gttacaacct   17040
gctcaaggac agcaccaaca ccgcgtaccg cagctggtac ctggcctaca actacggcga   17100
cccgtcgacg ggggtgcgct cctggaccct gctgtgcacg ccggacgtga cctgcggctc   17160
ggagcaggtg tactggtcgc tgcccgacat gatgcaagac cccgtgacct tccgctccac   17220
gcggcaggtc agcaacttcc cggtggtggg cgccgagctg ctgcccgtgc actccaagag   17280
cttctacaac gaccaggccg tctactccca gctcatccgc cagttcacct ctctgaccca   17340
cgtgttcaat cgctttcctg agaaccagat tctggcgcgc ccgcccgccc ccaccatcac   17400
caccgtcagt gaaaacgttc ctgctctcac agatcacggg acgctaccgc tgcgcaacag   17460
catcggagga gtccagcgag tgaccgttac tgacgccaga cgccgcacct gccctacgt   17520 ttacaaggcc ttgggcatag tctcgccgcg cgtcctttcc agccgcactt tttgagcaac   17580
accaccatca tgtccatcct gatctcaccc agcaataact ccggctgggg actgctgcgc   17640
gcgcccagca agatgttcgg aggggcgagg aagcgttccg agcagcaccc cgtgcgcgtg   17700
cgcgggcact tccgcgcccc ctggggagcg cacaaacgcg gccgcgcggg gcgcaccacc   17760
gtggacgacg ccatcgactc ggtggtggag caggcgcgca actacaggcc cgcggtctct   17820
accgtggacg cggccatcca gaccgtggtg cggggcgcgc ggcggtacgc caagctgaag   17880
agccgccgga agcgcgtggc ccgccgccac cgccgccgac ccggggccgc cgccaaacgc   17940
gccgccgcgg ccctgcttcg ccgggccaag cgcacgggcc gccgcgccgc catgagggcc   18000
gcgcgccgct tggccgccgg catcaccgcc gccaccatgg ccccccgtac ccgaagacgc   18060
gcggccgccg ccgccgccgc cgccatcagt gacatggcca gcaggcgccg gggcaacgtg   18120
tactgggtgc gcgactcggt gaccggcacg cgcgtgcccg tgcgcttccg ccccccgcgg   18180
acttgagatg atgtgaaaaa acaacactga gtctcctgct gttgtgtgta tcccagcggc   18240
ggcggcgcgc gcagcgtcat gtccaagcgc aaaatcaaag aagagatgct ccaggtcgtc   18300
gcgccggaga tctatgggcc cccgaagaag gaagagcagg attcgaagcc ccgcaagata   18360
aagcgggtca aaagaaaaa gaaagatgat gacgatgccg atggggaggt ggagttcctg   18420
cgcgccacgg cgcccaggcg cccggtgcag tggaagggcc ggcgcgtaaa gcgcgtcctg   18480
cgccccggca ccgcggtggt cttcacgccc ggcgagcgct ccacccggac tttcaagcgc   18540
gtctatgacg aggtgtacgg cgacgaagac ctgctggagc aggccaacga gcgcttcgga   18600
gagtttgctt acgggaagcg tcagcggcgc ctggggaagg aggacctgct ggcgctgccg   18660
ctggaccagg gcaaccccac ccccagtctg aagcccgtga ccctgcagca ggtgctgccg   18720
agcagcgcac cctccgaggc gaagcgggt ctgaagcgcg agggcggcga cctggcgccc   18780
accgtgcagc tcatggtgcc caagcggcag aggctggagg atgtgctgga gaaaatgaaa   18840
gtagaccccg gtctgcagcc ggacatcagg gtccgcccca tcaagcaggt ggcgccgggc   18900
```

```
ctcggcgtgc agaccgtgga cgtggtcatc cccaccggca actcccccgc cgccgccacc    18960
actaccgctg cctccacgga catggagaca cagaccgatc cgccgcagc cgcagccgca     19020
gccgccgccg cgacctcctc ggcggaggtg cagacggacc cctggctgcc gccggcgatg    19080
tcagctcccc gcgcgcgtcg cgggcgcagg aagtacggcg ccgccaacgc gctcctgccc    19140
gagtacgcct tgcatccttc catcgcgccc accccggct accgaggcta tacctaccgc     19200
ccgcgaagag ccaagggttc cacccgccgt ccccgccgac gcgccgccgc caccacccgc    19260
cgccgccgcc gcagacgcca gcccgcactg gctccagtct ccgtgaggaa gtggcgcgc     19320
gacggacaca ccctggtgct gcccagggcg cgctaccacc ccagcatcgt ttaaaagcct    19380
gttgtggttc ttgcagatat ggccctcact tgccgcctcc gtttcccggt gccgggatac    19440
cgaggaggaa gatcgcgccg caggaggggt ctggccggcc gcggcctgag cggaggcagc    19500
cgccgcgcgc accggcggcg acgcgccacc agccgacgca tgcgcggcgg ggtgctgccc    19560
ctgttaatcc ccctgatcgc cgcggcgatc ggcgccgtgc ccgggatcgc ctccgtggcc    19620
ttgcaagcgt cccagaggca ttgacagact tgcaaacttg caaatatgga aaaaaaaacc    19680
ccaataaaaa agtctagact ctcacgctcg cttggtcctg tgactatttt gtagaatgga    19740
agacatcaac tttgcgtcgc tggccccgcg tcacggctcg cgcccgttcc tgggacactg    19800
gaacgatatc ggcaccagca acatgagcgg tggcgccttc agttggggct ctctgtggag    19860
cggcattaaa agtatcgggt ctgccgttaa aaattacggc tcccgggcct ggaacagcag    19920
cacgggccag atgttgagag acaagttgaa agagcagaac ttccagcaga aggtggtgga    19980
gggcctggcc tccggcatca acggggtggt ggacctggcc aaccaggccg tgcagaataa    20040
gatcaacagc agactggacc cccggccgcc ggtggaggag gtgccgccgg cgctggagac    20100
ggtgtccccc gatgggcgtg gcgagaagcg cccgcgccc gatagggaag agaccactct     20160
ggtcacgcag accgatgagc cgccccgta tgaggaggcc ctgaagcaag gtctgcccac     20220
cacgcggccc atcgcgccca tggccaccgg ggtggtgggc cgccacaccc ccgccacgct    20280
ggacttgcct ccgcccgccg atgtgccgca gcagcagaag gcggcacagc cgggcccgcc    20340
cgcgaccgcc tcccgttcct ccgccggtcc tctgcgccgc gcggcagcg gccccgcgg     20400
gggggtcgcg aggcacggca actggcagag cacgctgaac agcatcgtgg gtctggggt     20460
gcggtccgtg aagcgccgcc gatgctactg aatagcttag ctaacgtgtt gtatgtgtgt    20520
atgcgcccta tgtcgccgcc agaggagctg ctgagtcgcc gccgttcgcg cgcccaccac    20580
caccgccact ccgcccctca agatggcgac cccatcgatg atgccgcagt ggtcgtacat    20640
gcacatctcg ggccaggacg cctcggagta cctgagcccc gggctggtgc agttcgcccg    20700
cgccaccgag agctacttca gcctgagtaa caagtttagg aaccccacgg tggcgcccac    20760
gcacgatgtg accaccgacc ggtctcagcg cctgacgctg cggttcattc ccgtggaccg    20820
cgaggacacc gcgtactcgt acaaggcgcg gttcacgctg gccgtgggcg acaaccgcgt    20880
gctggacatg gcctccacct actttgacat ccgcggggtg ctggaccggg gtcccacttt    20940
caagccctac tctggcaccg cctacaactc cctggccccc aagggcgctc ccaactcctg    21000
cgagtgggag caagaggaaa ctcaggcagt tgaagaagca gcagaagagg aagaagaaga    21060
tgctgacggt caagctgagg aagagcaagc agctaccaaa aagactcatg tatatgctca    21120
ggctcccctt tctggcgaaa aaattagtaa agatggtctg caaataggaa cggacgctac    21180
agctacagaa caaaaaccta tttatgcaga ccctacattc cagcccgaac cccaaatcgg    21240
ggagtcccag tggaatgagg cagatgctac agtcgccggc ggtagagtgc taaagaaatc    21300
```

```
tactcccatg aaaccatgct atggttccta tgcaagaccc acaaatgcta atggaggtca   21360
gggtgtacta acggcaaatg cccagggaca gctagaatct caggttgaaa tgcaattctt   21420
ttcaacttct gaaaacgccc gtaacgaggc taacaacatt cagcccaaat tggtgctgta   21480
tagtgaggat gtgcacatgg agaccccgga tacgcacctt tcttacaagc ccgcaaaaag   21540
cgatgacaat tcaaaaatca tgctgggtca gcagtccatg cccaacagac ctaattacat   21600
cggcttcaga gacaacttta tcggcctcat gtattacaat agcactggca acatgggagt   21660
gcttgcaggt caggcctctc agttgaatgc agtggtggac ttgcaagaca gaaacacaga   21720
actgtcctac cagctcttgc ttgattccat gggtgacaga accagatact tttccatgtg   21780
gaatcaggca gtggacagtt atgacccaga tgttagaatt attgaaaatc atggaactga   21840
agacgagctc cccaactatt gtttccctct gggtggcata ggggtaactg acacttacca   21900
ggctgttaaa accaacaatg caataacgg gggccaggtg acttggacaa aagatgaaac   21960
ttttgcagat cgcaatgaaa tagggtgggg aaacaatttc gctatggaga tcaacctcag   22020
tgccaacctg tggagaaact tcctgtactc caacgtggcg ctgtacctac cagacaagct   22080
taagtacaac ccctccaatg tggacatctc tgacaacccc aacacctacg attacatgaa   22140
caagcgagtg gtggccccgg ggctggtgga ctgctacatc aacctgggcg cgcgctggtc   22200
gctggactac atggacaacg tcaacccctt caaccaccac cgcaatgcgg gcctgcgcta   22260
ccgctccatg ctcctgggca cgggcgcta cgtgcccttc cacatccagg tgccccagaa   22320
gttctttgcc atcaagaacc tcctcctcct gccgggctcc tacacctacg agtggaactt   22380
caggaaggat gtcaacatgg tcctccagag ctctctgggt aacgatctca gggtggacgg   22440
ggccagcatc aagttcgaga gcatctgcct ctacgccacc ttcttcccca tggcccacaa   22500
cacggcctcc acgctcgagg ccatgctcag gaacgacacc aacgaccagt ccttcaatga   22560
ctacctctcc gccgccaaca tgctctaccc catacccgcc aacgccacca acgtccccat   22620
ctccatcccc tcgcgcaact gggcggcctt ccgcggctgg gccttcaccc gcctcaagac   22680
caaggagacc ccctccctgg gctcgggatt cgacccctac tacacctact cgggctccat   22740
tccctacctg gacggcacct tctacctcaa ccacactttc aagaaggtct cggtcacctt   22800
cgactcctcg gtcagctggc cgggcaacga ccgtctgctc accccaacg agttcgagat   22860
caagcgctcg gtcgacgggg agggctacaa cgtggcccag tgcaacatga ccaaggactg   22920
gttcctggtc cagatgctgg ccaactacaa catcggctac cagggcttct acatcccaga   22980
gagctacaag gacaggatgt actccttctt caggaacttc cagcccatga ccggcaggt   23040
ggtggaccag accaagtaca aggactacca ggaggtgggc atcatccacc agcacaacaa   23100
ctcgggcttc gtgggctacc tcgccccac catgcgcgag ggacaggcct accccgccaa   23160
cttcccctat ccgctcatag caagaccgc ggtcgacagc atcacccaga aaagttcct   23220
ctgcgaccgc accctctggc gcatccctt ctccagcaac ttcatgtcca tgggtgcgct   23280
ctcggacctg ggccagaact tgctctacgc caactccgcc cacgccctcg acatgacctt   23340
cgaggtcgac cccatggacg agcccaccct tctctatgtt ctgttcgaag tctttgacgt   23400
ggtccgggtc caccagccgc accgcggcgt catcgagacc gtgtacctgc gtacgcccctt   23460
ctcggccggc aacgccacca cctaaagaag caagccgcag tcatcgccgc ctgcatgccg   23520
tcgggttcca ccgagcaaga gctcaggcc atcgtcagag acctgggatg cgggccctat   23580
tttttgggca ccttcgacaa gcgcttccct ggctttgtct ccccacacaa gctggcctgc   23640
```

```
gccatcgtca acacggccgg ccgcgagacc gggggcgtgc actggctggc cttcgcctgg   23700
aacccgcgct ccaaaacatg cttcctcttt gaccccttcg gcttttcgga ccagcggctc   23760
aagcaaatct acgagttcga gtacgagggc ttgctgcgtc gcagcgccat cgcctcctcg   23820
cccgaccgct gcgtcaccct cgaaaagtcc acccagaccg tgcaggggcc cgactcggcc   23880
gcctgcggtc tcttctgctg catgtttctg cacgcctttg tgcactggcc tcagagtccc   23940
atggaccgca accccaccat gaacttgctg acggggtgc ccaactccat gctccagagc    24000
ccccaggtcg agcccaccct gcgccgcaac caggagcagc tctacagctt cctggagcgc   24060
cactcgcctt acttccgccg ccacagcgca cagatcagga gggccacctc cttctgccac   24120
ttgcaagaga tgcaagaagg gtaataacga tgtacacact tttttctca ataaatggca    24180
tcttttatt tatacaagct ctctggggta ttcatttccc accaccacc gccgttgtcg     24240
ccatctggct ctatttagaa atcgaaaggg ttctgccggg agtcgccgtg cgccacgggc   24300
agggacacgt tgcgatactg gtagcgggtg ccccacttga actcgggcac caccaggcga   24360
ggcagctcgg ggaagttttc gctccacagg ctgcgggtca gcaccagcgc gttcatcagg   24420
tcgggcgccg agatcttgaa gtcgcagttg gggccgccgc cctgcgcgcg cgagttgcgg   24480
tacaccgggt tgcagcactg gaacaccaac agcgccgggt gcttcacgct ggccagcacg   24540
ctgcggtcgg agatcagctc ggcgtccagg tcctccgcgt tgctcagcgc gaacggggtc   24600
atcttgggca cttgccgccc caggaagggc gcgtgccccg gtttcgagtt gcagtcgcag   24660
cgcagcggga tcagcaggtg cccgtgcccg gactcggcgt tggggtacag cgcgcgcatg   24720
aaggcctgca tctggcggaa ggccatctgg gccttgcgc cctccgagaa gaacatgccg    24780
caggacttgc ccgagaactg gtttgcgggg cagctggcgt cgtgcaggca gcagcgcgcg   24840
tcggtgttgg cgatctgcac cacgttgcgc ccccaccggt tcttcacgat cttggccttg   24900
gacgattgct ccttcagcgc gcgctgcccg ttctcgctgg tcacatccat ctcgatcaca   24960
tgttccttgt tcaccatgct gctgccgtgc agacacttca gctcgccctc cgtctcggtg   25020
cagcggtgct gccacagcgc gcagcccgtg ggctcgaaag acttgtaggt cacctccgcg   25080
aaggactgca ggtaccctg caaaaagcgg cccatcatgg tcacgaaggt cttgttgctg    25140
ctgaaggtca gctgcagccc gcggtgctcc tcgttcagcc aggtcttgca cacggccgcc   25200
agcgcctcca cctggtcggg cagcatcttg aagttcacct tcagctcatt ctccacgtgg   25260
tacttgtcca tcagcgtgcg cgccgcctcc atgcccttct cccaggccga caccagcggc   25320
aggctcacgg ggttcttcac catcaccgtg gccgccgcct ccgccgcgct ttcgcttttcc   25380
gccccgctgt tctcttcctc ttcctcctct tcctcgccgc cgcccactcg cagccccgc    25440
accacggggg cgtcttcctg caggcgctgc accttgcgct tgccgttgcg ccctgcttg    25500
atgcgcacgg gcgggttgct gaagcccacc atcaccagcg cggcctcttc ttgctcgtcc   25560
tcgctgtcca gaatgacctc cggggagggg gggttggtca tcctcagtac cgaggcacgc   25620
ttctttttct tcctgggggc gttcgccagc tccgcggctg cggccgctgc cgaggtcgaa   25680
ggccgagggc tgggcgtgcg cggcaccagc gcgtcctgcg agccgtcctc gtcctcctcg   25740
gactcgagac ggaggcgggc ccgcttcttc ggggcgcgc ggggcggcgg aggcggcggc    25800
ggcgacggag acgggacga gacatcgtcc agggtgggtg gacggcgggc cgcgccgcgt    25860
ccgcgctcgg gggtggtctc gcgctggtcc tcttcccgac tggccatctc ccactgctcc   25920
ttctcctata ggcagaaaga gatcatggag tctctcatgc gagtcgagaa ggaggaggac   25980
agcctaaccg cccccctctga gccctccacc accgccgcca ccaccgccaa tgccgccgcg   26040
```

```
gacgacgcgc ccaccgagac caccgccagt accaccctcc ccagcgacgc accccgctc      26100
gagaatgaag tgctgatcga gcaggacccg ggttttgtga gcggagagga ggatgaggtg      26160
gatgagaagg agaaggagga ggtcgccgcc tcagtgccaa agaggataa aaagcaagac       26220
caggacgacg cagataagga tgagacagca gtcgggcggg ggaacggaag ccatgatgct      26280
gatgacggct acctagacgt gggagacgac gtgctgctta agcacctgca ccgccagtgc      26340
gtcatcgtct gcgacgcgct gcaggagcgc tgcgaagtgc ccctggacgt ggcggaggtc      26400
agccgcgcct acgagcggca cctcttcgcg ccgcacgtgc cccccaagcg ccgggagaac      26460
ggcacctgcg agcccaaccc gcgtctcaac ttctacccgg tcttcgcggt acccgaggtg      26520
ctggccacct accacatctt tttccaaaac tgcaagatcc ccctctcctg ccgcgccaac      26580
cgcacccgcg ccgacaaaac cctgaccctg cggcagggcg cccacatacc tgatatcgcc      26640
tctctggagg aagtgcccaa gatcttcgag ggtctcggtc gcgacgagaa acgggcggcg      26700
aacgctctgc acggagacag cgaaaacgag agtcactcgg gggtgctggt ggagctcgag      26760
ggcgacaacg cgcgcctggc cgtactcaag cgcagcatag aggtcaccca ctttgcctac      26820
ccggcgctca acctgccccc caaggtcatg agtgtggtca tgggcgagct catcatgcgc      26880
cgcgcccagc ccctggccgc ggatgcaaac ttgcaagagt cctccgagga aggcctgccc      26940
gcggtcagcg acgagcagct ggcgcgctgg ctggagaccc gcgacccgc gcagctggag      27000
gagcggcgca agctcatgat ggccgcggtg ctggtcaccg tggagctcga gtgtctgcag      27060
cgcttcttcg cggacccga gatgcagcgc aagctcgagg agaccctgca ctacaccttc      27120
cgccagggct acgtgcgcca ggcctgcaag atctccaacg tggagctctg caacctggtc      27180
tcctacctgg gcatcctgca cgagaaccgc ctcgggcaga acgtcctgca ctccaccctc      27240
aaaggggagg cgcgccgcga ctacatccgc gactgcgcct acctcttcct ctgctacacc      27300
tggcagacgg ccatgggggt ctggcagcag tgcctggagg agcgcaacct caaggagctg      27360
gaaaagctcc tcaagcgcac cctcagggac ctctggacgg gcttcaacga gcgctcggtg      27420
gccgccgcgc tggcggacat catctttccc gagcgcctgc tcaagaccct gcagcagggc      27480
ctgcccgact tcaccagcca gagcatgctg cagaacttca ggactttcat cctggagcgc      27540
tcgggcatcc tgccggccac ttgctgcgcg ctgcccagcg acttcgtgcc catcaagtac      27600
agggagtgcc cgccgccgct ctggggccac tgctacctct tccagctggc caactacctc      27660
gcctaccact cggacctcat ggaagacgtg agcggcgagg gcctgctcga gtgccactgc      27720
cgctgcaacc tctgcacgcc ccaccgctct ctagtctgca acccgcagct gctcagcgag      27780
agtcagatta tcggtacctt cgagctgcag ggtccctcgc ctgacgagaa gtccgcggct      27840
ccagggctga aactcactcc ggggctgtgg acttccgcct acctacgcaa atttgtacct      27900
gaggactacc acgcccacga gatcaggttc tacgaagacc aatcccgccc gcccaaggcg      27960
gagctcaccg cctgcgtcat cacccagggg cacatcctgg gccaattgca agccatcaac      28020
aaagcccgcc gagagttctt gctgaaaaag ggtcgggggg tgtacctgga ccccagtcc       28080
ggcgaggagc taaacccgct acccccgccg ccgcccagc agcgggacct tgcttcccag       28140
gatggcaccc agaaagaagc agcagccgcc gccgccgccg cagccataca tgcttctgga      28200
ggaagaggag gaggactggg acagtcaggc agaggaggtt tcggacgagg agcaggagga      28260
gatgatggaa gactgggagg aggacagcag cctagacgag gaagcttcag aggccgaaga      28320
ggtggcagac gcaacaccat cgccctcggt cgcagccccc tcgccggggc ccctgaaatc      28380
```

```
ctccgaaccc agcaccagcg ctataacctc cgctcctccg gcgccggcgc cacccgcccg    28440
cagacccaac cgtagatggg acaccacagg aaccggggtc ggtaagtcca agtgcccgcc    28500
gccgccaccg cagcagcagc agcagcagcg ccagggctac cgctcgtggc gcgggcacaa    28560
gaacgccata gtcgcctgct tgcaagactg cgggggcaac atctctttcg cccgccgctt    28620
cctgctattc caccacgggg tcgcctttcc ccgcaatgtc ctgcattact accgtcatct    28680
ctacagcccc tactgcagcg gcgacccaga ggcggcagcg gcagccacag cggcgaccac    28740
cacctaggaa gatatcctcc gcgggcaaga cagcggcagc agcggccagg agacccgcgg    28800
cagcagcggc gggagcggtg ggcgcactgc gcctctcgcc caacgaaccc ctctcgaccc    28860
gggagctcag acacaggatc ttccccactt tgtatgccat cttccaacag agcagaggcc    28920
aggagcagga gctgaaaata aaaacagat ctctgcgctc cctcacccgc agctgtctgt     28980
atcacaaaag cgaagatcag cttcggcgca cgctggagga cgcggaggca ctcttcagca    29040
aatactgcgc gctcactctt aaagactagc tccgcgccct tctcgaattt aggcgggaga    29100
aaactacgtc atcgccggcc gccgcccagc ccgcccagcc gagatgagca aagagattcc    29160
cacgccatac atgtggagct accagccgca gatgggactc gcggcgggag cggcccagga    29220
ctactccacc cgcatgaact acatgagcgc gggaccccac atgatctcac aggtcaacgg    29280
gatccgcgcc cagcgaaacc aaatactgct ggaacaggcg gccataccg ccacgccccg     29340 ccataatctc aaccccgaa attggcccgc cgccctcgtg taccaggaaa ccccctccgc     29400
caccaccgta ctacttccgc gtgacgccca ggccgaagtc cagatgacta actcaggggc    29460
gcagctcgcg ggcggctttc gtcacggggc gcggccgctc cgaccaggta taagacacct    29520
gatgatcaga ggccgaggta tccagctcaa cgacgagtcg gtgagctctt cgctcggtct    29580
ccgtccggac ggaactttcc agctcgccgg atcggccgc tcttcgttca cgccccgcca     29640
ggcgtacctg actctgcaga cctcgtcctc ggagccccgc tccggcggca tcggaaccct    29700
ccagttcgtg gaggagttcg tgccctcggt ctacttcaac cccttctcgg gacctccgg    29760 acgctacccc gaccagttca ttccgaactt tgacgcggtg aaggactcgg cggacggcta    29820
cgactgaatg tcaggtgtcg aggcagagca gcttcgcctg agacacctcg agcactgccg    29880
ccgccacaag tgcttcgccc gcggttctgg tgagttctgc tactttcagc tacccgagga    29940
gcataccgag gggccggcgc acggcgtccg cctgaccacc cagggcgagg ttacctgttc    30000
cctcatccgg gagtttaccc tccgtcccct gctagtggag cgggagcggg gtccctgtgt    30060
cctaactatc gcctgcaact gccctaaccc tggattacat caagatcttt gctgtcatct    30120
ctgtgctgag tttaataaac gctgagatca gaatctactg gggctcctgt cgccatcctg    30180
tgaacgccac cgtcttcacc caccccgacc aggcccaggc gaacctcacc tgcggtctgc    30240
atcggagggc caagaagtac ctcacctggt acttcaacgg caccccctt gtggtttaca    30300 acagcttcga cggggacgga gtctcccctga aagaccagct ctccggtctc agctactcca    30360
tccacaagaa caccaccctc caactcttcc ctccctacct gccgggaacc tacgagtgcg    30420
tcaccggccg ctgcacccac ctcacccgcc tgatcgtaaa ccagagcttt ccgggaacag    30480
ataactccct cttccccaga acaggaggtg agctcaggaa actccccggg gaccaggcg     30540 gagacgtacc ttcgacccct tgtggggttag gattttttat taccgggttg ctggctcttt    30600
taatcaaagt ttccttgaga tttgttcttt ccttctacgt gtatgaacac ctcaacctcc    30660
aataactcta ccctttcttc ggaatcaggt gacttctctg aaatcgggct tggtgtgctg    30720
cttactctgt tgatttttttt ccttatcata ctcagccttc tgtgcctcag gctcgccgcc    30780
```

```
tgctgcgcac acatctatat ctactgctgg ttgctcaagt gcaggggtcg ccacccaaga   30840
tgaacaggta catggtccta tcgatcctag gcctgctggc cctggcggcc tgcagcgccg   30900
ccaaaaaaga gattaccttt gaggagcccg cttgcaatgt aactttcaag cccgagggtg   30960
accaatgcac caccctcgtc aaatgcgtta ccaatcatga gaggctgcgc atcgactaca   31020
aaaacaaaac tggccagttt gcggtctata gtgtgtttac gcccggagac ccctctaact   31080
actctgtcac cgtcttccag ggcggacagt ctaagatatt caattacact ttcccttttt   31140
atgagttatg cgatgcggtc atgtacatgt caaaacagta caacctgtgg cctccctctc   31200
cccaggcgtg tgtggaaaat actgggtctt actgctgtat ggctttcgca atcactacgc   31260
tcgctctaat ctgcacggtg ctatacataa aattcaggca gaggcgaatc tttatcgatg   31320
aaaagaaaat gccttgatcg ctaacaccgg ctttctatct gcagaatgaa tgcaatcacc   31380
tccctactaa tcaccaccac cctccttgcg attgccatg ggttgacacg aatcgaagtg    31440
ccagtggggt ccaatgtcac catggtgggc cccgccggca attccaccct catgtgggaa   31500
aaatttgtcc gcaatcaatg ggttcatttc tgctctaacc gaatcagtat caagcccaga   31560
gccatctgcg atgggcaaaa tctaactctg atcaatgtgc aaatgatgga tgctgggtac   31620
tattacgggc agcggggaga aatcattaat tactggcgac cccacaagga ctacatgctg   31680
catgtagtcg aggcacttcc cactaccacc cccactacca cctctcccac caccaccacc   31740
actactacta ctactactac tactactact actaccacta ccgctgcccg ccataccgc    31800 aaaagcacca tgattagcac aaagcccccct cgtgctcact cccacgccgg cgggcccatc   31860
ggtgcgacct cagaaaccac cgagctttgc ttctgccaat gcactaacgc cagcgctcat   31920
gaactgttcg acctggagaa tgaggatgtc cagcagagct ccgcttgcct gacccaggag   31980
gctgtggagc ccgttgccct gaagcagatc ggtgattcaa taattgactc ttcttctttt   32040
gccactcccg aataccctcc cgattctact ttccacatca cgggtaccaa agaccctaac   32100
ctctctttct acctgatgct gctgctctgt atctctgtgg tctcttccgc gctgatgtta   32160
ctggggatgt tctgctgcct gatctgccgc agaaagagaa aagctcgctc tcagggccaa   32220
ccactgatgc ccttcccta ccccccggat tttgcagata caagatatg agctcgctgc     32280 tgacactaac cgctttacta gcctgcgctc taacccttgt cgcttgcgac tcgagattcc   32340
acaatgtcac agctgtggca ggagaaaatg ttactttcaa ctccacggcc gatacccagt   32400
ggtcgtggag tggctcaggt agctacttaa ctatctgcaa tagctccact tcccccggca   32460
tatccccaac caagtaccaa tgcaatgcca gcctgttcac cctcatcaac gcttccaccc   32520
tggacaatgg actctatgta ggctatgtac cctttggtgg gcaaggaaag acccacgctt   32580
acaacctgga agttcgccag cccagaacca ctacccaagc ttctcccacc accaccacca   32640
ccaccaccat caccagcagc agcagcagca gcagccacag cagcagcagc agattattga   32700
ctttggtttt ggccagctca tctgccgcta cccaggccat ctacagctct gtgcccgaaa   32760
ccactcagat ccaccgccca gaaacgacca ccgccaccac cctacacacc tccagcgatc   32820
agatgccgac caacatcacc cccttggctc ttcaaatggg acttacaagc cccactccaa   32880
aaccagtgga tgcggccgag gtctccgccc tcgtcaatga ctgggcgggg ctgggaatgt   32940
ggtggttcgc cataggcatg atggcgctct gcctgcttct gctctggctc atctgctgcc   33000
tccaccgcag gcgagccaga cccccatct atagacccat cattgtcctg aaccccgata   33060
atgatgggat ccatagattg gatggcctga aaaacctact tttttctttt acagtatgat   33120
```

```
aaattgagac atgcctcgca ttttcttgta catgttcctt ctcccacctt ttctggggtg    33180
ttctacgctg gccgctgtgt ctcacctgga ggtagactgc ctctcaccct tcactgtcta    33240
cctgctttac ggattggtca ccctcactct catctgcagc ctaatcacag taatcatcgc    33300
cttcatccag tgcattgatt acatctgtgt gcgcctcgca tacttcagac accacccgca    33360
gtaccgagac aggaacattg cccaacttct aagactgctc taatcatgca taagactgtg    33420
atctgccttc tgatcctctg catcctgccc accctcacct cctgccagta caccacaaaa    33480
tctccgcgca aaagacatgc ctcctgccgc ttcacccaac tgtggaatat acccaaatgc    33540
tacaacgaaa agagcgagct ctccgaagct tggctgtatg gggtcatctg tgtcttagtt    33600
ttctgcagca ctgtctttgc cctcataatc taccoctact ttgatttggg atggaacgcg    33660
atcgatgcca tgaattaccc caccttccc gcacccgaga taattccact gcgacaagtt    33720
gtacccgttg tcgttaatca acgccccca tccctacgc ccactgaaat cagctacttt    33780
aacctaacag gcggagatga ctgacgccct agatctagaa atggacggca tcagtaccga    33840
gcagcgtctc ctagagaggc gcaggcaggc ggctgagcaa gagcgcctca atcaggagct    33900
ccgagatctc gttaacctgc accagtgcaa aagaggcatc ttttgtctgg taaagcaggc    33960
caaagtcacc tacgagaaga ccggcaacag ccaccgcctc agttacaaat tgcccaccca    34020
gcgccagaag ctggtgctca tggtgggtga gaatcccatc accgtcaccc agcactcggt    34080
agagaccgag gggtgtctgc actcccctg tcggggtcca gaagacctct gcaccctggt    34140
aaagaccctg tgcggtctca gagatttagt ccccttaac taatcaaaca ctggaatcaa    34200
taaaaagaat cacttactta aaatcagaca gcaggtctct gtccagttta ttcagcagca    34260
cctccttccc ctcctcccaa ctctggtact ccaaacgcct tctggcggca aacttcctcc    34320
acaccctgaa gggaatgtca gattcttgct cctgtccctc cgcacccact atcttcatgt    34380
tgttgcagat gaagcgcacc aaaacgtctg acgagagctt caaccccgtg taccoctatg    34440 acacggaaag cggccctccc tccgtcccctt tcctcacccc tcccttcgtg tctcccgatg    34500
gattccaaga aagtcccccc ggggtcctgt ctctgaacct ggccgagccc ctggtcactt    34560
cccacggcat gctcgccctg aaaatgggaa gtggcctctc cctggacgac gctggcaacc    34620
tcacctctca agatatcacc accgctagcc ctcccctcaa aaaaccaag accaacctca    34680 gcctagaaac ctcatccccc ctaactgtga gcacctcagg cgccctcacc gtagcagccg    34740
ccgctcccct ggcggtggcc ggcacctccc tcaccatgca atcagaggcc cccctgacag    34800
tacaggatgc aaaactcacc ctggccacca aaggcccct gaccgtgtct gaaggcaaac    34860
tggccttgca aacatcggcc ccgctgacgg ccgctgacag cagcacctc acagtcagtg    34920 ccacaccacc ccttagcaca agcaatggca gcttgggtat tgacatgcaa gcccccattt    34980
acaccaccaa tggaaaacta ggacttaact ttggcgctcc cctgcatgtg gtagacagcc    35040
taaatgcact gactgtagtt actggccaag gtcttacgat aaacggaaca gccctacaaa    35100
ctagagtctc aggtgccctc aactatgaca catcaggaaa cctagaattg agagctgcag    35160
ggggtatgcg agttgatgca aatggtcaac ttatccttga tgtagcttac ccatttgatg    35220
cacaaaacaa tctcagcctt aggcttggac agggaccct gtttgttaac tctgcccaca    35280
acttggatgt taactacaac agaggcctct acctgttcac atctggaaat accaaaaagc    35340
tagaagttaa tatcaaaaca gccaagggtc tcatttatga tgacactgct atagcaatca    35400
atgcgggtga tgggctacag tttgactcag gctcagatac aaatccatta aaaactaaac    35460
ttggattagg actggattat gactccagca gagccataat tgctaaactg ggaactggcc    35520
```

```
taagctttga caacacaggt gccatcacag taggcaacaa aaatgatgac aagcttacct    35580
tgtggaccac accagaccca tcccctaact gtagaatcta ttcagagaaa gatgctaaat    35640
tcacacttgt tttgactaaa tgcggcagtc aggtgttggc cagcgtttct gttttatctg    35700
taaaaggtag ccttgcgccc atcagtggca cagtaactag tgctcagatt gtcctcagat    35760
ttgatgaaaa tggagttcta ctaagcaatt cttcccttga ccctcaatac tggaactaca    35820
gaaaaggtga ccttacagag ggcactgcat ataccaacgc agtgggattt atgcccaacc    35880
tcacagcata cccaaaaaca cagagccaaa ctgctaaaag caacattgta agtcaggttt    35940
acttgaatgg ggacaaatcc aaacccatga ccctcaccat taccctcaat ggaactaatg    36000
aaacaggaga tgccacagta agcacttact ccatgtcatt ctcatggaac tggaatggaa    36060
gtaattacat taatgaaacg ttccaaacca actccttcac cttctcctac atcgcccaag    36120
aataaaaagc atgacgctgt tgatttgatt caatgtgttt ctgttttatt ttcaagcaca    36180
acaaaatcat tcaagtcatt cttccatctt agcttaatag acacagtagc ttaatagacc    36240
cagtagtgca aagccccatt ctagcttata actagtggag aagtactcgc ctacatgggg    36300
gtagagtcat aatcgtgcat caggataggg cggtggtgct gcagcagcgc gcgaataaac    36360
tgctgccgcc gccgctccgt cctgcaggaa tacaacatgg cagtggtctc ctcagcgatg    36420
attcgcaccg cccgcagcat aaggcgcctt gtcctccggg cacagcagcg caccctgatc    36480
tcacttaaat cagcacagta actgcagcac agcaccacaa tattgttcaa aatcccacag    36540
tgcaaggcgc tgtatccaaa gctcatggcg gggaccacag aacccacgtg gccatcatac    36600
cacaagcgca ggtagattaa gtggcgaccc ctcataaaca cgctggacat aaacattacc    36660
tcttttggca tgttgtaatt caccacctcc cggtaccata taaacctctg attaaacatg    36720
gcgccatcca ccaccatcct aaaccagctg gccaaaacct gcccgccggc tatacactgc    36780
agggaaccgg gactgaaaca atgacagtgg agagcccagg actcgtaacc atggatcatc    36840
atgctcgtca tgatatcaat gttggcacaa cacaggcaca cgtgcataca cttcctcagg    36900
attacaagct cctcccgcgt tagaaccata tcccagggaa caaccccatc ctgaatcagc    36960
gtaaatccca cactgcaggg aagacctcgc acgtaactca cgttgtgcat tgtcaaagtg    37020
ttacattcgg gcagcagcgg atgatcctcc agtatggtag cgcgggtttc tgtctcaaaa    37080
ggaggtagac gatccctact gtacggagtg cgccgagaca accagagatcg tgttggtcgt    37140
agtgtcatgc caaatggaac gccggacgta gtcatatttc ctgaagtctt agatctctca    37200
acgcagcacc agcaccaaca cttcgcagtg taaaaggcca agtgccgaga gagtatatat    37260
aggaataaaa agtgacgtaa acgggcaaag tccaaaaaac gcccagaaaa accgcacgcg    37320
aacctacgcc ccgaaacgaa agccaaaaaa cactagacac tcccttccgg cgtcaacttc    37380
cgctttccca cgctacgtca cttgccccag tcaaacaaac tacatatccc gaacttccaa    37440
gtcgccacgc ccaaaacacc gcctacacct ccccgcccgc cggcccgccc caaacccgc    37500
ctcccgcccc gcgccccgcc ccgcgccgcc catctcatta tcatattggc ttcaatccaa    37560
aataaggtat attattgatg atggtttaaa cggatcctct agagtcgacc tgcaggcatg    37620
caagcttgag tataaccccc ttgcggccgc ccgggccgtc gaccaattct catgtttgac    37680
agcttatcat cgaatttctg ccattcatcc gcttattatc acttattcag gcgtagcaac    37740
caggcgttta agggcaccaa taactgcctt aaaaaaatta cgcccgccc tgccactcat    37800
cgcagtactg ttgtaattca ttaagcattc tgccgacatg gaagccatca caaacggcat    37860
```

```
gatgaacctg aatcgccagc ggcatcagca ccttgtcgcc ttgcgtataa tatttgccca   37920
tggtgaaaac gggggcgaag aagttgtcca tattggccac gtttaaatca aaactggtga   37980
aactcaccca gggattggct gagacgaaaa acatattctc aataaaccct ttagggaaat   38040
aggccaggtt ttcaccgtaa cacgccacat cttgcgaata tatgtgtaga aactgccgga   38100
aatcgtcgtg gtattcactc cagagcgatg aaaacgtttc agtttgctca tggaaaacgg   38160
tgtaacaagg gtgaacacta tcccatatca ccagctcacc gtctttcatt gccatacgga   38220
attccggatg agcattcatc aggcgggcaa gaatgtgaat aaaggccgga taaaacttgt   38280
gcttattttt ctttacggtc tttaaaaagg ccgtaatatc cagctgaacg gtctggttat   38340
aggtacattg agcaactgac tgaaatgcct caaaatgttc tttacgatgc cattgggata   38400
tatcaacggt ggtatatcca gtgatttttt tctccatttt agcttcctta gctcctgaaa   38460
atctcgataa ctcaaaaaat acgcccggta gtgatcttat ttcattatgg tgaaagttgg   38520
aacctcttac gtgccgatca acgtctcatt ttcgccaaaa gttggcccag ggcttcccgg   38580
tatcaacagg gacaccagga tttatttatt ctgcgaagtg atcttccgtc acaggtattt   38640
attcgcgata agctcatgga gcggcgtaac cgtcgcacag gaaggacaga gaaagcgcgg   38700
atctgggaag tgacggacag aacggtcagg acctggattg gggaggcggt tgccgccgct   38760
gctgctgacg gtgtgacgtt ctctgttccg gtcacaccac atacgttccg ccattcctat   38820
gcgatgcaca tgctgtatgc cggtataccg ctgaaagttc tgcaaagcct gatgggacat   38880
aagtccatca gttcaacgga agtctacacg aaggtttttg cgctggatgt ggctgcccgg   38940
caccgggtgc agtttgcgat gccggagtct gatgcgttg cgatgctgaa acaattatcc    39000
tgagaataaa tgccttggcc tttatatgga aatgtggaac tgagtggata tgctgttttt   39060
gtctgttaaa cagagaagct ggctgttatc cactgagaag cgaacgaaac agtcgggaaa   39120
atctcccatt atcgtagaga tccgcattat taatctcagg agcctgtgta gcgtttatag   39180
gaagtagtgt tctgtcatga tgcctgcaag cggtaacgaa aacgattga atatgccttc    39240 aggaacaata gaaatcttcg tgcggtgtta cgttgaagtg gagcggatta tgtcagcaat   39300
ggacagaaca acctaatgaa cacagaacca tgatgtggtc tgtcctttta cagccagtag   39360
tgctcgccgc agtcgagcga cagggcgaag ccctcgagtg agcgaggaag caccagggaa   39420
cagcacttat atattctgct tacacacgat gcctgaaaaa acttcccttg ggttatccca   39480
cttatccacg gggatatttt tataattatt ttttttatag ttttttagatc ttcttttta   39540 gagcgccttg taggccttta tccatgctgg ttctagagaa ggtgttgtga caaattgccc   39600
tttcagtgtg acaaatcacc ctcaaatgac agtcctgtct gtgacaaatt gcccttaacc   39660
ctgtgacaaa ttgcccctcag aagaagctgt tttttcacaa agttatccct gcttattgac   39720
tcttttttat ttagtgtgac aatctaaaaa cttgtcacac ttcacatgga tctgtcatgg   39780
cggaaacagc ggttatcaat cacaagaaac gtaaaaatag cccgcgaatc gtccagtcaa   39840
acgacctcac tgaggcggca tatagtctct cccgggatca aaaacgtatg ctgtatctgt   39900
tcgttgacca gatcagaaaa tctgatggca ccctacagga acatgacggt atctgcgaga   39960
tccatgttgc taaatatgct gaaatattcg gattgacctc tgcggaagcc agtaaggata   40020
tacggcaggc attgaagagt ttcgcgggga aggaagtggt tttttatcgc cctgaagagg   40080
atgccggcga tgaaaaaggc tatgaatctt ttccttggtt tatcaaacgt gcgcacagtc   40140
catccagagg gctttacagt gtacatatca acccatatct cattcccttc tttatcgggt   40200
tacagaaccg gtttacgcag tttcggctta gtgaaacaaa agaaatcacc aatccgtatg   40260
```

```
ccatgcgttt atacgaatcc ctgtgtcagt atcgtaagcc ggatggctca ggcatcgtct   40320
ctctgaaaat cgactggatc atagagcgtt accagctgcc tcaaagttac cagcgtatgc   40380
ctgacttccg ccgccgcttc ctgcaggtct gtgttaatga gatcaacagc agaactccaa   40440
tgcgcctctc atacattgag aaaaagaaag gccgccagac gactcatatc gtatttcct    40500
tccgcgatat cacttccatg acgacaggat agtctgaggg ttatctgtca cagatttgag   40560
ggtggttcgt cacatttgtt ctgacctact gagggtaatt tgtcacagtt ttgctgtttc   40620
cttcagcctg catggatttt ctcatacttt ttgaactgta attttttaagg aagccaaatt  40680
tgagggcagt ttgtcacagt tgatttcctt ctctttccct tcgtcatgtg acctgatatc   40740
gggggttagt tcgtcatcat tgatgagggt tgattatcac agtttattac tctgaattgg   40800
ctatccgcgt gtgtacctct acctggagtt tttcccacgg tggatatttc ttcttgcgct   40860
gagcgtaaga gctatctgac agaacagttc ttctttgctt cctcgccagt tcgctcgcta   40920
tgctcggtta cacggctgcg gcgagcgcta gtgataataa gtgactgagg tatgtgctct   40980
tcttatctcc ttttgtagtg ttgctcttat tttaaacaac tttgcggttt tttgatgact   41040
ttgcgatttt gttgttgctt tgcagtaaat tgcaagattt aataaaaaaa cgcaaagcaa   41100
tgattaaagg atgttcagaa tgaaactcat ggaaacactt aaccagtgca taaacgctgg   41160
tcatgaaatg acgaaggcta tcgccattgc acagtttaat gatgacagcc cggaagcgag   41220
gaaaataacc cggcgctgga gaataggtga agcagcggat ttagttgggg tttcttctca   41280
ggctatcaga gatgccgaga aagcagggcg actaccgcac ccggatatgg aaattcgagg   41340
acgggttgag caacgtgttg gttatacaat tgaacaaatt aatcatatgc gtgatgtgtt   41400
tggtacgcga ttgcgacgtg ctgaagacgt atttccaccg gtgatcgggg ttgctgccca   41460
taaaggtggc gtttacaaaa cctcagtttc tgttcatctt gctcaggatc tggctctgaa   41520
ggggctacgt gttttgctcg tggaaggtaa cgacccccag ggaacagcct caatgtatca   41580
cggatgggta ccagatcttc atattcatgc agaagacact ctcctgcctt tctatcttgg   41640
ggaaaaggac gatgtcactt atgcaataaa gcccacttgc tggccggggc ttgacattat   41700
tccttcctgt ctggctctgc accgtattga aactgagtta atgggcaaat ttgatgaagg   41760
taaactgccc accgatccac acctgatgct ccgactggcc attgaaactg ttgctcatga   41820
ctatgatgtc atagttattg acagcgcgcc taacctgggt atcggcacga ttaatgtcgt   41880
atgtgctgct gatgtgctga ttgttcccac gcctgctgag ttgtttgact acacctccgc   41940
actgcagttt ttcgatatgc ttcgtgatct gctcaagaac gttgatctta aagggttcga   42000
gcctgatgta cgtatttttgc ttaccaaata cagcaatagt aatggctctc agtccccgtg   42060
gatgaggag caaattcggg atgcctgggg aagcatggtt ctaaaaaatg ttgtacgtga    42120
aacggatgaa gttggtaaag gtcagatccg gatgagaact gttttttgaac aggccattga  42180
tcaacgctct tcaactggtg cctggagaaa tgctcttttct atttgggaac ctgtctgcaa  42240
tgaaatttc gatcgtctga ttaaaccacg ctgggagatt agataatgaa gcgtgcgcct    42300
gttattccaa acatacgct caatactcaa ccggttgaag atacttcgtt atcgacacca    42360
gctgccccga tggtggattc gttaattgcg cgcgtaggga taatggctcg cggtaatgcc   42420
attactttgc ctgtatgtgg tcgggatgtg aagtttactc ttgaagtgct ccggggtgat   42480
agtgttgaga agacctctcg ggtatggtca ggtaatgaac gtgaccagga gctgcttact   42540
gaggacgcac tggatgatct catcccttct tttctactga ctggtcaaca gacaccggcg   42600
```

```
ttcggtcgaa gagtatctgg tgtcatagaa attgccgatg ggagtcgccg tcgtaaagct    42660
gctgcactta ccgaaagtga ttatcgtgtt ctggttggcg agctggatga tgagcagatg    42720
gctgcattat ccagattggg taacgattat cgcccaacaa gtgcttatga acgtggtcag    42780
cgttatgcaa gccgattgca gaatgaattt gctggaaata tttctgcgct ggctgatgcg    42840
gaaaatattt cacgtaagat tattacccgc tgtatcaaca ccgccaaatt gcctaaatca    42900
gttgttgctc tttttctca ccccggtgaa ctatctgccc ggtcaggtga tgcacttcaa    42960
aaagccttta cagataaaga ggaattactt aagcagcagg catctaacct tcatgagcag    43020
aaaaaagctg gggtgatatt tgaagctgaa gaagttatca ctcttttaac ttctgtgctt    43080
aaaacgtcat ctgcatcaag aactagttta agctcacgac atcagtttgc tcctggagcg    43140
acagtattgt ataagggcga taaaatggtg cttaacctgg acaggtctcg tgttccaact    43200
gagtgtatag agaaaattga ggccattctt aaggaacttg aaaagccagc accctgatgc    43260
gaccacgttt tagtctacgt ttatctgtct ttacttaatg tcctttgtta caggccagaa    43320
agcataactg gcctgaatat tctctctggg cccactgttc cacttgtatc gtcggtctga    43380
taatcagact gggaccacgg tcccactcgt atcgtcggtc tgattattag tctgggacca    43440
cggtcccact cgtatcgtcg gtctgattat tagtctggga ccacggtccc actcgtatcg    43500
tcggtctgat aatcagactg ggaccacggt cccactcgta tcgtcggtct gattattagt    43560
ctgggaccat ggtcccactc gtatcgtcgg tctgattatt agtctgggac cacggtccca    43620
ctcgtatcgt cggtctgatt attagtctgg aaccacggtc ccactcgtat cgtcggtctg    43680
attattagtc tgggaccacg gtcccactcg tatcgtcggt ctgattatta gtctgggacc    43740
acgatcccac tcgtgttgtc ggtctgatta tcggtctggg accacggtcc cacttgtatt    43800
gtcgatcaga ctatcagcgt gagactacga ttccatcaat gcctgtcaag gcaagtatt    43860 gacatgtcgt cgtaacctgt agaacggagt aacctcggtg tgcggttgta tgcctgctgt    43920
ggattgctgc tgtgtcctgc ttatccacaa cattttgcgc acggttatgt ggacaaaata    43980
cctggttacc caggccgtgc cggcacgctc ggtacccggg gatcctcgtt taaac         44035
```

<210> SEQ ID NO 51
<211> LENGTH: 41464
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"
<220> FEATURE:
<221> NAME/KEY: modified_base
<222> LOCATION: (16063)..(16063)
<223> OTHER INFORMATION: a, c, t, g, unknown or other

<400> SEQUENCE: 51

```
catcatcaat aatataccct attttggatt gaagccaata tgataatgag atgggcggcg     60
cggggcgggg cgcggggcgg gaggcgggtt tgggggcggg ccggcgggcg gggcggtgtg    120
gcggaagtgg actttgtaag tgtggcggat gtgacttgct agtgccgggc gcggtaaaag    180
tgacgttttc cgtgcgcgac aacgcccccg ggaagtgaca tttttcccgc ggtttttacc    240
ggatgttgta gtgaatttgg gcgtaaccaa gtaagatttg gccattttcg cgggaaaact    300
gaaacgggga agtgaaatct gattaatttt gcgttagtca taccgcgtaa tatttgtcta    360
gggccgaggg actttggccg attacgtgga ggactcgccc aggtgttttt tgaggtgaat    420
ttccgcgttc cgggtcaaag tctgcgtttt attattatag gatatcccat tgcatacgtt    480
```

```
gtatccatat cataatatgt acatttatat tggctcatgt ccaacattac cgccatgttg    540
acattgatta ttgactagtt attaatagta atcaattacg gggtcattag ttcatagccc    600
atatatggag ttccgcgtta cataacttac ggtaaatggc ccgcctggct gaccgcccaa    660 cgaccccgc ccattgacgt caataatgac gtatgttccc atagtaacgc caatagggac     720
tttccattga cgtcaatggg tggagtattt acggtaaact gcccacttgg cagtacatca    780
agtgtatcat atgccaagta cgccccctat tgacgtcaat gacggtaaat ggcccgcctg    840
gcattatgcc cagtacatga cctatgggac ttttcctact tggcagtaca tctacgtatt    900
agtcatcgct attaccatgg tgatgcggtt ttggcagtac atcaatgggc gtggatagcg    960
gtttgactca cggggatttc caagtctcca ccccattgac gtcaatggga gtttgttttg    1020
gcaccaaaat caacgggact ttccaaaatg tcgtaacaac tccgccccat tgacgcaaat    1080
gggcggtagg cgtgtacggt gggaggtcta tataagcaga gctctcccta tcagtgatag    1140 agatctcccct atcagtgata gagatcgcg acgagctcgt ttagtgaacc gtcagatcgc     1200
ctggagacgc catccacgct gttttgacct ccatagaaga caccgggacc gatccagcct    1260
ccgcggccgg gaacggtgca ttggaacgcg gattccccgt gccaagagtg agatcttccg    1320
tttatctagg taccagatat cgccaccatg agacctgctc cctggacacc taatcctccc    1380
aggtccccca gccagatgag cgtgagagac agactggcta ggctgagagc cgaggctcag    1440
gtcaagcagg ccagcgtcga ggtgcaaccc cctcagctca cccaggtgtc cccccagcag    1500
cctgtggccg gcattctgtt cattctggcc attctgaccg agtggggaag cggcaacaga    1560
acctacggcc ctgtcttcat gtgcctcgga ggactgctga caatggtggc tggcgccgtg    1620
tggctcaccg tcatgtccaa caccctgctc agcgcctgga ttctgaccgc cggattcctg    1680
atctttctga tcggattcgc tctctttggc gtcatcaggt gttgcaggta ctgttgctac    1740
tactgcctga ccctcgagag cgaggaaaga cccccccaccc cctacaggaa tacagtgagg    1800
aaacctcagc agcccgagag cctcgaggag tgcgatagcg agctggagat taaaaggtat    1860
aagaataggg tggcctccag gaagtgtagg gctaaattca aacagctcct gcaacactat    1920
agggaagtgg ccgccgccaa gtccagcgag attagggaca gaaggaggaa tcctgcctcc    1980
aggagagacc aggccaaatg gagactccaa acactcgccg ctggatggcc catgggctac    2040
caggcctata gctcctggat gtacagctac accgaccatc agacaacacc caccttcgtg    2100
catctgcagg ctacactggg ctgcaccgga ggcagaaggt gtcacgtgtt tctgggaatc    2160
gtgctgttca tctttggatg cctgctcgtg ctgggcatct ggatttatct cctggagatg    2220
ctctggagac tcggcgctac aatttggcag ctgctcgcct tttttctggc cttctttctg    2280
gacctgatcc tcctgatcat cgccctgtac ctccaacaga actggtggac cctcctggtg    2340
gatctgctgt ggctcctcct cttcctggcc atcctgatct ggatgtacta ccatggccag    2400
agaggaaggg tcgcttgcgc tcctgtccct gctcctgctg gccccatcgt gaggccttgg    2460
gagccttccc tcacacaggc cgccggccag gcctttgctc ccgtgaggcc ccagcacatg    2520
cctgtggaac ccgtgcccgt ccccacagtg gctctggaaa ggcctgtgta ccccaagccc    2580
gtgagacctg tcctctggct cagcagccct ggaggactcg gaacactcgg agccgctctc    2640
ctgacactgg ccgctgctct ggctctgctg ctagcctga tcctgggaac cctcaacctc      2700
accaccatgt ttctcctcat gctcctgtgg accctcgtgg tgctgctcat ctgttccagc    2760
tgctccagct gcccctgag caagatcctg ctggccaggc tgttcctgta cgccctcgcc    2820
```

```
ctcctgctgc tggctagcgc cctgatcgct ggcggaagca tcctccagac caatttcaag    2880
agcctctcct ccaccgagtt catccccaac ctgttctgta tgttactgct gatccatagc    2940
gacgagcacc atcatgacga ctccctgccc catcctcagc aggccacaga cgactccggc    3000
cacgagagcg acagcaatag caatgagggc aggcaccatc tgctcgtgtc cggagctcaa    3060
gtccccgagc ctcccaccat ccatctcgcc gcccagggaa tggcttaccc cctccacgag    3120
cagcacggca tggccccttg tcccgtcgct caagcccccc ctacacctct gcccttttc    3180 gccatttgtc tgacctggag aatcgaggac ccccccttca acagcctgct gttcgccctg    3240
ctcgccgccg ctggcggcct ccagggcatt tacgtcctcg tgatgctggt gctgctgatc    3300
ctcgcttaca ggagaagatg gaggagactg acagtgtgcg gcggcatcat gtttctcgcc    3360
tgcgtcctgg tcctgatcgt ggacgccgtc ctgcaactca gcccctcct gggagctgtg    3420 acagtggtct ccatgaccct gctgctgctg gccttcaacg accccacga tcctctgccc    3480 caagatcctg acaataccga cgataacggc cccaagacc ccgataacac cgacgacaat    3540
ggccctcacg accctctgcc ccatagccct tccgatagc ctggcaacga tggcggccct    3600
cctcagctga cagaggaggt ggaaaataag ggcggcgatc agggacccc cctgatgaca    3660 gatggcggag gaggacacag ccatgatagc ggacatggcg gaggcgatcc ccatctgcct    3720
accctcctcc tgggcagctc cggttctgga ggcgacgatg atgaccctca cggccctgtg    3780
cagctctcct actacgacgg caaaaggacc gaacaaggaa aagaggtcct ggagaaggcc    3840
aggggcagca catacggaac ccccaggcct cccatgtccg attggaccgg aggagccctg    3900
ctggtcctct acagcttcgc cctgatgctg atcattatca tcctgatcat ctttatcttc    3960
agaagggacc tgctgtgccc tctcggcgcc ctgtgcatcc tgctgctcat gatcacactc    4020
ctcctgatcg ccctctggaa cctgcacgga caagccctga tgtccgatga gggacctgga    4080
acaggacccg gaaacggact gggcgagaag ggagatacaa gcggccccga aggcagcggc    4140
ggaagcggac cccaaagaag gggcggcgac aaccacggaa gaggaagagg caggggcaga    4200
ggcagaggag gaggaagacc tggagcccct ggcggttctg gaagcggacc caggcacagg    4260
gacggagtga ggaggcctca aaaaagaccc agctgcatcg gctgcaaggg aacccactgg    4320
attgatgata ccccctccac agagaccgct caggcctgga cgccggctt cctgagggga    4380 agagcctatg gcatcgatct gctgaggacc gagggcgaac acgtggaggg agccaccgga    4440
gagacaaggg aggaaagcga agacacagaa agcgatggcg acgacgaaga cctgccctgc    4500
attgtgtcca ggggcggacc caaggtgaag aggccccccta tctttatcag aaggctccat    4560
agactgctcc tgatgagggc catgaaccct gtgtgcctgc ccgtgatcgt ggcccctac    4620 ctcttttggc tggccgccat tgccgctagc tgcttcaccg cctccgtgtc cacagtggtg    4680
acagccaccg gcctcgccct gagcctgctg ctcctcgctg ccgtggcctc cagctacgcc    4740
gctgctcaaa gaaagctcct gaccctgtc accgtcctga cagccgtcgt gaccaccttt    4800
tccgctggca ccttcaagct gcctaggtgc acacctggcg acaggcagtg gctctacgtg    4860
cagagctccg tgggcaatat tgtgcagagc tgcaatccca ggtacagcat ttttttcgac    4920
tacatggcca tccataggtc cctcaccaag atctgggagg atctgggagg cccttcccag    4980
gctcctctgc cctgcgtgct gtggcctgtg ctgcctgagc ctctgcccca aggccagctg    5040
acagcctatc acgtgtccac cgctcctaca ggttcttggt tcagcgctcc ccagcccgct    5100
cccgaaaacg cttaccaggc ttacgccgcc cccagctgt tccccgtctc cgacatctga    5160
tgatgagcgg ccgcgatctg ctgtgccttc tagttgccag ccatctgttg tttgcccctc    5220
```

```
ccccgtgcct tccttgaccc tggaaggtgc cactcccact gtcctttcct aataaaatga    5280
ggaaattgca tcgcattgtc tgagtaggtg tcattctatt ctgggggtg gggtggggca    5340 ggacagcaag gggaggatt gggaagacaa tagcaggcat gctgggatg cggtgggctc    5400 tatggccgat cagcgatcgc tgaggtgggt gagtgggcgt ggcctgggt ggtcatgaaa    5460 atatataagt tgggggtctt agggtctctt tatttgtgtt gcagagaccg ccggagccat    5520
gagcgggagc agcagcagca gcagtagcag cagcgccttg gatggcagca tcgtgagccc    5580
ttatttgacg acgcggatgc cccactgggc cggggtgcgt cagaatgtga tgggctccag    5640
catcgacggc cgaccgtcc tgcccgcaaa ttccgccacg ctgacctatg cgaccgtcgc    5700
ggggacgccg ttggacgcca ccgccgccgc cgccgccacc gcagccgcct cggccgtgcg    5760
cagcctggcc acggactttg cattcctggg accactggcg acaggggcta cttctcgggc    5820
cgctgctgcc gccgttcgcg atgacaagct gaccgccctg ctggcgcagt tggatgcgct    5880
tactcgggaa ctgggtgacc tttctcagca ggtcatggcc ctgcgccagc aggtctcctc    5940
cctgcaagct ggcgggaatg cttctcccac aaatgccgtt taagataaat aaaaccagac    6000
tctgtttgga ttaaagaaaa gtagcaagtg cattgctctc tttatttcat aattttccgc    6060
gcgcgatagg ccctagacca gcgttctcgg tcgttgaggg tgcggtgtat cttctccagg    6120
acgtggtaga ggtggctctg gacgttgaga tacatgggca tgagcccgtc ccggggtgg    6180 aggtagcacc actgcagagc ttcatgctcc ggggtggtgt tgtagatgat ccagtcgtag    6240
caggagcgct gggcatggtg cctaaaaatg tccttcagca gcaggccgat ggccagggg    6300 aggcccttgg tgtaagtgtt tacaaaacgg ttaagttggg aagggtgcat tcggggagag    6360
atgatgtgca tcttggactg tatttttaga ttggcgatgt ttccgcccag atcccttctg    6420
ggattcatgt tgtgcaggac caccagtaca gtgtatccgg tgcacttggg gaatttgtca    6480
tgcagcttag agggaaaagc gtggaagaac ttggagacgc ctttgtggcc tcccagattt    6540
tccatgcatt cgtccatgat gatggcaatg ggcccgcggg aggcagcttg ggcaaagata    6600 tttctgggt cgctgacgtc gtagttgtgt tccagggtga ggtcgtcata ggccattttt    6660
acaaagcgcg ggcggagggt gcccgactgg gggatgatg tccctctgg ccctggggcg    6720 tagttgccct cgcagatctg catttcccag gccttaatct cggagggggg aatcatatcc    6780
acctgcgggg cgatgaagaa aacggtttcc ggagccgggg agattaactg ggatgagagc    6840
aggtttctaa gcagctgtga ttttccacaa ccggtgggcc cataaataac acctataacc    6900
ggttgcagct ggtagtttag agagctgcag ctgccgtcgt cccggaggag ggggccacc    6960 tcgttgagca tgtccctgac gcgcatgttc tccccgacca gatccgccag aaggcgctcg    7020
ccgcccaggg acagcagctc ttgcaaggaa gcaaagtttt tcagcggctt gaggccgtcc    7080
gccgtgggca tgttttcag ggtctggctc agcagctcca ggcggtccca gagctcggtg    7140
acgtgctcta cggcatctct atccagcata tctcctcgtt tcgcgggttg gggcgactt    7200 cgctgtaggg caccaagcgg tggtcgtcca gcggggccag agtcatgtcc ttccatgggc    7260
gcagggtcct cgtcagggtg gtctgggtca cggtgaaggg gtgcgctccg ggctgagcgc    7320
ttgccaaggt gcgcttgagg ctggttctgc tggtgctgaa gcgctgccgg tcttcgccct    7380
gcgcgtcggc caggtagcat ttgaccatgg tgtcatagtc cagcccctcc gcggcgtgtc    7440
ccttggcgcg cagcttgccc ttggaggtgg cgccgcacga ggggcagagc aggtcttga    7500 gcgcgtagag cttgggggcg aggaagaccg attcggggga gtaggcgtcc gcgccgcaga    7560
```

```
ccccgcacac ggtctcgcac tccaccagcc aggtgagctc ggggcgcgcc gggtcaaaaa    7620
ccaggtttcc cccatgcttt ttgatgcgtt tcttacctcg ggtctccatg aggtggtgtc    7680
cccgctcggt gacgaagagg ctgtccgtgt ctccgtagac cgacttgagg ggtcttttct    7740
ccagggggg cccctcggtct tcctcgtaga ggaactcgga ccactctgag acgaaggccc    7800
gcgtccaggc caggacgaag gaggctatgt gggagggta gcggtcgttg tccactaggg    7860
ggtccacctt ctccaaggtg tgaagacaca tgtcgccttc ctcggcgtcc aggaaggtga    7920
ttggcttgta ggtgtaggcc acgtgaccgg gggttcctga cgggggggta taaaagggg    7980
tgggggcgcg ctcgtcgtca ctctcttccg catcgctgtc tgcgagggcc agctgctggg    8040
gtgagtattc cctctcgaag gcgggcatga cctccgcgct gaggttgtca gtttccaaaa    8100
acgaggagga tttgatgttc acctgtcccg aggtgatacc tttgaggta cccgcgtcca    8160
tctggtcaga aaacacgatc tttttattgt ccagcttggt ggcgaacgac ccgtagaggg    8220
cgttggagag cagcttggcg atggagcgca gggtctggtt cttgtccctg tcggcgcgct    8280
ccttggccgc gatgttgagc tgcacgtact cgcgcgcgac gcagcgccac tcggggaaga    8340
cggtggtgcg ctcgtcgggc accaggcgca cgcgccagcc gcggttgtgc agggtgacca    8400
ggtccacgct ggtggcgacc tcgccgcgca ggcgctcgtt ggtccagcag agacggccgc    8460
ccttgcgcga gcagaagggg ggcaggggt cgagctgggt ctcgtccggg gggtccgcgt    8520
ccacggtgaa aaccccgggg cgcaggcgcg cgtcgaagta gtctatcttg caaccttgca    8580
tgtccagcgc ctgctgccag tcgcgggcgg cgagcgcgcg ctcgtagggg ttgagcggcg    8640
ggccccaggg catggggtgg gtgagtgcgg aggcgtacat gccgcagatg tcatagacgt    8700
agagggctc ccgcaggacc ccgatgtagg tggggtagca gcggccgccg cggatgctgg    8760
cgcgcacgta gtcatacagc tcgtgcgagg gggcgaggag gtcggggccc aggttggtgc    8820
gggcggggcg ctccgcgcgg aagacgatct gcctgaagat ggcatgcgag ttggaagaga    8880
tggtggggcg ctggaagacg ttgaagctgg cgtcctgcag gccgacgcg tcgcgcacga    8940
aggaggcgta ggagtcgcgc agcttgtgta ccagctcggc ggtgacctgc acgtcgagcg    9000
cgcagtagtc gagggtctcg cggatgatgt catatttagc ctgccccttc ttttccaca    9060
gctcgcggtt gaggacaaac tcttcgcggt cttttccagta ctcttggatc gggaaaccgt    9120
ccggttccga acggtaagag cctagcatgt agaactggtt gacggcctgg taggcgcagc    9180
agcccttctc cacggggagg gcgtaggcct gcgcggcctt gcggagcgag gtgtgggtca    9240
gggcgaaggt gtccctgacc atgactttga ggtactggtg cttgaagtcg gagtcgtcgc    9300
agccgccccg ctcccagagc gagaagtcgg tgcgcttctt ggagcgggg ttgggcagag    9360
cgaaggtgac atcgttgaag aggattttgc ccgcgcgggg catgaagttg cgggtgatgc    9420
ggaagggccc cggcacttca gagcggttgt tgatgacctg ggcggcgagc acgatctcgt    9480
cgaagccgtt gatgttgtgg cccacgatgt agagttccag gaagcggggc cggcccttta    9540
cggtgggcag cttctttagc tcttcgtagg tgagctcctc gggcgaggcg aggccgtgct    9600
cggccagggc ccagtccgcg aggtgcgggt tgtctctgag gaaggacttc cagaggtcgc    9660
gggcaggag ggtctgcagg cggtctctga aggtcctgaa ctggcggccc acggccattt    9720
tttcggggt gatgcagtag aaggtgaggg ggtcttgctg ccagcggtcc cagtcgagct    9780
gcagggcgag gtcgcgcgcg gcggtgacca ggcgctcgtc gccccgaat ttcatgacca    9840
gcatgaaggg cacgagctgc tttccgaagg cccccatcca agtgtaggtc tctacatcgt    9900
aggtgacaaa gaggcgctcc gtgcgaggat gcgagccgat cgggaagaac tggatctccc    9960
```

```
gccaccagtt ggaggagtgg ctgttgatgt ggtggaagta gaagtcccgt cgccgggccg   10020
aacactcgtg ctggcttttg taaaagcgag cgcagtactg gcagcgctgc acgggctgta   10080
cctcatgcac gagatgcacc tttcgcccgc gcacgaggaa gccgagggga aatctgagcc   10140
ccccgcctgg ctcgcggcat ggctggttct cttctacttt ggatgcgtgt ccgtctccgt   10200
ctggctcctc gagggtgtt acggtggagc ggaccaccac gccgcgcgag ccgcaggtcc    10260
agatatcggc gcgcggcggt cggagtttga tgacgacatc gcgcagctgg gagctgtcca   10320
tggtctggag ctcccgcggc ggcggcaggt cagccgggag ttcttgcagg ttcacctcgc   10380
agagtcgggc cagggcgcgg ggcaggtcta ggtggtacct gatctctagg ggcgtgttgg   10440
tggcggcgtc gatggcttgc aggagcccgc agccccgggg ggcgacgacg gtgccccgcg   10500
gggtggtggt ggtggtggcg gtgcagctca gaagcggtgc cgcgggcggg ccccggagg    10560 tagggggggc tccggtcccg cgggcagggg cggcagcggc acgtcggcgt ggagcgcggg   10620
caggagttgg tgctgtgccc ggaggttgct ggcgaaggcg acgacgcggc ggttgatctc   10680
ctggatctgg cgcctctgcg tgaagacgac gggcccggtg agcttgaacc tgaaagagag   10740
ttcgacagaa tcaatctcgg tgtcattgac gcgggcctgg cgcaggatct cctgcacgtc   10800
tcccgagttg tcttggtagg cgatctcggc catgaactgc tcgatctctt cctcctggag   10860
gtctccgcgt ccgcgcgtt ccacggtggc cgccaggtcg ttggagatgc gccccatgag    10920
ctgcgagaag gcgttgagtc cgccctcgtt ccagactcgg ctgtagacca cgccccctg    10980 gtcatcgcgg gcgcgcatga ccacctgcgc gaggttgagc tccacgtgcc gcgcgaagac   11040
ggcgtagttg cgcagacgct ggaagaggta gttgagggtg gtggcggtgt gctcggccac   11100
gaagaagttc atgacccagc ggcgcaacgt ggattcgttg atgtccccca aggcctccag   11160
ccgttccatg gcctcgtaga agtccacggc gaagttgaaa aactgggagt tgcgcgccga   11220
cacggtcaac tcctcctcca gaagacggat gagctcggcg acggtgtcgc gcacctcgcg   11280
ctcgaaggct atgggatct cttcctccgc tagcatcacc acctcctcct cttcctcctc    11340
ttctggcact tccatgatgg cttcctcctc ttcgggggt ggcggcggcg gcggtggggg    11400 aggggcgct ctgcgccggc ggcggcgcac cgggaggcg tccacgaagc gcgcgatcat     11460
ctccccgcgg cggcggcgca tggtctcggt gacggcgcgg ccgttctccc ggggcgcag    11520 ttggaagacg ccgccggaca tctggtgctg ggcgggtgg ccgtgaggca gcgagacggc    11580
gctgacgatg catctcaaca attgctgcgt aggtacgccg ccgagggacc tgagggagtc   11640
catatccacc ggatccgaaa acctttcgag gaaggcgtct aaccagtcgc agtcgcaagg   11700
taggctgagc accgtggcgg gcggcggggg gtggggggag tgtctggcgg aggtgctgct   11760
gatgatgtaa ttgaagtagg cggacttgac acggcggatg tcgacagga gcaccatgtc    11820 cttgggtccg gcctgctgga tgcggaggcg gtcggctatg ccccaggctt cgttctggca   11880
tcggcgcagg tccttgtagt agtcttgcat gagcctttcc accggcacct cttctccttc   11940
ctcttctgct tcttccatgt ctgcttcggc cctggggcgg cgccgcgccc cctgccccc    12000 catgcgcgtg accccgaacc ccctgagcgg ttggagcagg gccaggtcgg cgacgacgcg   12060
ctcggccagg atggcctgct gcacctgcgt gagggtggtt tggaagtcat ccaagtccac   12120
gaagcggtgg taggcgcccg tgttgatggt gtaggtgcag ttggccatga cggaccagtt   12180
gacggtctgg tggcccggtt gcgacatctc ggtgtacctg agtcgcgagt aggcgcggga   12240
gtcgaagacg tagtcgttgc aagtccgcac caggtactgg tagcccacca ggaagtgcgg   12300
```

```
cggcggctgg cggtagaggg gccagcgcag ggtggcgggg gctccggggg ccaggtcttc   12360
cagcatgagg cggtggtagg cgtagatgta cctggacatc caggtgatac ccgcggcggt   12420
ggtggaggcg cgcgggaagt cgcgcacccg gttccagatg ttgcgcaggg gcagaaagtg   12480
ctccatggta ggcgtgctct gtccagtcag acgcgcgcag tcgttgatac tctagaccag   12540
ggaaaacgaa agccggtcag cgggcactct tccgtggtct ggtgaataga tcgcaagggt   12600
atcatggcgg agggcctcgg ttcgagcccc gggtccgggc cggacggtcc gccatgatcc   12660
acgcggttac cgcccgcgtg tcgaacccag gtgtgcgacg tcagacaacg gtggagtgtt   12720
ccttttggcg tttttctggc cgggcgccgg cgccgcgtaa gagactaagc cgcgaaagcg   12780
aaagcagtaa gtggctcgct ccccgtagcc ggagggatcc ttgctaaggg ttgcgttgcg   12840
gcgaaccccg gttcgaatcc cgtactcggg ccggccggac ccgcggctaa ggtgttggat   12900
tggcctcccc ctcgtataaa gaccccgctt gcggattgac tccggacacg gggacgagcc   12960
cctttatttt ttgctttccc cagatgcatc cggtgctgcg gcagatgcgc ccccgccc    13020 agcagcagca acaacaccag caagagcggc agcaacagca gcgggagtca tgcagggccc   13080
cctcacccac cctcggcggg ccggccacct cggcgtccgc ggccgtgtct ggcgcctgcg   13140
gcggcggcgg ggggccggct gacgaccccg aggagccccc gcggcgcagg gccagacact   13200
acctggacct ggaggagggc gagggcctgg cgcggctggg ggcgccgtct cccgagcgcc   13260
acccgcgggt gcagctgaag cgcgactcgc gcgaggcgta cgtgcctcgg cagaacctgt   13320
tcagggaccg cgcggggcgag gagcccgagg agatgcggga caggaggttc agcgcagggc   13380
gggagctgcg gcaggggctg aaccgcgagc ggctgctgcg cgaggaggac tttgagcccg   13440
acgcgcggac ggggatcagc cccgcgcgcg cgcacgtggc ggccgccgac ctggtgacgg   13500
cgtacgagca gacggtgaac caggagatca acttccaaaa gagtttcaac aaccacgtgc   13560
gcacgctggt ggcgcgcgag gaggtgacca tcgggctgat gcacctgtgg gactttgtaa   13620
gcgcgctggt gcagaacccc aacagcaagc ctctgacggc gcagctgttc ctgatagtgc   13680
agcacagcag ggacaacgag gcgtttaggg acgcgctgct gaacatcacc gagcccgagg   13740
gtcggtggct gctggacctg attaacatcc tgcagagcat agtggtgcag gagcgcagcc   13800
tgagcctggc cgacaaggtg gcggccatca actactcgat gctgagcctg gcaagttttt   13860
acgcgcgcaa gatctaccag acgccgtacg tgcccataga caaggaggtg aagatcgacg   13920 gttttacat gcgcatggcg ctgaaggtgc tcaccctgag cgacgacctg ggcgtgtacc   13980
gcaacgagcg catccacaag gccgtgagcg tgagccggcg gcgcgagctg agcgaccgcg   14040
agctgatgca cagcctgcag cgggcgctgg cgggcgccgg cagcggcgac agggaggcgg   14100
agtcctactt cgatgcgggg gcggacctgc gctgggcgcc cagccggcgg gccctggagg   14160 ccgcggggt ccgcgaggac tatgacgagg acggcgagga ggatgaggag tacgagctag   14220
aggagggcga gtacctggac taaaccgcgg gtggtgtttc cggtagatgc aagacccgaa   14280
cgtggtggac ccggcgctgc gggcggctct gcagagccag ccgtccggcc ttaactcctc   14340
agacgactgg cgacaggtca tggaccgcat catgtcgctg acggcgcgta acccggacgc   14400
gttccggcag cagccgcagg ccaacaggct ctccgccatc ctggaggcgg tggtgcctgc   14460
gcgctcgaac cccacgcacg agaaggtgct ggccatagtg aacgcgctgg ccgagaacag   14520
ggccatccgc ccggacgagg ccgggctggt gtacgacgcg ctgctgcagc gcgtggcccg   14580
ctacaacagc ggcaacgtgc agaccaacct ggaccggctg gtggggacg tgcgcgaggc   14640 ggtggcgcag cgcgagcgcg cggatcggca gggcaacctg ggctccatgg tggcgctgaa   14700
```

```
tgccttcctg agcacgcagc cggccaacgt gccgcggggg caggaagact acaccaactt   14760
tgtgagcgcg ctgcggctga tggtgaccga accccccag agcgaggtgt accagtcggg    14820
cccggactac ttcttccaga ccagcagaca gggcctgcag acggtgaacc tgagccaggc   14880
tttcaagaac ctgcggggc tgtggggcgt gaaggcgccc accggcgacc gggcgacggt    14940
gtccagcctg ctgacgccca actcgcgcct gctgctgctg ctgatcgcgc cgttcacgga   15000
cagcggcagc gtgtcccggg acacctacct ggggcacctg ctgaccctgt accgcgaggc   15060
catcgggcag gcgcaggtgg acgagcacac cttccaggag atcaccagcg tgagccgcgc   15120
gctggggcag gaggacacga gcagcctgga ggcgactctg aactacctgc tgaccaaccg   15180
gcggcagaag attccctcgc tgcacagcct gacctccgag gaggagcgca tcttgcgcta   15240
cgtgcagcag agcgtgagcc tgaacctgat gcgcgacggg gtgacgccca gcgtggcgct   15300
ggacatgacc gcgcgcaaca tggaaccggg catgtacgcc gcgcaccggc cttacatcaa   15360
ccgcctgatg gactacctgc atcgcgcggc ggccgtgaac cccgagtact ttaccaacgc   15420
catcctgaac ccgcactggc tcccgccgcc cgggttctac agcgggggct tcgaggtccc   15480
ggagaccaac gatggcttcc tgtgggacga catggacgac agcgtgttct ccccgcggcc   15540
gcaggcgctg gcggaagcgt ccctgctgcg tcccaagaag gaggaggagg aggaggcgag   15600
tcgccgccgc ggcagcagcg gcgtggcttc tctgtccgag ctgggggcgg cagccgccgc   15660
gcgccccggg tccctgggcg gcagcccctt ccgagcctg gtggggtctc tgcacagcga    15720
gcgcaccacc cgcccccggc tgctgggcga ggacgagtac ctgaataact ccctgctgca    15780
gccggtgcgg gagaaaaacc tgcctcccgc cttccccaac aacgggatag agagcctggt    15840
ggacaagatg agcagatgga agacctatgc gcaggagcac agggacgcgc ctgcgctccg    15900
gccgcccacg cggcgccagc gccacgaccg gcagcggggg ctggtgtggg atgacgagga    15960
ctccgcggac gatagcagcg tgctggacct ggggaggagc ggcaacccgt tcgcgcacct    16020
gcgcccccgc ctggggagga tgttttaaaa aaaaaaaaa aangcaagaa gcatgatgca    16080
aaaattaaat aaaactcacc aaggccatgg cgaccgagcg ttggtttctt gtgttcccct    16140
cagtatgcgc cgcgcggcga tgtaccagga gggacctcct ccctcttacg agagcgtggt    16200
gggcgcggcg gcggcggcgc cctcttctcc ctttgcgtcg cagctgctgg agccgccgta    16260
cgtgcctccg cgctacctgc ggcctacggg ggggagaaaa agcatccgtt actcggagct    16320
ggcgcccctg ttcgacacca cccgggtgta cctggtggac aacaagtcgg cggacgtggc    16380
ctccctgaac taccagaacg accacagcaa ttttttgacc acggtcatcc agaacaatga    16440
ctacagcccg agcgaggcca gcacccagac catcaatctg gatgaccggt cgcactgggg    16500
cggcgacctg aaaaccatcc tgcacaccaa catgcccaac gtgaacgagt tcatgttcac    16560
caataagttc aaggcgcggg tgatggtgtc gcgctcgcac accaaggaag accgggtgga    16620
gctgaagtac gagtggggtgg agttcgagct gccagagggc aactactccg agaccatgac    16680
cattgacctg atgaacaacg cgatcgtgga gcactatctg aaagtgggca ggcagaacgg    16740
ggtcctggag agcgacatcg gggtcaagtt cgacaccagg aacttccgcc tggggctgga    16800
ccccgtgacc gggctggtta tgcccggggt gtacaccaac gaggccttcc atcccgacat    16860
catcctgctg cccggctgcg gggtggactt cacttacagc cgcctgagca acctcctggg    16920
catccgcaag cggcagccct tccaggaggg cttcaggatc acctacgagg acctggaggg    16980
gggcaacatc cccgcgctcc tcgatgtgga ggcctaccag gatagcttga aggaaaatga    17040
```

```
ggcgggacag gaggataccg cccccgccgc ctccgccgcc gccgagcagg gcgaggatgc    17100
tgctgacacc gcggccgcgg acggggcaga ggccgacccc gctatggtgg tggaggctcc    17160
cgagcaggag gaggacatga atgacagtgc ggtgcgcgga cacccttcg tcacccgggg     17220 ggaggaaaag caagcggagg ccgaggccgc ggccgaggaa aagcaactgg cggcagcagc    17280
ggcggcggcg gcgttggccg cggcggaggc tgagtctgag gggaccaagc ccgccaagga    17340
gcccgtgatt aagcccctga ccgaagatag caagaagcgc agttacaacc tgctcaagga    17400
cagcaccaac accgcgtacc gcagctggta cctggcctac aactacggcg acccgtcgac    17460
gggggtgcgc tcctggaccc tgctgtgcac gccggacgtg acctgcgct cggagcaggt     17520 gtactggtcg ctgcccgaca tgatgcaaga ccccgtgacc ttccgctcca cgcggcaggt    17580
cagcaacttc ccggtggtgg gcgccgagct gctgccgtg cactccaaga gcttctacaa     17640
cgaccaggcc gtctactccc agctcatccg ccagttcacc tctctgaccc acgtgttcaa    17700
tcgctttcct gagaaccaga ttctggcgcg cccgcccgcc cccaccatca ccaccgtcag    17760
tgaaaacgtt cctgctctca cagatcacgg gacgctaccg ctgcgcaaca gcatcggagg    17820
agtccagcga gtgaccgtta ctgacgccag acgccgcacc tgcccctacg tttacaaggc    17880
cttgggcata gtctcgccgc gcgtcctttc cagccgcact ttttgagcaa caccaccatc    17940
atgtccatcc tgatctcacc cagcaataac tccggctggg gactgctgcg cgcgcccagc    18000
aagatgttcg gaggggcgag gaagcgttcc gagcagcacc ccgtgcgcgt gcgcgggcac    18060
ttccgcgccc cctggggagc gcacaaacgc ggccgcgcgg ggcgcaccac cgtggacgac    18120
gccatcgact cggtggtgga gcaggcgcgc aactacaggc ccgcggtctc taccgtggac    18180
gcggccatcc agaccgtggt gcggggcgcg cggcggtacg ccaagctgaa gagccgccgg    18240
aagcgcgtgg cccgccgcca ccgccgccga cccggggccg ccgccaaacg cgccgccgcg    18300
gccctgcttc gccgggccaa gcgcacgggc cgccgcgccg ccatgagggc cgcgcgccgc    18360
ttggccgccg gcatcaccgc cgccaccatg gcccccgta cccgaagacg cgcggccgcc     18420
gccgccgccg ccgccatcag tgacatggcc agcaggcgcc ggggcaacgt gtactgggtg    18480
cgcgactcgg tgaccggcac gcgcgtgccc gtgcgcttcc gccccccgcg gacttgagat    18540
gatgtgaaaa acaacactg agtctcctgc tgttgtgtgt atcccagcgg cggcggcgcg     18600
cgcagcgtca tgtccaagcg caaaatcaaa gaagagatgc tccaggtcgt cgcgccggag    18660
atctatgggc ccccgaagaa ggaagagcag gattcgaagc cccgcaagat aaagcgggtc    18720
aaaaagaaaa agaaagatga tgacgatgcc gatggggagg tggagttcct gcgcgccacg    18780
gcgcccaggc gcccggtgca gtggaagggc cggcgcgtaa agcgcgtcct gcgccccggc    18840
accgcggtgg tcttcacgcc cggcgagcgc tccacccgga ctttcaagcg cgtctatgac    18900
gaggtgtacg gcgacgaaga cctgctggag caggccaacg agcgcttcgg agagtttgct    18960
tacgggaagc gtcagcgggc gctggggaag gaggacctgc tggcgctgcc gctgaccag    19020 ggcaaccccca cccccagtct gaagcccgtg accctgcagc aggtgctgcc gagcagcgca    19080
ccctccgagg cgaagcgggg tctgaagcgc gagggcggcg acctggcgcc caccgtgcag    19140
ctcatggtgc ccaagcggca gaggctggag atgtgctgg agaaaatgaa agtagacccc    19200
ggtctgcagc cggacatcag ggtccgcccc atcaagcagg tggcgccggg cctcggcgtg    19260
cagaccgtgg acgtggtcat ccccaccggc aactcccccg ccgccgccac cactaccgct    19320
gcctccacgg acatggagac acagaccgat ccgccgcag ccgcagccgc agccgccgcc    19380
gcgacctcct cggcggaggt gcagacggac ccctggctgc cgccggcgat gtcagctccc    19440
```

```
cgcgcgcgtc gcgggcgcag gaagtacggc gccgccaacg cgctcctgcc cgagtacgcc   19500
ttgcatcctt ccatcgcgcc caccccggc taccgaggct atacctaccg cccgcgaaga    19560
gccaagggtt ccacccgccg tccccgccga cgcgccgccg ccaccacccg ccgccgccgc   19620
cgcagacgcc agcccgcact ggctccagtc tccgtgagga aagtggcgcg cgacggacac   19680
accctggtgc tgcccagggc gcgctaccac cccagcatcg tttaaaagcc tgttgtggtt   19740
cttgcagata tggccctcac ttgccgcctc cgtttcccgg tgccgggata ccaggagga    19800 agatcgcgcc gcaggagggg tctggccggc gcgcggctga gcggaggcag ccgccgcgcg   19860
caccggcggc gacgcgccac cagccgacgc atgcgcggcg gggtgctgcc cctgttaatc   19920 ccctgatcg ccgcggcgat cggcgccgtg cccgggatcg cctccgtggc cttgcaagcg    19980
tcccagaggc attgacagac ttgcaaactt gcaaatatgg aaaaaaaaac cccaataaaa   20040
aagtctagac tctcacgctc gcttggtcct gtgactattt tgtagaatgg aagacatcaa   20100
ctttgcgtcg ctggccccgc gtcacggctc gcgcccgttc ctgggacact ggaacgatat   20160
cggcaccagc aacatgagcg gtggcgcctt cagttgggc tctctgtgga gcggcattaa    20220
aagtatcggg tctgccgtta aaaattacgg ctcccgggcc tggaacagca gcacgggcca   20280
gatgttgaga gacaagttga aagagcagaa cttccagcag aaggtggtgg agggcctggc   20340
ctccggcatc aacggggtgg tggacctggc caaccaggcc gtgcagaata agatcaacag   20400
cagactggac ccccggccgc cggtggagga ggtgccgccg gcgctggaga cggtgtcccc   20460
cgatgggcgt ggcgagaagc gcccgcggcc cgatagggaa gagaccactc tggtcacgca   20520
gaccgatgag ccgccccgt atgaggaggc cctgaagcaa ggtctgccca ccacgcggcc    20580
catcgcgccc atggccaccg gggtggtggg ccgccacacc cccgcacgc tggacttgcc    20640 tccgcccgcc gatgtgccgc agcagcagaa ggcggcacag ccgggcccgc ccgcgaccgc   20700
ctcccgttcc tccgccggtc ctctgcgccg cgcggccagc ggcccccgcg gggggtcgc    20760 gaggcacggc aactggcaga gcacgctgaa cagcatcgtg ggtctggggg tgcggtccgt   20820
gaagcgccgc cgatgctact gaatagctta gctaacgtgt tgtatgtgtg tatgcgccct   20880
atgtcgccgc cagaggagct gctgagtcgc cgccgttcgc gcgcccacca ccaccgccac   20940
tccgcccctc aagatggcga ccccatcgat gatgccgcag tggtcgtaca tgcacatctc   21000
gggccaggac gcctcggagt acctgagccc cgggctggtg cagttcgccc gcgccaccga   21060
gagctacttc agcctgagta acaagtttag gaaccccacg gtggcgccca cgcacgatgt   21120
gaccaccgac cggtctcagc gcctgacgct gcggttcatt cccgtggacc gcgaggacac   21180
cgcgtactcg tacaaggcgc ggttcacccct ggccgtgggc gacaaccgcg tgctggacat  21240
ggcctccacc tactttgaca tccgcggggt gctggaccgg ggtcccactt tcaagcccta   21300
ctctggcacc gcctacaact ccctggcccc caagggcgct cccaactcct gcgagtggga   21360
gcaagaggaa actcaggcag ttgaagaagc agcagaagag gaagaagaag atgctgacgg   21420
tcaagctgag gaagagcaag cagctaccaa aaagactcat gtatatgctc aggctcccct   21480
ttctggcgaa aaaattagta aagatggtct gcaaatagga acggacgcta cagctacaga   21540
acaaaaacct atttatgcag accctacatt ccagcccgaa cccaaatcg gggagtccca    21600 gtggaatgag gcagatgcta cagtcgccgg cggtagagtg ctaaagaaat ctactcccat   21660
gaaaccatgc tatggttcct atgcaagacc cacaaatgct aatggaggtc agggtgtact   21720
aacggcaaat gcccagggac agctagaatc tcaggttgaa atgcaattct tttcaacttc   21780
```

```
tgaaaacgcc cgtaacgagg ctaacaacat tcagcccaaa ttggtgctgt atagtgagga    21840
tgtgcacatg gagaccccgg atacgcacct ttcttacaag cccgcaaaaa gcgatgacaa    21900
ttcaaaaatc atgctgggtc agcagtccat gcccaacaga cctaattaca tcggcttcag    21960
agacaacttt atcggcctca tgtattacaa tagcactggc aacatgggag tgcttgcagg    22020
tcaggcctct cagttgaatg cagtggtgga cttgcaagac agaaacacag aactgtccta    22080
ccagctcttg cttgattcca tgggtgacag aaccagatac ttttccatgt ggaatcaggc    22140
agtggacagt tatgacccag atgttagaat tattgaaaat catggaactg aagacgagct    22200
ccccaactat tgtttccctc tgggtggcat aggggtaact gacacttacc aggctgttaa    22260
aaccaacaat ggcaataacg ggggccaggt gacttggaca aaagatgaaa cttttgcaga    22320
tcgcaatgaa atagggtgg gaaacaattt cgctatggag atcaacctca gtgccaacct    22380
gtggagaaac ttcctgtact ccaacgtggc gctgtaccta ccagacaagc ttaagtacaa    22440
cccctccaat gtggacatct ctgacaaccc caacacctac gattacatga acaagcgagt    22500
ggtggccccg gggctggtgg actgctacat caacctgggc gcgcgctggt cgctggacta    22560
catggacaac gtcaacccct tcaaccacca ccgcaatgcg ggcctgcgct accgctccat    22620
gctcctgggc aacgggcgct acgtgccctt ccacatccag gtgccccaga gttctttgc    22680 catcaagaac ctcctcctcc tgccgggctc ctacacctac gagtggaact tcaggaagga    22740
tgtcaacatg gtcctccaga gctctctggg taacgatctc agggtggacg gggccagcat    22800
caagttcgag agcatctgcc tctacgccac cttcttcccc atgggcccaca acacggcctc    22860 cacgctcgag gccatgctca ggaacgacac caacgaccag tccttcaatg actacctctc    22920
cgccgccaac atgctctacc ccataccgc caacgccacc aacgtcccca tctccatccc    22980
ctcgcgcaac tgggcggcct tccgcggctg ggccttcacc cgcctcaaga ccaaggagac    23040
cccctccctg ggctcgggat tcgacccccta ctacacctac tcgggctcca ttccctacct    23100
ggacggcacc ttctacctca accacacttt caagaaggtc tcggtcacct tcgactcctc    23160
ggtcagctgg ccgggcaacg accgtctgct cacccccaac gagttcgaga tcaagcgctc    23220
ggtcgacggg gagggctaca cgtggcccca gtgcaacatg accaaggact ggttcctggt    23280
ccagatgctg gccaactaca acatcggcta ccagggcttc tacatcccag agagctacaa    23340
ggacaggatg tactccttct tcaggaactt ccagcccatg agccggcagg tggtggacca    23400
gaccaagtac aaggactacc aggaggtggg catcatccac cagcacaaca actcgggctt    23460
cgtgggctac ctcgccccca ccatgcgcga gggacaggcc taccccgcca cttccccta    23520 tccgctcata ggcaagaccg cggtcgacag catcacccag aaaaagttcc tctgcgaccg    23580 cacccctctgg cgcatcccct tctccagcaa cttcatgtcc atgggtgcgc tctcggacct    23640
gggccagaac ttgctctacg ccaactccgc ccacgccctc gacatgacct tcgaggtcga    23700
ccccatggac gagcccaccc ttctctatgt tctgttcgaa gtctttgacg tggtccgggt    23760
ccaccagccg caccgcggcg tcatcgagac cgtgtacctg cgtacgccct tctcggccgg    23820
caacgccacc acctaaagaa gcaagccgca gtcatcgccg cctgcatgcc gtcgggttcc    23880
accgagcaag agctcaggg catcgtcaga gacctgggat gcgggcccta ttttttgggc    23940
accttcgaca gcgcttccc tggctttgtc tccccacaca gctggcctg cgccatcgtc    24000 aacacgccc gccgcgagac cggggcgtg cactggctgg ccttcgcctg gaacccgcgc    24060
tccaaaacat gcttcctctt tgaccccttc ggcttttcgg accagcggct caagcaaatc    24120
tacgagttcg agtacgaggg cttgctgcgt cgcagcgcca tcgcctcctc gcccgaccgc    24180
```

```
tgcgtcaccc tcgaaaagtc cacccagacc gtgcaggggc ccgactcggc cgcctgcggt    24240
ctcttctgct gcatgtttct gcacgccttt gtgcactggc ctcagagtcc catggaccgc    24300
aaccccacca tgaacttgct gacggggtg cccaactcca tgctccagag cccccaggtc     24360
gagcccaccc tgcgccgcaa ccaggagcag ctctacagct tcctggagcg ccactcgcct    24420
tacttccgcc gccacagcgc acagatcagg agggccacct ccttctgcca cttgcaagag    24480
atgcaagaag ggtaataacg atgtacacac ttttttctc aataaatggc atcttttat      24540 ttatacaagc tctctggggt attcatttcc caccaccacc cgccgttgtc gccatctggc    24600
tctatttaga aatcgaaagg gttctgccgg gagtcgccgt gcgccacggg cagggacacg    24660
ttgcgatact ggtagcgggt gccccacttg aactcgggca ccaccaggcg aggcagctcg    24720
gggaagtttt cgctccacag gctgcgggtc agcaccagcg cgttcatcag gtcgggcgcc    24780
gagatcttga agtcgcagtt ggggccgccg ccctgcgcgc gcgagttgcg gtacaccggg    24840
ttgcagcact ggaacaccaa cagcgccggg tgcttcacgc tggccagcac gctgcggtcg    24900
gagatcagct cggcgtccag gtcctccgcg ttgctcagcg cgaacggggt catcttgggc    24960
acttgccgcc ccaggaaggg cgcgtgcccc ggtttcgagt tgcagtcgca gcgcagcggg    25020
atcagcaggt gcccgtgccc ggactcggcg ttggggtaca gcgcgcgcat gaaggcctgc    25080
atctggcgga aggccatctg ggccttggcg ccctccgaga agaacatgcc gcaggacttg    25140
cccgagaact ggtttgcggg gcagctggcg tcgtgcaggc agcagcgcgc gtcggtgttg    25200
gcgatctgca ccacgttgcg cccccaccgg ttcttcacga tcttggcctt ggacgattgc    25260
tccttcagcg cgcgctgccc gttctcgctg gtcacatcca tctcgatcac atgttccttg    25320
ttcaccatgc tgctgccgtg cagacacttc agctcgccct ccgtctcggt gcagcggtgc    25380
tgccacagcg cgcagcccgt gggctcgaaa gacttgtagg tcacctccgc gaaggactgc    25440
aggtacccct gcaaaaagcg gcccatcatg gtcacgaagg tcttgttgct gctgaaggtc    25500
agctgcagcc cgcggtgctc ctcgttcagc caggtcttgc acacggccgc cagcgcctcc    25560
acctggtcgg gcagcatctt gaagttcacc ttcagctcat tctccacgtg gtacttgtcc    25620
atcagcgtgc gcgccgcctc catgcccttc tcccaggccg acaccagcgg caggctcacg    25680
gggttcttca ccatcaccgt ggccgccgcc tccgccgcgc tttcgctttc cgcccgctg    25740 ttctcttcct cttcctcctc ttcctcgccg ccgcccactc gcagccccg caccacgggg   25800 tcgtcttcct gcaggcgctg caccttgcgc ttgccgttgc gcccctgctt gatgcgcacg    25860
ggcgggttgc tgaagcccac catcaccagc gcggcctctt cttgctcgtc ctcgctgtcc    25920
agaatgacct ccggggaggg ggggttggtc atcctcagta ccgaggcacg cttctttttc    25980
ttcctggggg cgttcgccag ctccgcggct cggccgctg ccgaggtcga aggccgaggg    26040
ctgggcgtgc gcggcaccag cgcgtcctgc gagccgtcct cgtcctcctc ggactcgaga    26100
cggaggcggg cccgcttctt cggggggcgcg cggggcggcg gaggcggcgg cggcgacgga    26160
gacggggacg agacatcgtc cagggtgggt ggacggcggg ccgcgccgcg tccgcgctcg    26220
ggggtggtct cgcgctggtc ctcttcccga ctggccatct cccactgctc cttctccctat   26280 aggcagaaag agatcatgga gtctctcatg cgagtcgaga aggaggagga cagcctaacc    26340 gcccctctg agccctccac caccgccgcc accaccgcca atgccgccgc ggacgacgcg     26400
cccaccgaga ccaccgccag taccacccte cccagcgacg cacccccgct cgagaatgaa    26460
gtgctgatcg agcaggaccc gggttttgtg agcggagagg aggatgaggt ggatgagaag    26520
```

```
gagaaggagg aggtcgccgc ctcagtgcca aaagaggata aaaagcaaga ccaggacgac  26580
gcagataagg atgagacagc agtcgggcgg gggaacggaa gccatgatgc tgatgacggc  26640
tacctagacg tgggagacga cgtgctgctt aagcacctgc accgccagtg cgtcatcgtc  26700
tgcgacgcgc tgcaggagcg ctgcgaagtg cccctggacg tggcgaggt cagccgcgcc  26760 tacgagcggc acctcttcgc gccgcacgtg ccccccaagc gccgggagaa cggcacctgc  26820
gagcccaacc cgcgtctcaa cttctacccg gtcttcgcgg tacccgaggt gctgccacc  26880 taccacatct tttccaaaa ctgcaagatc cccctctcct gccgcgccaa ccgcacccgc  26940
gccgacaaaa ccctgaccct gcggcagggc gcccacatac ctgatatcgc ctctctggag  27000
gaagtgccca agatcttcga gggtctcggt cgcgacgaga acgggcggc gaacgctctg  27060 cacggagaca gcgaaaacga gagtcactcg ggggtgctgg tggagctcga gggcgacaac  27120
gcgcgcctgg ccgtactcaa gcgcagcata gaggtcaccc actttgccta cccggcgctc  27180
aacctgcccc ccaaggtcat gagtgtggtc atgggcgagc tcatcatgcg ccgcgcccag  27240
cccctggccg cggatgcaaa cttgcaagag tcctccgagg aaggcctgcc cgcggtcagc  27300
gacgagcagc tggcgcgctg gctggagacc cgcgacccg cgcagctgga ggagcggcgc  27360
aagctcatga tggccgcggt gctggtcacc gtggagctcg agtgtctgca gcgcttcttc  27420
gcggaccccg agatgcagcg caagctcgag gagaccctgc actacacctt ccgccagggc  27480
tacgtgcgcc aggcctgcaa gatctccaac gtggagctct gcaacctggt ctcctacctg  27540
ggcatcctgc acgagaaccg cctcgggcag aacgtcctgc actccaccct caaaggggag  27600
gcgcgccgcg actacatccg cgactgcgcc tacctcttcc tctgctacac ctggcagacg  27660
gccatggggg tctggcagca gtgcctggag gagcgcaacc tcaaggagct ggaaaagctc  27720
ctcaagcgca ccctcaggga cctctggacg ggcttcaacg agcgctcggt ggccgccgcg  27780
ctggcggaca tcatctttcc cgagcgcctg ctcaagaccc tgcagcaggg cctgcccgac  27840
ttcaccagcc agagcatgct gcagaacttc aggactttca tcctggagcg ctcgggcatc  27900
ctgccggcca cttgctgcgc gctgcccagc gacttcgtgc ccatcaagta cagggagtgc  27960
ccgccgccgc tctggggcca ctgctacctc ttccagctgg ccaactacct cgcctaccac  28020
tcggacctca tggaagacgt gagcggcgag ggcctgctcg agtgccactg ccgctgcaac  28080
ctctgcacgc cccaccgctc tctagtctgc aacccgcagc tgctcagcga gagtcagatt  28140
atcggtacct tcgagctgca gggtccctcg cctgacgaga agtccgcggc tccagggctg  28200
aaactcactc cggggctgtg gacttccgcc tacctacgca aatttgtacc tgaggactac  28260
cacgcccacg agatcaggtt ctacgaagac caatcccgcc cgcccaaggc ggagctcacc  28320
gcctgcgtca tcacccaggg gcacatcctg gccaattgc aagccatcaa caaagcccgc  28380
cgagagttct tgctgaaaaa gggtcggggg gtgtacctgg accccagtc cggcgaggag  28440 ctaaacccgc tacccccgcc gccgccccag cagcgggacc ttgcttccca ggatggcacc  28500
cagaaagaag cagcagccgc cgccgccgcc gcagccatac atgcttctgg aggaagagga  28560
ggaggactgg gacagtcagg cagaggaggt ttcggacgag gagcaggagg agatgatgga  28620
agactgggag gaggacagca gcctagacga ggaagcttca gaggccgaag aggtggcaga  28680
cgcaacacca tcgccctcgg tcgcagcccc ctcgccgggg ccctgaaat cctccgaacc  28740 cagcaccagc gctataacct ccgctcctcc ggcgccggcg ccaccgccc gcagacccaa  28800 ccgtagatgg gacaccacag gaaccggggt cggtaagtcc aagtgcccgc cgccgccacc  28860
gcagcagcag cagcagcagc gccagggcta ccgctcgtgg cgcgggcaca agaacgccat  28920
```

```
agtcgcctgc ttgcaagact gcggggcaa catctctttc gcccgccgct tcctgctatt  28980
ccaccacggg gtcgcctttc cccgcaatgt cctgcattac taccgtcatc tctacagccc  29040
ctactgcagc ggcgacccag aggcggcagc ggcagccaca gcggcgacca ccacctagga  29100
agatatcctc cgcgggcaag acagcggcag cagcggccag gagacccgcg gcagcagcgg  29160
cgggagcggt gggcgcactg cgcctctcgc ccaacgaacc cctctcgacc cgggagctca  29220
gacacaggat cttccccact ttgtatgcca tcttccaaca gagcagaggc caggagcagg  29280
agctgaaaat aaaaaacaga tctctgcgct ccctcacccg cagctgtctg tatcacaaaa  29340
gcgaagatca gcttcggcgc acgctggagg acgcggaggc actcttcagc aaatactgcg  29400
cgctcactct taaagactag ctccgcgccc ttctcgaatt taggcgggag aaaactacgt  29460
catcgccggc cgccgcccag cccgcccagc cgagatgagc aaagagattc ccacgccata  29520
catgtggagc taccagccgc agatgggact cgcggcggga gcggcccagg actactccac  29580
ccgcatgaac tacatgagcg cgggacccca catgatctca caggtcaacg ggatccgcgc  29640
ccagcgaaac caaatactgc tggaacaggc ggccatcacc gccacgcccc gccataatct  29700
caacccccga aattggcccg ccgccctcgt gtaccaggaa acccctccg ccaccaccgt  29760
actacttccg cgtgacgccc aggccgaagt ccagatgact aactcagggg cgcagctcgc  29820
gggcggcttt cgtcacgggg cgcggccgct ccgaccaggt ataagacacc tgatgatcag  29880
aggccgaggt atccagctca acgacgagtc ggtgagctct tcgctcggtc tccgtccgga  29940
cggaactttc cagctcgccg gatccggccg ctcttcgttc acgccccgcc aggcgtacct  30000
gactctgcag acctcgtcct cggagccccg ctccggcggc atcggaaccc tccagttcgt  30060
ggaggagttc gtgccctcgg tctacttcaa cccttctcg ggacctcccg gacgctaccc  30120
cgaccagttc attccgaact ttgacgcggt gaaggactcg gcggacggct acgactgaat  30180
gtcaggtgtc gaggcagagc agcttcgcct gagacacctc gagcactgcc gccgccacaa  30240
gtgcttcgcc cgcggttctg gtgagttctg ctactttcag ctacccgagg agcataccga  30300
ggggccggcg cacggcgtcc gcctgaccac ccagggcgag gttacctgtt ccctcatccg  30360
ggagtttacc ctccgtcccc tgctagtgga gcgggagcgg ggtccctgtg tcctaactat  30420
cgcctgcaac tgcccctaacc ctggattaca tcaagatctt tgctgtcatc tctgtgctga  30480
gtttaataaa cgctgagatc agaatctact gggatttagt ccccttttaac taatcaaaca  30540
ctggaatcaa taaaaagaat cacttactta aaatcagaca gcaggtctct gtccagtta  30600
ttcagcagca cctccttccc ctcctcccaa ctctggtact ccaaacgcct tctggcggca  30660
aacttcctcc acaccctgaa gggaatgtca gattcttgct cctgtccctc cgcacccact  30720
atcttcatgt tgttgcagat gaagcgcacc aaaacgtctg acgagagctt caacccegtg  30780
taccctatg acacggaaag cggccctccc tccgtccctt tcctcacccc tcccttcgtg  30840
tctcccgatg gattccaaga aagtcccccc ggggtcctgt ctctgaacct ggccgagccc  30900
ctggtcactt cccacggcat gctcgccctg aaaatgggaa gtggcctctc cctggacgac  30960
gctggcaacc tcacctctca agatatcacc accgctagcc ctcccctcaa aaaaccaag  31020
accaacctca gcctagaaac ctcatccccc ctaactgtga gcacctcagg cgccctcacc  31080
gtagcagccg ccgctcccct ggcggtggcc ggcacctccc tcaccatgca atcagaggcc  31140
ccctgacag tacaggatgc aaaactcacc ctggccacca aaggcccct gaccgtgtct  31200
gaaggcaaac tggccttgca acatcggccc ccgctgacgg ccgctgacag cagcaccctc  31260
```

| | |
|---|---|
| acagtcagtg ccacaccacc ccttagcaca agcaatggca gcttgggtat tgacatgcaa | 31320 |
| gcccccattt acaccaccaa tggaaaacta ggacttaact ttggcgctcc cctgcatgtg | 31380 |
| gtagacagcc taaatgcact gactgtagtt actggccaag gtcttacgat aaacggaaca | 31440 |
| gccctacaaa ctagagtctc aggtgccctc aactatgaca catcaggaaa cctagaattg | 31500 |
| agagctgcag ggggtatgcg agttgatgca aatggtcaac ttatccttga tgtagcttac | 31560 |
| ccatttgatg cacaaaacaa tctcagcctt aggcttggac agggacccct gtttgttaac | 31620 |
| tctgcccaca acttggatgt taactacaac agaggcctct acctgttcac atctggaaat | 31680 |
| accaaaaagc tagaagttaa tatcaaaaca gccaagggtc tcatttatga tgacactgct | 31740 |
| atagcaatca atgcgggtga tgggctacag tttgactcag gctcagatac aaatccatta | 31800 |
| aaaactaaac ttggattagg actgattat gactccagca gagccataat tgctaaactg | 31860 |
| ggaactggcc taagctttga caacacaggt gccatcacag taggcaacaa aaatgatgac | 31920 |
| aagcttacct tgtggaccac accagaccca tcccctaact gtagaatcta ttcagagaaa | 31980 |
| gatgctaaat tcacacttgt tttgactaaa tgcggcagtc aggtgttggc cagcgtttct | 32040 |
| gttttatctg taaaggtag ccttgcgccc atcagtggca cagtaactag tgctcagatt | 32100 |
| gtcctcagat ttgatgaaaa tggagttcta ctaagcaatt cttcccttga ccctcaatac | 32160 |
| tggaactaca gaaaaggtga ccttacagag ggcactgcat ataccaacgc agtgggattt | 32220 |
| atgcccaacc tcacagcata cccaaaaaca cagagccaaa ctgctaaaag caacattgta | 32280 |
| agtcaggttt acttgaatgg ggacaaatcc aaacccatga ccctcaccat taccctcaat | 32340 |
| ggaactaatg aaacaggaga tgccacagta agcacttact ccatgtcatt ctcatggaac | 32400 |
| tggaatggaa gtaattacat taatgaaacg ttccaaacca actccttcac cttctcctac | 32460 |
| atcgcccaag aataaaaagc atgacgctgt tgatttgatt caatgtgttt ctgttttatt | 32520 |
| ttcaagcaca acaaaatcat tcaagtcatt cttccatctt agcttaatag acacagtagc | 32580 |
| ttaatagacc cagtagtgca aagccccatt ctagcttata actagtggag aagtactcgc | 32640 |
| ctacatgggg gtagagtcat aatcgtgcat caggataggg cggtggtgct gcagcagcgc | 32700 |
| gcgaataaac tgctgccgcc gccgctccgt cctgcaggaa tacaacatgg cagtggtctc | 32760 |
| ctcagcgatg attcgcaccg cccgcagcat aaggcgcctt gtcctccggg cacagcagcg | 32820 |
| cacccctgatc tcacttaaat cagcacagta actgcagcac agcaccacaa tattgttcaa | 32880 |
| aatcccacag tgcaaggcgc tgtatccaaa gctcatggcg gggaccacag aacccacgtg | 32940 |
| gccatcatac cacaagcgca ggtagattaa gtggcgaccc ctcataaaca cgctggacat | 33000 |
| aaacattacc tcttttggca tgttgtaatt caccacctcc cggtaccata taaacctctg | 33060 |
| attaaacatg gcgccatcca ccaccatcct aaaccagctg gccaaaacct gcccgccggc | 33120 |
| tatacactgc agggaaccgg gactggaaca atgacagtgg agagcccagg actcgtaacc | 33180 |
| atggatcatc atgctcgtca tgatatcaat gttggcacaa cacaggcaca cgtgcataca | 33240 |
| cttcctcagg attacaagct cctcccgcgt tagaaccata tcccagggaa caacccattc | 33300 |
| ctgaatcagc gtaaatccca cactgcaggg aagacctcgc acgtaactca cgttgtgcat | 33360 |
| tgtcaaagtg ttacattcgg gcagcagcgg atgatcctcc agtatggtag cgcgggtttc | 33420 |
| tgtctcaaaa ggaggtagac gatccctact gtacggagtg cgccgagaca accgagatcg | 33480 |
| tgttggtcgt agtgtcatgc caaatggaac gccggacgta gtcatatttc ctgaagtctt | 33540 |
| agatctctca acgcagcacc agcaccaaca cttcgcagtg taaaaggcca agtgccgaga | 33600 |
| gagtatatat aggaataaaa agtgacgtaa acgggcaaag tccaaaaaac gcccagaaaa | 33660 |

```
accgcacgcg aacctacgcc ccgaaacgaa agccaaaaaa cactagacac tcccttccgg    33720
cgtcaacttc cgctttccca cgctacgtca cttgccccag tcaaacaaac tacatatccc    33780
gaacttccaa gtcgccacgc ccaaaacacc gcctacacct ccccgcccgc cggcccgccc    33840
ccaaacccgc ctcccgcccc gcgcccgccc ccgcgccgcc catctcatta tcatattggc    33900
ttcaatccaa aataaggtat attattgatg atggtttaaa cggatcctct agagtcgacc    33960
tgcaggcatg caagcttgag tattctatag tgtcacctaa atagcttggc gtaatcatgg    34020
tcatagctgt ttcctgtgtg aaattgttat ccgctcacaa ttccacacaa catacgagcc    34080
ggaagcataa agtgtaaagc ctggggtgcc taatgagtga gctaactcac attaattgcg    34140
ttgcgctcac tgcccgcttt ccagtcggga acctgtcgt gccagctgca ttaatgaatc     34200
ggccaacgcg aacccttgc ggcgccgg gccgtcgacc aattctcatg tttgacagct       34260
tatcatcgaa tttctgccat tcatccgctt attatcactt attcaggcgt agcaaccagg    34320
cgtttaaggg caccaataac tgccttaaaa aaattacgcc ccgccctgcc actcatcgca    34380
gtactgttgt aattcattaa gcattctgcc gacatggaag ccatcacaaa cggcatgatg    34440
aacctgaatc gccagcggca tcagcacctt gtcgccttgc gtataatatt tgcccatggt    34500
gaaaacgggg gcgaagaagt tgtccatatt ggccacgttt aaatcaaaac tggtgaaact    34560
cacccaggga ttggctgaga cgaaaaacat attctcaata aaccctttag ggaaataggc    34620
caggttttca ccgtaacacg ccacatcttg cgaatatatg tgtagaaact gccggaaatc    34680
gtcgtggtat tcactccaga gcgatgaaaa cgtttcagtt tgctcatgga aaacggtgta    34740
acaagggtga acactatccc atatcaccag ctcaccgtct ttcattgcca tacggaattc    34800
cggatgagca ttcatcaggc gggcaagaat gtgaataaag gccggataaa acttgtgctt    34860
atttttcttt acggtcttta aaaaggccgt aatatccagc tgaacggtct ggttataggt    34920
acattgagca actgactgaa atgcctcaaa atgttcttta cgatgccatt gggatatatc    34980
aacggtggta tatccagtga ttttttttctc cattttagct tccttagctc ctgaaaatct    35040
cgataactca aaaaatacgc ccggtagtga tcttatttca ttatggtgaa agttggaacc    35100
tcttacgtgc cgatcaacgt ctcatttttcg ccaaaagttg gcccagggct tcccggtatc    35160 aacaggaca ccaggattta tttattctgc gaagtgatct tccgtcacag gtatttattc      35220
gcgataagct catggagcgg cgtaaccgtc gcacaggaag acagagaaa gcgcggatct     35280 gggaagtgac ggacagaacg gtcaggacct ggattgggga ggcggttgcc gccgctgctg    35340
ctgacggtgt gacgttctct gttccggtca caccacatac gttccgccat tcctatgcga    35400
tgcacatgct gtatgccggt ataccgctga agttctgca aagcctgatg ggacataagt     35460
ccatcagttc aacggaagtc tacacgaagg tttttgcgct ggatgtggct gcccggcacc    35520
gggtgcagtt tgcgatgccg gagtctgatg cggttgcgat gctgaaacaa ttatcctgag    35580
aataaatgcc ttggccttta tatggaaatg tggaactgag tggatatgct gttttttgtct   35640 gttaaacaga gaagctggct gttatccact gagaagcgaa cgaaacagtc gggaaaatct    35700
cccattatcg tagagatccg cattattaat ctcaggagcc tgtgtagcgt ttataggaag    35760
tagtgttctg tcatgatgcc tgcaagcggt aacgaaaacg atttgaatat gccttcagga    35820
acaatagaaa tcttcgtgcg gtgttacgtt gaagtggagc ggattatgtc agcaatggac    35880
agaacaacct aatgaacaca gaaccatgat gtggtctgtc cttttacagc cagtagtgct    35940
cgccgcagtc gagcgacagg gcgaagccct cgagtgagcg aggaagcacc agggaacagc    36000
```

```
acttatatat tctgcttaca cacgatgcct gaaaaaactt cccttggggt tatccactta   36060
tccacgggga tatttttata attatttttt ttatagtttt tagatcttct tttttagagc   36120
gccttgtagg cctttatcca tgctggttct agagaaggtg ttgtgacaaa ttgcccttc    36180 agtgtgacaa atcaccctca aatgacagtc ctgtctgtga caaattgccc ttaaccctgt   36240
gacaaattgc cctcagaaga agctgttttt tcacaaagtt atccctgctt attgactctt   36300
ttttatttag tgtgacaatc taaaaacttg tcacacttca catggatctg tcatggcgga   36360
aacagcggtt atcaatcaca agaaacgtaa aaatagcccg cgaatcgtcc agtcaaacga   36420
cctcactgag gcggcatata gtctctcccg ggatcaaaaa cgtatgctgt atctgttcgt   36480
tgaccagatc agaaaatctg atggcaccct acaggaacat gacggtatct gcgagatcca   36540
tgttgctaaa tatgctgaaa tattcggatt gacctctgcg gaagccagta aggatatacg   36600
gcaggcattg aagagtttcg cggggaagga agtggttttt tatcgccctg aagaggatgc   36660
cggcgatgaa aaaggctatg aatcttttcc ttggtttatc aaacgtgcgc acagtccatc   36720
cagagggctt tacagtgtac atatcaaccc atatctcatt cccttcttta tcgggttaca   36780
gaaccggttt acgcagtttc ggcttagtga aacaaaagaa atcaccaatc cgtatgccat   36840
gcgtttatac gaatccctgt gtcagtatcg taagccggat ggctcaggca tcgtctctct   36900
gaaaatcgac tggatcatag agcgttacca gctgcctcaa agttaccagc gtatgcctga   36960
cttccgccgc cgcttcctgc aggtctgtgt taatgagatc aacagcagaa ctccaatgcg   37020
cctctcatac attgagaaaa agaaaggccg ccagacgact catatcgtat tttccttccg   37080
cgatatcact tccatgacga caggatagtc tgagggttat ctgtcacaga tttgagggtg   37140
gttcgtcaca tttgttctga cctactgagg gtaatttgtc acagttttgc tgtttccttc   37200
agcctgcatg gattttctca tacttttga actgtaattt ttaaggaagc caaatttgag    37260
ggcagtttgt cacagttgat ttccttctct ttcccttcgt catgtgacct gatatcgggg   37320
gttagttcgt catcattgat gagggttgat tatcacagtt tattactctg aattggctat   37380
ccgcgtgtgt acctctacct ggagtttttc ccacggtgga tatttcttct tgcgctgagc   37440
gtaagagcta tctgacagaa cagttcttct ttgcttcctc gccagttcgc tcgctatgct   37500
cggttacacg gctgcggcga gcgctagtga taataagtga ctgaggtatg tgctcttctt   37560
atctcctttt gtagtgttgc tcttatttta aacaactttg cggttttttg atgactttgc   37620 gatttgttg ttgctttgca gtaaattgca agatttaata aaaaaacgca aagcaatgat    37680
taaaggatgt tcagaatgaa actcatggaa acacttaacc agtgcataaa cgctggtcat   37740
gaaatgacga aggctatcgc cattgcacag tttaatgatg acagcccgga agcgaggaaa   37800
ataacccggc gctggagaat aggtgaagca gcggatttag ttggggtttc ttctcaggct   37860
atcagagatg ccgagaaagc agggcgacta ccgcacccgg atatggaaat tcgaggacgg   37920
gttgagcaac gtgttggtta taacaattgaa caaattaatc atatgcgtga tgtgtttggt   37980
acgcgattgc gacgtgctga agacgtatt ccaccggtga tcggggttgc tgcccataaa    38040
ggtggcgttt acaaaacctc agtttctgtt catcttgctc aggatctggc tctgaagggg   38100
ctacgtgttt tgctcgtgga aggtaacgac ccccagggaa cagcctcaat gtatcacgga   38160
tgggtaccag atcttcatat tcatgcagaa gacactctcc tgcctttcta tcttggggaa   38220
aaggacgatg tcacttatgc aataaagccc acttgctggc cggggcttga cattattcct   38280
tcctgtctgg ctctgcaccg tattgaaact gagttaatgg gcaaatttga tgaaggtaaa   38340
ctgcccaccg atccacacct gatgctccga ctggccattg aaactgttgc tcatgactat   38400
```

```
gatgtcatag ttattgacag cgcgcctaac ctgggtatcg gcacgattaa tgtcgtatgt    38460
gctgctgatg tgctgattgt tcccacgcct gctgagttgt ttgactacac ctccgcactg    38520
cagtttttcg atatgcttcg tgatctgctc aagaacgttg atcttaaagg gttcgagcct    38580
gatgtacgta ttttgcttac caaatacagc aatagtaatg ctctcagtc cccgtggatg     38640 gaggagcaaa ttcgggatgc ctggggaagc atggttctaa aaaatgttgt acgtgaaacg    38700
gatgaagttg gtaaaggtca gatccggatg agaactgttt ttgaacaggc cattgatcaa    38760
cgctcttcaa ctggtgcctg agaaatgct ctttctattt gggaacctgt ctgcaatgaa     38820
attttcgatc gtctgattaa accacgctgg gagattagat aatgaagcgt gcgcctgtta    38880
ttccaaaaca tacgctcaat actcaaccgg ttgaagatac ttcgttatcg acaccagctg    38940
ccccgatggt ggattcgtta attgcgcgcg taggagtaat ggctcgcggt aatgccatta    39000
ctttgcctgt atgtggtcgg gatgtgaagt ttactcttga agtgctccgg ggtgatagtg    39060
ttgagaagac ctctcgggta tggtcaggta atgaacgtga ccaggagctg cttactgagg    39120
acgcactgga tgatctcatc ccttcttttc tactgactgg tcaacagaca ccggcgttcg    39180
gtcgaagagt atctggtgtc atagaaattg ccgatgggag tcgccgtcgt aaagctgctg    39240
cacttaccga aagtgattat cgtgttctgg ttggcgagct ggatgatgag cagatggctg    39300
cattatccag attgggtaac gattatcgcc caacaagtgc ttatgaacgt ggtcagcgtt    39360
atgcaagccg attgcagaat gaatttgctg gaaatatttc tgcgctggct gatgcggaaa    39420
atatttcacg taagattatt acccgctgta tcaacaccgc caaattgcct aaatcagttg    39480
ttgctctttt ttctcacccc ggtgaactat ctgcccggtc aggtgatgca cttcaaaaag    39540
cctttacaga taaagaggaa ttacttaagc agcaggcatc taaccttcat gagcagaaaa    39600
aagctggggt gatatttgaa gctgaagaag ttatcactct tttaacttct gtgcttaaaa    39660
cgtcatctgc atcaagaact agtttaagct cacgacatca gtttgctcct ggagcgcacg    39720
tattgtataa gggcgataaa atggtgctta acctggacag gtctcgtgtt ccaactgagt    39780
gtatagagaa aattgaggcc attcttaagg aacttgaaaa gccagcaccc tgatgcgacc    39840 acgtttagt ctacgtttat ctgtcttac ttaatgtcct ttgttacagg ccagaaagca      39900
taactggcct gaatattctc tctgggccca ctgttccact tgtatcgtcg gtctgataat    39960
cagactggga ccacggtccc actcgtatcg tcggtctgat tattagtctg ggaccacggt    40020
cccactcgta tcgtcggtct gattattagt ctgggaccac ggtcccactc gtatcgtcgg    40080
tctgataatc agactgggac cacggtccca ctcgtatcgt cggtctgatt attagtctgg    40140
gaccatggtc ccactcgtat cgtcggtctg attattagtc tgggaccacg gtcccactcg    40200
tatcgtcggt ctgattatta gtctggaacc acggtcccac tcgtatcgtc ggtctgatta    40260
ttagtctggg accacggtcc cactcgtatc gtcggtctga ttattagtct gggaccacga    40320
tcccactcgt gttgtcggtc tgattatcgg tctgggacca cggtcccact tgtattgtcg    40380
atcagactat cagcgtgaga ctacgattcc atcaatgcct gtcaagggca agtattgaca    40440
tgtcgtcgta acctgtagaa cggagtaacc tcggtgtgcg gttgtatgcc tgctgtggat    40500
tgctgctgtg tcctgcttat ccacaacatt ttgcgcacgg ttatgtggac aaaatacctg    40560
gttacccagg ccgtgccggc acgttaaccg ggctgcatcc gatgcaagtg tgtcgctgtc    40620
gacgagctcg cgagctcgga catgaggttg ccccgtattc agtgtcgctg atttgtattg    40680
tctgaagttg ttttttacgtt aagttgatgc agatcaatta atacgatacc tgcgtcataa    40740
```

```
ttgattattt gacgtggttt gatggcctcc acgcacgttg tgatatgtag atgataatca    40800 ttatcactttt acgggtcctt tccggtgatc cgacaggtta cggggcggcg acctcgcggg    40860
ttttcgctat ttatgaaaat tttccggttt aaggcgtttc cgttcttctt cgtcataact    40920
taatgttttt atttaaaata ccctctgaaa agaaaggaaa cgacaggtgc tgaaagcgag    40980 cttttttggcc tctgtcgttt cctttctctg tttttgtccg tggaatgaac aatggaagtc    41040
cgagctcatc gctaataact tcgtatagca tacattatac gaagttatat tcgatgcggc    41100
cgcaaggggt tcgcgtcagc gggtgttggc gggtgtcggg gctggcttaa ctatgcggca    41160
tcagagcaga ttgtactgag agtgcaccat atgcggtgtg aaataccgca cagatgcgta    41220
aggagaaaat accgcatcag gcgccattcg ccattcaggc tgcgcaactg ttgggaaggg    41280
cgatcggtgc gggcctcttc gctattacgc cagctggcga aggggggatg tgctgcaagg    41340
cgattaagtt gggtaacgcc agggttttcc cagtcacgac gttgtaaaac gacggccagt    41400
gaattgtaat acgactcact atagggcgaa ttcgagctcg tacccgggg atcctcgttt    41460 aaac                                                                 41464

<210> SEQ ID NO 52
<211> LENGTH: 43711
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (15388)..(15388)
<223> OTHER INFORMATION: a, c, t, g, unknown or other

<400> SEQUENCE: 52
catcatcaat aatataccttt attttggatt gaagccaata tgataatgag atgggcggcg      60
cggggcgggg cgcggggcgg gaggcgggtt tgggggcggg ccggcggggcg gggcggtgtg     120 gcggaagtgg actttgtaag tgtggcggat gtgacttgct agtgccgggc gcggtaaaag     180
tgacgttttc cgtgcgcgac aacgcccccg ggaagtgaca ttttttcccgc ggttttttacc     240 ggatgttgta gtgaatttgg gcgtaaccaa gtaagatttg gccattttcg cgggaaaact      300
gaaacgggga agtgaaatct gattaatttt gcgttagtca taccgcgtaa tatttgtcta     360
gggccgaggg actttggccg attacgtgga ggactcgccc aggtgttttt tgaggtgaat     420
ttccgcgttc cgggtcaaag tctgcgtttt attattatag gatatcccat tgcatacgtt     480
gtatccatat cataatatgt acatttatat tggctcatgt ccaacattac cgccatgttg     540
acattgatta ttgactagtt attaatagta atcaattacg gggtcattag ttcatagccc     600
atatatggag ttccgcgtta cataacttac ggtaaatggc ccgcctggct gaccgcccaa     660
cgacccccgc ccattgacgt caataatgac gtatgttccc atagtaacgc caatagggac     720
tttccattga cgtcaatggg tggagtattt acggtaaact gcccacttgg cagtacatca     780
agtgtatcat atgccaagta cgcccccctat tgacgtcaat gacggtaaat ggcccgcctg     840
gcattatgcc cagtacatga ccttatggga cttcctact tggcagtaca tctacgtatt     900
agtcatcgct attaccatgg tgatgcggtt ttggcagtac atcaatgggc gtggatagcg     960
gtttgactca cggggatttc caagtctcca ccccattgac gtcaatggga gtttgttttg    1020
gcaccaaaat caacgggact ttccaaaatg tcgtaacaac tccgccccat tgacgcaaat    1080
gggcggtagg cgtgtacggt gggaggtcta tataagcaga gctctcccta tcagtgatag    1140
```

```
agatctccct atcagtgata gagatcgtcg acgagctcgt ttagtgaacc gtcagatcgc    1200
ctggagacgc catccacgct gttttgacct ccatagaaga caccgggacc gatccagcct    1260
ccgcggccgg gaacggtgca ttggaacgcg gattccccgt gccaagagtg agatcttccg    1320
tttatctagg taccagatat cgccaccatg tccgaggact ttctgattct gatcgccatc    1380
ctggtgatcg tgattctcgt gggcacaatc acaaccctgg tgggcgccat cggcggcatt    1440
agggccagga ggagcttcct cttcatttgc atcttcttcc tgttcctctc cctcttcctg    1500
acaatcctcg ccctgctgct gggcttcagc tggctcctgc tggtggccat cctgttctgg    1560
gtgctctggc tggtcatcct cattctgctg ctgctggtgt accctattcc tcaccacccc    1620
ctgcccacct ccctcaggtt tagaatgaag cagagggtga gcagcgaccc cacaggttct    1680
gacagaagcc ctcagggcag ccataatagc ctgaactccc ccgatgagga ggaccccaag    1740
gatgacacca agcaacctct gtgcaacatg acccagggcg gacctcccgt caatggacag    1800
ctcctcggac aacatgctca atgcccccct cactatccct gctgccatat tcagcatccc    1860
gacggagagg attccgatgg agacgatggc aagtcctggg gcgatgccgg agaggaagac    1920
aatggcccta acgaccctaa caccgccagc accagagagt ccatttacga ggacctcaga    1980
taccccacaa gggacgccaa tggcgagtat gagaacgtgg ataccccccc tagggacgga    2040
gatgcccctc ataggctcgg agagcctgtg tatgacgatg tggagcaagc caccgctaac    2100
gaggtgagaa tctcccctct gttcagactg ccctacggaa gcgctttcgg acctggcccc    2160
cagcctggac ccattctgga gagctccaca tggggctttc tggtcttcac acagacctcc    2220
ctgttcgccg acgacattgc cgacgctatt agggactact gcacaaccca ccctggcccc    2280
acaaggaaca cccaggtggt cctcatgaac ttcgagggca gcggagtgcc cctgcctatg    2340
tttttttccc ctggagagga gacagaagag cagagagagg gcgatagagc tagcgactcc    2400
gacgagtccg aagacgctca gatcctgacc gtgttctgcc tgttttgcca gtggacactc    2460
tttatctgcc tgggaatcag gatgatctgt aactggaggg gcaaactcac caggatcatc    2520
tgcctgaagt tctgcctcta cggactgatt tccgcctccc tgtccttcgg ctggtacgct    2580 ttttctgaagg aagtgaccct ccccaccaca gccaccgttg atcctaggca actcccctg    2640 ttcctcttca tcctgagctc cgtgctggtg attctcgcca tcatgatgga gtttcaaaca    2700
tcctccagcc tcttcgctgc tctgttcgtg attatcgccg gaatgctgtg cgtcacagtg    2760
ggcgtgattt ttctgctggc tggcgtcaag cctctcctga gcggcatgat ctgcgcctcc    2820
ggcatcacaa tgctcgtgct cggcgtcgtg ctgctggtgg tgtgcaccag aagccccagc    2880
ccttgtcatc acagggatga acccccctcc agaagcccca gccctcaacc caccgtctcc    2940
gagcagtccc agcagtcccc caggcagcag agccctcaag gcacatccca gggttctaca    3000
agacctcagg tgcctggagg cgccaccacc agaaaaagag gcggcgtgag aggccaacct    3060
gccaagtgtc acggcaagta caccacaacc gccgagggac tgaccgctct cctgaatagg    3120
aggcacagcc ccaggacatc caacgagggc aggtggatga atggagtcat ggctgtgaac    3180
ctctccaaat ggcccctgta cagcctgagg agagccctgg ccctcgccat ggctcctaga    3240
aggaggctct ccgccctcc ctggctgaca gtgctgctgc tgctgtccac actgagcgtg    3300
gccgccctgc tgattctctt cctgattttc agcgccggcg ccaccattag cacagaagcc    3360
agcctgctgg tcctgctcct gctgtttgtg accctgctgc tgcctctcct gtcctccaac    3420
ggactccagc tccctgccgc cctgattctg atccagtgtt tcctcctggc cgctgattat    3480
```

```
ctcgcctacc tgattctgcc taccattatg cccaggggca gaagcacagg aaggaagggc    3540
agggacacag agaaagagag gagcagatcc cctctcagag ctcctggcgg ttctgatgga    3600
cccagcacaa gggctggctg tggagccgga ccctgtcagc tgagcagccc catcgccgga    3660
aacaacggca atgaaggcgg cgagggcgac gactacaaga gctggaggaa gcccgaggaa    3720
gaggacaacg gccccaatga ccccaatacc aacaacagga ttgaggatgg agacggcgac    3780
gacggaaaat cctggaggaa tcctgaggag gaggataaca gaaagcagga caggctgggc    3840
accaagcctt tcatggccgg ccactggtat gagagcgtga ttcccggcct gttcctctgc    3900
cccctgatcc tcccttccct gttctggatt tgctccctgc tgaccttcct ggtgggccac    3960
ggagccaata ttgtgagcgc cgtcctgttc ctcgtgctgg cttggtgtct cctcattgcc    4020
aactggaacg tgacaagaga ggacttcgtg tccggcagga aagctccat gagcagcctg    4080
tccgtggccg cttccaccgc cacagccatg ttcgccagct cctcacccct gagctttgat    4140
ggcctgggcc tgctgctgtt tggcaccgcc ctggtgatcc agacaattta cgtgctgtat    4200
ctggtggtca tggagatcac cgtgtggatc atgatgttta ggtatctcca cttttggatc    4260
accctgctgt tcctgctgag ccccattatt ctctccgtcg cctgtctcat catccaatcc    4320
tccgccctgc tgatcgaggc tgtggtcgtc accaccatca cagtcctggc cattttttctg    4380
tggctccctc ctcaaggcgc tgaggccgat ctcggcaccg ccctgctgat tctgaatacc    4440
gccctgtgcc tggtcgtgct gatcctgacc gctatcccta catgatgatg agcggccgcg    4500
atctgctgtg ccttctagtt gccagccatc tgttgtttgc ccctccccg tgccttcctt    4560
gaccctggaa ggtgccactc ccactgtcct ttcctaataa aatgaggaaa ttgcatcgca    4620
ttgtctgagt aggtgtcatt ctattctggg gggtggggtg gggcaggaca gcaaggggga    4680
ggattggaa gacaatagca ggcatgctgg ggatgcggtg ggctctatgg ccgatcagcg    4740
atcgctgagg tgggtgagtg ggcgtggcct ggggtggtca tgaaaatata aagttgggg    4800
gtcttagggt ctctttatt tgtgttgcaga gaccgccgga gccatgagcg ggagcagcag    4860
cagcagcagt agcagcagcg ccttggatgg cagcatcgtg agcccttatt tgacgacgcg    4920
gatgccccac tgggccgggg tgcgtcagaa tgtgatgggc tccagcatcg acggccgacc    4980
cgtcctgccc gcaaattccg ccacgctgac ctatgcgacc gtcgcgggga cgccgttgga    5040
cgccaccgcc gccgccgccg ccaccgcagc cgcctcggcc gtgcgcagcc tggccacgga    5100
ctttgcattc ctgggaccac tggcgacagg ggctacttct cgggccgctg ctgccgccgt    5160
tcgcgatgac aagctgaccg ccctgctggc gcagttggat gcgcttactc gggaactggg    5220
tgaccttcct cagcaggtca tggccctgcg ccagcaggtc tcctccctgc aagctggcgg    5280
gaatgcttct cccacaaatg ccgtttaaga taaataaaac cagactctgt ttggattaaa    5340
gaaaagtagc aagtgcattg ctctctttat ttcataattt tccgcgcgcg ataggcccta    5400
gaccagcgtt ctcggtcgtt gagggtgcgg tgtatcttct ccaggacgtg gtagaggtgg    5460
ctctggacgt tgagatacat gggcatgagc ccgtcccggg ggtggaggta gcaccactgc    5520
agagcttcat gctccggggt ggtgttgtag atgatccagt cgtagcagga gcgctgggca    5580
tggtgcctaa aaatgtcctt cagcagcagg ccgatgccca gggggaggcc cttggtgtaa    5640
gtgtttacaa aacggttaag ttgggaaggg tgcattcggg gagagatgat gtgcatcttg    5700
gactgtattt ttagattggc gatgtttccg cccagatccc ttctgggatt catgttgtgc    5760
aggaccacca gtacagtgta tccggtgcac ttggggaatt tgtcatgcag cttagaggga    5820
aaagcgtgga agaacttgga gacgcctttg tggcctccca gattttccat gcattcgtcc    5880
```

```
atgatgatgg caatgggccc gcgggaggca gcttgggcaa agatatttct ggggtcgctg    5940
acgtcgtagt tgtgttccag ggtgaggtcg tcataggcca tttttacaaa gcgcgggcgg    6000
agggtgcccg actggggggat gatggtcccc tctggccctg gggcgtagtt gccctcgcag    6060
atctgcattt cccaggcctt aatctcggag gggggaatca tatccacctg cggggcgatg    6120
aagaaaacgg tttccggagc cggggagatt aactgggatg agagcaggtt tctaagcagc    6180
tgtgattttc cacaaccggt gggcccataa ataacaccta taaccggttg cagctggtag    6240
tttagagagc tgcagctgcc gtcgtcccgg aggagggggg ccacctcgtt gagcatgtcc    6300
ctgacgcgca tgttctcccc gaccagatcc gccagaaggc gctcgccgcc cagggacagc    6360
agctcttgca aggaagcaaa gtttttcagc ggcttgaggc cgtccgccgt gggcatgttt    6420
ttcagggtct ggctcagcag ctccaggcgg tcccagagct cggtgacgtg ctctacggca    6480
tctctatcca gcatatctcc tcgtttcgcg ggttggggcg actttcgctg tagggcacca    6540
agcggtggtc gtccagcggg gccagagtca tgtccttcca tgggcgcagg gtcctcgtca    6600
gggtggtctg ggtcacggtg aagggggtgcg ctccgggctg agcgcttgcc aaggtgcgct    6660
tgaggctggt tctgctggtg ctgaagcgct gccggtcttc gccctgcgcg tcggccaggt    6720
agcatttgac catggtgtca tagtccagcc cctccgcggc gtgtcccttg gcgcgcagct    6780
tgcccttgga ggtggcgccg cacgaggggc agagcaggct cttgagcgcg tagagcttgg    6840
gggcgaggaa gaccgattcg ggggagtagg cgtccgcgcc gcagaccccg cacacggtct    6900
cgcactccac cagccaggtg agctcggggc gcgccgggtc aaaaaccagg tttcccccat    6960
gctttttgat gcgtttctta cctcgggtct ccatgaggtg gtgtccccgc tcggtgacga    7020
agaggctgtc cgtgtctccg tagaccgact tgaggggtct tttctccagg ggggtccctc    7080
ggtcttcctc gtagaggaac tcggaccact ctgagacgaa ggcccgcgtc caggccagga    7140
cgaaggaggc tatgtgggag gggtagcggt cgttgtccac taggggtcc accttctcca    7200 aggtgtgaag acacatgtcg ccttcctcgg cgtccaggaa ggtgattggc ttgtaggtgt    7260
aggccacgtg accggggggtt cctgacgggg gggtataaaa gggggtgggg gcgcgctcgt    7320
cgtcactctc ttccgcatcg ctgtctgcga gggccagctg ctggggtgag tattccctct    7380
cgaaggcggg catgacctcc gcgctgaggt tgtcagtttc caaaaacgag gaggatttga    7440
tgttcacctg tcccgaggtg atacctttga gggtacccgc gtccatctgg tcagaaaaca    7500
cgatcttttt attgtccagc ttggtggcga acgacccgta gagggcgttg gagagcagct    7560
tggcgatgga gcgcagggtc tggttcttgt ccctgtcggc gcgctccttg gccgcgatgt    7620
tgagctgcac gtactcgcgc gcgacgcagc gccactcggg gaagacggtg gtgcgctcgt    7680
cgggcaccag gcgcacgcgc cagccgcggt tgtgcagggt gaccaggtcc acgctggtgg    7740
cgacctcgcc gcgcaggcgc tcgttggtcc agcagagacg gccgcccttg cgcgagcaga    7800 agggggggcag ggggtcgagc tgggtctcgt ccgggggggtc cgcgtccacg gtgaaaaccc    7860
cggggcgcag gcgcgcgtcg aagtagtcta tcttgcaacc ttgcatgtcc agcgcctgct    7920
gccagtcgcg ggcggcgagc gcgcgctcgt aggggttgag cggcgggccc cagggcatgg    7980
ggtgggtgag tgcggaggcg tacatgccgc agatgtcata gacgtagagg ggctcccgca    8040
ggaccccgat gtaggtgggg tagcagcggc cgccgcggat gctggcgcgc acgtagtcat    8100
acagctcgtg cgagggggcg aggaggtcgg ggcccaggtt ggtgcgggcg gggcgctccg    8160
cgcggaagac gatctgcctg aagatggcat gcgagttgga agagatggtg gggcgctgga    8220
```

-continued

```
agacgttgaa gctggcgtcc tgcaggccga cggcgtcgcg cacgaaggag gcgtaggagt    8280
cgcgcagctt gtgtaccagc tcggcggtga cctgcacgtc gagcgcgcag tagtcgaggg    8340
tctcgcggat gatgtcatat ttagcctgcc ccttcttttt ccacagctcg cggttgagga    8400
caaactcttc gcggtctttc cagtactctt ggatcgggaa accgtccggt tccgaacggt    8460
aagagcctag catgtagaac tggttgacgg cctggtaggc gcagcagccc ttctccacgg    8520
ggagggcgta ggcctgcgcg gccttgcgga gcgaggtgtg ggtcagggcg aaggtgtccc    8580
tgaccatgac tttgaggtac tggtgcttga agtcggagtc gtcgcagccg ccccgctccc    8640
agagcgagaa gtcggtgcgc ttcttggagc ggggttggg cagagcgaag gtgacatcgt     8700
tgaagaggat tttgcccgcg cggggcatga agttgcgggt gatgcggaag ggccccggca    8760
cttcagagcg gttgttgatg acctgggcgg cgagcacgat ctcgtcgaag ccgttgatgt    8820
tgtggcccac gatgtagagt tccaggaagc ggggccggcc ctttacggtg gcagcttct    8880
ttagctcttc gtaggtgagc tcctcgggcg aggcgaggcc gtgctcggcc agggcccagt    8940
ccgcgaggtg cgggttgtct ctgaggaagg acttccagag gtcgcgggcc aggagggtct    9000
gcaggcggtc tctgaaggtc ctgaactggc ggcccacggc catttttcg ggggtgatgc     9060
agtagaaggt gaggggtct tgctgccagc ggtcccagtc gagctgcagg gcgaggtcgc     9120
gcgcggcggt gaccaggcgc tcgtcgcccc cgaatttcat gaccagcatg aagggcacga    9180
gctgcttcc gaaggccccc atccaagtgt aggtctctac atcgtaggtg acaaagaggc     9240
gctccgtgcg aggatgcgag ccgatcggga agaactggat ctcccgccac cagttggagg    9300
agtggctgtt gatgtggtgg aagtagaagt cccgtcgccg ggcgaacac tcgtgctggc     9360
ttttgtaaaa gcgagcgcag tactggcagc gctgcacggg ctgtacctca tgcacgagat    9420
gcacctttcg cccgcgcacg aggaagccga ggggaaatct gagcccccg cctggctcgc     9480
ggcatggctg gttctcttct actttggatg cgtgtccgtc tccgtctggc cctcgaggg     9540
gtgttacggt ggagcggacc accacgccgc gcgagccgca ggtccagata tcggcgcgcg    9600
gcggtcggag tttgatgacg acatcgcgca gctgggagct gtccatggtc tggagctccc    9660
gcggcggcgc caggtcagcc gggagttctt gcaggttcac ctcgcagagt cgggccaggg    9720
cgcggggcag gtctaggtgg tacctgatct ctaggggcgt gttggtggcg cgtcgatgg     9780
cttgcaggag cccgcagccc cggggggcga cgacggtgcc ccgcggggtg gtggtggtgg    9840
tggcggtgca gctcagaagc ggtgccgcgg gcgggccccc ggaggtaggg ggggctccgg    9900
tcccgcgggc aggggcggca gcggcacgtc ggcgtggagc gcgggcagga gttggtgctg    9960
tgcccggagg ttgctggcga aggcgacgac gcggcggttg atctcctgga tctggcgcct    10020
ctgcgtgaag acgacgggcc cggtgagctt gaacctgaaa gagagttcga cagaatcaat    10080
ctcggtgtca ttgaccgcgg cctggcgcag gatctcctgc acgtctcccg agttgtcttg    10140
gtaggcgatc tcggccatga actgctcgat ctcttcctcc tggaggtctc gcgtccggc     10200
gcgttccacg gtgccgcca ggtcgttgga gatgcgcccc atgagctgcg agaaggcgtt     10260
gagtccgccc tcgttccaga ctcggctgta gaccacgccc ccctggtcat cgcgggcgcg    10320
catgaccacc tgcgcgaggt tgagctccac gtgccgcgcg aagacggcgt agttgcgcag    10380
acgctggaag aggtagttga gggtggtggc ggtgtgctcg gccacgaaga agttcatgac    10440
ccagcggcgc aacgtggatt cgttgatgtc ccccaaggcc tccagccgtt ccatggcctc    10500
gtagaagtcc acgcgaagt tgaaaaactg ggagttgcgc gccgacacgg tcaactcctc     10560
ctccagaaga cggatgagct cggcgacggt gtcgcgcacc tcgcgctcga aggctatggg    10620
```

```
gatctcttcc tccgctagca tcaccacctc ctcctcttcc tcctcttctg gcacttccat   10680
gatggcttcc tcctcttcgg ggggtggcgg cggcggcggt gggggagggg gcgctctgcg   10740
ccggcggcgg cgcaccggga ggcggtccac gaagcgcgcg atcatctccc cgcggcggcg   10800
gcgcatggtc tcggtgacgg cgcggccgtt ctcccggggg cgcagttgga agacgccgcc   10860
ggacatctgg tgctggggcg ggtggccgtg aggcagcgag acggcgctga cgatgcatct   10920
caacaattgc tgcgtaggta cgccgccgag ggacctgagg gagtccatat ccaccggatc   10980
cgaaaacctt tcgaggaagg cgtctaacca gtcgcagtcg caaggtaggc tgagcaccgt   11040
ggcgggcggc gggggtggg gggagtgtct ggcggaggtg ctgctgatga tgtaattgaa    11100
gtaggcggac ttgacacggc ggatggtcga caggagcacc atgtccttgg gtccggcctg   11160
ctggatgcgg aggcggtcgg ctatgcccca ggcttcgttc tggcatcggc gcaggtcctt   11220
gtagtagtct tgcatgagcc tttccaccgg cacctcttct ccttcctctt ctgcttcttc   11280
catgtctgct tcggcctgg gcggcgccg cgccccctg cccccatgc gcgtgacccc       11340 gaacccctg agcggttgga gcagggccag gtcggcgacg acgcgctcgg ccaggatggc    11400
ctgctgcacc tgcgtgaggg tggtttggaa gtcatccaag tccacgaagc ggtggtaggc   11460
gcccgtgttg atggtgtagg tgcagttggc catgacggac cagttgacgg tctggtggcc   11520
cggttgcgac atctcggtgt acctgagtcg cgagtaggcg cggagtcga agacgtagtc    11580 gttgcaagtc cgcaccaggt actggtagcc caccaggaag tgcggcggcg gctggcggta   11640
gaggggccag cgcagggtgg cggggctcc ggggccagg tcttccagca tgaggcggtg     11700
gtaggcgtag atgtacctgg acatccaggt gatacccgcg gcggtggtgg aggcgcgcgg   11760
gaagtcgcgc acccggttcc agatgttgcg caggggcaga aagtgctcca tggtaggcgt   11820
gctctgtcca gtcagacgcg cgcagtcgtt gatactctag accagggaaa acgaaagccg   11880
gtcagcgggc actcttccgt ggtctggtga atagatcgca agggtatcat ggcggagggc   11940
ctcggttcga gccccgggtc cgggccggac ggtccgccat gatccacgcg gttaccgccc   12000
gcgtgtcgaa cccaggtgtg cgacgtcaga caacggtgga gtgttccttt tggcgttttt   12060
ctggccgggc gccggcgccg cgtaagagac taagccgcga aagcgaaagc agtaagtggc   12120
tcgctccccg tagccggagg gatccttgct aagggttgcg ttgcggcgaa ccccggttcg   12180
aatcccgtac tcgggccggc cggacccgcg gctaaggtgt tggattggcc tcccctcgt    12240 ataaagaccc cgcttgcgga ttgactccgg acacggggac gagccccttt tattttgct    12300 ttccccagat gcatccggtg ctgcggcaga tgcgcccccc gccccagcag cagcaacaac   12360
accagcaaga gcggcagcaa cagcagcggg agtcatgcag ggccccctca cccacccctcg  12420 gcgggccggc cacctcggcg tccgcggccg tgtctggcgc ctgcggcggc ggcggggggc   12480
cggctgacga ccccgaggag ccccgcggc gcagggccag acactacctg gacctggagg    12540
agggcgaggg cctggcgcgg ctgggggcgc cgtctcccga gcgccacccg cgggtgcagc   12600
tgaagcgcga ctcgcgcgag gcgtacgtgc ctcggcagaa cctgttcagg gaccgcgcgg   12660
gcgaggagcc cgaggagatg cgggacagga ggttcagcgc agggcgggag ctgcggcagg   12720
ggctgaaccg cgagcggctg ctgcgcgagg aggactttga gcccgacgcg cggacgggga   12780
tcagccccgc gcgcgcgcac gtggcggccg ccgacctggt gacggcgtac gagcagacgg   12840
tgaaccagga gatcaacttc caaaagagtt caacaaccca cgtgcgcacg ctggtggcgc   12900
gcgaggaggt gaccatcggg ctgatgcacc tgtgggactt tgtaagcgcg ctggtgcaga   12960
```

```
accccaacag caagcctctg acggcgcagc tgttcctgat agtgcagcac agcagggaca   13020
acgaggcgtt tagggacgcg ctgctgaaca tcaccgagcc cgagggtcgg tggctgctgg   13080
acctgattaa catcctgcag agcatagtgg tgcaggagcg cagcctgagc ctggccgaca   13140
aggtggcggc catcaactac tcgatgctga gcctgggcaa gttttacgcg cgcaagatct   13200
accagacgcc gtacgtgccc atagacaagg aggtgaagat cgacggtttt tacatgcgca   13260
tggcgctgaa ggtgctcacc ctgagcgacg acctgggcgt gtaccgcaac gagcgcatcc   13320
acaaggccgt gagcgtgagc cggcggcgcg agctgagcga ccgcgagctg atgcacagcc   13380
tgcagcgggc gctggcgggc gccggcagcg cgacaggga ggcggagtcc tacttcgatg   13440
cggggggcgga cctgcgctgg gcgcccagcc ggcgggccct ggaggccgcg ggggtccgcg   13500
aggactatga cgaggacggc gaggaggatg aggagtacga gctagaggag ggcgagtacc   13560
tggactaaac cgcgggtggt gtttccggta gatgcaagac ccgaacgtgg tggacccggc   13620
gctgcgggcg gctctgcaga gccagccgtc cggccttaac tcctcagacg actggcgaca   13680
ggtcatggac cgcatcatgt cgctgacggc gcgtaacccg gacgcgttcc ggcagcagcc   13740
gcaggccaac aggctctccg ccatcctgga ggcggtggtg cctgcgcgct cgaacccacc   13800
gcacgagaag gtgctggcca tagtgaacgc gctggccgag aacagggcca tccgcccgga   13860
cgaggccggg ctggtgtacg acgcgctgct gcagcgcgtg gcccgctaca acagcggcaa   13920
cgtgcagacc aacctggacc ggctggtggg ggacgtgcgc gaggcggtgg cgcagcgcga   13980
gcgcgcggat cggcagggca acctgggctc catggtggcg ctgaatgcct tcctgagcac   14040
gcagccggcc aacgtgccgc gggggcagga agactacacc aactttgtga gcgcgctgcg   14100
gctgatggtg accgagaccc cccagagcga ggtgtaccag tcgggcccgg actacttctt   14160
ccagaccagc agacagggcc tgcagacggt gaacctgagc caggctttca gaacctgcgg   14220
ggggctgtgg ggcgtgaagg cgcccaccgg cgaccgggcg acggtgtcca gcctgctgac   14280
gcccaactcg cgcctgctgc tgctgctgat cgcgccgttc acggacagcg gcagcgtgtc   14340
ccgggacacc tacctggggc acctgctgac cctgtaccgc gaggccatcg gcaggcgca   14400
ggtggacgag cacaccttcc aggagatcac cagcgtgagc cgcgcgctgg ggcaggagga   14460
cacgagcagc ctggaggcga ctctgaacta cctgctgacc aaccggcggc agaagattcc   14520
ctcgctgcac agcctgacct ccgaggagga gcgcatcttg cgctacgtgc agcagagcgt   14580
gagcctgaac ctgatgcgcg acggggtgac gcccagcgtg gcgctggaca tgaccgcgcg   14640
caacatggaa ccgggcatgt acgccgcgca ccggccttac atcaaccgcc tgatggacta   14700
cctgcatcgc gcggcggccg tgaaccccga gtactttacc aacgccatcc tgaacccgca   14760
ctggctcccg ccgcccgggt tctacagcgg gggcttcgag gtcccggaga ccaacgatgg   14820
cttcctgtgg gacgacatgg acgacagcgt gttctccccg cggccgcagg cgctggcgga   14880
agcgtccctg ctgcgtccca agaaggagga ggaggaggag gcgagtcgcc gccgcggcag   14940
cagcggcgtg gcttctctgt ccgagctggg ggcggcagcc gccgcgcgcc ccgggtccct   15000
gggcggcagc ccctttccga gcctggtggg gtctctgcac agcgagcgca ccacccgccc   15060
tcggctgctg ggcgaggacg agtacctgaa taactcctg ctgcagccgg tgcgggaaa    15120
aaacctgcct cccgccttcc ccaacaacgg gatagagagc ctggtggaca agatgagcag   15180
atggaagacc tatgcgcagg agcacaggga cgcgcctgcg ctccggccgc ccacgcggcg   15240
ccagcgccac gaccggcagc gggggctggt gtgggatgac gaggactccg cggacgatag   15300
cagcgtgctg gacctgggag ggagcggcaa cccgttcgcg cacctgcgcc ccgcctggg    15360
```

```
gaggatgttt taaaaaaaaa aaaaaaangc aagaagcatg atgcaaaaat taaataaaac   15420
tcaccaaggc catggcgacc gagcgttggt ttcttgtgtt cccttcagta tgcggcgcgc   15480
ggcgatgtac caggagggac ctcctccctc ttacgagagc gtggtgggcg cggcggcggc   15540
ggcgccctct tctcccttttg cgtcgcagct gctggagccg ccgtacgtgc ctccgcgcta   15600
cctgcggcct acgggggga gaaacagcat ccgttactcg gagctggcgc ccctgttcga   15660
caccacccgg gtgtacctgg tggacaacaa gtcggcggac gtggcctccc tgaactacca   15720
gaacgaccac agcaattttt tgaccacggt catccagaac aatgactaca gcccgagcga   15780
ggccagcacc cagaccatca atctggatga ccggtcgcac tggggcggcg acctgaaaac   15840
catcctgcac accaacatgc ccaacgtgaa cgagttcatg ttcaccaata agttcaaggc   15900
gcgggtgatg tgtcgcgct cgcacaccaa ggaagaccgg gtggagctga agtacgagtg   15960
ggtggagttc gagctgccag agggcaacta ctccgagacc atgaccattg acctgatgaa   16020
caacgcgatc gtggagcact atctgaaagt gggcaggcag aacggggtcc tggagagcga   16080
catcggggtc aagttcgaca ccaggaactt ccgcctgggg ctggaccccg tgaccgggct   16140
ggttatgccc ggggtgtaca ccaacgaggc cttccatccc gacatcatcc tgctgccgg   16200 ctgcgggtg gacttcactt acagccgcct gagcaacctc ctgggcatcc gcaagcggca   16260
gcccttccag gagggcttca ggatcaccta cgaggacctg gaggggggca acatccccgc   16320
gctcctcgat gtggaggcct accaggatag cttgaaggaa aatgaggcgg acaggagga   16380 taccgccccc gccgcctccg ccgccgccga gcagggcgag gatgctgctg acaccgcggc   16440
cgcggacggg gcagaggccg accccgctat ggtggtggag gctcccgagc aggaggagga   16500
catgaatgac agtgcggtgc gcggagacac cttcgtcacc cgggggagg aaaagcaagc   16560 ggaggccgag gccgcggccg aggaaaagca actggcggca gcagcggcgg cggcggcgtt   16620
ggccgcggcg gaggctgagt ctgagggac caagcccgcc aaggagcccg tgattaagcc   16680
cctgaccgaa gatagcaaga agcgcagtta caacctgctc aaggacagca ccaacaccgc   16740
gtaccgcagc tggtacctgg cctacaacta cggcgacccg tcgacggggg tgcgctcctg   16800
gaccctgctg tgcacgccgg acgtgacctg cggctcggag caggtgtact ggtcgctgcc   16860
cgacatgatg caagcccccg tgaccttccg ctccacgcgg caggtcagca acttcccggt   16920
ggtgggcgcc gagctgctgc ccgtgcactc caagagcttc tacaacgacc aggccgtcta   16980
ctcccagctc atccgccagt tcacctctct gacccacgtg ttcaatcgct ttcctgagaa   17040
ccagattctg gcgcgcccgc ccgccccac catcaccacc gtcagtgaaa cgttcctgc   17100 tctcacagat cacgggacgc taccgctgcg caacagcatc ggaggagtcc agcgagtgac   17160
cgttactgac gccagacgcc gcacctgccc ctacgtttac aaggccttgg gcatagtctc   17220
gccgcgcgtc ctttccagcc gcacttttttg agcaacacca ccatcatgtc catcctgatc   17280
tcacccagca ataactccgg ctggggactg ctgcgcgcgc ccagcaagat gttcggaggg   17340
gcgaggaagc gttccgagca gcaccccgtg cgcgtgcgcg ggcacttccg cgccccctgg   17400
ggagcgcaca aacgcggccg cgcgggggcgc accaccgtgg acgacgccat cgactcggtg   17460
gtggagcagg cgcgcaacta caggcccgcg gtctctaccg tggacgcggc catccagacc   17520
gtggtgcggg gcgcgcggcg gtacgccaag ctgaagagcc gccggaagcg cgtggcccgc   17580
cgccaccgcc gccgacccgg ggccgccgcc aaacgcgccg ccgcggccct gcttcgccgg   17640
gccaagcgca cgggccgccg cgccgccatg agggccgcgc gccgcttggc cgccggcatc   17700
```

```
accgccgcca ccatggcccc ccgtacccga agacgcgcgg ccgccgccgc cgccgccgcc   17760
atcagtgaca tggccagcag gcgccggggc aacgtgtact gggtgcgcga ctcggtgacc   17820
ggcacgcgcg tgcccgtgcg cttccgcccc ccgcggactt gagatgatgt gaaaaaacaa   17880
cactgagtct cctgctgttg tgtgtatccc agcggcggcg gcgcgcgcag cgtcatgtcc   17940
aagcgcaaaa tcaaagaaga gatgctccag gtcgtcgcgc cggagatcta tgggcccccg   18000
aagaaggaag agcaggattc gaagcccgc aagataaagc gggtcaaaaa gaaaagaaa    18060 gatgatgacg atgccgatgg ggaggtggag ttcctgcgcg ccacggcgcc caggcgcccg   18120
gtgcagtgga agggccggcg cgtaaagcgc gtcctgcgcc ccggcaccgc ggtggtcttc   18180
acgcccggcg agcgctccac ccggactttc aagcgcgtct atgacgaggt gtacggcgac   18240
gaagacctgc tggagcaggc caacgagcgc ttcggagagt ttgcttacgg gaagcgtcag   18300
cgggcgctgg ggaaggagga cctgctggcg ctgccgctgg accagggcaa ccccaccccc   18360
agtctgaagc ccgtgaccct gcagcaggtg ctgccgagca gcgcaccctc cgaggcgaag   18420
cggggtctga agcgcgaggg cggcgacctg gcgcccaccg tgcagctcat ggtgcccaag   18480
cggcagaggc tggaggatgt gctggagaaa atgaaagtag accccggtct gcagccggac   18540
atcagggtcc gccccatcaa gcaggtggcg ccgggcctcg gcgtgcagac cgtggacgtg   18600
gtcatcccca ccggcaactc cccgccgcc gccaccacta ccgctgcctc cacggacatg   18660
gagacacaga ccgatcccgc cgcagccgca gccgcagccg ccgccgcgac ctcctcggcg   18720
gaggtgcaga cggaccctg gctgccgccg gcgatgtcag ctccccgcgc gcgtcgcggg   18780
cgcaggaagt acgcgccgc caacgcgctc ctgcccgagt acgccttgca tccttccatc   18840
gcgcccaccc ccggctaccg aggctatacc taccgcccgc gaagagccaa gggttccacc   18900
cgccgtcccc gccgacgcgc cgccgccacc cccgccgcc gccgccgcag acgccagccc   18960
gcactggctc cagtctccgt gaggaaagtg gcgcgcgacg acacaccct ggtgctgccc    19020 agggcgcgct accaccccag catcgtttaa aagcctgttg tggttcttgc agatatggcc   19080
ctcacttgcc gcctccgttt cccggtgccg ggataccgag gaggaagatc gcgccgcagg   19140
aggggtctgg ccggccgcgg cctgagcgga ggcagccgcc gcgcgcaccg gcggcgacgc   19200
gccaccagcc gacgcatgcg cggcggggtg ctgcccctgt taatccccct gatcgccgcg   19260
gcgatcggcg ccgtgcccgg gatcgcctcc gtggccttgc aagcgtccca gaggcattga   19320
cagacttgca aacttgcaaa tatggaaaaa aaaacccaa taaaaagtc tagactctca    19380 cgctcgcttg gtcctgtgac tattttgtag aatggaagac atcaactttg cgtcgctggc   19440
cccgcgtcac ggctcgcgcc cgttcctggg acactggaac gatatcggca ccagcaacat   19500
gagcggtggc gccttcagtt ggggctctct gtggagcggc attaaaagta tcgggtctgc   19560
cgttaaaaat tacggctccc gggcctggaa cagcagcacg ggccagatgt tgagagacaa   19620
gttgaaagag cagaacttcc agcagaaggt ggtggagggc ctggcctccg gcatcaacgg   19680
ggtggtggac ctgccaacc aggccgtgca gaataagatc aacagcagac tggaccccg     19740 gccgccggtg gaggaggtgc cgccggcgct ggagacggtg tccccgatg ggcgtggcga    19800 gaagcgcccg cggcccgata gggaagagac cactctggtc acgcagaccg atgagccgcc   19860
cccgtatgag gaggccctga agcaaggtct gcccaccacg cggcccatcg cgcccatggc   19920 caccgggggtg gtgggccgcc acaccccgc cacgctggac ttgcctccgc ccgccgatgt   19980
gccgcagcag cagaaggcgg cacagccggg cccgcccgcg accgcctccc gttcctccgc   20040
cggtcctctg cgccgcgcgg ccagcggccc ccgcgggggg gtcgcgaggc acggcaactg   20100
```

```
gcagagcacg ctgaacagca tcgtgggtct gggggtgcgg tccgtgaagc gccgccgatg    20160
ctactgaata gcttagctaa cgtgttgtat gtgtgtatgc gccctatgtc gccgccagag    20220
gagctgctga gtcgccgccg ttcgcgcgcc caccaccacc gccactccgc ccctcaagat    20280
ggcgacccca tcgatgatgc cgcagtggtc gtacatgcac atctcgggcc aggacgcctc    20340
ggagtacctg agccccgggc tggtgcagtt cgcccgcgcc accgagagct acttcagcct    20400
gagtaacaag tttaggaacc ccacggtggc gcccacgcac gatgtgacca ccgaccggtc    20460
tcagcgcctg acgctgcggt tcattcccgt ggaccgcgag gacaccgcgt actcgtacaa    20520
ggcgcggttc accctggccg tgggcgacaa ccgcgtgctg gacatggcct ccacctactt    20580
tgacatccgc ggggtgctgg accggggtcc cactttcaag ccctactctg gcaccgccta    20640
caactccctg gcccccaagg gcgctcccaa ctcctgcgcg tgggagcaag aggaaactca    20700
ggcagttgaa gaagcagcag aagaggaaga agaagatgct gacggtcaag ctgaggaaga    20760
gcaagcagct accaaaaaga ctcatgtata tgctcaggct ccccttcctg gcgaaaaaat    20820
tagtaaagat ggtctgcaaa taggaacgga cgctacagct acagaacaaa aacctattta    20880
tgcagaccct acattccagc ccgaaccca aatcggggag tcccagtgga atgaggcaga    20940
tgctacagtc gccggcggta gagtgctaaa gaaatctact cccatgaaac catgctatgg    21000
ttcctatgca agacccacaa atgctaatgg aggtcagggt gtactaacgg caaatgccca    21060
gggacagcta gaatctcagg ttgaaatgca attcttttca acttctgaaa cgcccgtaa    21120 cgaggctaac aacattcagc ccaaattggt gctgtatagt gaggatgtgc acatggagac    21180
cccggatacg caccttctt acaagcccgc aaaaagcgat gacaattcaa aaatcatgct    21240
gggtcagcag tccatgccca acagacctaa ttacatcggc ttcagagaca ctttatcgg    21300 cctcatgtat tacaatagca ctggcaacat gggagtgctt gcaggtcagg cctctcagtt    21360
gaatgcagtg gtggacttgc aagacagaaa cacagaactg tcctaccagc tcttgcttga    21420
ttccatgggt gacagaacca gatactttc catgtggaat caggcagtgg acagttatga    21480
cccagatgtt agaattattg aaaatcatgg aactgaagac gagctcccca actattgttt    21540
ccctctgggt ggcataggg taactgacac ttaccaggct gttaaaacca acaatggcaa    21600
taacgggggc caggtgactt ggacaaaaga tgaaactttt gcagatcgca atgaaatagg    21660
ggtgggaaac aatttcgcta tggagatcaa cctcagtgcc aacctgtgga gaaacttcct    21720
gtactccaac gtggcgctgt acctaccaga caagcttaag tacaaccct ccaatgtgga    21780 catctctgac aaccccaaca cctacgatta catgaacaag cgagtggtgg ccccggggct    21840
ggtggactgc tacatcaacc tgggcgcgcg ctggtcgctg gactacatgg acaacgtcaa    21900
ccccttcaac caccaccgca atgcgggcct gcgctaccgc tccatgctcc tgggcaacgg    21960
gcgctacgtg cccttccaca tccaggtgcc ccagaagttc tttgccatca gaacctcct    22020 cctcctgccg ggctcctaca cctacgagtg gaacttcagg aaggatgtca catggtcct    22080 ccagagctct ctgggtaacg atctcagggt ggacggggcc agcatcaagt tcgagagcat    22140
ctgcctctac gccaccttct tccccatggc ccacaacacg gcctcacgc tcgaggccat    22200 gctcaggaac gacaccaacg accagtcctt caatgactac ctctccgccg ccacatgct    22260 ctaccccata cccgccaacg ccaccaacgt ccccatctcc atcccctcgc gcaactgggc    22320
ggccttccgc ggctgggcct tcacccgcct caagaccaag agacccccct ccctgggctc    22380
gggattcgac ccctactaca cctactcggg ctccattccc tacctggacg gcaccttcta    22440
```

```
cctcaaccac actttcaaga aggtctcggt caccttcgac tcctcggtca gctggccggg    22500
caacgaccgt ctgctcaccc ccaacgagtt cgagatcaag cgctcggtcg acggggaggg    22560
ctacaacgtg gcccagtgca acatgaccaa ggactggttc ctggtccaga tgctggccaa    22620
ctacaacatc ggctaccagg gcttctacat cccagagagc tacaaggaca ggatgtactc    22680
cttcttcagg aacttccagc ccatgagccg gcaggtggtg gaccagacca agtacaagga    22740
ctaccaggag gtgggcatca tccaccagca caacaactcg ggcttcgtgg gctacctcgc    22800
ccccaccatg cgcgagggac aggcctaccc cgccaacttc ccctatccgc tcataggcaa    22860
gaccgcggtc gacagcatca cccagaaaaa gttcctctgc gaccgcaccc tctggcgcat    22920 cccccttctcc agcaacttca tgtccatggg tgcgctctcg gacctgggcc agaacttgct    22980
ctacgccaac tccgcccacg ccctcgacat gaccttcgag gtcgacccca tggacgagcc    23040 caccttctc tatgttctgt tcgaagtctt tgacgtggtc cgggtccacc agccgcaccg    23100
cggcgtcatc gagaccgtgt acctgcgtac gcccttctcg gccggcaacg ccaccaccta    23160
aagaagcaag ccgcagtcat cgccgcctgc atgccgtcgg gttccaccga gcaagagctc    23220
agggccatcg tcagagacct gggatgcggg ccctattttt tgggcaccttc cgacaagcgc    23280 ttccctggct ttgtctcccc acacaagctg gcctgcgcca tcgtcaacac ggccggccgc    23340
gagaccgggg gcgtgcactg gctggccttc gcctggaacc gcgctccaa aacatgcttc    23400 ctctttgacc ccttcggctt ttcggaccag cggctcaagc aaatctacga gttcgagtac    23460
gagggcttgc tgcgtcgcag cgccatcgcc tcctcgcccg accgctgcgt caccctcgaa    23520
aagtccaccc agaccgtgca ggggcccgac tcggccgcct gcggtctctt ctgctgcatg    23580
tttctgcacg ccttgtgtgca ctggcctcag agtcccatgg accgcaaccc caccatgaac    23640
ttgctgacgg gggtgcccaa ctccatgctc cagagccccc aggtcgagcc caccctgcgc    23700
cgcaaccagg agcagctcta cagcttcctg gagcgccact cgccttactt ccgccgccac    23760
agcgcacaga tcaggagggc cacctccttc tgccacttgc aagagatgca agaagggtaa    23820
taacgatgta cacactttt ttctcaataa atggcatctt tttatttata caagctctct    23880
ggggtattca tttcccacca ccacccgccg ttgtcgccat ctggctctat ttagaaatcg    23940
aaagggttct gccgggagtc gccgtgcgcc acgggcaggg acacgttgcg atactggtag    24000
cgggtgcccc acttgaactc gggcaccacc aggcgaggca gctcgggaa gttttcgctc    24060 cacaggctgc gggtcagcac cagcgcgttc atcaggtcgg gcgccgagat cttgaagtcg    24120
cagttggggc cgccgccctg cgcgcgcgag ttgcggtaca ccgggttgca gcactggaac    24180
accaacagcg ccgggtgctt cacgctggcc agcacgctgc ggtcggagat cagctcggcg    24240
tccaggtcct ccgcgttgct cagcgcgaac ggggtcatct tgggcacttg ccgccccagg    24300
aagggcgcgt gccccggttt cgagttgcag tcgcagcgca gcgggatcag caggtgcccg    24360
tgcccggact cggcgttggg gtacagcgcg cgcatgaagg cctgcatctg gcggaaggcc    24420
atctgggcct tggcgccctc cgagaagaac atgccgcagg acttgcccga gaactggttt    24480
gcggggcagc tggcgtcgtg caggcagcag cgcgcgtcgg tgttggcgat ctgcaccacg    24540
ttgcgccccc accggttctt cacgatcttg gccttggacg attgctcctt cagcgcgcgc    24600
tgcccgttct cgctggtcac atccatctcg atcacatgtt ccttgttcac catgctgctg    24660
ccgtgcagac acttcagctc gccctccgtc tcggtcagc ggtgctgcca cagcgcgcag    24720
cccgtgggct cgaaagactt gtaggtcacc tccgcgaagg actgcaggta cccctgcaaa    24780
aagcggccca tcatggtcac gaaggtcttg ttgctgctga aggtcagctg cagcccgcgg    24840
```

```
tgctcctcgt tcagccaggt cttgcacacg gccgccagcg cctccacctg gtcgggcagc    24900
atcttgaagt tcaccttcag ctcattctcc acgtggtact tgtccatcag cgtgcgcgcc    24960
gcctccatgc ccttctccca ggccgacacc agcggcaggc tcacggggtt cttcaccatc    25020
accgtggccg ccgcctccgc cgcgcttccg ctttccgccc cgctgttctc ttcctcttcc    25080
tcctcttcct cgccgccgcc cactcgcagc ccccgcacca cggggtcgtc ttcctgcagg    25140
cgctgcacct tgcgcttgcc gttgcgcccc tgcttgatgc gcacgggcgg gttgctgaag    25200
cccaccatca ccagcgcggc ctcttcttgc tcgtcctcgc tgtccagaat gacctccggg    25260
gagggggggt tggtcatcct cagtaccgag gcacgcttct ttttcttcct gggggcgttc    25320
gccagctccg cggctgcggc cgctgccgag gtcgaaggcc gagggctggg cgtgcgcggc    25380
accagcgcgt cctgcgagcc gtcctcgtcc tcctcggact cgagacggag gcgggcccgc    25440
ttcttcgggg gcgcgcgggg cggcggaggc ggcggcggcg acggagacgg ggacgagaca    25500
tcgtccaggg tgggtggacg gcgggccgcg ccgcgtccgc gctcggggt ggtctcgcgc     25560 tggtcctctt cccgactggc catctcccac tgctccttct cctataggca gaaagagatc    25620
atggagtctc tcatgcgagt cgagaaggag gaggacagcc taaccgcccc ctctgagccc    25680
tccaccaccg ccgccaccac cgccaatgcc gccgcggacg acgcgcccac cgagaccacc    25740
gccagtacca ccctccccag cgacgcaccc ccgctcgaga tgaagtgct  gatcgagcag    25800 gacccgggtt ttgtgagcgg agaggaggat gaggtggatg agaaggagaa ggaggaggtc    25860
gccgcctcag tgccaaaaga ggataaaaag caagaccagg acgacgcaga taaggatgag    25920
acagcagtcg ggcggggggaa cggaagccat gatgctgatg acggctacct agacgtggga    25980
gacgacgtgc tgcttaagca cctgcaccgc cagtgcgtca tcgtctgcga cgcgctgcag    26040
gagcgctgcg aagtgcccct ggacgtggcg gaggtcagcc gcgcctacga gcggcacctc    26100
ttcgcgccgc acgtgccccc caagcgccgg gagaacggca cctgcgagcc caacccgcgt    26160
ctcaacttct acccggtctt cgcggtaccc gaggtgctgg ccacctacca catcttttc    26220 caaaactgca agatccccct ctcctgccgc gccaaccgca cccgcgccga caaaaccctg    26280
accctgcggc agggcgccca catacctgat atcgcctctc tggaggaagt gcccaagatc    26340
ttcgagggtc tcggtcgcga cgagaaacgg gcggcgaacg ctctgcacgg agacagcgaa    26400
aacgagagtc actcggggt gctggtggag ctcgagggcg acaacgcgcg cctggccgta    26460
ctcaagcgca gcatagaggt cacccacttt gcctacccgg cgctcaacct gccccccaag    26520
gtcatgagtg tggtcatggg cgagctcatc atgcgccgcg cccagcccct ggccgcggat    26580
gcaaacttgc aagagtcctc cgaggaaggc ctgcccgcgg tcagcgacga gcagctggcg    26640
cgctggctgg agacccgcga ccccgcgcag ctggaggagc ggcgcaagct catgatggcc    26700
gcggtgctgg tcaccgtgga gctcgagtgt ctgcagcgct tcttcgcgga ccccgagatg    26760
cagcgcaagc tcgaggagac cctgcactac accttccgcc agggctacgt gcgccaggcc    26820
tgcaagatct ccaacgtgga gctctgcaac ctggtctcct acctgggcat cctgcacgag    26880
aaccgcctcg gcagaacgt  cctgcactcc accctcaaag gggaggcgcg ccgcgactac    26940
atccgcgact gcgcctacct cttcctctgc tacacctggc agacggccat gggggtctgg    27000
cagcagtgcc tggaggagcg caacctcaag gagctggaaa agctcctcaa gcgcaccctc    27060
agggacctct ggacgggctt caacgagcgc tcggtgccg ccgcgctggc ggacatcatc    27120
tttcccgagc gcctgctcaa gaccctgcag cagggcctgc ccgacttcac cagccagagc    27180
```

```
atgctgcaga acttcaggac tttcatcctg gagcgctcgg gcatcctgcc ggccacttgc   27240
tgcgcgctgc ccagcgactt cgtgcccatc aagtacaggg agtgcccgcc gccgctctgg   27300
ggccactgct acctcttcca gctggccaac tacctcgcct accactcgga cctcatggaa   27360
gacgtgagcg gcgagggcct gctcgagtgc cactgccgct gcaacctctg cacgccccac   27420
cgctctctag tctgcaaccc gcagctgctc agcgagagtc agattatcgg taccttcgag   27480
ctgcagggtc cctcgcctga cgagaagtcc gcggctccag ggctgaaact cactccgggg   27540
ctgtggactt ccgcctacct acgcaaattt gtacctgagg actaccacgc ccacgagatc   27600
aggttctacg aagaccaatc ccgcccgccc aaggcggagc tcaccgcctg cgtcatcacc   27660
caggggcaca tcctgggcca attgcaagcc atcaacaaag cccgccgaga gttcttgctg   27720
aaaaagggtc gggggtgta cctggacccc cagtccggcg aggagctaaa cccgctaccc   27780
ccgccgccgc cccagcagcg ggaccttgct tcccaggatg gcacccagaa agaagcagca   27840
gccgccgccg ccgccgcagc catacatgct tctggaggaa gaggaggagg actgggacag   27900
tcaggcagag gaggtttcgg acgaggagca ggaggagatg atggaagact gggaggagga   27960
cagcagccta gacgaggaag cttcagaggc cgaagaggtg gcagacgcaa caccatcgcc   28020
ctcggtcgca gcccctcgc cggggcccct gaaatcctcc gaacccagca ccagcgctat   28080
aacctccgct cctccggcgc cggcgccacc cgcccgcaga cccaaccgta gatgggacac   28140
cacaggaacc ggggtcggta agtccaagtg cccgccgccg ccaccgcagc agcagcagca   28200
gcagcgccag ggctaccgct cgtggcgcgg gcacaagaac gccatagtcg cctgcttgca   28260
agactgcggg gcaacatct cttcgcccg ccgcttcctg ctattccacc acggggtcgc   28320
cttcccccgc aatgtcctgc attactaccg tcatctctac agccctact gcagcggcga   28380
cccagaggcg gcagcggcag ccacagcggc gaccaccacc taggaagata tcctccgcgg   28440
gcaagacagc ggcagcagcg gccaggagac ccgcggcagc agcggcggga cggtgggcg   28500
cactgcgcct ctcgcccaac gaaccccctct cgacccggga gctcagacac aggatcttcc   28560
ccactttgta tgccatcttc caacagagca gaggccagga gcaggagctg aaaataaaaa   28620
acagatctct gcgctccctc acccgcagct gtctgtatca caaaagcgaa gatcagcttc   28680
ggcgcacgct ggaggacgcg gaggcactct tcagcaaata ctgcgcgctc actcttaaag   28740
actagctccg cgcccttctc gaatttaggc gggagaaaac tacgtcatcg ccggccgccg   28800
cccagcccgc ccagccgaga tgagcaaaga gattcccacg ccatacatgt ggagctacca   28860
gccgcagatg ggactcgcgg cgggagcggc ccaggactac tccacccgca tgaactacat   28920
gagcgcggga ccccacatga tctcacaggt caacgggatc cgcgcccagc gaaaccaaat   28980
actgctggaa caggcggcca tcaccgccac gccccgccat aatctcaacc cccgaaattg   29040
gcccgccgcc ctcgtgtacc aggaaacccc ctccgccacc accgtactac ttccgcgtga   29100
cgccaggcc gaagtccaga tgactaactc aggggcgcag ctcgcgggcg gctttcgtca   29160
cggggcgcgg ccgctccgac caggtataag acacctgatg atcagaggcc gaggtatcca   29220
gctcaacgac gagtcggtga gctcttcgct cggtctccgt ccggacggaa cttctccagct   29280
cgccggatcc ggccgctctt cgttcacgcc ccgccaggcg tacctgactc tgcagacctc   29340
gtcctcggag ccccgctccg gcggcatcgg aaccctccag ttcgtggagg agttcgtgcc   29400
ctcggtctac ttcaacccct tctcgggacc tccggacgc tacccgacc agttcattcc   29460
gaactttgac gcggtgaagg actcggcgga cggctacgac tgaatgtcag gtgtcgaggc   29520
agagcagctt cgcctgagac acctcgagca ctgccgccgc cacaagtgct tcgcccgcgg   29580
```

```
ttctggtgag ttctgctact ttcagctacc cgaggagcat accgaggggc cggcgcacgg   29640
cgtccgcctg accacccagg gcgaggttac ctgttccctc atccgggagt ttaccctccg   29700
tcccctgcta gtggagcggg agcggggtcc ctgtgtccta actatcgcct gcaactgccc   29760
taaccctgga ttacatcaag atctttgctg tcatctctgt gctgagttta ataaacgctg   29820
agatcagaat ctactggggc tcctgtcgcc atcctgtgaa cgccaccgtc ttcacccacc   29880
ccgaccaggc ccaggcgaac ctcacctgcg gtctgcatcg gagggccaag aagtacctca   29940
cctggtactt caacggcacc cccttgtgg tttacaacag cttcgacggg gacggagtct   30000
ccctgaaaga ccagctctcc ggtctcagct actccatcca caagaacacc ccctccaac   30060 tcttccctcc ctacctgccg ggaacctacg agtgcgtcac cggccgctgc acccacctca   30120
cccgcctgat cgtaaaccag agctttccgg gaacagataa ctccctcttc cccagaacag   30180
gaggtgagct caggaaactc cccggggacc agggcggaga cgtaccttcg acccttgtgg   30240
ggttaggatt ttttattacc gggttgctgg ctcttttaat caaagtttcc ttgagatttg   30300
ttctttcctt ctacgtgtat gaacacctca acctccaata actctaccct ttcttcggaa   30360
tcaggtgact tctctgaaat cgggcttggt gtgctgctta ctctgttgat tttttttcctt   30420 atcatactca gccttctgtg cctcaggctc gccgcctgct gcgcacacat ctatatctac   30480
tgctggttgc tcaagtgcag gggtcgccac ccaagatgaa caggtacatg gtcctatcga   30540
tcctaggcct gctggccctg gcggcctgca gcgccgccaa aaagagatt cctttgagg   30600 agcccgcttg caatgtaact ttcaagcccg agggtgacca atgcaccacc ctcgtcaaat   30660
gcgttaccaa tcatgagagg ctgcgcatcg actacaaaaa caaaactggc cagtttgcgg   30720
tctatagtgt gtttacgccc ggagacccct ctaactactc tgtcaccgtc ttccagggcg   30780
gacagtctaa gatattcaat tacactttcc cttttttatga gttatgcgat gcggtcatgt   30840
acatgtcaaa acagtacaac ctgtggcctc cctctcccca ggcgtgtgtg gaaaatactg   30900
ggtcttactg ctgtatggct ttcgcaatca ctacgctcgc tctaatctgc acggtgctat   30960
acataaaatt caggcagagg cgaatcttta tcgatgaaaa gaaaatgcct tgatcgctaa   31020
caccggcttt ctatctgcag aatgaatgca atcacctccc tactaatcac caccaccctc   31080
cttgcgattg cccatgggtt gacacgaatc gaagtgccag tggggtccaa tgtcaccatg   31140
gtgggccccg ccggcaattc cacccctcatg tgggaaaaat ttgtccgcaa tcaatgggtt   31200
catttctgct ctaaccgaat cagtatcaag cccagagcca tctgcgatgg gcaaaatcta   31260
actctgatca atgtgcaaat gatggatgct gggtactatt acgggcagcg gggagaaatc   31320
attaattact ggcgaccccca caaggactac atgctgcatg tagtcgaggc acttcccact   31380
accaccccca ctaccacctc tcccaccacc accaccacta ctactactac tactactact   31440
actactacta ccactaccgc tgcccgccat acccgcaaaa gcaccatgat tagcacaaag   31500 cccccctcgtg ctcactccca cgccggcggg cccatcggtg cgacctcaga aaccaccgag   31560
ctttgcttct gccaatgcac taacgccagc gctcatgaac tgttcgacct ggagaatgag   31620
gatgtccagc agagctccgc ttgcctgacc caggaggctg tggagcccgt tgccctgaag   31680
cagatcggtg attcaataat tgactcttct tcttttgcca ctcccgaata ccctcccgat   31740
tctactttcc acatcacggg taccaaagac cctaacctct cttctacct gatgctgctg   31800 ctctgtatct ctgtggtctc ttccgcgctg atgttactgg ggatgttctg ctgcctgatc   31860
tgccgcagaa agagaaaagc tcgctctcag ggccaaccac tgatgcccctt cccctacccc   31920
```

```
ccggattttg cagataacaa gatatgagct cgctgctgac actaaccgct ttactagcct   31980
gcgctctaac ccttgtcgct tgcgactcga gattccacaa tgtcacagct gtggcaggag   32040
aaaatgttac tttcaactcc acggccgata cccagtggtc gtggagtggc tcaggtagct   32100
acttaactat ctgcaatagc tccacttccc ccggcatatc cccaaccaag taccaatgca   32160
atgccagcct gttcacccte atcaacgctt ccaccctgga caatggactc tatgtaggct   32220
atgtaccctt tggtgggcaa ggaaagaccc acgcttacaa cctggaagtt cgccagccca   32280
gaaccactac ccaagcttct cccaccacca ccaccaccac caccatcacc agcagcagca   32340
gcagcagcag ccacacgcagc agcagcagat tattgacttt ggttttggcc agctcatctg   32400
ccgctaccca ggccatctac agctctgtgc ccgaaaccac tcagatccac cgcccagaaa   32460
cgaccaccgc caccacccta cacacctcca gcgatcagat gccgaccaac atcaccccct   32520
tggctcttca aatgggactt acaagcccca ctccaaaacc agtggatgcg gccgaggtct   32580
ccgccctcgt caatgactgg gcggggctgg aatgtggtg gttcgccata ggcatgatgg   32640
cgctctgcct gcttctgctc tggctcatct gctgcctcca ccgcaggcga gccagacccc   32700
ccatctatag acccatcatt gtcctgaacc ccgataatga tgggatccat agattggatg   32760
gcctgaaaaa cctacttttt tcttttacag tatgataaat tgagacatgc ctcgcatttt   32820
cttgtacatg ttccttctcc cacctttict ggggtgttct acgctggccg ctgtgtctca   32880
cctggaggta gactgcctct caccctteac tgtctacctg ctttacggat tggtcaccct   32940
cactctcatc tgcagcctaa tcacagtaat catcgccttc atccagtgca ttgattacat   33000
ctgtgtgcgc ctcgcatact tcagacacca cccgcagtac cgagacagga acattgccca   33060
acttctaaga ctgctctaat catgcataag actgtgatct gccttctgat cctctgcatc   33120
ctgcccaccc tcacctcctg ccagtacacc acaaaatctc cgcgcaaaag acatgcctcc   33180
tgccgcttca cccaactgtg gaatataccc aaatgctaca acgaaaagag cgagctctcc   33240
gaagcttggc tgtatggggt catctgtgtc ttagttttct gcagcactgt ctttgccctc   33300
ataatctacc cctacttga tttgggatgg aacgcgatcg atgccatgaa ttaccccacc   33360
tttcccgcac ccgagataat tccactgcga caagttgtac ccgttgtcgt taatcaacgc   33420 ccccccatccc ctacgcccac tgaaatcagc tactttaacc taacaggcgg agatgactga   33480
cgccctagat ctagaaatgg acggcatcag taccgagcag cgtctcctag agaggcgcag   33540
gcaggcggct gagcaagagc gcctcaatca ggagctccga gatctcgtta acctgcacca   33600
gtgcaaaaga ggcatctttt gtctggtaaa gcaggccaaa gtcacctacg agaagaccgg   33660
caacagccac cgcctcagtt acaaattgcc cacccagcgc cagaagctgg tgctcatggt   33720
gggtgagaat cccatcaccg tcacccagca ctcggtagag accgaggggt gtctgcactc   33780 ccctgtcgg ggtccagaag acctctgcac cctggtaaag accctgtgcg gtctcagaga   33840
tttagtcccc tttaactaat caaacactgg aatcaataaa aagaatcact tacttaaaat   33900
cagacagcag gtctctgtcc agtttattca gcagcacctc cttccectcc tcccaactct   33960 ggtactccaa acgccttctg gcggcaaact tcctccacac cctgaaggga atgtcagatt   34020
cttgctcctg tccctccgca cccactatct tcatgttgtt gcagatgaag cgcaccaaaa   34080
cgtctgacga gagcttcaac cccgtgtacc cctatgacac ggaaagcggc cctccctccg   34140 tcccctttcct cacccctccc ttcgtgtctc ccgatggatt ccaagaaagt cccccgggg   34200 tcctgtctct gaacctggcc gagccctgg tcacttccca cggcatgctc gccctgaaaa   34260
tgggaagtgg cctctccctg gacgacgctg gcaacctcac ctctcaagat atcaccaccg   34320
```

```
ctagccctcc cctcaaaaaa accaagacca acctcagcct agaaacctca tccccctaa    34380 ctgtgagcac ctcaggcgcc ctcaccgtag cagccgccgc tccctggcg gtggccggca    34440 cctccctcac catgcaatca gaggcccccc tgacagtaca ggatgcaaaa ctcaccctgg   34500
ccaccaaagg ccccctgacc gtgtctgaag gcaaactggc cttgcaaaca tcggcccgc    34560 tgacggccgc tgacagcagc accctcacag tcagtgccac accacccctt agcacaagca   34620
atggcagctt gggtattgac atgcaagccc ccatttacac caccaatgga aaactaggac   34680
ttaactttgg cgctcccctg catgtggtag acagcctaaa tgcactgact gtagttactg   34740
gccaaggtct tacgataaac ggaacagccc tacaaactag agtctcaggt gccctcaact   34800
atgacacatc aggaaaccta gaattgagag ctgcaggggg tatgcgagtt gatgcaaatg   34860
gtcaacttat ccttgatgta gcttacccat ttgatgcaca aaacaatctc agccttaggc   34920
ttggacaggg accctgtttt gttaactctg cccacaactt ggatgttaac tacaacagag   34980
gcctctacct gttcacatct ggaaatacca aaaagctaga agttaatatc aaaacagcca   35040
agggtctcat ttatgatgac actgctatag caatcaatgc gggtgatggg ctacagtttg   35100
actcaggctc agatacaaat ccattaaaaa ctaaacttgg attaggactg gattatgact   35160
ccagcagagc cataattgct aaactgggaa ctggcctaag ctttgacaac acaggtgcca   35220
tcacagtagg caacaaaaat gatgacaagc ttaccttgtg gaccacacca gacccatccc   35280
ctaactgtag aatctattca gagaaagatg ctaaattcac acttgttttg actaaatgcg   35340
gcagtcaggt gttggccagc gtttctgttt tatctgtaaa aggtagcctt gcgcccatca   35400
gtggcacagt aactagtgct cagattgtcc tcagatttga tgaaaatgga gttctactaa   35460
gcaattcttc ccttgaccct caatactgga actacagaaa aggtgacctt acagagggca   35520
ctgcatatac caacgcagtg ggatttatgc ccaacctcac agcatccca aaaacacaga    35580 gccaaactgc taaaagcaac attgtaagtc aggtttactt gaatgggac aaatccaaac    35640 ccatgaccct caccattacc ctcaatggaa ctaatgaaac aggagatgcc acagtaagca   35700
cttactccat gtcattctca tggaactgga atggaagtaa ttacattaat gaaacgttcc   35760
aaaccaactc cttcaccttc tcctacatcg cccaagaata aaaagcatga cgctgttgat   35820
ttgattcaat gtgtttctgt tttattttca agcacaacaa aatcattcaa gtcattcttc   35880
catcttagct taatagacac agtagcttaa tagacccagt agtgcaaagc ccattctag   35940 cttataacta gtggagaagt actcgcctac atggggtag agtcataatc gtgcatcagg    36000 ataggcggt ggtgctgcag cagcgcgcga ataaactgct gccgccgccg ctccgtcctg    36060
caggaataca acatggcagt ggtctcctca gcgatgattc gcaccgcccg cagcataagg   36120
cgccttgtcc tccgggcaca gcagcgcacc ctgatctcac ttaaatcagc acagtaactg   36180
cagcacagca ccacaatatt gttcaaaatc ccacagtgca aggcgctgta tccaaagctc   36240
atggcgggga ccacagaacc cacgtggcca tcataccaca agcgcaggta gattaagtgg   36300
cgacccctca taaacacgct ggacataaac attacctctt ttggcatgtt gtaattcacc   36360
acctcccggt accatataaa cctctgatta aacatggcgc catccaccac catcctaaac   36420
cagctggcca aaacctgccc gccggctata cactgcaggg aaccgggact ggaacaatga   36480
cagtggagag cccaggactc gtaaccatgg atcatcatgc tcgtcatgat atcaatgttg   36540
gcacaacaca ggcacacgtg catacacttc ctcaggatta caagctcctc ccgcgttaga   36600
accatatccc agggaacaac ccattcctga atcagcgtaa atcccacact gcagggaaga   36660
```

-continued

```
cctcgcacgt aactcacgtt gtgcattgtc aaagtgttac attcgggcag cagcggatga   36720
tcctccagta tggtagcgcg ggtttctgtc tcaaaaggag gtagacgatc cctactgtac   36780
ggagtgcgcc gagacaaccg agatcgtgtt ggtcgtagtg tcatgccaaa tggaacgccg   36840
gacgtagtca tatttcctga agtcttagat ctctcaacgc agcaccagca ccaacacttc   36900
gcagtgtaaa aggccaagtg ccgagagagt atatatagga ataaaagtg acgtaaacgg    36960 gcaaagtcca aaaacgccc agaaaaaccg cacgcgaacc tacgcccga aacgaaagcc     37020 aaaaaacact agacactccc ttccggcgtc aacttccgct ttcccacgct acgtcacttg   37080
ccccagtcaa acaaactaca tatcccgaac ttccaagtcg ccacgcccaa acaccgcct    37140 acacctcccc gcccgccggc cgcccccaa accgcctcc cgccccgcgc ccgccccgc      37200 gccgcccatc tcattatcat attggcttca atccaaaata aggtatatta ttgatgatgg   37260
tttaaacgga tcctctagag tcgacctgca ggcatgcaag cttgagtata accccttgc    37320 ggccgcccgg gccgtcgacc aattctcatg tttgacagct tatcatcgaa tttctgccat   37380
tcatccgctt attatcactt attcaggcgt agcaaccagg cgtttaaggg caccaataac   37440
tgccttaaaa aaattacgcc ccgccctgcc actcatcgca gtactgttgt aattcattaa   37500
gcattctgcc gacatggaag ccatcacaaa cggcatgatg aacctgaatc gccagcggca   37560
tcagcacctt gtcgccttgc gtataatatt tgcccatggt gaaaacgggg gcgaagaagt   37620
tgtccatatt ggccacgttt aaatcaaaac tggtgaaact cacccaggga ttggctgaga   37680
cgaaaaacat attctcaata aacccttag ggaaataggc caggttttca ccgtaacacg    37740
ccacatcttg cgaatatatg tgtagaaact gccggaaatc gtcgtggtat tcactccaga   37800
gcgatgaaaa cgtttcagtt tgctcatgga aaacggtgta acaagggtga acactatccc   37860
atatcaccag ctcaccgtct ttcattgcca tacggaattc cggatgagca ttcatcaggc   37920
gggcaagaat gtgaataaag gccggataaa acttgtgctt atttttcttt acggtcttta   37980
aaaaggccgt aatatccagc tgaacggtct ggttataggt acattgagca actgactgaa   38040
atgcctcaaa atgttcttta cgatgccatt gggatatatc aacggtggta tatccagtga   38100 ttttttctc cattttagct tccttagctc ctgaaaatct cgataactca aaaaatacgc    38160
ccggtagtga tcttatttca ttatggtgaa agttggaacc tcttacgtgc cgatcaacgt   38220 ctcatttttcg ccaaaagttg gcccagggct tcccggtatc aacagggaca ccaggattta  38280
tttattctgc gaagtgatct tccgtcacag gtatttattc gcgataagct catggagcgg   38340
cgtaaccgtc gcacaggaag gacagagaaa gcgcggatct gggaagtgac ggacagaacg   38400
gtcaggacct ggattgggga ggcggttgcc gccgctgctg ctgacggtgt gacgttctct   38460
gttccggtca caccacatac gttccgccat tcctatgcga tgcacatgct gtatgccggt   38520
ataccgctga aagttctgca aagcctgatg gacataagt ccatcagttc aacggaagtc    38580
tacacgaagg tttttgcgct ggatgtggct gcccggcacc gggtgcagtt tgcgatgccg   38640
gagtctgatg cggttgcgat gctgaaacaa ttatcctgag aataaatgcc ttggcccttta  38700 tatggaaatg tggaactgag tggatatgct gttttgtct gttaaacaga gaagctggct    38760
gttatccact gagaagcgaa cgaaacagtc gggaaaatct cccattatcg tagagatccg   38820
cattattaat ctcaggagcc tgtgtagcgt ttataggaag tagtgttctg tcatgatgcc   38880
tgcaagcggt aacgaaaacg atttgaatat gccttcagga acaatagaaa tcttcgtgcg   38940
gtgttacgtt gaagtggagc ggattatgtc agcaatggac agaacaacct aatgaacaca   39000
gaaccatgat gtggtctgtc cttttacagc cagtagtgct cgccgcagtc gagcgacagg   39060
```

```
gcgaagccct cgagtgagcg aggaagcacc agggaacagc acttatatat tctgcttaca    39120
cacgatgcct gaaaaaactt cccttggggt tatccactta tccacgggga tatttttata    39180
attattttt  ttatagtttt tagatcttct tttttagagc gccttgtagg cctttatcca    39240
tgctggttct agagaaggtg ttgtgacaaa ttgcccttc agtgtgacaa atcaccctca     39300
aatgacagtc ctgtctgtga caaattgccc ttaaccctgt gacaaattgc cctcagaaga    39360
agctgttttt tcacaaagtt atccctgctt attgactctt ttttatttag tgtgacaatc    39420
taaaaacttg tcacacttca catggatctg tcatggcgga aacagcggtt atcaatcaca    39480
agaaacgtaa aaatagcccg cgaatcgtcc agtcaaacga cctcactgag gcggcatata    39540
gtctctcccg ggatcaaaaa cgtatgctgt atctgttcgt tgaccagatc agaaaatctg    39600
atggcaccct acaggaacat gacggtatct gcgagatcca tgttgctaaa tatgctgaaa    39660
tattcggatt gacctctgcg gaagccagta aggatatacg gcaggcattg aagagtttcg    39720
cggggaagga agtggttttt tatcgccctg aagaggatgc cggcgatgaa aaaggctatg    39780
aatcttttcc ttggtttatc aaacgtgcgc acagtccatc cagagggctt tacagtgtac    39840
atatcaaccc atatctcatt cccttcttta tcgggttaca gaaccggttt acgcagtttc    39900
ggcttagtga aacaaaagaa atcaccaatc cgtatgccat gcgtttatac gaatccctgt    39960
gtcagtatcg taagccggat ggctcaggca tcgtctctct gaaaatcgac tggatcatag    40020
agcgttacca gctgcctcaa agttaccagc gtatgcctga cttccgccgc cgcttcctgc    40080
aggtctgtgt taatgagatc aacagcagaa ctccaatgcg cctctcatac attgagaaaa    40140
agaaaggccg ccagacgact catatcgtat tttccttccg cgatatcact tccatgacga    40200
caggatagtc tgagggttat ctgtcacaga tttgagggtg ttcgtcaca tttgttctga     40260
cctactgagg gtaatttgtc acagttttgc tgtttccttc agcctgcatg gattttctca    40320
tacttttga actgtaattt ttaaggaagc caaatttgag ggcagtttgt cacagttgat     40380
ttccttctct ttcccttcgt catgtgacct gatatcgggg gttagttcgt catcattgat    40440
gagggttgat tatcacagtt tattactctg aattggctat ccgcgtgtgt acctctacct    40500
ggagttttc ccacggtgga tatttcttct tgcgctgagc gtaagagcta tctgacgaa      40560
cagttcttct ttgcttcctc gccagttcgc tcgctatgct cggttacacg gctgcggcga    40620
gcgctagtga taataagtga ctgaggtatg tgctcttctt atctcctttt gtagtgttgc    40680
tcttatttta aacaactttg cggttttttg atgactttgc gattttgttg ttgctttgca    40740
gtaaattgca agatttaata aaaaaacgca agcaatgat taaaggatgt tcagaatgaa     40800
actcatggaa acacttaacc agtgcataaa cgctggtcat gaaatgacga aggctatcgc    40860
cattgcacag tttaatgatg acagcccgga agcgaggaaa ataacccggc gctgagaat     40920
aggtgaagca gcggatttag ttggggtttc ttctcaggct atcagagatg ccgagaaagc    40980
agggcgacta ccgcacccgg atatggaaat tcgaggacgg gttgagcaac gtgttggtta    41040
tacaattgaa caaattaatc atatgcgtga tgtgtttggt acgcgattgc gacgtgctga    41100
agacgtattt ccaccggtga tcggggttgc tgcccataaa ggtggcgttt acaaaacctc    41160
agtttctgtt catcttgctc aggatctggc tctgaagggg ctacgtgttt tgctcgtgga    41220
aggtaacgac ccccagggaa cagcctcaat gtatcacgga tgggtaccag atcttcatat    41280
tcatgcagaa gacactctcc tgcctttcta tcttggggaa aaggacgatg tcacttatgc    41340
aataaagccc acttgctggc cggggcttga cattattcct tcctgtctgg ctctgcaccg    41400
```

-continued

```
tattgaaact gagttaatgg gcaaatttga tgaaggtaaa ctgcccaccg atccacacct    41460
gatgctccga ctggccattg aaactgttgc tcatgactat gatgtcatag ttattgacag    41520
cgcgcctaac ctgggtatcg gcacgattaa tgtcgtatgt gctgctgatg tgctgattgt    41580
tcccacgcct gctgagttgt ttgactacac ctccgcactg cagttttcg atatgcttcg     41640
tgatctgctc aagaacgttg atcttaaagg gttcgagcct gatgtacgta ttttgcttac    41700
caaatacagc aatagtaatg gctctcagtc cccgtggatg gaggagcaaa ttcgggatgc    41760
ctggggaagc atggttctaa aaaatgttgt acgtgaaacg gatgaagttg gtaaaggtca    41820
gatccggatg agaactgttt ttgaacaggc cattgatcaa cgctcttcaa ctggtgcctg    41880
gagaaatgct ctttctattt gggaacctgt ctgcaatgaa attttcgatc gtctgattaa    41940
accacgctgg gagattagat aatgaagcgt gcgcctgtta ttccaaaaca tacgctcaat    42000
actcaaccgg ttgaagatac ttcgttatcg acaccagctg ccccgatggt ggattcgtta    42060
attgcgcgcg taggagtaat ggctcgcggt aatgccatta cttttgcctgt atgtggtcgg   42120
gatgtgaagt ttactcttga agtgctccgg ggtgatagtt ttgagaagac ctctcgggta   42180
tggtcaggta atgaacgtga ccaggagctg cttactgagg acgcactgga tgatctcatc   42240
ccttctttc tactgactgg tcaacagaca ccggcgttcg gtcgaagagt atctggtgtc     42300
atagaaattg ccgatgggag tcgccgtcgt aaagctgctg cacttaccga aagtgattat   42360
cgtgttctgg ttggcgagct ggatgatgag cagatggctg cattatccag attgggtaac   42420
gattatcgcc caacaagtgc ttatgaacgt ggtcagcgtt atgcaagccg attgcagaat   42480
gaatttgctg gaaatatttc tgcgctggct gatgcggaaa atatttcacg taagattatt   42540
acccgctgta tcaacaccgc caaattgcct aaatcagttg ttgctctttt ttctcacccc   42600
ggtgaactat ctgcccggtc aggtgatgca cttcaaaaag cctttacaga taagaggaa    42660
ttacttaagc agcaggcatc taaccttcat gagcagaaaa aagctggggt gatatttgaa   42720
gctgaagaag ttatcactct tttaacttct gtgcttaaaa cgtcatctgc atcaagaact   42780
agtttaagct cacgacatca gtttgctcct ggagcgacag tattgtataa gggcgataaa   42840
atggtgctta acctggacag gtctcgtgtt ccaactgagt gtatagagaa aattgaggcc   42900
attcttaagg aacttgaaaa gccagcaccc tgatgcgacc acgttttagt ctacgtttat   42960
ctgtctttac ttaatgtcct tgttacagg ccagaaagca taactggcct gaatattctc    43020
tctgggccca ctgttccact tgtatcgtcg gtctgataat cagactggga ccacggtccc   43080
actcgtatcg tcggtctgat tattagtctg ggaccacggt cccactcgta tcgtcggtct   43140
gattattagt ctgggaccac ggtcccactc gtatcgtcgg tctgataatc agactgggac   43200
cacggtccca ctcgtatcgt cggtctgatt attagtctgg accatggtc ccactcgtat    43260
cgtcggtctg attattagtc tgggaccacg gtcccactcg tatcgtcggt ctgattatta   43320
gtctggaacc acggtcccac tcgtatcgtc ggtctgatta ttagtctggg accacggtcc   43380
cactcgtatc gtcggtctga ttattagtct gggaccacga tcccactcgt gttgtcggtc   43440
tgattatcgg tctgggacca cggtcccact tgtattgtcg atcagactat cagcgtgaga   43500
ctacgattcc atcaatgcct gtcaagggca agtattgaca tgtcgtcgta acctgtagaa   43560
cggagtaacc tcggtgtgcg gttgtatgcc tgctgtggat tgctgctgtg tcctgcttat   43620
ccacaacatt tgcgcacgg ttatgtggac aaaatacctg gttacccagg ccgtgccggc    43680
acgctcggta cccggggatc ctcgtttaaa c                                  43711
```

-continued

```
<210> SEQ ID NO 53
<211> LENGTH: 41545
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (16144)..(16144)
<223> OTHER INFORMATION: a, c, t, g, unknown or other

<400> SEQUENCE: 53
catcatcaat aatataccctt attttggatt gaagccaata tgataatgag atgggcggcg      60
cggggcgggg cgcggggcgg gaggcgggtt tgggggcggg ccggcgggcg ggcggtgtg      120 gcggaagtgg actttgtaag tgtggcggat gtgacttgct agtgccgggc gcggtaaaag    180
tgacgttttc cgtgcgcgac aacgcccccg ggaagtgaca ttttttcccgc ggttttttacc    240 ggatgttgta gtgaatttgg gcgtaaccaa gtaagatttg gccattttcg cgggaaaact    300
gaaacgggga agtgaaatct gattaatttt gcgttagtca taccgcgtaa tatttgtcta    360
gggccgaggg actttggccg attacgtgga ggactcgccc aggtgttttt tgaggtgaat    420
ttccgcgttc cgggtcaaag tctgcgtttt attattatag gatatcccat tgcatacgtt    480
gtatccatat cataatatgt acatttatat tggctcatgt ccaacattac cgccatgttg    540
acattgatta ttgactagtt attaatagta atcaattacg gggtcattag ttcatagccc    600
atatatggag ttccgcgtta cataacttac ggtaaatggc ccgcctggct gaccgcccaa    660
cgacccccgc ccattgacgt caataatgac gtatgttccc atagtaacgc caatagggac    720
tttccattga cgtcaatggg tggagtatt  acggtaaact gcccacttgg cagtacatca    780
agtgtatcat atgccaagta cgccccctat tgacgtcaat gacggtaaat ggcccgcctg    840
gcattatgcc cagtacatga ccttatggga ctttcctact tggcagtaca tctacgtatt    900
agtcatcgct attaccatgg tgatgcggtt ttggcagtac atcaatgggc gtggatagcg    960
gtttgactca cggggatttc caagtctcca ccccattgac gtcaatggga gtttgttttg   1020
gcaccaaaat caacgggact ttccaaaatg tcgtaacaac tccgcccat tgacgcaaat     1080 gggcggtagg cgtgtacggt gggaggtcta taagcagag ctctcccta tcagtgatag      1140 agatctcccct atcagtgata gagatcgtcg acgagctcgt ttagtgaacc gtcagatcgc   1200
ctggagacgc catccacgct gttttgacct ccatagaaga caccgggacc gatccagcct   1260
ccgcggccgg gaacggtgca ttggaacgcg gattccccgt gccaagagtg agatcttccg   1320
tttatctagg taccagatat cgccaccatg tccgaggact ttctgattct gatcgccatc   1380
ctggtgatcg tgattctcgt gggcacaatc acaaccctgg tgggcgccat cggcggcatt   1440
agggccagga ggagcttcct cttcatttgc atcttcttcc tgttcctctc cctcttcctg   1500
acaatcctcg ccctgctgct gggcttcagc tggctcctgc tggtggccat cctgttctgg   1560
gtgctctggc tggtcatcct cattctgctg ctgctggtgt accctattcc tcaccacccc   1620
ctgcccacct ccctcaggtt tagaatgaag cagagggtga gcagcgaccc cacaggttct   1680
gacagaagcc ctcagggcag ccataatagc ctgaactccc ccgatgagga ggaccccaag   1740
gatgacacca agcaacctct gtgcaacatg acccagggcg acctcccgt caatggacag   1800 ctcctcggac aacatgctca atgcccccct cactatccct gctgccatat tcagcatccc   1860
gacggagagg attccgatgg agacgatggc aagtcctggg gcgatgccgg agaggaagac   1920
```

```
aatggcccta acgaccctaa caccgccagc accagagagt ccatttacga ggacctcaga    1980
taccccacaa gggacgccaa tggcgagtat gagaacgtgg gatacccccc tagggacgga    2040
gatgcccctc ataggctcgg agagcctgtg tatgacgatg tggagcaagc caccgctaac    2100
gaggtgagaa tctcccctct gttcagactg ccctacggaa gcgctttcgg acctggcccc    2160
cagcctggac ccattctgga gagctccaca tggggctttc tggtcttcac acagacctcc    2220
ctgttcgccg acgacattgc cgacgctatt agggactact gcacaaccca ccctggcccc    2280
acaaggaaca cccaggtggt cctcatgaac ttcgagggca gcggagtgcc cctgcctatg    2340
ttttttcccc ctggagagga gacagaagag cagagagagg gcgatagagc tagcgactcc    2400
gacgagtccg aagacgctca gatcctgacc gtgttctgcc tgttttgcca gtggacactc    2460
tttatctgcc tgggaatcag gatgatctgt aactggaggg gcaaactcac caggatcatc    2520
tgcctgaagt tctgcctcta cggactgatt tccgcctccc tgtccttcgg ctggtacgct    2580
tttctgaagg aagtgaccct ccccaccaca gccaccgttg atcctaggca actcccctg    2640 ttcctcttca tcctgagctc cgtgctggtg attctcgcca tcatgatgga gtttcaaaca    2700
tcctccagcc tcttcgctgc tctgttcgtg attatcgccg gaatgctgtg cgtcacagtg    2760
ggcgtgattt ttctgctggc tggcgtcaag cctctcctga gcggcatgat ctgcgcctcc    2820
ggcatcacaa tgctcgtgct cggcgtcgtg ctgctggtgg tgtgcaccag agatgagcac    2880
gctatttccg ccagccacca tgctagcgat ggctccgtga atcagcagaa ggaaaatcag    2940
ccccagaccc tggaggaatg caagacagat caggagagga agaggtacag gaacaggctg    3000
gcctccagga ggtgtagagc taagttcagg aaccagctgg aacattttag gacagtcgcc    3060
gctgctaaga cagaggagaa caacaggctc agggtgctca tcaggcagat gtgtcctaca    3120
ctggacgtgg aatccatcgt cccctccacc tccgccggct accacgagcc tctgaatcac    3180
ctgacccaca gccccagccc ttgtcatcac agggatgaac ccccctccag aagccccagc    3240
cctcaaccca ccgtctccga gcagtcccag cagtccccca ggcagcagag ccctcaaggc    3300
acatcccagg gttctacaag acctcaggtg cctggaggcg ccaccaccag aaaaagaggc    3360
ggcgtgagag ccaacctgc caagtgtcac ggcaagtaca ccacaaccgc cgagggactg    3420
accgctctcc tgaataggag gcacagcccc aggacatcca acgagggcag gtggatgaat    3480
ggagtcatgg ctgtgaacct ctccaaatgg ccctgtaca gcctgaggag agccctggcc    3540
ctcgccatgg ctcctagaag gaggctctcc ggccctccct ggctgacagt gctgctgctg    3600
ctgtccacac tgagcgtggc cgccctgctg attctcttcc tgattttcag cgccggcgcc    3660
accattagca cagaagccag cctgctggtc ctgctcctgc tgtttgtgac cctgctgctg    3720
cctctcctgt cctccaacgg actccagctc cctgccgccc tgattctgat ccagtgtttc    3780
ctcctggccg ctgattatct cgcctacctg attctgccta ccattatgcc caggggcaga    3840
agcacaggaa ggaagggcag ggacacagag aaagagagga gcagatcccc tctcagagct    3900
cctggcggtt ctgatggacc cagcacaagg gctggctgtg gagccggacc ctgtcagctg    3960
agcagcccca tcgccggaaa caacggcaat gaaggcggcg agggcgacga ctacaagagc    4020
tggaggaagc ccgaggaaga ggacaacggc cccaatgacc ccaataccaa caacaggatt    4080
gaggatggag acggcgacga cggaaaatcc tggaggaatc ctgaggagga ggataacaga    4140
aagcaggaca ggctgggcac caagcctttc atggacctcg acggaaccgg cggaggcgag    4200
ggctacagcc agatggtccc tatcgccacc gcccccggaa gcggccacgc cgctacctat    4260
caggatctcc aggccgcccc ttacatcatc tggcctctcc agaccgattg ccagcctgtg    4320
```

-continued

```
gctaccacct tcgcctcccc cggacagatc cagtggtata caagcgccgt ccccagccc   4380
acagagcatt gctcccagtt tacaaacgct cccaccgtca accagcagca gcctattagc   4440
caacccagc  ccgaaaatcc ccctgctttc acctttaccc agcccgcttc catcattccc   4500
ggcgtcatta gcgcctccaa cctgaacgtg agcgcttccc ctatcatccc tagcgaccat   4560
gtcctcccca tcattacctc cgtgaccagc ctcgcccaac ctaataacat ggccggccac   4620
tggtatgaga gcgtgattcc cggcctgttc ctctgccccc tgatcctccc ttccctgttc   4680
tggatttgct ccctgctgac cttcctggtg ggccacggag ccaatattgt gagcgccgtc   4740
ctgttcctcg tgctggcttg gtgtctcctc attgccaact ggaacgtgac aagagaggac   4800
ttcgtgtccg gcaggagaag ctccatgagc agcctgtccg tggccgcttc caccgccaca   4860
gccatgttcg ccagcttcct caccctgagc tttgatggcc tgggcctgct gctgtttggc   4920
accgccctgg tgatccagac aatttacgtg ctgtatctgg tggtcatgga gatcaccgtg   4980
tggatcatga tgtttaggta tctccacttt tggatcaccc tgctgttcct gctgagcccc   5040
attattctct ccgtcgcctg tctcatcatc caatcctccg ccctgctgat cgaggctgtg   5100
gtcgtcacca ccatcacagt cctggccatt tttctgtggc tccctcctca aggcgctgag   5160
gccgatctcg gcaccgccct gctgattctg aataccgccc tgtgcctggt cgtgctgatc   5220
ctgaccgcta tccctacatg atgatgagcg gccgcgatct gctgtgcctt ctagttgcca   5280
gccatctgtt gtttgcccct ccccgtgcc  ttccttgacc ctggaaggtg ccactcccac   5340
tgtcctttcc taataaaatg aggaaattgc atcgcattgt ctgagtaggt gtcattctat   5400
tctggggggt ggggtggggc aggacagcaa gggggaggat tgggaagaca atagcaggca   5460
tgctggggat gcggtgggct ctatggccga tcagcgatcg ctgaggtggg tgagtgggcg   5520
tggcctgggg tggtcatgaa aatatataag ttgggggtct tagggtctct ttatttgtgt   5580
tgcagagacc gccggagcca tgagcggag  cagcagcagc agcagtagca gcagcgcctt   5640
ggatggcagc atcgtgagcc cttatttgac gacgcggatg ccccactggg ccggggtgcg   5700
tcagaatgtg atgggctcca gcatcgacgg ccgacccgtc ctgcccgcaa attccgccac   5760
gctgacctat gcgaccgtcg cggggacgcc gttggacgcc accgccgccg ccgccgccac   5820
cgcagccgcc tcggccgtgc gcagcctggc cacggacttt gcattcctgg gaccactggc   5880
gacagggct  acttctcggg ccgctgctgc cgccgttcgc gatgacaagc tgaccgccct   5940
gctggcgcag ttggatgcgc ttactcggga actgggtgac cttttctcagc aggtcatggc   6000
cctgcgccag caggtctcct ccctgcaagc tggcgggaat gcttctccca caaatgccgt   6060
ttaagataaa taaaaccaga ctctgtttgg attaaagaaa agtagcaagt gcattgctct   6120
ctttatttca taattttccg cgcgcgatag gccctagacc agcgttctcg gtcgttgagg   6180
gtgcggtgta tcttctccag gacgtggtag aggtggctct ggacgttgag atacatgggc   6240
atgagcccgt cccgggggtg gaggtagcac cactgcagag cttcatgctc cggggtggtg   6300
ttgtagatga tccagtcgta gcaggagcgc tgggcatggt gcctaaaaat gtccttcagc   6360
agcaggccga tggccagggg gaggcccttg gtgtaagtgt ttacaaaacg gttaagttgg   6420
gaagggtgca ttcggggaga gatgatgtgc atcttggact gtattttag  attggcgatg   6480
tttccgccca gatcccttct gggattcatg ttgtgcagga ccaccagtac agtgtatccg   6540
gtgcacttgg ggaatttgtc atgcagctta gagggaaaag cgtggaagaa cttgagacg    6600
cctttgtggc ctcccagatt ttccatgcat tcgtccatga tgatggcaat gggcccgcgg   6660
```

```
gaggcagctt gggcaaagat atttctgggg tcgctgacgt cgtagttgtg ttccagggtg    6720
aggtcgtcat aggccatttt tacaaagcgc gggcggaggg tgcccgactg ggggatgatg    6780
gtcccctctg gccctggggc gtagttgccc tcgcagatct gcatttccca ggccttaatc    6840
tcggaggggg gaatcatatc cacctgcggg gcgatgaaga aaacggtttc cggagccggg    6900
gagattaact gggatgagag caggtttcta agcagctgtg attttccaca accggtgggc    6960
ccataaataa cacctataac cggttgcagc tggtagttta gagagctgca gctgccgtcg    7020
tcccggagga gggggggccac ctcgttgagc atgtccctga cgcgcatgtt ctccccgacc    7080
agatccgcca gaaggcgctc gccgcccagg gacagcagct cttgcaagga agcaaagttt    7140
ttcagcggct tgaggccgtc cgccgtgggc atgttttttca gggtctggct cagcagctcc    7200
aggcggtccc agagctcggt gacgtgctct acggcatctc tatccagcat atctcctcgt    7260
ttcgcgggtt ggggcgactt tcgctgtagg gcaccaagcg gtggtcgtcc agcggggcca    7320
gagtcatgtc cttccatggg cgcagggtcc tcgtcagggt ggtctgggtc acggtgaagg    7380
ggtgcgctcc gggctgagcg cttgccaagg tgcgcttgag gctggttctg ctggtgctga    7440
agcgctgccg gtcttcgccc tgcgcgtcgg ccaggtagca tttgaccatg gtgtcatagt    7500
ccagcccctc cgcggcgtgt cccttggcgc gcagcttgcc cttggaggtg gcgccgcacg    7560
aggggcagag caggctcttg agcgcgtaga gcttgggggc gaggaagacc gattcggggg    7620
agtaggcgtc cgcgccgcag accccgcaca cggtctcgca ctccaccagc caggtgagct    7680
cggggcgcgc cgggtcaaaa accaggtttc ccccatgctt tttgatgcgt ttcttacctc    7740
gggtctccat gaggtggtgt ccccgctcgg tgacgaagag gctgtccgtg tctccgtaga    7800
ccgacttgag gggtcttttc tccagggggg tccctcggtc ttcctcgtag aggaactcgg    7860
accactctga gacgaaggcc cgcgtccagg ccaggacgaa ggaggctatg tgggagggt    7920
agcggtcgtt gtccactagg gggtccacct tctccaaggt gtgaagacac atgtcgcctt    7980
cctcggcgtc caggaaggtg attggcttgt aggtgtaggc cacgtgaccg ggggttcctg    8040
acggggggt ataaaagggg gtgggggcgc gctcgtcgtc actctcttcc gcatcgctgt    8100
ctgcgagggc cagctgctgg ggtgagtatt ccctctcgaa ggcgggcatg acctccgcgc    8160
tgaggttgtc agtttccaaa aacgaggagg atttgatgtt cacctgtccc gaggtgatac    8220
ctttgagggt acccgcgtcc atctggtcag aaaacacgat cttttttattg tccagcttgg    8280
tggcgaacga cccgtagagg gcgttggaga gcagcttggc gatggagcgc agggtctggt    8340
tcttgtccct gtcggcgcgc tccttggccg cgatgttgag ctgcacgtac tcgcgcgcga    8400
cgcagcgcca ctcggggaag acggtggtgc gctcgtcggg caccaggcgc acgcgccagc    8460
cgcggttgtg cagggtgacc aggtccacgc tggtggcgac ctcgccgcgc aggcgctcgt    8520
tggtccagca gagacggccg cccttgcgcg agcagaaggg gggcaggggg tcgagctggg    8580
tctcgtccgg ggggtccgcg tccacggtga aacccgggg gcgcaggcgc gcgtcgaagt    8640
agtctatctt gcaaccttgc atgtccacgc cctgctgcca gtcgcgggcg gcgagcgcgc    8700
gctcgtaggg gttgagcggc gggccccagg gcatggggtg ggtgagtgcg gaggcgtaca    8760
tgccgcagat gtcatagacg tagagggggct cccgcaggac cccgatgtag gtgggggtagc    8820
agcggccgcc gcggatgctg gcgcgcacgt agtcatacag ctcgtgcgag ggggcgagga    8880
ggtcgggggc caggttggtg cgggcggggc gctccgcgcg gaagacgatc tgcctgaaga    8940
tggcatcgca gttggaagag atggtggggc gctggaagac gttgaagctg gcgtcctgca    9000
ggccgacggc gtcgcgcacg aaggaggcgt aggagtcgcg cagcttgtgt accagctcgg    9060
```

```
cggtgacctg cacgtcgagc gcgcagtagt cgagggtctc gcggatgatg tcatatttag   9120
cctgccccctt ctttttccac agctcgcggt tgaggacaaa ctcttcgcgg tctttccagt   9180
actcttggat cgggaaaccg tccggttccg aacggtaaga gcctagcatg tagaactggt   9240
tgacggcctg gtaggcgcag cagcccttct ccacggggag ggcgtaggcc tgcgcggcct   9300
tgcggagcga ggtgtgggtc agggcgaagg tgtccctgac catgactttg aggtactggt   9360
gcttgaagtc ggagtcgtcg cagccgcccc gctcccagag cgagaagtcg gtgcgcttct   9420
tggagcgggg gttgggcaga gcgaaggtga catcgttgaa gaggattttg cccgcgcggg   9480
gcatgaagtt gcgggtgatg cggaagggcc ccggcacttc agagcggttg ttgatgacct   9540
gggcggcgag cacgatctcg tcgaagccgt tgatgttgtg gcccacgatg tagagttcca   9600
ggaagcgggg ccggccctttt acggtgggca gcttctttag ctcttcgtag gtgagctcct   9660
cgggcgaggc gaggccgtgc tcggccaggg cccagtccgc gaggtgcggg ttgtctctga   9720
ggaaggactt ccagaggtcg cgggccagga gggtctgcag gcggtctctg aaggtcctga   9780
actggcggcc cacggccatt ttttcggggg tgatgcagta aaggtgagg gggtcttgct    9840
gccagcggtc ccagtcgagc tgcagggcga ggtcgcgcgc ggcggtgacc aggcgctcgt   9900
cgccccccgaa tttcatgacc agcatgaagg gcacgagctg ctttccgaag gcccccatcc   9960
aagtgtaggt ctctacatcg taggtgacaa agaggcgctc cgtgcgagga tgcgagccga  10020
tcgggaagaa ctggatctcc cgccaccagt tggaggagtg gctgttgatg tggtggaagt  10080
agaagtcccg tcgccgggcc gaacactcgt gctggctttt gtaaaagcga gcgcagtact  10140
ggcagcgctg cacgggctgt acctcatgca cgagatgcac ctttcgcccg cgcacgagga  10200
agccgagggg aaatctgagc cccccgcctg gctcgcggca tggctggttc tcttctactt  10260
tggatgcgtg tccgtctccg tctggctcct cgaggggtgt tacggtggag cggaccacca  10320
cgccgcgcga gccgcaggtc cagatatcgg cgcgcggcgg tcggagtttg atgacgacat  10380
cgcgcagctg ggagctgtcc atggtctgga gctcccgcgg cggcggcagg tcagccggga  10440
gttcttgcag gttcacctcg cagagtcggg ccagggcgcg gggcaggtct aggtggtacc  10500
tgatctctag gggcgtgttg gtggcggcgt cgatggcttg caggagcccg cagcccccggg  10560
gggcgacgac ggtgccccgc ggggtggtgg tggtggtggc ggtgcagctc agaagcggtg  10620
ccgcgggcgg gccccccggag gtaggggggg ctccggtccc gcgggcaggg gcggcagcgg  10680
cacgtcggcg tggagcgcgg gcaggagttg gtgctgtgcc cggaggttgc tggcgaaggc  10740
gacgacgcgcg cggttgatct cctggatctg gcgcctctgc gtgaagacga cgggcccggt  10800
gagcttgaac ctgaaagaga gttcgacaga atcaatctcg gtgtcattga ccgcggcctg  10860
gcgcaggatc tcctgcacgt ctcccgagtt gtcttggtag gcgatctcgg ccatgaactg  10920
ctcgatctct tcctcctgga ggtctccgcg tccggcgcgt tccacggtgg ccgccaggtc  10980
gttggagatg cgcccatga gctgcagaa ggcgttgagt ccgccctcgt tccagactcg  11040
gctgtagacc acgccccct ggtcatcgcg ggcgcgcatg accacctgcg cgaggttgag  11100
ctccacgtgc cgcgcgaaga cggcgtagtt gcgcagacgc tggaagaggt agttgagggt  11160
ggtggcggtg tgctcggcca cgaagaagtt catgacccag cggcgcaacg tggattcgtt  11220
gatgtccccc aaggcctcca gccgttccat ggcctcgtag aagtccacgg cgaagttgaa  11280
aaactgggag ttgcgcgccg acacggtcaa ctcctcctcc agaagacgga tgagctcggc  11340
gacggtgtcg cgcacctcgc gctcgaaggc tatgggatc tcttcctccg ctagcatcac  11400
```

```
cacctcctcc tcttcctcct cttctggcac ttccatgatg gcttcctcct cttcgggggg   11460
tggcggcggc ggcggtgggg gaggggggcgc tctgcgccgg cggcggcgca ccggaggcgc   11520
gtccacgaag cgcgcgatca tctccccgcg gcggcggcgc atggtctcgg tgacggcgcg   11580
gccgttctcc cggggggcgca gttggaagac gccgccggac atctggtgct ggggcgggtg   11640
gccgtgaggc agcgagacgg cgctgacgat gcatctcaac aattgctgcg taggtacgcc   11700
gccgagggac ctgagggagt ccatatccac cggatccgaa aacctttcga ggaaggcgtc   11760
taaccagtcg cagtcgcaag gtaggctgag caccgtggcg ggcggcgggg ggtggggggga   11820 gtgtctggcg gaggtgctgc tgatgatgta attgaagtag gcggacttga cacggcggat   11880
ggtcgacagg agcaccatgt ccttgggtcc ggcctgctgg atgcggaggc ggtcggctat   11940
gccccaggct tcgttctggc atcggcgcag gtccttgtag tagtcttgca tgagcctttc   12000
caccggcacc tcttctcctt cctcttctgc ttcttccatg tctgcttcgg ccctggggcg   12060
gcgccgcgcc cccctgcccc ccatgcgcgt gaccccgaac cccctgagcg gttggagcag   12120
ggccaggtcg gcgacgacgc gctcggccag gatggcctgc tgcacctgcg tgagggtggt   12180
ttggaagtca tccaagtcca cgaagcggtg gtaggcgccc gtgttgatgg tgtaggtgca   12240
gttggccatg acgaccagt tgacggtctg gtggcccggt tgcgacatct cggtgtacct   12300
gagtcgcgag taggcgcggg agtcgaagac gtagtcgttg caagtccgca ccaggtactg   12360
gtagcccacc aggaagtgcg gcggcggctg gcggtagagg ggccagcgca gggtggcggg   12420
ggctccgggg gccaggtctt ccagcatgag gcggtggtag gcgtagatgt acctggacat   12480
ccaggtgata cccgcggcgg tggtggaggc gcgcggggaag tcgcgcaccc ggttccagat   12540
gttgcgcagg ggcagaaagt gctccatggt aggcgtgctc tgtccagtca gacgcgcgca   12600
gtcgttgata ctctagacca gggaaaacga aagccggtca gcgggcactc ttccgtggtc   12660
tggtgaatag atcgcaaggg tatcatggcg gagggcctcg gttcgagccc cgggtccggg   12720
ccggacggtc cgccatgatc cacgcggtta ccgcccgcgt gtcgaaccca ggtgtgcgac   12780
gtcagacaac ggtggagtgt tccttttggc gttttttctgg ccgggcgccg cgccgcgta   12840 agagactaag ccgcgaaagc gaaagcagta agtggctcgc tccccgtagc cggagggatc   12900
cttgctaagg gttgcgttgc ggcgaacccc ggttcgaatc ccgtactcgg gccggccgga   12960
cccgcggcta aggtgttgga ttggcctccc cctcgtataa agaccccgct tgcggattga   13020
ctccggacac ggggacgagc cccttttatt tttgctttcc ccagatgcat ccggtgctgc   13080
ggcagatgcg ccccccgccc cagcagcagc aacaacacca gcaagagcgg cagcaacagc   13140
agcgggagtc atgcagggcc ccctcaccca ccctcggcgg gccggccacc tcggcgtccg   13200
cggccgtgtc tggcgcctgc ggcggcgcg ggggccggc tgacgacccc gaggagcccc   13260
cgcggcgcag ggccagacac tacctggacc tggaggaggg cgagggcctg gcgcggctgg   13320
gggcgccgtc tcccgagcgc caccgcgggg tgcagctgaa gcgcgactcg cgcgaggcgt   13380
acgtgcctcg gcagaacctg ttcagggacc cgcgcgggcga ggagcccgag gagatgcggg   13440
acaggaggtt cagcgcaggg cgggagctgc ggcaggggct gaaccgcgag cggctgctgc   13500
gcgaggagga ctttgagccc gacgcgcgga cggggatcag ccccgcgcgc gcgcacgtgg   13560
cggccgccga cctggtgacg gcgtacgagc agacggtgaa ccaggagatc aacttccaaa   13620
agagtttcaa caaccacgtg cgcacgctgg tggcgcgcga ggaggtgacc atcgggctga   13680
tgcacctgtg ggactttgta agcgcgctgg tgcagaaccc caacagcaag cctctgacgg   13740
cgcagctgtt cctgatagtg cagcacagca gggacaacga ggcgtttagg gacgcgctgc   13800
```

```
tgaacatcac cgagcccgag ggtcggtggc tgctggacct gattaacatc ctgcagagca   13860
tagtggtgca ggagcgcagc ctgagcctgg ccgacaaggt ggcggccatc aactactcga   13920
tgctgagcct gggcaagttt tacgcgcgca agatctacca gacgccgtac gtgcccatag   13980
acaaggaggt gaagatcgac ggttttttaca tgcgcatggc gctgaaggtg ctcaccctga   14040
gcgacgacct gggcgtgtac cgcaacgagc gcatccacaa ggccgtgagc gtgagccggc   14100
ggcgcgagct gagcgaccgc gagctgatgc acagcctgca gcgggcgctg gcgggcgccg   14160
gcagcggcga cagggaggcg gagtcctact tcgatgcggg ggcggacctg cgctgggcgc   14220
ccagccggcg ggccctggag gccgcggggg tccgcgagga ctatgacgag gacggcgagg   14280
aggatgagga gtacgagcta gaggagggcg agtacctgga ctaaaccgcg ggtggtgttt   14340
ccggtagatg caagacccga acgtggtgga cccggcgctg cggcggctc tgcagagcca    14400
gccgtccggc cttaactcct cagacgactg gcgacaggtc atggaccgca tcatgtcgct   14460
gacggcgcgt aacccggacg cgttccgca gcagccgcag gccaacaggc tctccgccat    14520
cctggaggcg gtggtgcctg cgcgctcgaa ccccacgcac gagaaggtgc tggccatagt   14580
gaacgcgctg gccgagaaca gggccatccg cccggacgag gccgggctgg tgtacgacgc   14640
gctgctgcag cgcgtggccc gctacaacag cggcaacgtg cagaccaacc tggaccggct   14700
ggtgggggac gtgcgcgagg cggtggcgca gcgcgagcgc gcggatcggc agggcaacct   14760
gggctccatg gtggcgctga atgccttcct gagcacgcag ccggccaacg tgccgcgggg   14820
gcaggaagac tacaccaact tgtgagcgc gctgcggctg atggtgaccg agacccccca   14880
gagcgaggtg taccagtcgg gcccggacta cttcttccag accagcagac agggcctgca   14940
gacggtgaac ctgagccagg cttttcaagaa cctgcgggggg ctgtggggcg tgaaggcgcc   15000
caccggcgac cgggcgacgg tgtccagcct gctgacgccc aactcgcgcc tgctgctgct   15060
gctgatcgcg ccgttcacgg acagcggcag cgtgtcccgg acacctacc tggggcacct   15120
gctgaccctg taccgcgagg ccatcgggca ggcgcaggtg gacgagcaca ccttccagga   15180
gatcaccagc gtgagccgcg cgctggggca ggaggacacg agcagcctgg aggcgactct   15240
gaactacctg ctgaccaacc ggcggcagaa gattccctcg ctgcacagcc tgacctccga   15300
ggaggagcgc atcttgcgct acgtgcagca gagcgtgagc ctgaacctga tgcgcgacgg   15360
ggtgacgccc agcgtggcgc tggacatgac cgcgcgcaac atggaaccgg gcatgtacgc   15420
cgcgcaccgg ccttacatca accgcctgat ggactacctg catcgcgcgg cggccgtgaa   15480
ccccgagtac tttaccaacg ccatcctgaa cccgcactgg ctcccgccgc ccgggttcta   15540
cagcggggggc ttcgaggtcc cggagaccaa cgatggcttc ctgtgggacg acatggacga   15600
cagcgtgttc tccccgcggc cgcaggcgct ggcggaagcg tccctgctgc gtcccaagaa   15660
ggaggaggag gaggaggcga gtcgccgccg cggcagcagc ggcgtggctt ctctgtccga   15720
gctgggggcg gcagccgccg cgcgccccgg gtccctgggc ggcagcccct ttccgagcct   15780
ggtgggggtct ctgcacagcg agcgcaccac ccgccctcgg ctgctgggcg aggacgagta   15840
cctgaataac tccctgctgc agccggtgcg ggagaaaaac ctgcctcccg ccttcccaa    15900
caacgggata gagagcctgg tggacaagat gagcagatgg aagacctatg cgcaggagca   15960
cagggacgcg cctgcgctcc ggccgcccac gcggcgccag cgccacgacc ggcagcgggg   16020
gctggtgtgg gatgacgagg actccgcgga cgatagcagc gtgctggacc tgggagggag   16080
cggcaacccg ttcgcgcacc tgcgcccccg cctggggagg atgttttaaa aaaaaaaaa    16140
```

```
aaangcaaga agcatgatgc aaaaattaaa taaaactcac caaggccatg gcgaccgagc  16200
gttggtttct tgtgttccct tcagtatgcg gcgcgcggcg atgtaccagg agggacctcc  16260
tccctcttac gagagcgtgg tgggcgcggc ggcggcggcg ccctcttctc cctttgcgtc  16320
gcagctgctg gagccgccgt acgtgcctcc gcgctacctg cggcctacgg gggggagaaa  16380
cagcatccgt tactcggagc tggcgcccct gttcgacacc acccgggtgt acctggtgga  16440
caacaagtcg gcggacgtgg cctccctgaa ctaccagaac gaccacagca attttttgac  16500
cacggtcatc cagaacaatg actacagccc gagcgaggcc agcacccaga ccatcaatct  16560
ggatgaccgg tcgcactggg gcggcgacct gaaaaccatc ctgcacacca acatgcccaa  16620
cgtgaacgag ttcatgttca ccaataagtt caaggcgcgg gtgatggtgt cgcgctcgca  16680
caccaaggaa gaccgggtgg agctgaagta cgagtgggtg gagttcgagc tgccagaggg  16740
caactactcc gagaccatga ccattgacct gatgaacaac gcgatcgtgg agcactatct  16800
gaaagtgggc aggcagaacg gggtcctgga gagcgacatc ggggtcaagt tcgacaccag  16860
gaacttccgc ctggggctgg accccgtgac cgggctggtt atgccggggg tgtacaccaa  16920
cgaggccttc catcccgaca tcatcctgct gcccggctgc ggggtggact tcacttacag  16980
ccgcctgagc aacctcctgg gcatccgcaa gcggcagccc ttccaggagg gcttcaggat  17040
cacctacgag gacctggagg ggggcaacat ccccgcgctc ctcgatgtgg aggcctacca  17100
ggatagcttg aaggaaaatg aggcgggaca ggaggatacc gccccgccg cctccgccgc  17160 cgccgagcag ggcgaggatg ctgctgacac cgcggccgcg gacggggcag aggccgaccc  17220
cgctatggtg gtggaggctc ccgagcagga ggaggacatg aatgacagtg cggtgcgcgg  17280
agacaccttc gtcacccggg gggaggaaaa gcaagcggag gccgaggccg cggccgagga  17340
aaagcaactg gcggcagcag cggcggcggc ggcgttggcc gcggcggagg ctgagtctga  17400
ggggaccaag cccgccaagg agcccgtgat taagcccctg accgaagata gcaagaagcg  17460
cagttacaac ctgctcaagg acagcaccaa caccgcgtac cgcagctggt acctggccta  17520
caactacggc gacccgtcga cggggggtgcg ctcctggacc ctgctgtgca cgccggacgt  17580
gacctgcggc tcggagcagg tgtactggtc gctgcccgac atgatgcaag accccgtgac  17640
cttccgctcc acgcggcagg tcagcaactt cccggtggtg ggcgccgagc tgctgcccgt  17700
gcactccaag agcttctaca cgaccaggc cgtctactcc cagctcatcc gccagttcac  17760
ctctctgacc cacgtgttca atcgctttcc tgagaaccag attctggcgc gcccgcccgc  17820
ccccaccatc accaccgtca gtgaaaaacgt tcctgctctc acagatcacg ggacgctacc  17880
gctgcgcaac agcatcggag gagtccagcg agtgaccgtt actgacgcca gacgccgcac  17940
ctgcccctac gtttacaagg ccttgggcat agtctcgccg cgcgtccttt ccagccgcac  18000
tttttgagca acaccaccat catgtccatc ctgatctcac ccagcaataa ctccggctgg  18060
ggactgctgc gcgcgcccag caagatgttc ggaggggcga ggaagcgttc cgagcagcac  18120
cccgtgcgcg tgcgcgggca cttccgcgcc ccctggggag cgcacaaacg cggccgcgcg  18180
gggcgcacca ccgtggacga cgccatcgac tcggtggtgg agcaggcgcg caactacagg  18240
cccgcggtct ctaccgtgga cgcggccatc cagaccgtgg tgcggggcgc gcggcggtac  18300
gccaagctga agagccgccg gaagcgcgtg gcccgccgcc accgccgccg acccggggcc  18360
gccgccaaac gcgccgccgc ggccctgctt cgccgggcca agcgcacggg ccgccgcgcc  18420
gccatgaggg ccgcgcgccg cttggccgcc ggcatcaccg ccgccaccat ggcccccgt  18480 acccgaagac gcgcggccgc cgccgccgcc gccgccatca gtgacatggc cagcaggcgc  18540
```

```
cggggcaacg tgtactgggt gcgcgactcg gtgaccggca cgcgcgtgcc cgtgcgcttc   18600
cgccccccgc ggacttgaga tgatgtgaaa aacaacact gagtctcctg ctgttgtgtg    18660
tatcccagcg gcggcggcgc gcgcagcgtc atgtccaagc gcaaaatcaa agaagagatg   18720
ctccaggtcg tcgcgccgga gatctatggg cccccgaaga aggaagagca ggattcgaag   18780
ccccgcaaga taaagcgggt caaaaagaaa aagaaagatg atgacgatgc cgatggggag   18840
gtggagttcc tgcgcgccac ggcgcccagg cgcccggtgc agtggaaggg ccggcgcgta   18900
aagcgcgtcc tgcgccccgg caccgcggtg gtcttcacgc ccggcgagcg ctccacccgg   18960
actttcaagc gcgtctatga cgaggtgtac ggcgacgaag acctgctgga gcaggccaac   19020
gagcgcttcg gagagtttgc ttacgggaag cgtcagcggg cgctggggaa ggaggacctg   19080
ctggcgctgc cgctggacca gggcaacccc accccagtc tgaagcccgt gaccctgcag    19140
caggtgctgc cgagcagcgc accctccgag gcgaagcggg gtctgaagcg cgagggcggc   19200
gacctggcgc ccaccgtgca gctcatggtg cccaagcggc agaggctgga ggatgtgctg   19260
gagaaaatga agtagaccc cggtctgcag ccggacatca gggtccgccc catcaagcag    19320
gtggcgccgg gcctcggcgt gcagaccgtg gacgtggtca tccccaccgg caactccccc   19380
gccgccgcca ccactaccgc tgcctccacg gacatggaga cacagaccga tcccgccgca   19440
gccgcagccg cagccgccgc cgcgacctcc tcgcggagg tgcagacgga ccctggctg     19500 ccgccggcga tgtcagctcc ccgcgcgcgt gcgggcgca ggaagtacgg cgccgccaac    19560
gcgctcctgc ccgagtacgc cttgcatcct tccatcgcgc ccaccccgg ctaccgaggc    19620 tatacctacc gcccgcgaag agccaagggt tccacccgcc gtccccgccg acgcgccgcc   19680
gccaccaccc gccgccgccg ccgcagacgc cagcccgcac tggctccagt ctccgtgagg   19740
aaagtggcgc gcgacggaca caccctggtg ctgcccaggg cgcgctacca ccccagcatc   19800
gtttaaaagc ctgttgtggt tcttgcagat atggccctca cttgccgcct ccgtttcccg   19860
gtgccgggat accgaggagg aagatcgcgc cgcaggaggg gtctggccgg ccgcggcctg   19920
agcggaggca gccgccgcgc gcaccggcgg cgacgcgcca ccagccgacg catgcgcggc   19980
ggggtgctgc ccctgttaat cccctgatc gccgcggcga tcggcgccgt gcccgggatc    20040
gcctccgtgg ccttgcaagc gtcccagagg cattgacaga cttgcaaact tgcaaatatg   20100
gaaaaaaaaa ccccaataaa aaagtctaga ctctcacgct cgcttggtcc tgtgactatt   20160
ttgtagaatg gaagacatca actttgcgtc gctggccccg cgtcacggct cgcgcccgtt   20220
cctgggacac tggaacgata tcggcaccag caacatgagc ggtggcgcct tcagttgggg   20280
ctctctgtgg agcggcatta aaagtatcgg gtctgccgtt aaaaattacg gctcccgggc   20340
ctggaacagc agcacgggcc agatgttgag agacaagttg aaagagcaga acttccagca   20400
gaaggtggtg gagggcctgg cctccggcat caacggggtg gtggacctgg ccaaccaggc   20460
cgtgcagaat aagatcaaca gcagactgga ccccgccg ccggtggagg aggtgccgcc     20520
ggcgctggag acggtgtccc ccgatgggcg tggcgagaag cgcccgcggc ccgatagga    20580 agagaccact ctggtcacgc agaccgatga gccgcccccg tatgaggagg ccctgaagca   20640
aggtctgccc accacgcggc ccatcgcgcc catggccacc ggggtggtgg gccgccacac   20700
ccccgccacg ctggacttgc ctccgcccgc cgatgtgccg cagcagcaga aggcggcaca   20760
gccgggcccg cccgcgaccg cctccgttc ctccgccggt cctctgcgcc gcgcggccag    20820
cggccccgcc gggggggtcg cgaggcacgg caactggcag agcacgctga acagcatcgt   20880
```

```
gggtctgggg gtgcggtccg tgaagcgccg ccgatgctac tgaatagctt agctaacgtg   20940
ttgtatgtgt gtatgcgccc tatgtcgccg ccagaggagc tgctgagtcg ccgccgttcg   21000
cgcgcccacc accaccgcca ctccgcccct caagatggcg accccatcga tgatgccgca   21060
gtggtcgtac atgcacatct cgggccagga cgcctcggag tacctgagcc ccgggctggt   21120
gcagttcgcc cgcgccaccg agagctactt cagcctgagt aacaagttta ggaaccccac   21180
ggtggcgccc acgcacgatg tgaccaccga ccggtctcag cgcctgacgc tgcggttcat   21240
tcccgtggac cgcgaggaca ccgcgtactc gtacaaggcg cggttcaccc tggccgtggg   21300
cgacaaccgc gtgctggaca tggcctccac ctactttgac atccgcgggg tgctggaccg   21360
gggtcccact ttcaagccct actctggcac cgcctacaac tccctggccc caagggcgc    21420
tcccaactcc tgcgagtggg agcaagagga aactcaggca gttgaagaag cagcagaaga   21480
ggaagaagaa gatgctgacg gtcaagctga ggaagagcaa gcagctacca aaaagactca   21540
tgtatatgct caggctcccc tttctggcga aaaaattagt aaagatggtc tgcaaatagg   21600
aacggacgct acagctacag aacaaaaacc tatttatgca gaccctacat ccagcccga    21660
accccaaatc ggggagtccc agtggaatga ggcagatgct acagtcgccg gcggtagagt   21720
gctaaagaaa tctactccca tgaaaccatg ctatggttcc tatgcaagac ccacaaatgc   21780
taatggaggt cagggtgtac taacggcaaa tgcccaggga cagctagaat ctcaggttga   21840
aatgcaattc ttttcaactt ctgaaaacgc ccgtaacgag ctaacaaca ttcagcccaa     21900
attggtgctg tatagtgagg atgtgcacat ggagaccccg gatacgcacc tttcttacaa   21960
gcccgcaaaa agcgatgaca attcaaaaat catgctgggt cagcagtcca tgcccaacag   22020
acctaattac atcggcttca gagacaactt tatcggcctc atgtattaca atagcactgg   22080
caacatggga gtgcttgcag gtcaggcctc tcagttgaat gcagtggtgg acttgcaaga   22140
cagaaacaca gaactgtcct accagctctt gcttgattcc atgggtgaca gaaccagata   22200
cttttccatg tggaatcagg cagtggacag ttatgaccca gatgttagaa ttattgaaaa   22260
tcatggaact gaagacgagc tccccaacta ttgtttccct ctgggtggca tagggtaac    22320
tgacacttac caggctgtta aaaccaacaa tggcaataac gggggccagg tgacttggac   22380
aaaagatgaa acttttgcag atcgcaatga aatagggtg ggaaacaatt tcgctatgga    22440
gatcaacctc agtgccaacc tgtggagaaa cttcctgtac tccaacgtgg cgctgtacct   22500
accagacaag cttaagtaca cccctccaa tgtggacatc tctgacaacc ccaacaccta    22560
cgattacatg aacaagcgag tggtggcccc ggggctggtg gactgctaca tcaacctggg   22620
cgcgcgctgg tcgctggact acatggacaa cgtcaacccc ttcaaccacc accgcaatgc   22680
gggcctgcgc taccgctcca tgctcctggg caacgggcgc tacgtgccct tccacatcca   22740
ggtgccccag aagttctttg ccatcaagaa cctcctcctc ctgccgggct cctacaccta   22800
cgagtggaac ttcaggaagg atgtcaacat ggtcctccag agctctctgg gtaacgatct   22860
cagggtggac ggggccagca tcaagttcga gagcatctgc ctctacgcca ccttcttccc   22920
catggcccac aacacggcct ccacgctcga ggccatgctc aggaacgaca ccaacgacca   22980
gtccttcaat gactacctct ccgccgccaa catgctctac cccataccgg ccaacgccac   23040
caacgtcccc atctccatcc cctcgcgcaa ctgggcggcc ttccgcggct gggccttcac   23100
ccgcctcaag accaaggaga ccccctcct gggctcggga ttcgacccct actacctta    23160
ctcgggctcc attccctacc tggacggcac cttctacctc aaccacactt tcaagaaggt   23220
ctcggtcacc ttcgactcct cggtcagctg gccgggcaac gaccgtctgc tcacccccaa   23280
```

```
cgagttcgag atcaagcgct cggtcgacgg ggagggctac aacgtggccc agtgcaacat   23340
gaccaaggac tggttcctgg tccagatgct ggccaactaa acatcggct accagggctt    23400
ctacatccca gagagctaca aggacaggat gtactccttc ttcaggaact tccagcccat   23460
gagccggcag gtggtggacc agaccaagta caaggactac caggaggtgg gcatcatcca   23520
ccagcacaac aactcgggct tcgtgggcta cctcgccccc accatgcgcg agggacaggc   23580
ctaccccgcc aacttcccct atccgctcat aggcaagacc gcggtcgaca gcatcaccca   23640
gaaaaagttc ctctgcgacc gcaccctctg gcgcatcccc ttctccagca acttcatgtc   23700
catgggtgcg ctctcggacc tgggccagaa cttgctctac gccaactccg cccacgccct   23760
cgacatgacc ttcgaggtcg accccatgga cgagcccacc cttctctatg ttctgttcga   23820
agtctttgac gtggtccggg tccaccagcc gcaccgcggc gtcatcgaga ccgtgtacct   23880
gcgtacgccc ttctcggccg gcaacgccac cacctaaaga agcaagccgc agtcatcgcc   23940
gcctgcatgc cgtcgggttc caccgagcaa gagctcaggg ccatcgtcag agacctggga   24000
tgcgggccct atttttggg caccttcgac aagcgcttcc ctggctttgt ctccccacac    24060
aagctggcct cgccatcgt caacacggcc ggccgcgaga ccggggcgt gcactggctg     24120
gccttcgcct ggaacccgcg ctccaaaaca tgcttcctct ttgacccctt cggcttttcg   24180
gaccagcggc tcaagcaaat ctacgagttc gagtacgagg gcttgctgcg tcgcagcgcc   24240
atcgcctcct cgcccgaccg ctgcgtcacc ctcgaaaagt ccacccagac cgtgcagggg   24300
cccgactcgg ccgcctgcgg tctcttctgc tgcatgtttc tgcacgcctt tgtgcactgg   24360
cctcagagtc ccatggaccg caaccccacc atgaacttgc tgacggggt gcccaactcc    24420
atgctccaga gccccaggt cgagcccacc ctgcgccgca accaggagca gctctacagc    24480
ttcctggagc gccactcgcc ttacttccgc cgccacagcg cacagatcag gagggccacc   24540
tccttctgcc acttgcaaga gatgcaagaa gggtaataac gatgtacaca ctttttttct   24600
caataaatgg catcttttta tttatacaag ctctctgggg tattcatttc ccaccaccac   24660
ccgccgttgt cgccatctgg ctctatttag aaatcgaaag ggttctgccg ggagtcgccg   24720
tgcgccacgg gcagggacac gttgcgatac tggtagcggg tgcccacctt gaactcgggc   24780
accaccaggc gaggcagctc ggggaagttt tcgctccaca ggctgcgggt cagcaccagc   24840
gcgttcatca ggtcgggcgc cgagatcttg aagtcgcagt tggggccgcc gcctgcgcg    24900
cgcgagttgc ggtacaccgg gttgcagcac tggaacacca acagcgccgg gtgcttcacg   24960
ctggccagca cgctgcggtc ggagatcagc tcggcgtcca ggtcctccgc gttgctcagc   25020
gcgaacgggg tcatcttggg cacttgccgc cccaggaagg gcgcgtgccc cggtttcgag   25080
ttgcagtcgc agcgcagcgg gatcagcagg tgcccgtgcc cggactcggc gttggggtac   25140
agcgcgcgca tgaaggcctg catctggcgg aaggccatct gggccttggc gccctccgag   25200
aagaacatgc cgcaggactt gcccgagaac tggtttgcgg ggcagctggc gtcgtgcagg   25260
cagcagcgcg cgtcggtgtt ggcgatctgc accacgttgc gcccccaccg gttcttcacg   25320
atcttggcct tggacgattg ctccttcagc gcgcgctgcc cgttctcgct ggtcacatcc   25380
atctcgatca catgttcctt gttcaccatg ctgctgccgt gcagacactt cagctcgccc   25440
tccgtctcgg tgcagcggtg ctgccacagc gcgcagcccg tgggctcgaa agacttgtag   25500
gtcacctccg cgaaggactg caggtacccc tgcaaaaagc ggcccatcat ggtcacgaag   25560
gtcttgttgc tgctgaaggt cagctgcagc ccgcggtgct cctcgttcag ccaggtcttg   25620
```

```
cacacggccg ccagcgcctc cacctggtcg ggcagcatct tgaagttcac cttcagctca  25680
ttctccacgt ggtacttgtc catcagcgtg cgcgccgcct ccatgccctt ctcccaggcc  25740
gacaccagcg gcaggctcac ggggttcttc accatcaccg tggccgccgc ctccgccgcg  25800
ctttcgcttt ccgccccgct gttctcttcc tcttcctcct cttcctcgcc gccgcccact  25860
cgcagccccc gcaccacggg gtcgtcttcc tgcaggcgct gcaccttgcg cttgccgttg  25920
cgccctgct tgatgcgcac gggcggggttg ctgaagccca ccatcaccag cgcggcctct  25980
tcttgctcgt cctcgctgtc cagaatgacc tccggggagg gggggttggt catcctcagt  26040
accgaggcac gcttctttt cttcctgggg gcgttcgcca gctccgcggc tgcggccgct  26100
gccgaggtcg aaggccgagg gctgggcgtg cgcggcacca gcgcgtcctg cgagccgtcc  26160
tcgtcctcct cggactcgag acggaggcgg gcccgcttct tcgggggcgc gcggggcggc  26220
ggaggcggcg gcggcgacgg agacggggac gagacatcgt ccagggtggg tggacggcgg  26280
gccgcgccgc gtccgcgctc gggggtggtc tcgcgctggt cctcttcccg actggccatc  26340
tcccactgct ccttctccta taggcagaaa gagatcatgg agtctctcat gcgagtcgag  26400
aaggaggagg acagcctaac cgcccctct gagccctcca ccaccgccgc caccaccgcc  26460
aatgccgcca cggacgacgc gcccaccgag accaccgcca gtaccaccct cccagcgac  26520
gcaccccgc tcgagaatga agtgctgatc gagcaggacc cgggttttgt gagcggagag  26580
gaggatgagg tggatgagaa ggagaaggag gaggtcgccg cctcagtgcc aaaagaggat  26640
aaaaagcaag accaggacga cgcagataag gatgagacag cagtcgggcg ggggaacgga  26700
agccatgatg ctgatgacgg ctacctagac gtgggagacg acgtgctgct taagcacctg  26760
caccgccagt gcgtcatcgt ctgcgacgcg ctgcaggagc gctgcgaagt gccccttggac  26820
gtggcggagg tcagccgcgc ctacgagcgg cacctcttcg cgccgcacgt gccccccaag  26880
cgccgggaga acggcacctg cgagcccaac ccgcgtctca acttctaccc ggtcttcgcg  26940
gtacccgagg tgctgccac ctaccacatc tttttccaaa actgcaagat cccctctcc  27000
tgccgcgcca accgcacccg cgccgacaaa accctgaccc tgcggcaggg cgcccacata  27060
cctgatatcg cctctctgga ggaagtgccc aagatcttcg agggtctcgg tcgcgacgag  27120
aaacgggcgg cgaacgctct gcacggagac agcgaaaacg agagtcactc gggggtgctg  27180
gtggagctcg agggcgacaa cgcgcgcctg ccgtactca agcgcagcat agaggtcacc  27240
cactttgcct acccggcgct caacctgccc cccaaggtca tgagtgtggt catgggcgag  27300
ctcatcatgc gccgcgccca gcccctggcc gcggatgcaa acttgcaaga gtcctccgag  27360
gaaggcctgc ccgcggtcag cgacgagcag ctggcgcgct ggctggagac ccgcgacccc  27420
gcgcagctgg aggagcggcg caagctcatg atggccgcgg tgctggtcac cgtgagctc  27480
gagtgtctgc agcgcttctt cgcggacccc gagatgcagc gcaagctcga ggagaccctg  27540
cactacacct tccgccaggg ctacgtgcgc caggcctgca agatctccaa cgtggagctc  27600
tgcaacctgg tctcctacct gggcatcctg cacgagaacc gcctcgggca gaacgtcctg  27660
cactccaccc tcaaagggga ggcgcgccgc gactacatcc gcgactgcgc ctacctcttc  27720
ctctgctaca cctggcagac ggccatgggg gtctggcagc agtgcctgga ggagcgcaac  27780
ctcaaggagc tggaaaagct cctcaagcgc accctcaggg acctctggac gggcttcaac  27840
gagcgctcgg tggccgccgc gctggcggac atcatctttc ccgagcgcct gctcaagacc  27900
ctgcagcagg gcctgcccga cttcaccagc cagagcatgc tgcagaactt caggactttc  27960
atcctggagc gctcgggcat cctgccggcc acttgctgcg cgctgcccag cgacttcgtg  28020
```

```
cccatcaagt acagggagtg cccgccgccg ctctggggcc actgctacct cttccagctg    28080
gccaactacc tcgcctacca ctcggacctc atggaagacg tgagcggcga gggcctgctc    28140
gagtgccact gccgctgcaa cctctgcacg ccccaccgct ctctagtctg caacccgcag    28200
ctgctcagcg agagtcagat tatcggtacc ttcgagctgc agggtccctc gcctgacgag    28260
aagtccgcgg ctccagggct gaaactcact ccggggctgt ggacttccgc ctacctacgc    28320
aaatttgtac ctgaggacta ccacgcccac gagatcaggt tctacgaaga ccaatcccgc    28380
ccgcccaagg cggagctcac cgcctgcgtc atcacccagg ggcacatcct gggccaattg    28440
caagccatca acaaagcccg ccgagagttc ttgctgaaaa agggtcgggg ggtgtacctg    28500
gaccccagt ccggcgagga gctaaacccg ctaccccgc cgccgcccca gcagcgggac       28560
cttgcttccc aggatggcac ccagaaagaa gcagcagccg ccgccgccgc cgcagccata    28620
catgcttctg gaggaagagg aggaggactg ggacagtcag gcagaggagg tttcggacga    28680
ggagcaggag gagatgatgg aagactggga ggaggacagc agcctagacg aggaagcttc    28740
agaggccgaa gaggtggcag acgcaacacc atcgccctcg gtcgcagccc cctcgccggg    28800
gccccctgaaa tcctccgaac ccagcaccag cgctataacc tccgctcctc cggcgccggc    28860
gccacccgcc cgcagaccca accgtagatg ggacaccaca ggaaccgggg tcggtaagtc    28920
caagtgcccg ccgccgccac cgcagcagca gcagcagcag cgccagggct accgctcgtg    28980
gcgcgggcac aagaacgcca tagtcgcctg cttgcaagac tgcgggggca acatctcttt    29040
cgcccgccgc ttcctgctat tccaccacgg ggtcgccttt ccccgcaatg tcctgcatta    29100
ctaccgtcat ctctacagcc cctactgcag cggcgaccca gaggcggcag cggcagccac    29160
agcggcgacc accacctagg aagatatcct ccgcgggcaa gacagcggca gcagcggcca    29220
ggagacccgc ggcagcagcg gcgggagcgg tgggcgcact gcgcctctcg cccaacgaac    29280
ccctctcgac ccgggagctc agacacagga tcttccccac tttgtatgcc atcttccaac    29340
agagcagagg ccaggagcag gagctgaaaa taaaaaacag atctctgcgc tccctcaccc    29400
gcagctgtct gtatcacaaa agcgaagatc agcttcggcg cacgctggag gacgcggagg    29460
cactcttcag caaatactgc gcgctcactc ttaaagacta gctccgcgcc cttctcgaat    29520
ttaggcggga gaaaactacg tcatcgccgg ccgccgccca gcccgcccag ccgagatgag    29580
caaagagatt cccacgccat acatgtggag ctaccagccg cagatgggac tcgcggcggg    29640
agcggcccag gactactcca cccgcatgaa ctacatgagc gcggacccc acatgatctc     29700
acaggtcaac gggatccgcg cccagcgaaa ccaaatactg ctggaacagg cggccatcac    29760
cgccacgccc cgccataatc tcaaccccg aaattggccc gccgccctcg tgtaccagga    29820
aaccccctcc gccaccaccg tactacttcc gcgtgacgcc caggccgaag tccagatgac    29880
taactcaggg gcgcagctcg cgggcggctt tcgtcacggg gcgcggccgc tccgaccagg    29940
tataagacac ctgatgatca gaggccgagg tatccagctc aacgacgagt cggtgagctc    30000
ttcgctcggt ctccgtccgg acggaacttt ccagctcgcc ggatccggcc gctcttcgtt    30060
cacgccccgc caggcgtacc tgactctgca gacctcgtcc tcggagcccc gctccggcgg    30120
catcggaacc ctccagttcg tggaggagtt cgtgccctcg gtctacttca accccttctc    30180
gggacctccc ggacgctacc ccgaccagtt cattccgaac tttgacgcgg tgaaggactc    30240
ggcggacggc tacgactgaa tgtcaggtgt cgaggcagag cagcttcgcc tgagacacct    30300
cgagcactgc cgccgccaca agtgcttcgc ccgcggttct ggtgagttct gctactttca    30360
```

```
gctacccgag gagcataccg aggggccggc gcacggcgtc cgcctgacca cccagggcga   30420
ggttacctgt tccctcatcc gggagtttac cctccgtccc ctgctagtgg agcgggagcg   30480
gggtccctgt gtcctaacta tcgcctgcaa ctgccctaac cctggattac atcaagatct   30540
ttgctgtcat ctctgtgctg agtttaataa acgctgagat cagaatctac tgggatttag   30600 tccccttaa ctaatcaaac actggaatca ataaaaagaa tcacttactt aaaatcagac   30660
agcaggtctc tgtccagttt attcagcagc acctccttcc cctcctccca actctggtac   30720
tccaaacgcc ttctggcggc aaacttcctc cacaccctga agggaatgtc agattcttgc   30780
tcctgtccct ccgcacccac tatcttcatg ttgttgcaga tgaagcgcac caaaacgtct   30840
gacgagagct tcaaccccgt gtaccsctat gacacggaaa gcggccctcc ctccgtccct   30900
ttcctcaccc ctcccttcgt gtctcccgat ggattccaag aaagtccccc cggggtcctg   30960
tctctgaacc tggccgagcc cctggtcact tcccacggca tgctcgccct gaaaatggga   31020
agtggcctct ccctggacga cgctggcaac ctcacctctc aagatatcac caccgctagc   31080
cctcccctca aaaaaaccaa gaccaacctc agcctagaaa cctcatcccc cctaactgtg   31140
agcacctcag gcgccctcac cgtagcagcc gccgctcccc tggcggtggc cggcacctcc   31200
ctcaccatgc aatcagaggc ccccctgaca gtacaggatg caaaactcac cctggccacc   31260
aaaggccccc tgaccgtgtc tgaaggcaaa ctggccttgc aaacatcggc cccgctgacg   31320
gccgctgaca gcagcaccct cacagtcagt gccacaccac cccttagcac aagcaatggc   31380
agcttgggta ttgacatgca agccccccatt tacaccacca atggaaaact aggacttaac   31440
tttggcgctc ccctgcatgt ggtagacagc ctaaatgcac tgactgtagt tactggccaa   31500
ggtcttacga taaacggaac agccctacaa actagagtct caggtgccct caactatgac   31560
acatcaggaa acctagaatt gagagctgca gggggtatgc gagttgatgc aaatggtcaa   31620
cttatccttg atgtagctta cccatttgat gcacaaaaca atctcagcct taggcttgga   31680
cagggacccc tgtttgttaa ctctgcccac aacttggatg ttaactacaa cagaggcctc   31740
tacctgttca catctggaaa taccaaaaag ctagaagtta atatcaaaac agccaagggt   31800
ctcatttatg atgacactgc tatagcaatc aatgcgggtg atgggctaca gtttgactca   31860
ggctcagata caaatccatt aaaaactaaa cttggattag gactggatta tgactccagc   31920
agagccataa ttgctaaact gggaactggc ctaagctttg acaacacagg tgccatcaca   31980
gtaggcaaca aaaatgatga caagcttacc ttgtggacca caccagaccc atcccctaac   32040
tgtagaatct attcagagaa agatgctaaa ttcacacttg ttttgactaa atgcggcagt   32100
caggtgttgg ccagcgtttc tgttttatct gtaaaaggta gccttgcgcc catcagtggc   32160
acagtaacta gtgctcagat tgtcctcaga tttgatgaaa atggagttct actaagcaat   32220
tcttcccttg accctcaata ctggaactac agaaaaggtg accttacaga gggcactgca   32280
tataccaacg cagtgggatt tatgcccaac ctcacagcat acccaaaaac acagagccaa   32340
actgctaaaa gcaacattgt aagtcaggtt acttgaatg gggacaaatc caaacccatg   32400
accctcacca ttaccctcaa tggaactaat gaaacaggag atgccacagt aagcacttac   32460
tccatgtcat tctcatggaa ctggaatgga agtaattaca ttaatgaaac gttccaaacc   32520
aactccttca ccttctccta catcgcccaa gaataaaaag catgacgctg ttgatttgat   32580
tcaatgtgtt tctgttttat tttcaagcac aacaaaatca ttcaagtcat tcttccatct   32640
tagcttaata gacacagtag cttaatagac ccagtagtgc aaagcccat tctagcttat   32700 aactagtgga gaagtactcg cctacatggg ggtagagtca taatcgtgca tcaggatagg   32760
```

```
gcggtggtgc tgcagcagcg cgcgaataaa ctgctgccgc cgccgctccg tcctgcagga   32820
atacaacatg gcagtggtct cctcagcgat gattcgcacc gcccgcagca taaggcgcct   32880
tgtcctccgg gcacagcagc gcaccctgat ctcacttaaa tcagcacagt aactgcagca   32940
cagcaccaca atattgttca aaatcccaca gtgcaaggcg ctgtatccaa agctcatggc   33000
ggggaccaca gaacccacgt ggccatcata ccacaagcgc aggtagatta agtggcgacc   33060
cctcataaac acgctggaca taaacattac ctcttttggc atgttgtaat tcaccacctc   33120
ccggtaccat ataaacctct gattaaacat ggcgccatcc accaccatcc taaaccagct   33180
ggccaaaacc tgcccgccgg ctatacactg cagggaaccg ggactggaac aatgacagtg   33240
gagagcccag gactcgtaac catggatcat catgctcgtc atgatatcaa tgttggcaca   33300
acacaggcac acgtgcatac acttcctcag gattacaagc tcctcccgcg ttagaaccat   33360
atcccaggga acaacccatt cctgaatcag cgtaaatccc acactgcagg gaagacctcg   33420
cacgtaactc acgttgtgca ttgtcaaagt gttacattcg ggcagcagcg gatgatcctc   33480
cagtatggta gcgcgggttt ctgtctcaaa aggaggtaga cgatccctac tgtacggagt   33540
gcgccgagac aaccgagatc gtgttggtcg tagtgtcatg ccaaatggaa cgccggacgt   33600
agtcatattt cctgaagtct tagatctctc aacgcagcac cagcaccaac acttcgcagt   33660
gtaaaaggcc aagtgccgag agagtatata taggaataaa aagtgacgta aacgggcaaa   33720
gtccaaaaaa cgcccagaaa aaccgcacgc gaacctacgc cccgaaacga aagccaaaaa   33780
acactagaca ctcccttccg gcgtcaactt ccgctttccc acgctacgtc acttgcccca   33840
gtcaaacaaa ctacatatcc cgaacttcca agtcgccacg cccaaaacac cgcctacacc   33900
tccccgcccg ccggcccgcc cccaaacccg cctcccgccc cgcgcccgc ccgcgccgc    33960 ccatctcatt atcatattgg cttcaatcca aaataaggta tattattgat gatggtttaa   34020
acggatcctc tagagtcgac ctgcaggcat gcaagcttga gtattctata gtgtcaccta   34080
aatagcttgg cgtaatcatg gtcatagctg tttcctgtgt gaaattgtta tccgctcaca   34140
attccacaca acatacgagc cggaagcata aagtgtaaag cctggggtgc ctaatgagtg   34200
agctaactca cattaattgc gttgcgctca ctgcccgctt tccagtcggg aaacctgtcg   34260
tgccagctgc attaatgaat cggccaacgc gaacccttg cggccgcccg gccgtcgac    34320 caattctcat gtttgacagc ttatcatcga atttctgcca ttcatccgct tattatcact   34380
tattcaggcg tagcaaccag gcgtttaagg gcaccaataa ctgccttaaa aaaattacgc   34440
cccgccctgc cactcatcgc agtactgttg taattcatta agcattctgc cgacatggaa   34500
gccatcacaa acggcatgat gaacctgaat cgccagcggc atcagcacct tgtcgccttg   34560
cgtataatat ttgcccatgg tgaaaacggg ggcgaagaag ttgtccatat tggccacgtt   34620
taaatcaaaa ctggtgaaac tcacccaggg attggctgag acgaaaaaca tattctcaat   34680
aaacccttta gggaaatagg ccaggttttc accgtaacac gccacatctt gcgaatatat   34740
gtgtagaaac tgccggaaat cgtcgtggta ttcactccag agcgatgaaa acgtttcagt   34800
ttgctcatgg aaaacggtgt aacaagggtg aacactatcc catatcacca gctcaccgtc   34860
tttcattgcc atacggaatt ccggatgagc attcatcagg cgggcaagaa tgtgaataaa   34920
ggccggataa aacttgtgct tatttttctt tacggtcttt aaaaaggccg taatatccag   34980
ctgaacggtc tggttatagg tacattgagc aactgactga atgcctcaa aatgttcttt   35040 acgatgccat tgggatatat caacggtggt atatccagtg atttttttct ccatttagc    35100
```

```
ttccttagct cctgaaaatc tcgataactc aaaaaatacg cccggtagtg atcttatttc   35160
attatggtga aagttggaac ctcttacgtg ccgatcaacg tctcatttttc gccaaaagtt   35220
ggcccagggc ttcccggtat caacagggac accaggattt atttattctg cgaagtgatc   35280
ttccgtcaca ggtatttatt cgcgataagc tcatggagcg gcgtaaccgt cgcacaggaa   35340
ggacagagaa agcgcggatc tgggaagtga cggacagaac ggtcaggacc tggattgggg   35400
aggcggttgc cgccgctgct gctgacggtg tgacgttctc tgttccggtc acaccacata   35460
cgttccgcca ttcctatgcg atgcacatgc tgtatgccgg tataccgctg aaagttctgc   35520
aaagcctgat gggacataag tccatcagtt caacggaagt ctacacgaag gtttttgcgc   35580
tggatgtggc tgcccggcac cgggtgcagt ttgcgatgcc ggagtctgat gcggttgcga   35640
tgctgaaaca attatcctga gaataaatgc cttggccttt atatggaaat gtggaactga   35700
gtggatatgc tgttttttgtc tgttaaacag agaagctggc tgttatccac tgagaagcga   35760
acgaaacagt cgggaaaatc tcccattatc gtagagatcc gcattattaa tctcaggagc   35820
ctgtgtagcg tttataggaa gtagtgttct gtcatgatgc ctgcaagcgg taacgaaaac   35880
gatttgaata tgccttcagg aacaatagaa atcttcgtgc ggtgttacgt tgaagtggag   35940
cggattatgt cagcaatgga cagaacaacc taatgaacac agaaccatga tgtggtctgt   36000
cctttacag ccagtagtgc tcgccgcagt cgagcgacag ggcgaagccc tcgagtgagc   36060
gaggaagcac cagggaacag cacttatata ttctgcttac acacgatgcc tgaaaaaact   36120
tcccttgggg ttatccactt atccacgggg atatttttat aattattttt tttatagttt   36180
ttagatcttc ttttttagag cgccttgtag gcctttatcc atgctggttc tagagaaggt   36240
gttgtgacaa attgcccttt cagtgtgaca aatcaccctc aaatgacagt cctgtctgtg   36300
acaaattgcc cttaaccctg tgacaaattg ccctcagaag aagctgtttt ttcacaaagt   36360
tatccctgct tattgactct ttttttattta gtgtgacaat ctaaaaactt gtcacacttc   36420
acatggatct gtcatggcgg aaacagcggt tatcaatcac aagaaacgta aaaatagccc   36480
gcgaatcgtc cagtcaaacg acctcactga ggcggcatat agtctctccc gggatcaaaa   36540
acgtatgctg tatctgttcg ttgaccagat cagaaaatct gatggcaccc tacaggaaca   36600
tgacggtatc tgcgagatcc atgttgctaa atatgctgaa atattcggat tgacctctgc   36660
ggaagccagt aaggatatac ggcaggcatt gaagagtttc gcggggaagg aagtggtttt   36720
ttatcgccct gaagaggatg ccggcgatga aaaaggctat gaatcttttc cttggttat   36780
caaacgtgcg cacagtccat ccagagggct ttacagtgta catatcaacc catatctcat   36840
tcccttcttt atcgggttac agaaccggtt tacgcagttt cggcttagtg aaacaaaaga   36900
aatcaccaat ccgtatgcca tgcgtttata cgaatccctg tgtcagtatc gtaagccgga   36960
tggctcaggc atcgtctctc tgaaaatcga ctggatcata gagcgttacc agctgcctca   37020
aagttaccag cgtatgcctg acttccgccg ccgcttcctg caggtctgtg ttaatgagat   37080
caacagcaga actccaatgc gcctctcata cattgagaaa agaaaggcc gccagacgac   37140
tcatatcgta ttttccttcc gcgatatcac ttccatgacg acaggatagt ctgagggtta   37200
tctgtcacag atttgagggt ggttcgtcac atttgttctg acctactgag ggtaaatttgt   37260
cacagttttg ctgtttcctt cagcctgcat ggattttctc atactttttg aactgtaatt   37320
tttaaggaag ccaaatttga gggcagtttg tcacagttga tttccttctc tttcccttcg   37380
tcatgtgacc tgatatcggg ggttagttcg tcatcattga tgagggttga ttatcacagt   37440
ttattactct gaattggcta tccgcgtgtg tacctctacc tggagttttt cccacggtgg   37500
```

```
atatttcttc ttgcgctgag cgtaagagct atctgacaga acagttcttc tttgcttcct    37560
cgccagttcg ctcgctatgc tcggttacac ggctgcggcg agcgctagtg ataataagtg    37620
actgaggtat gtgctcttct tatctccttt tgtagtgttg ctcttatttt aaacaacttt    37680 gcggttttt  gatgactttg cgattttgtt gttgctttgc agtaaattgc aagatttaat    37740 aaaaaacgc  aaagcaatga ttaaaggatg ttcagaatga aactcatgga aacacttaac    37800
cagtgcataa acgctggtca tgaaatgacg aaggctatcg ccattgcaca gtttaatgat    37860
gacagcccgg aagcgaggaa ataacccgg  cgctggagaa taggtgaagc agcggattta    37920
gttgggtttt cttctcaggc tatcagagat gccgagaaag cagggcgact accgcacccg    37980
gatatggaaa ttcgaggacg ggttgagcaa cgtgttggtt atacaattga acaaattaat    38040
catatgcgtg atgtgtttgg tacgcgattg cgacgtgctg aagacgtatt tccaccggtg    38100
atcggggttg ctgcccataa aggtggcgtt tacaaaacct cagtttctgt tcatcttgct    38160
caggatctgg ctctgaaggg gctacgtgtt ttgctcgtgg aaggtaacga cccccaggga    38220
acagcctcaa tgtatcacgg atgggtacca gatcttcata ttcatgcaga agacactctc    38280 ctgccttct  atcttgggga aaaggacgat gtcacttatg caataaagcc cacttgctgg    38340
ccggggcttg acattattcc ttcctgtctg gctctgcacc gtattgaaac tgagttaatg    38400
ggcaaatttg atgaaggtaa actgcccacc gatccacacc tgatgctccg actgccatt     38460 gaaactgttg ctcatgacta tgatgtcata gttattgaca gcgcgcctaa cctgggtatc    38520
ggcacgatta atgtcgtatg tgctgctgat gtgctgattg ttcccacgcc tgctgagttg    38580
tttgactaca cctccgcact gcagttttc  gatatgcttc gtgatctgct caagaacgtt    38640
gatcttaaag ggttcgagcc tgatgtacgt attttgctta ccaaatacag caatagtaat    38700
ggctctcagt ccccgtggat ggaggagcaa attcgggatg cctggggaag catggttcta    38760
aaaaatgttg tacgtgaaac ggatgaagtt ggtaaaggtc agatccggat gagaactgtt    38820
tttgaacagg ccattgatca acgctcttca actggtgcct ggagaaatgc tctttctatt    38880
tgggaacctg tctgcaatga aattttcgat cgtctgatta aaccacgctg ggagattaga    38940
taatgaagcg tgcgcctgtt attccaaaac atacgctcaa tactcaaccg gttgaagata    39000
cttcgttatc gacaccagct gccccgatgg tggattcgtt aattgcgcgc gtaggagtaa    39060
tggctcgcgg taatgccatt actttgcctg tatgtggtcg ggatgtgaag tttactcttg    39120
aagtgctccg gggtgatagt gttgagaaga cctctcgggt atggtcaggt aatgaacgtg    39180
accaggagct gcttactgag gacgcactgg atgatctcat cccttctttt ctactgactg    39240
gtcaacagac accggcgttc ggtcgaagag tatctggtgt catagaaatt gccgatggga    39300
gtcgccgtcg taaagctgct gcacttaccg aaagtgatta tcgtgttctg gttggcgagc    39360
tggatgatga gcagatggct gcattatcca gattgggtaa cgattatcgc ccaacaagtg    39420
cttatgaacg tggtcagcgt tatgcaagcc gattgcagaa tgaatttgct ggaaatattt    39480
ctgcgctggc tgatgcggaa aatatttcac gtaagattat tacccgctgt atcaacaccg    39540
ccaaattgcc taaatcagtt gttgctcttt tttctcaccc cggtgaacta tctgcccggt    39600
caggtgatgc acttcaaaaa gcctttacag ataaagagga attacttaag cagcaggcat    39660
ctaaccttca tgagcagaaa aaagctgggg tgatatttga agctgaagaa gttatcactc    39720
ttttaacttc tgtgcttaaa acgtcatctg catcaagaac tagtttaagc tcacgacatc    39780
agtttgctcc tggagcgaca gtattgtata agggcgataa aatggtgctt aacctggaca    39840
```

```
ggtctcgtgt tccaactgag tgtatagaga aaattgaggc cattcttaag gaacttgaaa    39900
agccagcacc ctgatgcgac cacgttttag tctacgttta tctgtcttta cttaatgtcc    39960
tttgttacag gccagaaagc ataactggcc tgaatattct ctctgggccc actgttccac    40020
ttgtatcgtc ggtctgataa tcagactggg accacggtcc cactcgtatc gtcggtctga    40080
ttattagtct gggaccacgg tcccactcgt atcgtcggtc tgattattag tctgggacca    40140
cggtcccact cgtatcgtcg gtctgataat cagactggga ccacggtccc actcgtatcg    40200
tcggtctgat tattagtctg gaccatggt cccactcgta tcgtcggtct gattattagt     40260
ctgggaccac ggtcccactc gtatcgtcgg tctgattatt agtctggaac cacggtccca    40320
ctcgtatcgt cggtctgatt attagtctgg gaccacggtc ccactcgtat cgtcggtctg    40380
attattagtc tgggaccacg atcccactcg tgttgtcggt ctgattatcg gtctgggacc    40440
acggtcccac ttgtattgtc gatcagacta tcagcgtgag actacgattc catcaatgcc    40500
tgtcaagggc aagtattgac atgtcgtcgt aacctgtaga acggagtaac ctcggtgtgc    40560
ggttgtatgc ctgctgtgga ttgctgctgt gtcctgctta ccacaacat tttgcgcacg     40620 gttatgtgga caaaatacct ggttacccag gccgtgccgg cacgttaacc gggctgcatc    40680
cgatgcaagt gtgtcgctgt cgacgagctc gcgagctcgg acatgaggtt gccccgtatt    40740
cagtgtcgct gatttgtatt gtctgaagtt gttttacgt taagttgatg cagatcaatt     40800
aatacgatac ctgcgtcata attgattatt tgacgtggtt tgatggcctc cacgcacgtt    40860
gtgatatgta gatgataatc attatcactt tacgggtcct ttccggtgat ccgacaggtt    40920
acggggcggc gacctcgcgg gttttcgcta tttatgaaaa tttccggtt taaggcgttt     40980 ccgttcttct tcgtcataac ttaatgtttt tatttaaaat accctctgaa agaaaggaa     41040 acgacaggtg ctgaaagcga gcttttggc ctctgtcgtt tcctttctct gttttgtcc     41100 gtggaatgaa caatggaagt ccgagctcat cgctaataac ttcgtatagc atacattata    41160
cgaagttata ttcgatgcgg ccgcaagggg ttcgcgtcag cgggtgttgg cgggtgtcgg    41220
ggctggctta actatgcggc atcagagcag attgtactga gagtgcacca tatgcggtgt    41280
gaaataccgc acagatgcgt aaggagaaaa taccgcatca ggcgccattc gccattcagg    41340
ctgcgcaact gttgggaagg gcgatcggtg cgggcctctt cgctattacg ccagctggcg    41400
aaagggggat gtgctgcaag gcgattaagt tgggtaacgc cagggttttc ccagtcacga    41460
cgttgtaaaa cgacggccag tgaattgtaa tacgactcac tataggcgga attcgagctc    41520
ggtacccggg gatcctcgtt taaac                                          41545
```

<210> SEQ ID NO 54
<211> LENGTH: 42220
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (16789)..(16789)
<223> OTHER INFORMATION: a, c, t, g, unknown or other

<400> SEQUENCE: 54

```
catcatcaat aatatacctt attttggatt gaagccaata tgataatgag atgggcggcg      60
cggggcgggg cgcggggcgg gaggcggggtt tgggggcggg ccggcgggcg gggcggtgtg    120
gcggaagtgg actttgtaag tgtggcggat gtgacttgct agtgccgggc gcggtaaaag    180
```

```
tgacgttttc cgtgcgcgac aacgcccccg ggaagtgaca ttttcccgc ggttttacc      240 ggatgttgta gtgaatttgg gcgtaaccaa gtaagatttg gccattttcg cgggaaaact     300
gaaacgggga agtgaaatct gattaatttt gcgttagtca taccgcgtaa tatttgtcta     360
gggccgaggg actttggccg attacgtgga ggactcgccc aggtgttttt tgaggtgaat     420
ttccgcgttc cgggtcaaag tctgcgtttt attattatag gatatcccat tgcatacgtt     480
gtatccatat cataatatgt acatttatat tggctcatgt ccaacattac cgccatgttg     540
acattgatta ttgactagtt attaatagta atcaattacg gggtcattag ttcatagccc     600
atatatggag ttccgcgtta cataacttac ggtaaatggc ccgcctggct gaccgcccaa     660
cgacccccgc ccattgacgt caataatgac gtatgttccc atagtaacgc caatagggac     720
tttccattga cgtcaatggg tggagtattt acggtaaact gcccacttgg cagtacatca     780
agtgtatcat atgccaagta cgccccctat tgacgtcaat gacggtaaat ggcccgcctg     840
gcattatgcc cagtacatga ccttatggga ctttcctact tggcagtaca tctacgtatt     900
agtcatcgct attaccatgg tgatgcggtt ttggcagtac atcaatgggc gtggatagcg     960
gtttgactca cggggatttc caagtctcca ccccattgac gtcaatggga gtttgttttg    1020
gcaccaaaat caacgggact ttccaaaatg tcgtaacaac tccgccccat tgacgcaaat    1080
gggcggtagg cgtgtacggt gggaggtcta tataagcaga gctctcccta tcagtgatag    1140
agatctccct atcagtgata gagatcgtcg acgagctcgt ttagtgaacc gtcagatcgc    1200
ctggagacgc catccacgct gttttgacct ccatagaaga caccgggacc gatccagcct    1260
ccgcggccgg gaacggtgca ttggaacgcg gattccccgt gccaagagtg agatcttccg    1320
tttatctagg taccagatat cgccaccatg gacgaccagc gggacctgat cagcaacaac    1380
gagcagctgc ccatgctggg ccagaggcct ggcgcccctg agagcaagtg tagcagaggc    1440
gccgtgtaca ccgtgttcag catcctggtg gccctgctgc tggccggaca ggccaccacc    1500
gcctactttc tgtatcagca gcaggacggc ctggacaagc tgaccgtgac cagccagaac    1560
ctgcagctgg aaaacctgcg gatgaagctg cccaagcccg ccaagcccct gagccagatg    1620
agaatggcca cccccctgct gatgcaggcc ctgcctatgg ccggcctgcc ccagaaaccc    1680
atgcagaacg ccaccaagca cggcaacatg accgaggacc acgtgatgca tctgctgctg    1740
aacgccgacc cctgaaggt gtaccccca ctgaagggca gcctgagcga gaacctgaag    1800
cacctgaaga acaccatgga aaccatggac tggaaggtgt tcgagagctg gctgcaccac    1860
tggctgctgt tcgagatgag caagcacagc ctggaacaga gcccaccgga gcccctcccc    1920
aaagagagcc tggaactgga agatcccagc agcggcctgg gcgtgaccaa gcaggatctg    1980
ggccccgtgg ctatgtccga ggactttctg attctgatcg ccatcctggt gatcgtgatt    2040
ctcgtgggca caatcacaac cctggtgggc gccatcggcg gcattagggc caggaggagc    2100
ttcctcttca tttgcatctt cttcctgttc ctctccctct tcctgacaat cctcgccctg    2160
ctgctgggct tcagctggct cctgctggtg gccatcctgt tctgggtgct ctggctggtc    2220
atcctcattc tgctgctgct ggtgtaccct attcctcacc accccctgcc cacctccctc    2280
aggtttagaa tgaagcagag ggtgagcagc gaccccacag gttctgacag aagccctcag    2340
ggcagccata atagcctgaa ctcccccgat gaggaggacc caaggatgga caccaagcaa    2400
cctctgtgca acatgaccca gggcggacct ccgtcaatg acagctcct cggacaacat    2460 gctcaatgcc cccctcacta tccctgctgc catattcagc atcccgacgg agaggattcc    2520
```

```
gatggagacg atggcaagtc ctggggcgat gccggagagg aagacaatgg ccctaacgac    2580
cctaacaccg ccagcaccag agagtccatt tacgaggacc tcagataccc acaagggac     2640 gccaatggcg agtatgagaa cgtgggatac cccctaggg acggagatgc ccctcatagg     2700
ctcggagagc ctgtgtatga cgatgtggag caagccaccg ctaacgaggt gagaatctcc    2760
cctctgttca gactgcccta cggaagcgct tcggacctg gccccagcc tggacccatt      2820 ctggagagct ccacatgggg ctttctggtc ttcacacaga cctccctgtt cgccgacgac    2880
attgccgacg ctattaggga ctactgcaca acccacccctg gccccacaag gaacacccag   2940
gtggtcctca tgaacttcga gggcagcgga gtgcccctgc ctatgttttt tcccccctgga  3000 gaggagacag aagagcagag agagggcgat agagctagcg actccgacga gtccgaagac    3060
gctcagatcc tgaccgtgtt ctgcctgttt tgccagtgga cactctttat ctgcctggga    3120
atcaggatga tctgtaactg gagggggcaaa ctcaccagga tcatctgcct gaagttctgc   3180
ctctacggac tgatttccgc ctccctgtcc ttcggctggt acgcttttct gaaggaagtg    3240
accctcccca ccacagccac cgttgatcct aggcaactcc ccctgttcct cttcatcctg    3300
agctccgtgc tggtgattct cgccatcatg atggagtttc aaacatcctc cagcctcttc    3360
gctgctctgt tcgtgattat cgccggaatg ctgtgcgtca cagtgggcgt gattttctg     3420 ctggctggcg tcaagcctct cctgagcggc atgatctgcg cctccggcat cacaatgctc    3480
gtgctcggcg tcgtgctgct ggtggtgtgc accagagatg agcacgctat ttccgccagc    3540
caccatgcta gcgatggctc cgtgaatcag cagaaggaaa atcagcccca gaccctggag    3600
gaatgcaaga cagatcagga gaggaagagg tacaggaaca ggctggcctc caggaggtgt    3660
agagctaagt tcaggaacca gctggaacat tttaggacag tcgccgctgc taagacagag    3720
gagaacaaca ggctcagggt gctcatcagg cagatgtgtc ctacactgga cgtggaatcc    3780 atcgtccccct ccacctccgc cggctaccac gagcctctga atcacctgac ccacagcccc   3840
agcccttgtc atcacaggga tgaacccccc tccagaagcc ccagccctca acccaccgtc    3900
tccgagcagt cccagcagtc cccaggcag cagagccctc aaggcacatc ccagggttct     3960
acaagacctc aggtgcctgg aggcgccacc accagaaaaa gaggcggcgt gagaggccaa    4020
cctgccaagt gtcacggcaa gtacaccaca accgccgagg gactgaccgc tctcctgaat    4080
aggaggcaca gccccaggac atccaacgag ggcaggtgga tgaatggagt catggctgtg    4140
aacctctcca aatggcccct gtacagcctg aggagagccc tggccctcgc catggctcct    4200
agaaggaggc tctccggccc tccctggctg acagtgctgc tgctgctgtc cacactgagc    4260
gtggccgccc tgctgattct cttcctgatt ttcagcgccg gcgccaccat tagcacagaa    4320
gccagcctgc tggtcctgct cctgctgttt gtgaccctgc tgctgcctct cctgtcctcc    4380
aacggactcc agctccctgc cgccctgatt ctgatccagt gtttcctcct ggccgctgat    4440
tatctcgcct acctgattct gcctaccatt atgcccaggg gcagaagcac aggaaggaag    4500
ggcagggaca cagagaaaga gaggagcaga tcccctctca gagctcctgg cggttctgat    4560
ggacccagca caagggctgg ctgtggagcc ggaccctgtc agctgagcag ccccatcgcc    4620
ggaaacaacg gcaatgaagg cggcgagggc gacgactaca agagctggag gaagcccgag    4680
gaagaggaca acggccccaa tgaccccaat accaacaaca ggattgagga tggagacggc    4740
gacgacggaa atcctggag gaatcctgag gaggaggata acagaaagca ggacaggctg    4800
ggcaccaagc ctttcatgga cctcgacgga accggcggag cgagggcta cagccagatg    4860 gtccctatcg ccaccgcccc cggaagcggc cacgccgcta cctatcagga tctccaggcc    4920
```

```
gcccccttaca tcatctggcc tctccagacc gattgccagc ctgtggctac caccttcgcc    4980
tcccccggac agatccagtg gtatacaagc gccgtccccc agcccacaga gcattgctcc    5040
cagtttacaa acgctcccac cgtcaaccag cagcagccta ttagccaacc ccagcccgaa    5100 aatcccctg  ctttcacctt tacccagccc gcttccatca ttcccggcgt cattagcgcc    5160
tccaacctga acgtgagcgc ttcccctatc atccctagcg accatgtcct ccccatcatt    5220
acctccgtga ccagcctcgc ccaacctaat aacatggccg ccactggta tgagagcgtg    5280 attcccggcc tgttcctctg cccctgatc ctcccttccc tgttctggat ttgctccctg    5340
ctgaccttcc tggtgggcca cggagccaat attgtgagcg ccgtcctgtt cctcgtgctg    5400
gcttggtgtc tcctcattgc caactggaac gtgacaagag aggacttcgt gtccggcagg    5460
agaagctcca tgagcagcct gtccgtggcc gcttccaccg ccacagccat gttcgccagc    5520
ttcctcaccc tgagctttga tggcctgggc ctgctgctgt ttggcaccgc cctggtgatc    5580
cagacaattt acgtgctgta tctggtggtc atggagatca ccgtgtggat catgatgttt    5640
aggtatctcc acttttggat caccctgctg ttcctgctga gcccattat tctctccgtc    5700 gcctgtctca tcatccaatc ctccgccctg ctgatcgagg ctgtggtcgt caccaccatc    5760
acagtcctgg ccattttct gtggctccct cctcaaggcg ctgaggccga tctcggcacc    5820
gccctgctga ttctgaatac cgccctgtgc ctggtcgtgc tgatcctgac cgctatccct    5880
acatgatgat gagcggccgc gatctgctgt gccttctagt tgccagccat ctgttgtttg    5940
cccctccccc gtgccttcct tgaccctgga aggtgccact cccactgtcc tttcctaata    6000
aaatgaggaa attgcatcgc attgtctgag taggtgtcat tctattctgg ggggtgggt    6060 ggggcaggac agcaagggg aggattggga agacaatagc aggcatgctg gggatgcggt    6120
gggctctatg gccgatcagc gatcgctgag gtgggtgagt gggcgtggcc tggggtggtc    6180
atgaaaatat ataagttggg ggtcttaggg tctctttatt tgtgttgcag agaccgccgg    6240
agccatgagc gggagcagca gcagcagcag tagcagcagc gccttggatg gcagcatcgt    6300
gagcccttat ttgacgacgc ggatgcccca ctgggccggg gtgcgtcaga atgtgatggg    6360
ctccagcatc gacggccgac ccgtcctgcc cgcaaattcc gccacgctga cctatgcgac    6420
cgtcgcgggg acgccgttgg acgccaccgc cgccgccgcc gccaccgcag ccgcctcggc    6480
cgtgcgcagc ctggccacgg actttgcatt cctgggacca ctggcgacag gggctacttc    6540
tcgggccgct gctgccgccg ttcgcgatga caagctgacc gccctgctgg cgcagttgga    6600
tgcgcttact cgggaactgg gtgacctttc tcagcaggtc atggccctgc ccagcaggt    6660 ctcctccctg caagctggcg ggaatgcttc tcccacaaat gccgtttaag ataaataaaa    6720
ccagactctg tttggattaa agaaaagtag caagtgcatt gctctctta tttcataatt    6780 ttccgcgcgc gataggccct agaccagcgt tctcggtcgt tgagggtgcg gtgtatcttc    6840
tccaggacgt ggtagaggtg gctctggacg ttgagataca tgggcatgag cccgtcccgg    6900
gggtggaggt agcaccactg cagagcttca tgctccgggg tggtgttgta gatgatccag    6960
tcgtagcagg agcgctgggc atggtgccta aaaatgtcct tcagcagcag gccgatggcc    7020
agggggaggc ccttggtgta agtgtttaca aaacggttaa gttgggaagg gtgcattcgg    7080
ggagagatga tgtgcatctt ggactgtatt tttagattgg cgatgtttcc gcccagatcc    7140
cttctgggat tcatgttgtg caggaccacc agtacagtgt atccggtgca cttggggaat    7200
ttgtcatgca gcttagaggg aaaagcgtgg aagaacttgg agacgccttt gtggcctccc    7260
```

```
agatttttcca tgcattcgtc catgatgatg gcaatgggcc cgcgggaggc agcttgggca    7320
aagatatttc tggggtcgct gacgtcgtag ttgtgttcca gggtgaggtc gtcataggcc    7380
atttttacaa agcgcgggcg gagggtgccc gactggggga tgatggtccc ctctggccct    7440
ggggcgtagt tgccctcgca gatctgcatt tcccaggcct taatctcgga gggggggaatc   7500
atatccacct gcgggcgat gaagaaaacg gtttccggag ccggggagat taactgggat     7560
gagagcaggt ttctaagcag ctgtgatttt ccacaaccgg tgggcccata aataacacct    7620
ataaccggtt gcagctggta gtttagagag ctgcagctgc cgtcgtcccg gaggaggggg    7680
gccacctcgt tgagcatgtc cctgacgcgc atgttctccc cgaccagatc cgccagaagg    7740
cgctcgccgc ccagggacag cagctcttgc aaggaagcaa agttttttcag cggcttgagg   7800
ccgtccgccg tgggcatgtt tttcagggtc tggctcagca gctccaggcg gtcccagagc    7860
tcggtgacgt gctctacggc atctctatcc agcatatctc ctcgtttcgc gggttggggc    7920
gactttcgct gtagggcacc aagcggtggt cgtccagcgg ggccagagtc atgtccttcc    7980
atgggcgcag ggtcctcgtc agggtggtct gggtcacggt gaaggggtgc gctccgggct    8040
gagcgcttgc caaggtgcgc ttgaggctgg ttctgctggt gctgaagcgc tgccggtctt    8100
cgccctgcgc gtcggccagg tagcatttga ccatggtgtc atagtccagc ccctccgcgg    8160
cgtgtccctt ggcgcgcagc ttgcccttgg aggtggcgcc gcacgagggg cagagcaggc    8220
tcttgagcgc gtagagcttg ggggcgagga agaccgattc gggggagtag gcgtccgcgc    8280
cgcagacccc gcacacggtc tcgcactcca ccagccaggt gagctcgggg cgcgccgggt    8340
caaaaaccag gtttccccca tgcttttga tgcgtttctt acctcgggtc tccatgaggt     8400
ggtgtccccg ctcggtgacg aagaggctgt ccgtgtctcc gtagaccgac ttgaggggtc    8460
ttttctccag gggggtccct cggtcttcct cgtagaggaa ctcggaccac tctgagacga    8520
aggcccgcgt ccaggccagg acgaaggagg ctatgtggga ggggtagcgg tcgttgtcca    8580
ctaggggtc caccttctcc aaggtgtgaa gacacatgtc gccttcctcg gcgtccagga     8640
aggtgattgg cttgtaggtg taggccacgt gaccgggggt tcctgacggg ggggtataaa    8700
aggggggtggg ggcgcgctcg tcgtcactct cttccgcatc gctgtctgcg agggccagct   8760
gctggggtga gtattccctc tcgaaggcgg gcatgacctc cgcgctgagg ttgtcagttt    8820
ccaaaaacga ggaggatttg atgttcacct gtcccgaggt gatacctttg agggtacccg    8880
cgtccatctg gtcagaaaac acgatctttt tattgtccag cttggtggcg aacgacccgt    8940
agagggcgtt ggagagcagc ttggcgatgg agcgcagggt ctggttcttg tccctgtcgg    9000
cgcgctcctt ggccgcgatg ttgagctgca cgtactcgcg cgcgacgcag cgccactcgg    9060
ggaagacggt ggtgcgctcg tcgggcacca ggcgcacgcg ccagccgcgg ttgtgcaggg    9120
tgaccaggtc cacgctggtg gcgacctcgc cgcgcaggcg ctcgttggtc cagcagagac    9180
ggccgccctt gcgcgagcag aagggggggca ggggtcgag ctgggtctcg tccgggggt     9240
ccgcgtccac ggtgaaaacc ccggggcgca ggcgcgcgtc gaagtagtct atcttgcaac    9300
cttgcatgtc cagcgcctgc tgccagtcgc gggcggcgag cgcgcgctcg tagggggttga   9360
gcggcgggcc ccagggcatg gggtgggtga gtgcggaggc gtacatgccg cagatgtcat    9420
agacgtagag gggctcccgc aggaccccga tgtaggtggg gtagcagcgg ccgccgcgga    9480
tgctggcgcg cacgtagtca tacagctcgt gcgaggggc gaggaggtcg ggcccaggt      9540
tggtgcgggc ggggcgctcc gcgcggaaga cgatctgcct gaagatggca tgcgagttgg    9600
aagagatggt ggggcgctgg aagacgttga agctggcgtc ctgcaggccg acggcgtcgc    9660
```

-continued

```
gcacgaagga ggcgtaggag tcgcgcagct tgtgtaccag ctcggcgtg acctgcacgt      9720 cgagcgcgca gtagtcgagg gtctcgcgga tgatgtcata tttagcctgc cccttctttt      9780
tccacagctc gcggttgagg acaaactctt cgcggtcttt ccagtactct tggatcggga      9840
aaccgtccgg ttccgaacgg taagagccta gcatgtagaa ctggttgacg gcctggtagg      9900
cgcagcagcc cttctccacg ggagggcgt aggcctgcgc ggccttgcgg agcgaggtgt       9960
gggtcagggc gaaggtgtcc ctgaccatga ctttgaggta ctggtgcttg aagtcggagt     10020
cgtcgcagcc gccccgctcc cagagcgaga agtcggtgcg cttcttggag cggggttgg      10080 gcagagcgaa ggtgacatcg ttgaagagga ttttgcccgc gcggggcatg aagttgcggg     10140
tgatgcggaa gggccccggc acttcagagc ggttgttgat gacctgggcg gcgagcacga     10200
tctcgtcgaa gccgttgatg ttgtggccca cgatgtagag ttccaggaag cggggccggc     10260
cctttacggt gggcagcttc tttagctctt cgtaggtgag ctcctcgggc gaggcgaggc     10320
cgtgctcggc cagggcccag tccgcgaggt gcgggttgtc tctgaggaag acttccaga     10380 ggtcgcgggc caggagggtc tgcaggcggt ctctgaaggt cctgaactgg cggcccacgg     10440
ccattttttc gggggtgatg cagtagaagg tgagggggtc ttgctgccag cggtcccagt     10500
cgagctgcag ggcgaggtcg cgcgcggcgg tgaccaggcg ctcgtcgccc ccgaatttca     10560
tgaccagcat gaagggcacg agctgctttc cgaaggcccc catccaagtg taggtctcta     10620
catcgtaggt gacaaagagg cgctccgtgc gaggatgcga gccgatcggg aagaactgga     10680
tctcccgcca ccagttggag gagtggctgt tgatgtggtg gaagtagaag tcccgtcgcc     10740
gggccgaaca ctcgtgctgg cttttgtaaa agcgagcgca gtactggcag cgctgcacgg     10800
gctgtacctc atgcacgaga tgcacctttc gcccgcgcac gaggaagccg aggggaaatc     10860
tgagcccccc gcctggctcg cggcatggct ggttctcttc tactttggat gcgtgtccgt     10920
ctccgtctgg ctcctcgagg ggtgttacgg tggagcggac caccacgccg cgcgagccgc     10980
aggtccagat atcggcgcgc ggcggtcgga gtttgatgac gacatcgcgc agctgggagc     11040
tgtccatggt ctggagctcc cgcggcggcg gcaggtcagc cgggagttct tgcaggttca     11100
cctcgcagag tcgggccagg gcgcggggca ggtctaggtg gtacctgatc tctaggggcg     11160
tgttggtggc ggcgtcgatg gcttgcagga gcccgcagcc ccggggggcg acgacggtgc     11220
cccgcggggt ggtggtggtg gtggcggtgc agctcagaag cggtgccgcg ggcgggcccc     11280
cggaggtagg gggggctccg gtcccgcggg caggggcggc agcggcacgt cggcgtggag     11340
cgcgggcagg agttggtgct gtgcccggag gttgctggcg aaggcgacga cgcggcggtt     11400
gatctcctgg atctggcgcc tctgcgtgaa gacgacgggc ccggtgagct tgaacctgaa     11460
agagagttcg acagaatcaa tctccggtgtc attgaccgcg gcctggcgca ggatctcctg     11520
cacgtctccc gagttgtctt ggtaggcgat ctcggccatg aactgctcga tctcttcctc     11580
ctggaggtct ccgcgtccgg cgcgttccac ggtggccgcc aggtcgttgg agatgcgccc     11640
catgagctgc gagaaggcgt tgagtccgcc ctcgttccag actcggctgt agaccacgcc     11700
cccctggtca tcgcgggcgc gcatgaccac ctgcgcgagg ttgagctcca cgtgccgcgc     11760
gaagacggcg tagttgcgca gacgctgaa gaggtagttg agggtggtgg cggtgtgctc     11820
ggccacgaag aagttcatga cccagcggcg caacgtggat tcgttgatgt cccccaaggc     11880
ctccagccgt tccatggcct cgtagaagtc cacggcgaag ttgaaaaact gggagttgcg     11940
cgccgacacg gtcaactcct cctccagaag acggatgagc tcggcgacgg tgtcgcgcac     12000
```

-continued

```
ctcgcgctcg aaggctatgg ggatctcttc ctccgctagc atcaccacct cctcctcttc   12060
ctcctcttct ggcacttcca tgatggcttc ctcctcttcg ggggtggcg gcggcggcgg    12120 tgggggaggg ggcgctctgc gccggcggcg gcgcaccggg aggcggtcca cgaagcgcgc   12180
gatcatctcc ccgcggcggc ggcgcatggt ctcggtgacg gcgcggccgt tctcccgggg   12240
gcgcagttgg aagacgccgc cggacatctg gtgctggggc gggtggccgt gaggcagcga   12300
gacggcgctg acgatgcatc tcaacaattg ctgcgtaggt acgccgccga gggacctgag   12360
ggagtccata tccaccggat ccgaaaacct ttcgaggaag gcgtctaacc agtcgcagtc   12420
gcaaggtagg ctgagcaccg tggcgggcgg cgggggtgg ggggagtgtc tggcggaggt    12480
gctgctgatg atgtaattga agtaggcgga cttgacacgg cggatggtcg acaggagcac   12540
catgtccttg ggtccggcct gctggatgcg gaggcggtcg gctatgcccc aggcttcgtt   12600
ctggcatcgg cgcaggtcct tgtagtagtc ttgcatgagc ctttccaccg gcacctcttc   12660
tccttcctct tctgcttctt ccatgtctgc ttcggccctg gggcggcgcc gcgccccct    12720 gccccccatg cgcgtgaccc cgaacccct gagcggttgg agcagggcca ggtcggcgac    12780
gacgcgctcg gccaggatgg cctgctgcac ctgcgtgagg gtggtttgga agtcatccaa   12840
gtccacgaag cggtggtagg cgcccgtgtt gatggtgtag gtgcagttgg ccatgacgga   12900
ccagttgacg gtctggtggc ccggttgcga catctcggtg tacctgagtc gcgagtaggc   12960
gcgggagtcg aagacgtagt cgttgcaagt ccgcaccagg tactggtagc ccaccaggaa   13020
gtgcggcggc ggctggcggt agaggggcca gcgcagggtg gcggggctc cggggccag    13080 gtcttccagc atgaggcggt ggtaggcgta gatgtacctg gacatccagg tgatacccgc   13140
ggcggtggtg gaggcgcgcg ggaagtcgcg caccggttc cagatgttgc gcaggggcag    13200
aaagtgctcc atggtaggcg tgctctgtcc agtcagacgc gcgcagtcgt tgatactcta   13260
gaccagggaa aacgaaagcc ggtcagcggg cactcttccg tggtctggtg aatagatcgc   13320
aagggtatca tggcggaggg cctcggttcg agccccgggt ccgggccgga cggtccgcca   13380
tgatccacgc ggttaccgcc cgcgtgtcga acccaggtgt gcgacgtcag acaacggtgg   13440
agtgttcctt ttggcgtttt tctggccggg cgccggcgcc gcgtaagaga ctaagccgcg   13500
aaagcgaaag cagtaagtgg ctcgctcccc gtagccggag ggatccttgc taagggttgc   13560
gttgcggcga accccggttc gaatcccgta ctcgggccgg ccggaccgc ggctaaggtg    13620 ttggattggc ctcccctcg tataaagacc ccgcttgcgg attgactccg gacacgggga    13680 cgagccctt ttattttgc tttccccaga tgcatccggt gctgcggcag atgcgccccc     13740
cgccccagca gcagcaacaa caccagcaag agcggcagca acagcagcgg gagtcatgca   13800 gggcccctc acccacctc ggcggccgg ccacctcggc gtccgcgcc gtgtctggcg       13860 cctgcggcgg cggcggggg ccggctgacg acccgagga gccccgcgg cgcagggcca     13920 gacactacct ggacctggag gagggcgagg gcctggcgcg gctggggcg ccgtctcccg    13980 agcgccaccc gcgggtgcag ctgaagcgcg actcgcgcga ggcgtacgtg cctcggcaga   14040
acctgttcag ggaccgcgcg ggcgaggagc ccgaggagat gcgggacagg aggttcagcg   14100
cagggcggga gctgcggcag gggctgaacc gcgagcggct gctgcgcgag gaggactttg   14160
agcccgacgc gcggacgggg atcagccccg cgcgcgcgca cgtggcggcc gccgacctgg   14220
tgacggcgta cgagcagacg gtgaaccagg agatcaactt ccaaaagagt ttcaacaacc   14280
acgtgcgcac gctggtggcg cgcgaggagg tgaccatcgg gctgatgcac ctgtgggact   14340
ttgtaagcgc gctggtgcag aaccccaaca gcaagcctct gacggcgcag ctgttcctga   14400
```

```
tagtgcagca cagcagggac aacgaggcgt ttagggacgc gctgctgaac atcaccgagc    14460
ccgagggtcg gtggctgctg gacctgatta acatcctgca gagcatagtg gtgcaggagc    14520
gcagcctgag cctggccgac aaggtggcgg ccatcaacta ctcgatgctg agcctgggca    14580
agttttacgc gcgcaagatc taccagacgc cgtacgtgcc catagacaag gaggtgaaga    14640
tcgacggttt ttacatgcgc atggcgctga aggtgctcac cctgagcgac gacctgggcg    14700
tgtaccgcaa cgagcgcatc cacaaggccg tgagcgtgag ccgcggcgc gagctgagcg    14760 accgcgagct gatgcacagc ctgcagcggg cgctggcggg cgccggcagc ggcgacaggg    14820
aggcggagtc ctacttcgat gcgggggcgg acctgcgctg ggcgcccagc cggcgggccc    14880
tggaggccgc gggggtccgc gaggactatg acgaggacgg cgaggaggat gaggagtacg    14940
agctagagga gggcgagtac ctggactaaa ccgcgggtgg tgtttccggt agatgcaaga    15000
cccgaacgtg gtggacccgg cgctgcgggc ggctctgcag agccagccgt ccggccttaa    15060
ctcctcagac gactggcgac aggtcatgga ccgcatcatg tcgctgacgg cgcgtaaccc    15120
ggacgcgttc cggcagcagc cgcaggccaa caggctctcc gccatcctgg aggcggtggt    15180
gcctgcgcgc tcgaacccca cgcacgagaa ggtgctggcc atagtgaacg cgctggccga    15240
gaacagggcc atccgcccgg acgaggccgg gctggtgtac gacgcgctgc tgcagcgcgt    15300
ggcccgctac aacagcggca acgtgcagac caacctggac cggctggtgg gggacgtgcg    15360
cgaggcggtg gcgcagcgcg agcgcgcgga tcggcagggc aacctgggct ccatggtggc    15420
gctgaatgcc ttcctgagca cgcagccggc caacgtgccg cggggcagg aagactacac    15480 caactttgtg agcgcgctgc ggctgatggt gaccgagacc ccccagagcg aggtgtacca    15540
gtcgggcccg gactacttct tccagaccag cagacagggc ctgcagacgg tgaacctgag    15600
ccaggctttc aagaacctgc gggggctgtg gggcgtgaag gcgcccaccg cgaccgggc    15660 gacggtgtcc agcctgctga cgcccaactc gcgcctgctg ctgctgctga tcgcgccgtt    15720
cacggacagc ggcagcgtgt cccgggacac ctacctgggg cacctgctga ccctgtaccg    15780
cgaggccatc gggcaggcgc aggtggacga gcacaccttc caggagatca ccagcgtgag    15840
ccgcgcgctg gggcaggagg acacgagcag cctggaggcg actctgaact acctgctgac    15900
caaccggcgg cagaagattc cctcgctgca cagcctgacc tccgaggagg agcgcatctt    15960
gcgctacgtg cagcagagcg tgagcctgaa cctgatgcgc gacggggtga cgcccagcgt    16020
ggcgctggac atgaccgcgc gcaacatgga accgggcatg tacgccgcgc accggcctta    16080
catcaaccgc ctgatggact acctgcatcg cgcggcggcc gtgaacccg agtactttac    16140 caacgccatc ctgaacccgc actggctccc gccgcccggg ttctacagcg ggggcttcga    16200
ggtcccggag accaacgatg gcttcctgtg ggacgacatg gacgacagcg tgttctcccc    16260
gcggccgcag gcgctggcgg aagcgtccct gctgcgtccc aagaaggagg aggaggagga    16320
ggcgagtcgc cgccgcggca gcagcggcgt ggcttctctg tccgagctgg gggcggcagc    16380
cgccgcgcgc cccgggtccc tgggcggcag ccccttccg agcctggtgg ggtctctgca    16440
cagcgagcgc accacccgcc ctcggctgct gggcgaggac gagtacctga ataactccct    16500
gctgcagccg gtgcgggaga aaaacctgcc tcccgccttc cccaacaacg ggatagagag    16560
cctggtggac aagatgagca gatggaagac ctatgcgcag gagcacaggg acgcgcctgc    16620
gctccggccg cccacgcggc gccagcgcca cgaccggcag cggggctgg tgtgggatga    16680 cgaggactcc gcggacgata gcagcgtgct ggacctggga gggagcggca accgttcgc    16740
```

```
gcacctgcgc ccccgcctgg ggaggatgtt ttaaaaaaaa aaaaaaaang caagaagcat    16800
gatgcaaaaa ttaaataaaa ctcaccaagg ccatggcgac cgagcgttgg tttcttgtgt    16860
tcccttcagt atgcggcgcg cggcgatgta ccaggaggga cctcctccct cttacgagag    16920
cgtggtgggc gcggcggcgg cggcgccctc ttctcccttt gcgtcgcagc tgctggagcc    16980
gccgtacgtg cctccgcgct acctgcggcc tacgggggg agaaacagca tccgttactc    17040
ggagctggcg cccctgttcg acaccacccg ggtgtacctg gtggacaaca agtcggcgga    17100
cgtggcctcc ctgaactacc agaacgacca cagcaatttt ttgaccacgg tcatccagaa    17160
caatgactac agcccgagcg aggccagcac ccagaccatc aatctggatg accggtcgca    17220
ctggggcggc gacctgaaaa ccatcctgca caccaacatg cccaacgtga acgagttcat    17280
gttcaccaat aagttcaagg cgcggtgat ggtgtcgcgc tcgcacacca aggaagaccg    17340
ggtggagctg aagtacgagt gggtggagtt cgagctgcca gagggcaact actccgagac    17400
catgaccatt gacctgatga caacgcgat cgtggagcac tatctgaaag tgggcaggca    17460
gaacggggtc ctggagagcg acatcggggt caagttcgac accaggaact tccgcctggg    17520
gctggacccc gtgaccgggc tggttatgcc cggggtgtac accaacgagg ccttccatcc    17580
cgacatcatc ctgctgcccg gctgcggggt ggacttcact tacagccgcc tgagcaacct    17640
cctgggcatc cgcaagcggc agcccttcca ggagggcttc aggatcacct acgaggacct    17700 ggagggggc aacatccccg cgctcctcga tgtggaggcc taccaggata gcttgaagga    17760
aaatgaggcg ggacaggagg ataccgcccc cgccgcctcc gccgccgccg agcagggcga    17820
ggatgctgct gacaccgcgg ccgcggacgg ggcagaggcc gacccgcta tggtggtgga    17880 ggctcccgag caggaggagg acatgaatga cagtgcggtg cgcggagaca ccttcgtcac    17940
ccggggggag gaaaagcaag cggaggccga ggccgcggcc gaggaaaagc aactggcggc    18000
agcagcggcg gcggcggcgt tggccgcggc ggaggctgag tctgagggga ccaagcccgc    18060
caaggagccc gtgattaagc ccctgaccga agatagcaag aagcgcagtt acaacctgct    18120
caaggacagc accaacaccg cgtaccgcag ctggtacctg cctacaact acggcgaccc    18180 gtcgacgggg gtgcgctcct ggaccctgct gtgcacgccg acgtgacct gcggctcgga    18240 gcaggtgtac tggtcgctgc ccgacatgat gcaagacccc gtgaccttcc gctccacgcg    18300
gcaggtcagc aacttcccgg tggtgggcgc cgagctgctg cccgtgcact ccaagagctt    18360
ctacaacgac caggccgtct actcccagct catccgccag ttcacctctc tgacccacgt    18420
gttcaatcgc tttcctgaga accagattct ggcgcgcccg cccgccccca ccatcaccac    18480
cgtcagtgaa aacgttcctg ctctcacaga tcacgggacg ctaccgctgc gcaacagcat    18540
cggaggagtc cagcgagtga ccgttactga cgccagacgc cgcacctgcc cctacgttta    18600
caaggccttg ggcatagtct cgccgcgcgt ccttccagc cgcactttt gagcaacacc    18660 accatcatgt ccatcctgat ctcacccagc aataactccg gctggggact gctgcgcgcg    18720
cccagcaaga tgttcggagg ggcgaggaag cgttccgagc agcaccccgt gcgcgtgcgc    18780
gggcacttcc gcgcccctg gggagcgcac aaacgcggcc gcgcggggcg caccaccgtg    18840
gacgacgcca tcgactcggt ggtggagcag gcgcgcaact acaggccgc ggtctctacc    18900 gtggacgcgg ccatccagac cgtggtgcgg ggcgcgcggc ggtacgccaa gctgaagagc    18960
cgccggaagc gcgtggcccg ccgccaccgc gccgaccg gggccgccgc caaacgcgcg    19020
gccgcggccc tgcttcgccg ggccaagcgc acgggccgcc gcgccgccat gagggccgcg    19080
cgccgcttgg ccgccggcat caccgccgcc accatggccc cccgtacccg aagacgcgcg    19140
```

```
gccgccgccg ccgccgccgc catcagtgac atggccagca ggcgccgggg caacgtgtac   19200
tgggtgcgcg actcggtgac cggcacgcgc gtgcccgtgc gcttccgccc ccgcggact    19260 tgagatgatg tgaaaaaaca acactgagtc tcctgctgtt gtgtgtatcc cagcggcggc   19320
ggcgcgcgca gcgtcatgtc caagcgcaaa atcaaagaag agatgctcca ggtcgtcgcg   19380
ccggagatct atgggccccc gaagaaggaa gagcaggatt cgaagcccg caagataaag    19440 cgggtcaaaa agaaaagaa agatgatgac gatgccgatg ggaggtgga gttcctgcgc    19500 gccacggcgc ccaggcgccc ggtgcagtgg aagggccggc gcgtaaagcg cgtcctgcgc   19560
cccggcaccg cggtggtctt cacgcccggc gagcgctcca cccggactt caagcgcgtc    19620 tatgacgagg tgtacggcga cgaagacctg ctggagcagg ccaacgagcg cttcggagag   19680
tttgcttacg ggaagcgtca gcgggcgctg gggaaggagg acctgctggc gctgccgctg   19740
gaccagggca accccacccc cagtctgaag cccgtgaccc tgcagcaggt gctgccgagc   19800
agcgcaccct ccgaggcgaa gcggggtctg aagcgcgagg gcggcgacct ggcgcccacc   19860
gtgcagctca tggtgcccaa gcggcagagg ctggaggatg tgctggagaa aatgaaagta   19920
gaccccggtc tgcagccgga catcagggtc cgccccatca gcaggtggc gccgggcctc    19980 ggcgtgcaga ccgtggacgt ggtcatcccc accggcaact cccccgccgc cgccaccact   20040
accgctgcct ccacggacat ggagacacag accgatcccg ccgcagccgc agccgcagcc   20100
gccgccgcga cctcctcggc ggaggtgcag acggacccct ggctgccgcc ggcgatgtca   20160
gctccccgcg cgcgtcgcgg gcgcaggaag tacggcgccg ccaacgcgct cctgcccgag   20220
tacgccttgc atccttccat cgcgcccacc cccggctacc gaggctatac ctaccgcccg   20280
cgaagagcca agggttccac ccgccgtccc cgccgacgcg ccgccgccac cacccgccgc   20340
cgccgccgca gacgccagcc cgcactggct ccagtctccg tgaggaaagt ggcgcgcgac   20400
ggacacaccc tggtgctgcc cagggcgcgc taccaccca gcatcgtta aaagcctgtt    20460 gtggttcttg cagatatggc cctcacttgc cgcctccgtt tcccggtgcc gggataccga   20520
ggaggaagat cgcgccgcag gaggggtctg gccggccgcg gcctgagcgg aggcagccgc   20580
cgcgcgcacc ggcggcgacg cgccaccagc cgacgcatgc gcggcggggt gctgcccctg   20640
ttaatccccc tgatcgccgc ggcgatcggc gccgtgcccg ggatcgcctc cgtggccttg   20700
caagcgtccc agaggcattg acagacttgc aaacttgcaa atatgaaaaa aaaaccccca   20760 ataaaaagt ctagactctc acgctcgctt ggtcctgtga ctatttgta gaatggaaga    20820 catcaacttt gcgtcgctgg ccccgcgtca cggctcgcgc ccgttcctgg gacactggaa   20880
cgatatcggc accagcaaca tgagcggtgg cgccttcagt tggggctctc tgtggagcgg   20940
cattaaaagt atcgggtctg ccgttaaaaa ttacggctcc cgggcctgga acagcagcac   21000
gggccagatg ttgagagaca agttgaaaga gcagaacttc cagcagaagg tggtggaggg   21060
cctggcctcc ggcatcaacg gggtggtgga cctggcaac caggccgtgc agaataagat    21120
caacagcaga ctggacccc ggccgccggt ggaggaggtg ccgccggcgc tggagacggt    21180
gtcccccgat gggcgtggcg agaagcgccc gcggcccgat agggaagaga ccactctggt   21240
cacgcagacc gatgagccgc cccgtatga ggaggccctg aagcaaggtc tgcccaccac    21300
gcggcccatc gcgcccatgg ccaccggggt ggtgggccgc cacacccccg ccacgctgga   21360
cttgcctccg cccgccgatg tgccgcagca gcagaaggcg gcagagcggg gcccgcccgc   21420
gaccgcctcc cgttcctccg ccggtcctct gcgccgcgcg ccagcggcc cccgcggggg   21480
```

```
ggtcgcgagg cacggcaact ggcagagcac gctgaacagc atcgtgggtc tgggggtgcg   21540
gtccgtgaag cgccgccgat gctactgaat agcttagcta acgtgttgta tgtgtgtatg   21600
cgccctatgt cgccgccaga ggagctgctg agtcgccgcc gttcgcgcgc ccaccaccac   21660
cgccactccg cccctcaaga tggcgacccc atcgatgatg ccgcagtggt cgtacatgca   21720
catctcgggc caggacgcct cggagtacct gagccccggg ctggtgcagt tcgcccgcgc   21780
caccgagagc tacttcagcc tgagtaacaa gtttaggaac cccacggtgg cgcccacgca   21840
cgatgtgacc accgaccggt ctcagcgcct gacgctgcgg ttcattcccg tggaccgcga   21900
ggacaccgcg tactcgtaca aggcgcggtt caccctggcc gtgggcgaca accgcgtgct   21960
ggacatggcc tccacctact ttgacatccg cggggtgctg gaccggggtc ccactttcaa   22020
gccctactct ggcaccgcct acaactccct ggccccaag  ggcgctccca actcctgcga   22080
gtgggagcaa gaggaaactc aggcagttga agaagcagca gaagaggaag aagaagatgc   22140
tgacggtcaa gctgaggaag agcaagcagc taccaaaaag actcatgtat atgctcaggc   22200 tccccttttct ggcgaaaaaa ttagtaaaga tggtctgcaa ataggaacgg acgctacagc   22260
tacagaacaa aaacctattt atgcagaccc tacattccag cccgaacccc aaatcgggga   22320
gtcccagtgg aatgaggcag atgctacagt cgccggcggt agagtgctaa agaaatctac   22380
tcccatgaaa ccatgctatg gttcctatgc aagacccaca aatgctaatg gaggtcaggg   22440
tgtactaacg gcaaatgccc agggacagct agaatctcag gttgaaatgc aattcttttc   22500
aacttctgaa acgcccgta acgaggctaa caacattcag cccaaattgg tgctgtatag   22560
tgaggatgtg cacatggaga ccccggatac gcacctttct tacaagcccg caaaaagcga   22620
tgacaattca aaaatcatgc tgggtcagca gtccatgccc aacagaccta attcatcgg   22680 cttcagagac aactttatcg gcctcatgta ttacaatagc actggcaaca tgggagtgct   22740
tgcaggtcag gcctctcagt tgaatgcagt ggtggacttg caagacagaa acacagaact   22800
gtcctaccag ctcttgcttg attccatggg tgacagaacc agatactttt ccatgtggaa   22860
tcaggcagtg gacagttatg acccagatgt tagaattatt gaaaatcatg gaactgaaga   22920
cgagctcccc aactattgtt tccctctggg tggcataggg gtaactgaca cttaccaggc   22980
tgttaaaacc aacaatggca ataacggggg ccaggtgact tggacaaaag atgaaacttt   23040
tgcagatcgc aatgaaatag gggtggaaa caatttcgct atggagatca acctcagtgc   23100
caacctgtgg agaaacttcc tgtactccaa cgtggcgctg tacctaccag acaagcttaa   23160
gtacaacccc tccaatgtgg acatctctga caaccccaac acctacgatt acatgaacaa   23220
gcgagtggtg gccccggggc tggtggactg ctacatcaac ctgggcgcgc gctggtcgct   23280
ggactacatg gacaacgtca cccccttcaa ccaccaccgc aatgcgggcc tgcgctaccg   23340
ctccatgctc ctgggcaacg ggcgctacgt gcccttccac atccaggtgc cccagaagtt   23400
ctttgccatc aagaacctcc tcctcctgcc gggctcctac acctacgagt ggaacttcag   23460
gaaggatgtc aacatggtcc tccagagctc tctgggtaac gatctcaggg tggacggggc   23520
cagcatcaag ttcgagagca tctgcctcta cgccaccttc ttccccatgg cccacaacac   23580
ggcctccacg ctcgaggcca tgctcaggaa cgacaccaac gaccagtcct caatgactca   23640
cctctccgcc gccaacatgc tctaccccat acccgccaac gccaccaacg tcccatctc  23700 catccccctcg cgcaactggg cggccttccg cggctgggcc ttcacccgcc tcaagaccaa   23760
ggagaccccc tccctgggct cgggattcga ccccctactac acctactcgg ctccattcc   23820 ctacctggac ggcaccttct acctcaacca cactttcaag aaggtctcgg tcaccttcga   23880
```

```
ctcctcggtc agctggccgg gcaacgaccg tctgctcacc cccaacgagt tcgagatcaa   23940
gcgctcggtc gacggggagg gctacaacgt ggcccagtgc aacatgacca aggactggtt   24000
cctggtccag atgctggcca actacaacat cggctaccag ggcttctaca tcccagagag   24060
ctacaaggac aggatgtact ccttcttcag gaacttccag cccatgagcc ggcaggtggt   24120
ggaccagacc aagtacaagg actaccagga ggtgggcatc atccaccagc acaacaactc   24180
gggcttcgtg ggctacctcg cccccaccat gcgcgaggga caggcctacc cgccaacttt   24240
cccctatccg ctcataggca agaccgcggt cgacagcatc acccagaaaa agttcctctg   24300
cgaccgcacc ctctggcgca tcccttctc cagcaacttc atgtccatgg gtgcgctctc   24360
ggacctgggc cagaacttgc tctacgccaa ctccgcccac gccctcgaca tgaccttcga   24420
ggtcgacccc atggacgagc ccaccccttct ctatgttctg ttcgaagtct ttgacgtggt   24480
ccgggtccac cagccgcacc gcggcgtcat cgagaccgtg tacctgcgta cgcccttctc   24540
ggccggcaac gccaccacct aaagaagcaa gccgcagtca tcgccgcctg catgccgtcg   24600
ggttccaccg agcaagagct cagggccatc gtcagagacc tgggatgcgg ccctattttt   24660
ttgggcacct tcgacaagcg cttccctggc tttgtctccc cacacaagct ggcctgcgcc   24720
atcgtcaaca cggccggccg cgagaccggg ggcgtgcact ggctggcctt cgcctggaac   24780
ccgcgctcca aaacatgctt cctctttgac cccttcggct tttcggacca gcggctcaag   24840
caaatctacg agttcgagta cgagggcttg ctgcgtcgca gcgccatcgc ctcctcgccc   24900
gaccgctgcg tcaccctcga aaagtccacc cagaccgtgc aggggcccga ctcggccgcc   24960
tgcggtctct tctgctgcat gtttctgcac gcctttgtgc actggcctca gagtcccatg   25020
gaccgcaacc ccaccatgaa cttgctgacg ggggtgccca actccatgct ccagagcccc   25080
caggtcgagc ccaccctgcg ccgcaaccag gagcagctct acagcttcct ggagcgccac   25140
tcgccttact tccgccgcca cagcgcacag atcaggaggg ccacctcctt ctgccacttg   25200
caagagatgc aagaagggta ataacgatgt acacactttt tttctcaata aatggcatct   25260 tttatttat acaagctctc tggggtattc atttcccacc accacccgcc gttgtcgcca   25320
tctggctcta tttagaaatc gaaagggttc tgccgggagt cgccgtgcgc cacgggcagg   25380
gacacgttgc gatactggta gcgggtgccc cacttgaact cgggcaccac caggcgaggc   25440
agctcgggga agttttcgct ccacaggctg cgggtcagca ccagcgcgtt catcaggtcg   25500
ggcgccgaga tcttgaagtc gcagttgggg ccgccgccct gcgcgcgcga gttgcggtac   25560
accgggttgc agcactggaa caccaacagc gccgggtgct tcacgctggc cagcacgctg   25620
cggtcggaga tcagctcggc gtccaggtcc tccgcgttgc tcagcgcgaa cggggtcatc   25680
ttgggcactt gccgcccag gaagggcgcg tgccccggtt tcgagttgca gtcgcagcgc   25740
agcgggatca gcaggtgccc gtgcccggac tcggcgttgg ggtacagcgc gcgcatgaag   25800
gcctgcatct ggcggaaggc catctgggcc ttggcgccct ccgagaagaa catgccgcag   25860
gacttgcccg agaactggtt tgcggggcag ctggcgtcgt gcaggcagca gcgcgcgtcg   25920
gtgttggcga tctgcaccac gttgcgcccc caccggttct tcacgatctt ggccttggac   25980
gattgctcct tcagcgcgcg ctgccgcgttc tgctggtca catccatctc gatcacatgt   26040
tccttgttca ccatgctgct gccgtgcaga cacttcagct cgccctccgt ctcggtgcag   26100
cggtgctgcc acagcgcgca gcccgtgggc tcgaaagact tgtaggtcac ctccgcgaag   26160
gactgcaggt accctgcaa aaagcggccc atcatggtca cgaaggtctt gttgctgctg   26220
```

```
aaggtcagct gcagcccgcg gtgctcctcg ttcagccagg tcttgcacac ggccgccagc   26280
gcctccacct ggtcgggcag catcttgaag ttcaccttca gctcattctc cacgtggtac   26340
ttgtccatca gcgtgcgcgc cgcctccatg cccttctccc aggccgacac cagcggcagg   26400
ctcacggggt tcttcaccat caccgtggcc gccgcctccg ccgcgctttc gctttccgcc   26460
ccgctgttct cttcctcttc ctcctcttcc tcgccgccgc ccactcgcag cccccgcacc   26520
acggggtcgt cttcctgcag gcgctgcacc ttgcgcttgc cgttgcgccc ctgcttgatg   26580
cgcacgggcg ggttgctgaa gcccaccatc accagcgcgg cctcttcttg ctcgtcctcg   26640
ctgtccagaa tgacctccgg ggagggggggg ttggtcatcc tcagtaccga ggcacgcttc   26700
tttttcttcc tgggggcgtt cgccagctcc gcggctgcgg ccgctgccga ggtcgaaggc   26760
cgagggctgg gcgtgcgcgg caccagcgcg tcctgcgagc cgtcctcgtc ctcctcggac   26820
tcgagacgga ggcgggcccg cttcttcggg ggcgcgcggg gcggcggagg cggcggcggc   26880
gacggagacg gggacgagac atcgtccagg gtgggtggac ggcgggccgc gccgcgtccg   26940
cgctcggggg tggtctcgcg ctggtcctct tcccgactgg ccatctccca ctgctccttc   27000
tcctataggc agaaagagat catggagtct ctcatgcgag tcgagaagga ggaggacagc   27060
ctaaccgccc cctctgagcc ctccaccacc gccgccacca ccgccaatgc cgccgcgac   27120 gacgcgccca ccgagaccac cgccagtacc accctcccca gcgacgcacc cccgctcgag   27180
aatgaagtgc tgatcgagca ggacccgggt tttgtgagcg gagaggagga tgaggtggat   27240
gagaaggaga aggaggaggt cgccgcctca gtgccaaaag aggataaaaa gcaagaccag   27300
gacgacgcag ataaggatga cacagcagtc gggcggggga acgaagcca tgatgctgat   27360 gacggctacc tagacgtggg agacgacgtg ctgcttaagc acctgcaccg ccagtgcgtc   27420
atcgtctgcg acgcgctgca ggagcgctgc gaagtgcccc tggacgtggc ggaggtcagc   27480
cgcgcctacg agcggcacct cttcgcgccg cacgtgcccc ccaagcgccg ggagaacggc   27540
acctgcgagc ccaacccgcg tctcaacttc tacccggtct tcgcggtacc cgaggtgctg   27600
gccacctacc acatcttttt ccaaaactgc aagatccccc tctcctgccg cgccaaccgc   27660
acccgcgccc acaaaaccct gaccctgcgg cagggcgccc acatacctga tatcgcctct   27720
ctggaggaag tgcccaagat cttcgagggt ctcggtcgcg acgagaaacg ggcggcgaac   27780
gctctgcacg gagacagcga aaacgagagt cactcggggg tgctggtgga gctcgagggc   27840
gacaacgcgc gcctggccgt actcaagcgc agcatagagg tcacccactt tgcctacccg   27900
gcgctcaacc tgccccccaa ggtcatgagt gtggtcatgg gcgagctcat catgcgccgc   27960
gcccagcccc tggccgcgga tgcaaacttg caagagtcct ccgaggaagg cctgcccgcg   28020
gtcagcgacg agcagctggc gcgctggctg gagacccgcg accccgcgca gctggaggag   28080
cggcgcaagc tcatgatggc cgcggtgctg gtcaccgtgg agctcgagtg tctgcagcgc   28140
ttcttcgcgg accccgagat gcagcgcaag ctcgaggaga ccctgcacta caccttccgc   28200
cagggctacg tgcgccaggc ctgcaagatc tccaacgtgg agctctgcaa cctggtctcc   28260
tacctgggca tcctgcacga gaaccgcctc gggcagaacg tcctgcactc caccctcaaa   28320
ggggaggcgc gccgcgacta catccgcgac tgcgcctacc tcttcctctg ctacacctgg   28380
cagacggcca tggggtctg gcagcagtgc ctggaggagc gcaacctcaa ggagctggaa   28440
aagctcctca gcgcaccct cagggacctc tggacgggct tcaacgagcg ctcggtggcc   28500
gccgcgctgc cggacatcat cttccccgag cgcctgctca gaccctgca gcagggcctg   28560 cccgacttca ccagccagag catgctgcag aacttcagga cttttcatcct ggagcgctcg   28620
```

```
ggcatcctgc cggccacttg ctgcgcgctg cccagcgact tcgtgcccat caagtacagg   28680
gagtgcccgc cgccgctctg gggccactgc tacctcttcc agctggccaa ctacctcgcc   28740
taccactcgg acctcatgga agacgtgagc ggcgagggcc tgctcgagtg ccactgccgc   28800
tgcaacctct gcacgcccca ccgctctcta gtctgcaacc cgcagctgct cagcgagagt   28860
cagattatcg gtaccttcga gctgcagggt ccctcgcctg acgagaagtc cgcggctcca   28920
gggctgaaac tcactccggg gctgtggact tccgcctacc tacgcaaatt tgtacctgag   28980
gactaccacg cccacgagat caggttctac gaagaccaat cccgcccgcc caaggcggag   29040
ctcaccgcct gcgtcatcac ccaggggcac atcctgggcc aattgcaagc catcaacaaa   29100
gcccgccgag agttcttgct gaaaaagggt cgggggggtgt acctggaccc ccagtccggc   29160
gaggagctaa acccgctacc cccgccgccg cccagcagc gggaccttgc ttcccaggat   29220
ggcacccaga aagaagcagc agccgccgcc gccgccgcag ccatacatgc ttctggagga   29280
agaggaggag gactgggaca gtcaggcaga ggaggtttcg gacgaggagc aggaggagat   29340
gatggaagac tgggaggagg acagcagcct agacgaggaa gcttcagagg ccgaagaggt   29400
ggcagacgca acaccatcgc cctcggtcgc agcccctcg ccggggcccc tgaaatcctc   29460
cgaacccagc accagcgcta taacctccgc tcctccggcg ccggcgccac ccgcccgcag   29520
acccaaccgt agatgggaca ccacaggaac cgggtcggt aagtccaagt gcccgccgcc   29580
gccaccgcag cagcagcagc agcagcgcca gggctaccgc tcgtggcgcg gcacaagaa   29640 cgccatagtc gcctgcttgc aagactgcgg gggcaacatc tctttcgccc gccgcttcct   29700
gctattccac cacggggtcg cctttccccg caatgtcctg cattactacc gtcatctcta   29760
cagcccctac tgcagcggcg acccagaggc ggcagcggca gccacagcgg cgaccaccac   29820
ctaggaagat atcctccgcg ggcaagacag cggcagcagc ggccaggaga cccgcggcag   29880
cagcggcggg agcggtgggc gcactgcgcc tctcgcccaa cgaacccctc tcgacccggg   29940
agctcagaca caggatcttc cccactttgt atgccatctt ccaacagagc agaggccagg   30000
agcaggagct gaaataaaa aacagatctc tgcgctccct caccgcagc tgtctgtatc   30060 acaaaagcga agatcagctt cggcgcacgc tggaggacgc ggaggcactc ttcagcaaat   30120
actgcgcgct cactcttaaa gactagctcc gcgcccttct cgaatttagg cgggagaaaa   30180
ctacgtcatc gccggccgcc gcccagcccg cccagccgag atgagcaaag agattcccac   30240
gccatacatg tggagctacc agccgcagat gggactcgcg gcgggagcgg cccaggacta   30300
ctccacccgc atgaactaca tgagcgcggg acccacatg atctcacagg tcaacggat   30360 ccgcgcccag cgaaaccaaa tactgctgga acaggcggcc atcaccgcca cgccccgcca   30420
taatctcaac ccccgaaatt ggcccgccgc cctcgtgtac caggaaaccc cctccgccac   30480
caccgtacta cttccgcgtg acgcccaggc cgaagtccag atgactaact caggggcgca   30540
gctcgcgggc ggctttcgtc acggggcgcg ccgctccga ccaggtataa gacacctgat   30600
gatcagaggc cgaggtatcc agctcaacga cgagtcggtg agctcttcgc tcggtctccg   30660
tccggacgga actttccagc tcgccggatc cggccgctct tcgttcacgc cccgccaggc   30720
gtacctgact ctgcagacct cgtcctcgga gccccgctcc ggcggcatcg gaaccctcca   30780
gttcgtggag gagttcgtgc cctcggtcta cttcaaccc ttctcgggac ctcccggacg   30840
ctaccccgac cagttcattc cgaactttga cgcggtgaag gactcggcgg acggctacga   30900
ctgaatgtca ggtgtcgagg cagagcagct tcgcctgaga caccctcgagc actgccgccg   30960
```

```
ccacaagtgc ttcgcccgcg gttctggtga gttctgctac tttcagctac ccgaggagca   31020
taccgagggg ccggcgcacg gcgtccgcct gaccacccag ggcgaggtta cctgttccct   31080
catccgggag tttaccctcc gtcccctgct agtggagcgg gagcggggtc cctgtgtcct   31140
aactatcgcc tgcaactgcc ctaaccctgg attacatcaa gatctttgct gtcatctctg   31200
tgctgagttt aataaacgct gagatcagaa tctactggga tttagtcccc tttaactaat   31260
caaacactgg aatcaataaa agaatcact tacttaaaat cagacagcag gtctctgtcc   31320
agtttattca gcagcacctc cttcccctcc tcccaactct ggtactccaa acgccttctg   31380
gcggcaaact tcctccacac cctgaaggga atgtcagatt cttgctcctg tccctccgca   31440
cccactatct tcatgttgtt gcagatgaag cgcaccaaaa cgtctgacga gagcttcaac   31500
cccgtgtacc cctatgacac ggaaagcggc cctccctccg tccctttcct cacccctccc   31560
ttcgtgtctc ccgatggatt ccaagaaagt cccccggg tcctgtctct gaacctggcc   31620
gagcccctgg tcacttccca cggcatgctc gccctgaaaa tgggaagtgg cctctccctg   31680
gacgacgctg gcaacctcac ctctcaagat atcaccaccg ctagccctcc cctcaaaaaa   31740
accaagacca acctcagcct agaaacctca tccccctaa ctgtgagcac ctcaggcgcc   31800
ctcaccgtag cagccgccgc tcccctggcg gtggccggca cctccctcac catgcaatca   31860
gaggcccccc tgacagtaca ggatgcaaaa ctcaccctgg ccaccaaagg cccctgacc    31920 gtgtctgaag gcaaactggc cttgcaaaca tcggccccgc tgacggccgc tgacagcagc   31980
accctcacag tcagtgccac accaccccctt agcacaagca atggcagctt gggtattgac   32040
atgcaagccc ccatttacac caccaatgga aaactaggac ttaactttgg cgctcccctg   32100
catgtggtag acagcctaaa tgcactgact gtagttactg gccaaggtct tacgataaac   32160
ggaacagccc tacaaactag agtctcaggt gccctcaact atgacacatc aggaaaccta   32220
gaattgagag ctgcagggg tatgcgagtt gatgcaaatg gtcaacttat ccttgatgta   32280
gcttacccat ttgatgcaca aaacaatctc agccttaggc ttggacaggg accctgttt    32340 gttaactctg cccacaactt ggatgttaac tacaacagag gcctctacct gttcacatct   32400
ggaaatacca aaaagctaga agttaatatc aaaacagcca agggtctcat ttatgatgac   32460
actgctatag caatcaatgc gggtgatggg ctacagtttg actcaggctc agatacaaat   32520
ccattaaaaa ctaaacttgg attaggactg gattatgact ccagcagagc cataattgct   32580
aaactgggaa ctggcctaag cttttgacaac acaggtgcca tcacagtagg caacaaaaat   32640
gatgacaagc ttaccttgtg gaccacacca gacccatccc ctaactgtag aatctattca   32700
gagaaagatg ctaaattcac acttgttttg actaaatgcg gcagtcaggt gttggccagc   32760
gtttctgttt tatctgtaaa aggtagcctt gcgcccatca gtggcacagt aactagtgct   32820
cagattgtcc tcagatttga tgaaaatgga gttctactaa gcaattcttc ccttgaccct   32880
caatactgga actacagaaa aggtgacctt acagagggca ctgcatatac caacgcagtg   32940
ggatttatgc ccaacctcac agcatacca aaaacacaga gccaaactgc taaaagcaac   33000
attgtaagtc aggtttactt gaatgggac aaatccaaac ccatgaccct caccattacc   33060
ctcaatggaa ctaatgaaac aggagatgcc acagtaagca cttactccat gtcattctca   33120
tggaactgga atggaagtaa ttacattaat gaaacgttcc aaaccaactc cttcaccttc   33180
tcctacatcg cccaagaata aaaagcatga cgctgttgat ttgattcaat gtgtttctgt   33240
tttattttca agcacaacaa aatcattcaa gtcattcttc catcttagct taatagacac   33300
agtagcttaa tagacccagt agtgcaaagc cccattctag cttataacta gtggagaagt   33360
```

```
actcgcctac atggggtag agtcataatc gtgcatcagg ataggcggt ggtgctgcag    33420
cagcgcgcga ataaactgct gccgccgccg ctccgtcctg caggaataca acatggcagt    33480
ggtctcctca gcgatgattc gcaccgcccg cagcataagg cgccttgtcc tccgggcaca    33540
gcagcgcacc ctgatctcac ttaaatcagc acagtaactg cagcacagca ccacaatatt    33600
gttcaaaatc ccacagtgca aggcgctgta tccaaagctc atggcgggga ccacagaacc    33660
cacgtggcca tcataccaca agcgcaggta gattaagtgg cgaccctca taaacacgct    33720
ggacataaac attacctctt ttggcatgtt gtaattcacc acctcccggt accatataaa    33780
cctctgatta aacatggcgc catccaccac catcctaaac cagctggcca aaacctgccc    33840
gccggctata cactgcaggg aaccgggact ggaacaatga cagtggagag cccaggactc    33900
gtaaccatgg atcatcatgc tcgtcatgat atcaatgttg gcacaacaca ggcacacgtg    33960
catacacttc ctcaggatta caagctcctc ccgcgttaga accatatccc agggaacaac    34020
ccattcctga atcagcgtaa atcccacact gcagggaaga cctcgcacgt aactcacgtt    34080
gtgcattgtc aaagtgttac attcgggcag cagcggatga tcctccagta tggtagcgcg    34140
ggtttctgtc tcaaaaggag gtagacgatc cctactgtac ggagtgcgcc gagacaaccg    34200
agatcgtgtt ggtcgtagtg tcatgccaaa tggaacgccg gacgtagtca tatttcctga    34260
agtcttagat ctctcaacgc agcaccagca ccaacacttc gcagtgtaaa aggcaagtg    34320
ccgagagagt atatatagga ataaaagtg acgtaaacgg gcaaagtcca aaaaacgccc    34380
agaaaaaccg cacgcgaacc tacgcccga aacgaaagcc aaaaaacact agacactccc    34440
ttccggcgtc aacttccgct ttcccacgct acgtcacttg ccccagtcaa acaaactaca    34500
tatcccgaac ttccaagtcg ccacgcccaa aacaccgcct acacctcccc gcccgccggc    34560
ccgcccccaa accgcctcc cgccccgcgc ccgccccgc gccgcccatc tcattatcat    34620
attggcttca atccaaaata aggtatatta ttgatgatgg tttaaacgga tcctctagag    34680
tcgacctgca ggcatgcaag cttgagtatt ctatagtgtc acctaaatag cttggcgtaa    34740
tcatggtcat agctgttcc tgtgtgaaat tgttatccgc tcacaattcc acacaacata    34800
cgagccggaa gcataaagtg taaagcctgg ggtgcctaat gagtgagcta actcacatta    34860
attgcgttgc gctcactgcc cgctttccag tcgggaaacc tgtcgtgcca gctgcattaa    34920
tgaatcggcc aacgcgaacc ccttgcgccc gcccggccg tcgaccaatt ctcatgtttg    34980
acagcttatc atcgaatttc tgccattcat ccgcttatta tcacttattc agctcggtac    35040
ccggggatcc tcgtttaaac aggcgtagca accaggcgtt taagggcacc aataactgcc    35100
ttaaaaaaat tacgccccgc cctgccactc atcgcagtac tgttgtaatt cattaagcat    35160
tctgccgaca tggaagccat cacaaacggc atgatgaacc tgaatcgcca gcggcatcag    35220
caccttgtcg ccttgcgtat aatatttgcc catggtgaaa acgggggcga agaagttgtc    35280
catattggcc acgtttaaat caaaactggt gaaactcacc cagggattgg ctgagacgaa    35340
aaacatattc tcaataaacc ctttagggaa ataggccagg ttttcaccgt aacacgccac    35400
atcttgcgaa tatatgtgta gaaactgccg gaaatcgtcg tggtattcac tccagagcga    35460
tgaaaacgtt tcagtttgct catggaaaac ggtgtaacaa gggtgaacac tatcccatat    35520
caccagctca ccgtctttca ttgccatacg gaattccgga tgagcattca tcaggcgggc    35580
aagaatgtga ataaaggccg gataaaactt gtgcttattt ttctttacgg tctttaaaaa    35640
ggccgtaata tccagctgaa cggtctggtt ataggtacat tgagcaactg actgaaatgc    35700
```

```
ctcaaaatgt tctttacgat gccattggga tatatcaacg gtggtatatc cagtgatttt    35760
tttctccatt ttagcttcct tagctcctga aaatctcgat aactcaaaaa atacgcccgg    35820
tagtgatctt atttcattat ggtgaaagtt ggaacctctt acgtgccgat caacgtctca    35880
ttttcgccaa aagttggccc agggcttccc ggtatcaaca gggacaccag gatttattta    35940
ttctgcgaag tgatcttccg tcacaggtat ttattcgcga taagctcatg gagcggcgta    36000
accgtcgcac aggaaggaca gagaaagcgc ggatctggga agtgacggac agaacggtca    36060
ggacctggat tggggaggcg gttgccgccg ctgctgctga cggtgtgacg ttctctgttc    36120
cggtcacacc acatacgttc cgccattcct atgcgatgca catgctgtat gccggtatac    36180
cgctgaaagt tctgcaaagc ctgatgggac ataagtccat cagttcaacg gaagtctaca    36240
cgaaggtttt tgcgctggat gtggctgccc ggcaccgggt gcagtttgcg atgccggagt    36300
ctgatgcggt tgcgatgctg aaacaattat cctgagaata aatgccttgg cctttatatg    36360
gaaatgtgga actgagtgga tatgctgttt ttgtctgtta aacagagaag ctggctgtta    36420
tccactgaga agcgaacgaa acagtcggga aaatctccca ttatcgtaga gatccgcatt    36480
attaatctca ggagcctgtg tagcgtttat aggaagtagt gttctgtcat gatgcctgca    36540
agcggtaacg aaaacgattt gaatatgcct tcaggaacaa tagaaatctt cgtgcggtgt    36600
tacgttgaag tggagcggat tatgtcagca atggacagaa caacctaatg aacacagaac    36660
catgatgtgg tctgtccttt tacagccagt agtgctcgcc gcagtcgagc gacagggcga    36720
agccctcgag tgagcgagga agcaccaggg aacagcactt atatattctg cttacacacg    36780
atgcctgaaa aaacttccct tggggttatc cacttatcca cggggatatt tttataatta    36840 tttttttat agtttttaga tcttcttttt tagagcgcct tgtaggcctt tatccatgct    36900
ggttctagaa aaggtgttgt gacaaattgc cctttcagtg tgacaaatca ccctcaaatg    36960
acagtcctgt ctgtgacaaa ttgcccttaa ccctgtgaca aattgccctc agaagaagct    37020
gttttttcac aaagttatcc ctgcttattg actctttttt atttagtgtg acaatctaaa    37080
aacttgtcac acttcacatg gatctgtcat ggcggaaaca gcggttatca atcacaagaa    37140
acgtaaaaat agcccgcgaa tcgtccagtc aaacgacctc actgaggcgg catatagtct    37200
ctcccgggat caaaaacgta tgctgtatct gttcgttgac cagatcagaa atctgatgg    37260 caccctacag gaacatgacg gtatctgcga gatccatgtt gctaaatatg ctgaaatatt    37320
cggattgacc tctgcggaag ccagtaagga tatacggcag gcattgaaga gtttcgcggg    37380
gaaggaagtg gttttttatc gccctgaaga ggatgccggc gatgaaaaag gctatgaatc    37440
ttttccttgg tttatcaaac gtgcgcacag tccatccaga gggctttaca gtgtacatat    37500
caacccatat ctcattccct tctttatcgg gttacagaac cggtttacgc agtttcggct    37560
tagtgaaaca aaagaaatca ccaatccgta tgccatgcgt ttatacgaat ccctgtgtca    37620
gtatcgtaag ccggatggct caggcatcgt ctctctgaaa atcgactgga tcatagagcg    37680
ttaccagctg cctcaaagtt accagcgtat gcctgacttc cgccgccgct tcctgcaggt    37740
ctgtgttaat gagatcaaca gcagaactcc aatgcgcctc tcatacattg agaaaaagaa    37800
aggccgccag acgactcata tcgtattttc cttccgcgat atcacttcca tgacgacagg    37860
atagtctgag ggttatctgt cacagatttg agggtggttc gtcacatttg ttctgaccta    37920
ctgagggtaa tttgtcacag ttttgctgtt ccttcagcc tgcatggatt ttctcatact    37980
ttttgaactg taattttaa ggaagccaaa tttgagggca gtttgtcaca gttgatttcc    38040
ttctctttcc cttcgtcatg tgacctgata tcggggggtta gttcgtcatc attgatgagg    38100
```

```
gttgattatc acagtttatt actctgaatt ggctatccgc gtgtgtacct ctacctggag    38160
ttttccccac ggtggatatt tcttcttgcg ctgagcgtaa gagctatctg acagaacagt    38220
tcttctttgc ttcctcgcca gttcgctcgc tatgctcggt tacacggctg cggcgagcgc    38280
tagtgataat aagtgactga ggtatgtgct cttcttatct cctttgtag tgttgctctt     38340 attttaaaca actttgcggt tttttgatga ctttgcgatt tgttgttgc tttgcagtaa     38400 attgcaagat ttaataaaaa aacgcaaagc aatgattaaa ggatgttcag aatgaaactc    38460
atggaaacac ttaaccagtg cataaacgct ggtcatgaaa tgacgaaggc tatcgccatt    38520
gcacagttta atgatgacag cccggaagcg aggaaaataa cccggcgctg gagaataggt    38580
gaagcagcgg atttagttgg ggtttcttct caggctatca gagatgccga aaagcaggg    38640 cgactaccgc acccggatat ggaaattcga ggacgggttg agcaacgtgt tggttataca    38700
attgaacaaa ttaatcatat gcgtgatgtg tttggtacgc gattgcgacg tgctgaagac    38760
gtatttccac cggtgatcgg ggttgctgcc cataaaggtg gcgtttacaa aacctcagtt    38820
tctgttcatc ttgctcagga tctggctctg aaggggctac gtgttttgct cgtggaaggt    38880
aacgaccccc agggaacagc ctcaatgtat cacggatggg taccagatct tcatattcat    38940
gcagaagaca ctctcctgcc tttctatctt ggggaaaagg acgatgtcac ttatgcaata    39000
aagcccactt gctggccggg gcttgacatt attccttcct gtctggctct gcaccgtatt    39060
gaaactgagt taatgggcaa atttgatgaa ggtaaactgc ccaccgatcc acacctgatg    39120
ctccgactgg ccattgaaac tgttgctcat gactatgatg tcatagttat tgacagcgcg    39180
cctaacctgg gtatcggcac gattaatgtc gtatgtgctg ctgatgtgct gattgttccc    39240
acgcctgctg agttgtttga ctacacctcc gcactgcagt ttttcgatat gcttcgtgat    39300
ctgctcaaga acgttgatct taaagggttc gagcctgatg tacgtatttt gcttaccaaa    39360
tacagcaata gtaatggctc tcagtccccg tggatggagg agcaaattcg ggatgcctgg    39420
ggaagcatgg ttctaaaaaa tgttgtacgt gaaacggatg aagttggtaa aggtcagatc    39480
cggatgagaa ctgttttga acaggccatt gatcaacgct cttcaactgg tgcctggaga    39540
aatgctcttt ctatttggga acctgtctgc aatgaaattt tcgatcgtct gattaaacca    39600
cgctgggaga ttagataatg aagcgtgcgc ctgttattcc aaaacatacg ctcaatactc    39660
aaccggttga agatacttcg ttatcgacac cagctgcccc gatggtggat tcgttaattg    39720
cgcgcgtagg agtaatggct cgcggtaatg ccattacttt gcctgtatgt ggtcgggatg    39780
tgaagtttac tcttgaagtg ctccggggtg atagtgttga aagacctct cgggtatggt     39840 caggtaatga acgtgaccag gagctgctta ctgaggacgc actggatgat ctcatcccctt   39900 cttttctact gactggtcaa cagacaccgg cgttcggtcg aagagtatct ggtgtcatag    39960
aaattgccga tgggagtcgc cgtcgtaaag ctgctgcact taccgaaagt gattatcgtg    40020
ttctggttgg cgagctggat gatgagcaga tggctgcatt atccagattg ggtaacgatt    40080
atcgcccaac aagtgcttat gaacgtggtc agcgttatgc aagccgattg cagaatgaat    40140
ttgctggaaa tatttctgcg ctggctgatg cggaaaatat ttcacgtaag attattaccc    40200
gctgtatcaa caccgccaaa ttgcctaaat cagttgttgc tcttttttct caccccggtg    40260
aactatctgc ccggtcaggt gatgcacttc aaaaagcctt tacagataaa gaggaattac    40320
ttaagcagca ggcatctaac cttcatgagc agaaaaagc tggggtgata tttgaagctg    40380
aagaagttat cactctttta acttctgtgc ttaaaacgtc atctgcatca agaactagtt    40440
```

```
taagctcacg acatcagttt gctcctggag cgacagtatt gtataagggc gataaaatgg    40500
tgcttaacct ggacaggtct cgtgttccaa ctgagtgtat agagaaaatt gaggccattc    40560
ttaaggaact tgaaaagcca gcaccctgat gcgaccacgt tttagtctac gtttatctgt    40620
ctttacttaa tgtcctttgt tacaggccag aaagcataac tggcctgaat attctctctg    40680
ggcccactgt tccacttgta tcgtcggtct gataatcaga ctgggaccac ggtcccactc    40740
gtatcgtcgg tctgattatt agtctgggac cacggtccca ctcgtatcgt cggtctgatt    40800
attagtctgg gaccacggtc ccactcgtat cgtcggtctg ataatcagac tgggaccacg    40860
gtcccactcg tatcgtcggt ctgattatta gtctgggacc atggtcccac tcgtatcgtc    40920
ggtctgatta ttagtctggg accacggtcc cactcgtatc gtcggtctga ttattagtct    40980
ggaaccacgg tcccactcgt atcgtcggtc tgattattag tctgggacca cggtcccact    41040
cgtatcgtcg gtctgattat tagtctggga ccacgatccc actcgtgttg tcggtctgat    41100
tatcggtctg ggaccacggt cccacttgta ttgtcgatca gactatcagc gtgagactac    41160
gattccatca atgcctgtca agggcaagta ttgacatgtc gtcgtaacct gtagaacgga    41220
gtaacctcgg tgtgcggttg tatgcctgct gtggattgct gctgtgtcct gcttatccac    41280
aacattttgc gcacggttat gtggacaaaa tacctggtta cccaggccgt gccggcacgt    41340
taaccgggct gcatccgatg caagtgtgtc gctgtcgacg agctcgcgag ctcggacatg    41400
aggttgcccc gtattcagtg tcgctgattt gtattgtctg aagttgtttt tacgttaagt    41460
tgatgcagat caattaatac gatacctgcg tcataattga ttatttgacg tggtttgatg    41520
gcctccacg acgttgtgat atgtagatga taatcattat cactttacgg gtcctttccg    41580
gtgatccgac aggttacggg gcggcgacct cgcgggtttt cgctatttat gaaaattttc    41640
cggtttaagg cgtttccgtt cttcttcgtc ataacttaat gttttatttt aaaatacccc    41700
ctgaaaagaa aggaaacgac aggtgctgaa agcgagcttt ttggcctctg tcgtttcctt    41760
tctctgtttt tgtccgtgga atgaacaatg gaagtccgag ctcatcgcta ataacttcgt    41820
atagcataca ttatacgaag ttatattcga tgcggccgca aggggttcgc gtcagcgggt    41880
gttggcgggt gtcggggctg gcttaactat gcggcatcag agcagattgt actgagagtg    41940
caccatatgc ggtgtgaaat accgcacaga tgcgtaagga gaaaataccg catcaggcgc    42000
cattcgccat tcaggctgcg caactgttgg gaagggcgat cggtgcgggc ctcttcgcta    42060
ttacgccagc tggcgaaagg gggatgtgct gcaaggcgat taagttgggt aacgccaggg    42120
ttttcccagt cacgacgttg taaaacgacg gccagtgaat tgtaatacga ctcactatag    42180
ggcgaattcg agctcggtac ccggggatcc tcgtttaaac                          42220
```

EPSTEIN-BARR VIRUS ANTIGEN CONSTRUCTS

CROSS-REFERENCE TO RELATED APPLICATIONS

This application is filed pursuant to 35 U.S.C. § 371 as a United States National Phase Application of International Application No. PCT/IB2018/060101 filed Dec. 14, 2018 which claims priority from U.S. Provisional No. 62/608,038 filed Dec. 20, 2017.

STATEMENT OF GOVERNMENT INTEREST

This invention was created in the performance of a Cooperative Research and Development Agreement with the National Institutes of Health, an Agency of the Department of Health and Human Services. The Government of the United States has certain rights in this invention.

SEQUENCE LISTING

The instant application contains a Sequence Listing which has been submitted electronically in ASCII format and is hereby incorporated by reference in its entirety. Said ASCII copy, created on Dec. 5, 2018, is named VU66487_WO_SL.txt and is 419,960 bytes in size.

FIELD OF THE INVENTION

This invention is in the field of treating and preventing viral infections. In particular, the present invention relates to Epstein Barr Virus antigen constructs. It includes the use of Epstein-Barr Virus antigen constructs for treating and preventing Epstein-Barr Virus infections and Epstein-Barr Virus-associated diseases.

BACKGROUND

Epstein-Barr Virus (EBV), also known as human herpesvirus 4 (HHV-4), is one of the most common viruses in humans, infecting at least 90% of adults. EBV establishes asymptomatic latent infection in most infected individuals, but is also known as the primary causative agent of infectious mononucleosis.

More significantly, EBV infection is associated with certain types of malignancies (e.g., gastric carcinoma, nasopharyngeal carcinoma, Hodgkin's lymphoma, non-Hodgkin's lymphoma, Burkitt's lymphoma) as well as an increased risk of multiple sclerosis (MS), systemic lupus erythematosus (SLE), rheumatoid arthritis (RA) and Sjögren's syndrome.

Like other members of the herpesvirus family, EBV contains a double-stranded DNA genome of about 192 kilobases encoding about 85 genes. The EBV genome is encased in a protein nucleocapsid surrounded by a viral tegument. An outer envelope layer comprises lipids and surface glycoproteins which are thought to be involved in targeting the virus to its primary host cells, B lymphocytes and epithelial cells.

The EBV viral replication cycle is well-characterized. After initial infection of host cells, EBV enters a stage of active production of infectious virions, termed the lytic replication stage (or lytic stage). During the lytic stage, EBV gene expression is characterized by expression of one or more lytic gene products, including ZEBRA, BRLF1, BNLF2, BCRF1, and viral capsid antigens (VCAs); as well as envelope glycoproteins such as gp350 and gp110.

Following a period of lytic replication, EBV enters a state of persistent viral infection without active viral production, termed latency (or the latent phase). Latent EBV infection is accompanied by characteristic gene expression programs, including expression of one or more latent gene products such as EBNA1, EBNA2, EBNA3A, EBNA3B, EBNA3C, EBNA leader protein (EBNA-LP), LMP1, and/or LMP2. Latently-infected cells can be reactivated to lytic viral production by triggers which are not yet understood.

A number of EBV vaccine candidates have been evaluated in animal models and human trials. Most prophylactic vaccine candidates have focused on the major EBV envelope glycoprotein gp350 as the immunogen. Gu et al. reported that a recombinant live vaccinia virus expressing EBV gp350 elicited EBV neutralizing antibodies and modest protection in children, but not in adults. Gu et al., Dev. Biol. Stand. 1995; 84: 171-177. A recombinant gp350 vaccine was found not to protect against EBV infection, but reduced the occurrence of infectious mononucleosis. Sokal et al., J. Infect. Dis. 2007; 196(12):1749-1753.

Therapeutic EBV vaccine candidates have primarily targeted T-cell epitopes of EBV nuclear antigen-1 (EBNA1) and LMP2. For example, Taylor et al. have described a modified vaccinia virus Ankara (MVA) vector expressing a peptide fragment of EBNA1 fused to the full-length LMP2 protein. The so-called MVA-EL vaccine was reported to induce antigen-specific CD4+ and CD8+ T cell responses in early clinical trials. Taylor et al., J. Virol. January 2004, p. 768-778. Similarly, a recombinant human adenoviral vector expressing full length LMP2 protein was reported to induce antigen-specific T-cell responses in vitro and in in mice. Pan et al., Biochem Biophys Res Commun. 2006 Sep. 1; 347 (3):551-7.

Despite the clear need in the art, no EBV vaccine has yet been licensed for use in humans. Thus, there remains a need for an EBV vaccine for use in preventing EBV infection as well as in treating EBV-associated malignancies and EBV-associated diseases, such as multiple sclerosis.

SUMMARY OF THE INVENTION

The present inventors provide EBV antigen polypeptides, polynucleotides and vectors useful as components of immunogenic compositions for the induction of an immune response in a subject against Epstein-Barr Virus (EBV) infection; methods for their use in prevention and treatment of EBV infection and EBV-associated diseases; and processes for their manufacture.

There is provided a polynucleotide encoding an EBV antigen polypeptide comprising:
  (a) at least one fragment of at least 8 amino acids of SEQ ID NO: 1,
  (b) at least one fragment of at least 8 amino acids of SEQ ID NO: 6,
  (c) at least one fragment of at least 8 amino acids of SEQ ID NO: 11, and
  (d) at least one fragment of at least 8 amino acids of SEQ ID NO: 13;
wherein the polynucleotide is operatively linked to one or more sequences which direct expression of said polypeptide in a host cell. In some embodiments, the polypeptide further comprises at least one fragment of at least 8 amino acids of SEQ ID NO: 21.

Also provided is a polynucleotide encoding an EBV antigen polypeptide comprising:

(a) at least two LMP1 fragments of at least 8 amino acids of SEQ ID NO: 1, wherein the LMP1 fragments are not adjacent to each other,
(b) at least two LMP2 fragments of at least 8 amino acids of SEQ ID NO: 6, wherein the LMP2 fragments are not adjacent to each other,
(c) at least two EBNA1 fragments of at least 8 amino acids of SEQ ID NO: 11, wherein the EBNA1 fragments are not adjacent to each other,
(d) at least two EBNA3A fragments of at least 8 amino acids of SEQ ID NO: 13, wherein the EBNA3A fragments are not adjacent to each other, and/or
(e) at least two ZEBRA fragments of at least 8 amino acids of SEQ ID NO: 21, wherein the ZEBRA fragments are not adjacent to each other;

wherein the polynucleotide is operatively linked to one or more sequences which direct expression of said polypeptide in a host cell.

Also provided is a polynucleotide as described above, wherein the EBV antigen polypeptide comprises:
(a) a first fragment of LMP1 consisting of SEQ ID NO: 2,
(b) a second fragment of LMP1 consisting of SEQ ID NO: 3,
(c) a third fragment of LMP1 consisting of SEQ ID NO: 4,
(d) a fourth fragment of LMP1 consisting of SEQ ID NO: 5,
(e) a first fragment of LMP2 consisting of SEQ ID NO: 7,
(f) a second fragment of LMP2 consisting of SEQ ID NO: 8,
(g) a third fragment of LMP2 consisting of SEQ ID NO: 9,
(h) a fourth fragment of LMP2 consisting of SEQ ID NO: 10,
(i) a first fragment of EBNA1 consisting of SEQ ID NO: 12,
(j) a first fragment of EBNA3A consisting of SEQ ID NO: 14,
(k) a second fragment of EBNA3A consisting of SEQ ID NO: 15,
(l) a third fragment of EBNA3A consisting of SEQ ID NO: 16,
(m) a fourth fragment of EBNA3A consisting of SEQ ID NO: 17,
(n) a fifth fragment of EBNA3A consisting of SEQ ID NO: 18,
(o) a sixth fragment of EBNA3A consisting of SEQ ID NO: 19, and
(p) a seventh fragment of EBNA3A consisting of SEQ ID NO: 20;

wherein the first, second, third and fourth LMP1 fragments are not adjacent to each other; the first, second, third and fourth LMP2 fragments are not adjacent to each other; and the first, second, third, fourth, fifth, sixth, and seventh EBNA3A fragments are not adjacent to each other. Optionally, the polypeptide further comprises: (a) a first fragment of ZEBRA consisting of SEQ ID NO: 22, and (b) a second fragment of ZEBRA consisting of SEQ ID NO: 23; wherein the first and second ZEBRA fragments are not adjacent to each other.

Also provided is a polynucleotide as described above, wherein the EBV antigen polypeptide is at least 80% identical to SEQ ID NO: 24 or SEQ ID NO: 26.

Also provided are vectors comprising the polynucleotides as described herein, including, for example, adenovirus vectors (e.g., non-human simian adenovirus vectors) and vaccinia virus vectors (e.g., modified vaccinia Ankara (MVA) vectors).

Also provided are EBV antigen polypeptides encoded by the polynucleotides and vectors as described herein, such as polypeptides at least 80% identical to SEQ ID NO: 24 or SEQ ID NO: 26.

Also provided are compositions comprising polynucleotides, vectors and polypeptides described herein; and a pharmaceutically acceptable excipient. Such compositions optionally comprise one or more adjuvants.

Also provided are uses of the polynucleotides, vectors, polypeptides and compositions as described herein, in the manufacture of a medicament for the treatment or prophylaxis of a disease caused by Epstein-Barr Virus infection.

Also described are methods of inducing an immune response in a subject comprising administering the polynucleotides, vectors, polypeptides and compositions as described herein to the subject.

Also provided are methods of treating or preventing an EBV-associated disease in a subject, comprising administering the polynucleotides, vectors, polypeptides and compositions as described herein to the subject. EBV-associated diseases include, for example, EBV-associated diseases (e.g., multiple sclerosis, rheumatoid arthritis and systemic lupus erythematosus).

Also provided are the polynucleotides, vectors, polypeptides and compositions as described herein, for use in the treatment or prophylaxis of a disease caused by Epstein-Barr Virus infection.

Also provided are methods of inducing an immune response in a subject comprising:
(a) administering an adenovirus comprising a polynucleotide encoding an EBV antigen polypeptide as described herein, and
(b) administering a vaccinia virus comprising a polynucleotide encoding an EBV antigen polypeptide as described herein;
wherein steps (a) and (b) are conducted in either order.

Also provided is a method of treating or preventing an EBV-associated disease in a
subject, comprising:
(a) administering an adenovirus comprising a polynucleotide encoding an EBV antigen polypeptide as described herein, and
(b) administering a vaccinia virus comprising a polynucleotide encoding an EBV antigen polypeptide as described herein;
wherein steps (a) and (b) are conducted in either order.

Figure 1:
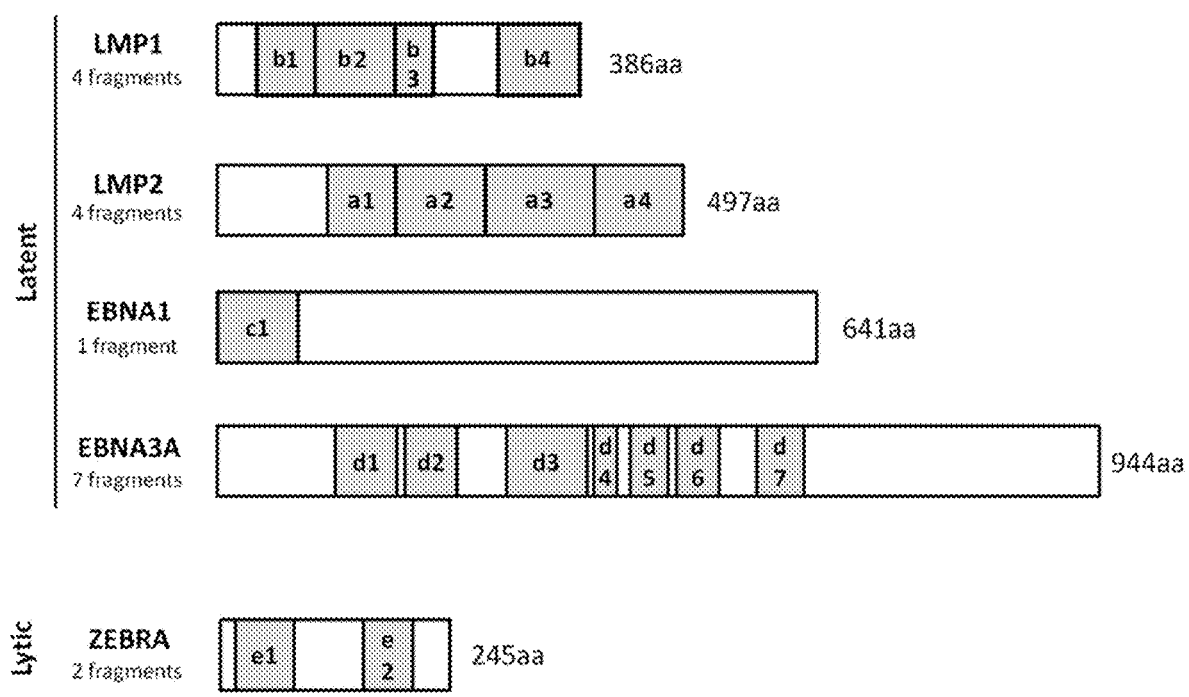
FIG. 1: Schematic representation of EBV latent (LMP1, LMP2, EBNA1 and EBNA3A) and lytic (ZEBRA) proteins. Numbered regions indicate immunogenic fragments used to construct polyvalent EBV antigen polypeptides. Alphanumeric identifiers (e.g., a1, a2, b1, b2) correspond to the fragments represented in polyvalent constructs shown in FIG. 2A-B.

FIG. 5A: T-cell responses in mice immunized with adenoviral vectors encoding EBV antigen constructs at doses of $10^6$, $10^7$ and $10^8$ viral particles (vp). ChAd155-EBV-L and ChAd155-EBV-LLy elicited interferon gamma (IFNγ) secretion from splenocytes in a dose-dependent manner. T-cell activation in response to stimulation with peptide pools covering LMP1, LMP2, EBNA1 and EBNA3A was observed to each of the EBV latent antigens in both EBV-L and EBV-LLy immunized mice. T-cell responses to the EBV lytic protein, ZEBRA, were only detected in EBV-LLy immunized mice. No responses were detected to the EBV junctional peptides (Ej) or to DMSO (dimethyl sulfoxide), the peptide pool diluent, used as a negative control.

FIG. 5B: T-cell responses in mice immunized with adenoviral vectors encoding CalHV3 antigen constructs at doses of $10^6$, $10^7$ and 10 vp. ChAd155-CalHV3-L and ChAd155-CalHV3-LLy elicited IFNγ secretion from splenocytes in a dose-dependent manner. T-cell responses to peptide pools covering CalHV3 latent antigens C1, C7 and ORF39 were detected in both CalHV3-L and CalHV3-LLy immunized mice. However, T-cell responses to the CalHV3 lytic protein, ORF43, were only detected in CalHV3-LLy immunized mice. No responses were detected to the CalHV3 junctional peptides (Cj) or the negative control, DMSO.

FIG. 6A-B: Effect of prime-boost dosing on EBV-LLy immunogenicity in mice. Immunization with ChAd155-EBV-LLy on day 0 followed by a boost immunization with MVA-EBV-LLy on day 21 (week 3) produced a significant increase in EBV-specific interferon gamma release, as compared to unboosted mice or mice receiving a “boost” injection of an MVA vector encoding an EBV-unrelated antigen. FIG. 6A presents the cumulative T-cell responses to all antigens (LMP1, LMP2, EBNA1, EBNA3A and ZEBRA), and FIG. 6B shows the responses to individual antigens and to the negative control, DMSO.

FIG. 7: Effect of prime-boost dosing on CalHV3-LLy immunogenicity in mice. Immunization with ChAd155-CalHV3-LLy (“prime”) on day 0 followed by a boost immunization with either the same antigen construct (ChAd155-CalHV3-LLy) or MVA-CalHV3-LLy on day 42 (week 6) produced a significant increase in CalHV3-specific IFNγ release measured at week 7, as compared to unboosted mice or mice receiving a “boost” injection of an MVA vector encoding a CalHV3-unrelated antigen.

FIG. 8: Cumulative T-cell responses in mice two weeks after immunization with an invariant chain-CalHV3-LLy fusion protein (ChAd155-li-CalHV3-LLy). At the lower dose of antigen ($5\times10^6$ vp), ChAd155-li-CalHV3-LLy elicited significantly greater IFNγ release and a higher proportion (100%) of responding mice than ChAd155-CalHV3-LLy. No differences were observed at the higher antigen dose tested ($5\times10^7$ vp).

FIG. 9: Cumulative T-cell responses in CalHV3-infected marmosets. Prior to immunization (w0), animals exhibited baseline CalHV3-specific T-cell responses, consistent with the fact that the animals are virus carriers. Three weeks after ChAd155-CalHV3-LLy immunization (w3 pp), CalHV3-immunized animals exhibited significant expansion of pre-existing CalHV3-specific T cell responses. T-cell responses continued to be elevated above baseline 1 week post-boost (w1 pb) with MVA-CalHV3-LLy, and after contraction were still above baseline 7 weeks after boost.

FIG. 10: The enhanced cumulative T-cell response to ChAd155-CalHV3-LLy shown in FIG. 9 was determined to be polyspecific, i.e., against CalHV3-LLy antigens C1, C7, ORF39 and ORF 43.

FIG. 11: EBV peptide pools corresponding to antigens encoded by ChAd155 and MVA latent+lytic EBV vaccines elicit IFNγ release in PBMCs from human healthy donors.

DESCRIPTION OF THE SEQUENCES

SEQ ID NO: 1 EBV LMP1 protein (Genbank No. P03230)
SEQ ID NO: 2 immunogenic fragment of EBV LMP1 protein
SEQ ID NO: 3 immunogenic fragment of EBV LMP1 protein
SEQ ID NO: 4 immunogenic fragment of EBV LMP1 protein
SEQ ID NO: 5 immunogenic fragment of EBV LMP1 protein
SEQ ID NO: 6 EBV LMP2 protein (Genbank No. P13285)
SEQ ID NO: 7 immunogenic fragment of EBV LMP2 protein
SEQ ID NO: 8 immunogenic fragment of EBV LMP2 protein
SEQ ID NO: 9 immunogenic fragment of EBV LMP2 protein
SEQ ID NO: 10 immunogenic fragment of EBV LMP2 protein
SEQ ID NO: 11 EBV EBNA1 protein (Genbank No. P03211)
SEQ ID NO: 12 immunogenic fragment of EBV EBNA1 protein
SEQ ID NO: 13 EBV EBNA3A protein (Genbank No. YP401669)
SEQ ID NO: 14 immunogenic fragment of EBV EBNA3A protein
SEQ ID NO: 15 immunogenic fragment of EBV EBNA3A protein
SEQ ID NO: 16 immunogenic fragment of EBV EBNA3A protein
SEQ ID NO: 17 immunogenic fragment of EBV EBNA3A protein
SEQ ID NO: 18 immunogenic fragment of EBV EBNA3A protein
SEQ ID NO: 19 immunogenic fragment of EBV EBNA3A protein
SEQ ID NO: 20 immunogenic fragment of EBV EBNA3A protein SEQ ID NO: 21 EBV ZEBRA protein (Genbank No. P03206)
SEQ ID NO: 22 immunogenic fragment of EBV ZEBRA protein
SEQ ID NO: 23 immunogenic fragment of EBV ZEBRA protein
SEQ ID NO: 24 EBV-L antigen polypeptide
SEQ ID NO: 25 DNA encoding EBV-L antigen polypeptide
SEQ ID NO: 26 EBV-LLy antigen polypeptide
SEQ ID NO: 27 DNA encoding EBV-LLy antigen polypeptide
SEQ ID NO: 28 CalHV3 C1 protein (Genbank No. NP_733852)
SEQ ID NO: 29 immunogenic fragment of CalHV3 C1 protein
SEQ ID NO: 30 immunogenic fragment of CalHV3 C1 protein
SEQ ID NO: 31 immunogenic fragment of CalHV3 C1 protein
SEQ ID NO: 32 CalHV3 C7 protein (Genbank No. NP_733851)
SEQ ID NO: 33 immunogenic fragment of CalHV3 C7 protein
SEQ ID NO: 34 immunogenic fragment of CalHV3 C7 protein
SEQ ID NO: 35 immunogenic fragment of CalHV3 C7 protein
SEQ ID NO: 36 CalHV3 ORF39 (Genbank No. NP_733892)
SEQ ID NO: 37 immunogenic fragment of CalHV3 ORF39
SEQ ID NO: 38 immunogenic fragment of CalHV3 ORF39
SEQ ID NO: 39 immunogenic fragment of CalHV3 ORF39
SEQ ID NO: 40 CalHv3 ORF43 protein (Genbank No. NP_733896)
SEQ ID NO: 41 immunogenic fragment of CalHv3 ORF43 protein
SEQ ID NO: 42 immunogenic fragment of CalHv3 ORF43 protein
SEQ ID NO: 43 marmoset invariant chain polypeptide
SEQ ID NO: 44 CalHv3_L antigen polypeptide
SEQ ID NO: 45 DNA encoding CalHV3_L antigen polypeptide
SEQ ID NO: 46 CalHV3_LLy antigen polypeptide
SEQ ID NO: 47 DNA encoding CalHV3_LLy antigen polypeptide
SEQ ID NO: 48 li_CalHV3_LLy antigen polypeptide
SEQ ID NO: 49 DNA encoding li_CalHV3_LLy antigen polypeptide
SEQ ID NO: 50 pChAd155 (ΔE1, ΔE4_Ad5E4 orf6) TetO hCMV-EBV-L expression vector
SEQ ID NO: 51 pChAd155 (ΔE1, ΔE3, ΔE4_Ad5E4 orf6) TetO hCMV-EBV-LLy expression vector
SEQ ID NO: 52 pChAd155 (ΔE1, ΔE4_Ad5E4 orf6) TetO hCMV-CalHV3-L expression vector
SEQ ID NO: 53 pChAd155 (ΔE1, ΔE3, ΔE4_Ad5E4 orf6) TetO hCMV-CalHV3-LLy expression vector
SEQ ID NO: 54 pChAd155 (ΔE1, ΔE3, ΔE4_Ad5E4 orf6) TetO hCMV-mli-CalHV3-LLy expression vector

DETAILED DESCRIPTION OF THE INVENTION

Epstein-Barr Virus Antigen Polypeptides

EBV antigen polypeptides of the invention include polypeptides comprising immunogenic fragments of one or more EBV latent and/or lytic proteins. EBV latent proteins include, for example, Latent Membrane Proteins (LMP1 and LMP2); and EBV Nuclear Antigens (EBNA1, EBNA2, EBNA3A, EBNA3B and EBNA3C). EBV lytic proteins include, for example, ZEBRA (encoded by the BZLF1 gene).

An "immunogenic fragment" of an EBV protein, as used herein, means a fragment smaller than a full-length EBV protein that is capable of inducing an immune response, for example a humoral (e.g., antibody) and/or cell-mediated (e.g., a cytotoxic T cell) response. Immunogenic fragments include fragments of at least 8, at least 9, at least 10, at least 11, at least 12, at least 13, at least 14, at least 15, at least 20, at least 30, at least 40, at least 50, at least 60, at least 70, at least 80, at least 90 and at least 100 amino acids of the full length protein. In some embodiments, immunogenic fragments consist of about 8, about 9, about 10, about 11, about 12, about 13, about 14, about 15, about 20, about 30, about 40, about 50, about 60, about 70, about 80, about 90 and about 100 amino acids of the full length protein. One aspect of the invention is to provide EBV antigen polypeptides capable of inducing T-cell responses against B-cells harboring latent EBV infection. Thus, in some embodiments, immunogenic fragments of EBV proteins comprise one or more T-cell epitopes capable of inducing an antigen-specific T-cell response.

Immunogenic fragments may have one or more substitutions, deletions or insertions relative to the full length protein from which the fragment is derived. Thus, immunogenic fragments include fragments at least 80%, at least 85%, at least 90%, at least 95% or at least 99% identical to the corresponding region of the full length protein.

In one embodiment, an EBV antigen polypeptide of the invention comprises a Latent Membrane Protein 1 (LMP1) antigen. LMP1 is a 386 amino acid protein expressed during the latent stage of the EBV viral life cycle. Immunogenic fragments of LMP1 suitable for use in the EBV antigen polypeptides of the invention include fragments of at least 8, at least 9, at least 10, at least 11, at least 12, at least 13, at least 14, at least 15, at least 20, at least 30, at least 40, at least 50, at least 60, at least 70, at least 80, at least 90 and at least 100 amino acids of SEQ ID NO: 1. In some embodiments, immunogenic fragments of LMP1 consist of about 8, about 9, about 10, about 11, about 12, about 13, about 14, about 15, about 20, about 30, about 40, about 50, about 60, about 70, about 80, about 90 and about 100 amino acids of SEQ ID NO: 1. In some embodiments, immunogenic fragments of LMP1 include fragments at least 80%, at least 85%, at least 90%, at least 95% or at least 99% identical to the corresponding region of SEQ ID NO: 1.

In some embodiments, an immunogenic fragment of LMP1 comprises one or more T-cell epitopes. In preferred embodiments, immunogenic epitopes of LMP1 include, but are not limited to, SEQ ID Nos: 2-5 and fragments at least 80%, at least 85%, at least 90%, at least 95% or at least 99% identical to SEQ ID Nos: 2-5.

In one embodiment, an EBV antigen polypeptide of the invention comprises a Latent Membrane Protein 2 (LMP2) antigen. LMP2 is a 497 amino acid protein expressed during the latent stage of the EBV viral life cycle. Immunogenic fragments of LMP2 suitable for use in the EBV antigen polypeptides of the invention include fragments of at least 8, at least 9, at least 10, at least 11, at least 12, at least 13, at least 14, at least 15, at least 20, at least 30, at least 40, at least 50, at least 60, at least 70, at least 80, at least 90 and at least 100 amino acids of SEQ ID NO: 6. In some embodiments, immunogenic fragments of LMP2 consist of about 8, about 9, about 10, about 11, about 12, about 13, about 14, about 15, about 20, about 30, about 40, about 50, about 60, about 70, about 80, about 90 and about 100 amino acids of SEQ ID NO: 6. In some embodiments, immunogenic fragments of LMP2 include fragments at least 80%, at least 85%, at least 90%, at least 95% or at least 99% identical to the corresponding region of SEQ ID NO: 6.

In some embodiments, an immunogenic fragment of LMP2 comprises one or more T-cell epitopes. In preferred embodiments, immunogenic epitopes of LMP2 include, but are not limited to, SEQ ID Nos: 7-10, and fragments at least 80%, at least 85%, at least 90%, at least 95% or at least 99% identical to SEQ ID Nos: 7-10.

In one embodiment, an EBV antigen polypeptide of the invention comprises an Epstein-Barr Nuclear Antigen 1 (EBNA1) antigen. EBNA1 is a 641 amino acid protein expressed during the latent stage of the EBV viral life cycle. Immunogenic fragments of EBNA1 suitable for use in the EBV antigen polypeptides of the invention include fragments of at least 8, at least 9, at least 10, at least 11, at least 12, at least 13, at least 14, at least 15, at least 20, at least 30, at least 40, at least 50, at least 60, at least 70, at least 80, at least 90 and at least 100 amino acids of SEQ ID NO: 11. In some embodiments, immunogenic fragments of EBNA1 consist of about 8, about 9, about 10, about 11, about 12, about 13, about 14, about 15, about 20, about 30, about 40, about 50, about 60, about 70, about 80, about 90 and about 100 amino acids of SEQ ID NO: 11. In some embodiments, immunogenic fragments of EBNA1 include fragments at least 80%, at least 85%, at least 90%, at least 95% or at least 99% identical to the corresponding region of SEQ ID NO: 11.

In some embodiments, an immunogenic fragment of EBNA1 comprises one or more T-cell epitopes. In preferred embodiments, immunogenic epitopes of EBNA1 include, but are not limited to, SEQ ID No: 12, and fragments at least 80%, at least 85%, at least 90%, at least 95% or at least 99% identical to SEQ ID No: 12.

In one embodiment, an EBV antigen polypeptide of the invention comprises an Epstein-Barr Nuclear Antigen 3A (EBNA3A) antigen. EBNA3A is a 944 amino acid protein expressed during the latent stage of the EBV viral life cycle. Immunogenic fragments of EBNA3A suitable for use in the EBV antigen polypeptides of the invention include fragments of at least 8, at least 9, at least 10, at least 11, at least 12, at least 13, at least 14, at least 15, at least 20, at least 30, at least 40, at least 50, at least 60, at least 70, at least 80, at least 90 and at least 100 amino acids of SEQ ID NO: 13. In some embodiments, immunogenic fragments of EBNA3A consist of about 8, about 9, about 10, about 11, about 12, about 13, about 14, about 15, about 20, about 30, about 40, about 50, about 60, about 70, about 80, about 90 and about 100 amino acids of SEQ ID NO: 13. In some embodiments, immunogenic fragments of EBNA3A include fragments at least 80%, at least 85%, at least 90%, at least 95% or at least 99% identical to the corresponding region of SEQ ID NO: 13.

In some embodiments, an immunogenic fragment of EBNA3A comprises one or more T-cell epitopes. In preferred embodiments, immunogenic epitopes of EBNA3A include, but are not limited to, SEQ ID Nos: 14-20, and fragments at least 80%, at least 85%, at least 90%, at least 95% or at least 99% identical to SEQ ID Nos: 14-20.

In one embodiment, an EBV antigen polypeptide of the invention comprises a ZEBRA antigen. ZEBRA is a 245 amino acid protein expressed during the lytic stage of the EBV viral life cycle. Immunogenic fragments of ZEBRA suitable for use in the EBV antigen polypeptides of the invention include fragments of at least 8, at least 9, at least 10, at least 11, at least 12, at least 13, at least 14, at least 15, at least 20, at least 30, at least 40, at least 50, at least 60, at least 70, at least 80, at least 90 and at least 100 amino acids of SEQ ID NO: 21. In some embodiments, immunogenic fragments of ZEBRA consist of about 8, about 9, about 10, about 11, about 12, about 13, about 14, about 15, about 20, about 30, about 40, about 50, about 60, about 70, about 80, about 90 and about 100 amino acids of SEQ ID NO: 21. In some embodiments, immunogenic fragments of ZEBRA include fragments at least 80%, at least 85%, at least 90%, at least 95% or at least 99% identical to the corresponding region of SEQ ID NO: 21.

In some embodiments, an immunogenic fragment of ZEBRA comprises one or more T-cell epitopes. In preferred embodiments, immunogenic epitopes of ZEBRA include, but are not limited to, SEQ ID Nos: 22-23, and fragments at least 80%, at least 85%, at least 90%, at least 95% or at least 99% identical to SEQ ID Nos: 22-23.

In some embodiments, an EBV antigen polypeptide is a polyvalent EBV antigen polypeptide. By "polyvalent" is intended a polypeptide comprising immunogenic fragments of two, three, four, five or more EBV proteins. By "fragment" is intended a fragment of at least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of the full-length protein.

Thus, in one embodiment is provided a polypeptide comprising:
  (a) at least one fragment of least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of SEQ ID NO: 1,
  (b) at least one fragment of least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of SEQ ID NO: 6,
  (c) at least one fragment of least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of SEQ ID NO: 11, and
  (d) at least one fragment of least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of SEQ ID NO: 13.

Optionally, the polypeptide further comprises at least one fragment of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 21.

In some embodiments, a polyvalent EBV antigen polypeptide comprises at least two, at least three, at least four, at least five, at least six, at least seven, at least eight, at least nine, or at least ten fragments of one or more EBV proteins. Thus, in one embodiment, a polyvalent EBV antigen is a polypeptide comprising:
  (a) at least two fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 1,
  (b) at least two fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 6,
(c) at least two fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 11,
(d) at least two fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 13, or
(e) at least two fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 21.

In one embodiment, a polyvalent EBV antigen is a polypeptide comprising:
(a) at least three fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 1,
(b) at least three fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 6,
(c) at least three fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 11,
(d) at least three fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 13, or
(e) at least three fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 21.

In one embodiment, a polyvalent EBV antigen is a polypeptide comprising:
(a) at least four fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 1,
(b) at least four fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 6,
(c) at least four fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 11,
(d) at least four fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 13, or
(e) at least four fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 21.

In one embodiment, a polyvalent EBV antigen is a polypeptide comprising:
(a) at least five fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 1,
(b) at least five fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 6,
(c) at least five fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 11,
(d) at least five fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 13, or
(e) at least five fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 21.

In one embodiment, a polyvalent EBV antigen is a polypeptide comprising:
(a) at least six fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 1,
(b) at least six fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 6,
(c) at least six fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 11,
(d) at least six fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 13, or
(e) at least six fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 21.

In one embodiment, a polyvalent EBV antigen is a polypeptide comprising:
(a) at least seven fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 1, (b) at least seven fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 6, (c) at least seven fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 11, (d) at least seven fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 13, or (e) at least seven fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 21.

In one embodiment, a polyvalent EBV antigen is a polypeptide comprising:
(a) at least eight fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 1, (b) at least eight fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 6, (c) at least eight fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 11, (d) at least eight fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 13, or (e) at least eight fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 21.

In one embodiment, a polyvalent EBV antigen is a polypeptide comprising:
(a) at least nine fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 1, (b) at least nine fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 6, (c) at least nine fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 11, (d) at least nine fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 13, or (e) at least nine fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 21.

In one embodiment, a polyvalent EBV antigen is a polypeptide comprising:
(a) at least ten fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 1, (b) at least ten fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 6, (c) at least ten fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 11, (d) at least ten fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 13, or (e) at least ten fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 21.

In some embodiments, the polyvalent EBV antigen polypeptide comprises at least two immunogenic fragments derived from the same EBV protein, wherein the at least two immunogenic fragments are not adjacent to each other in the polyvalent EBV antigen polypeptide. By "not adjacent" is intended to mean that the at least two immunogenic fragments do not form a contiguous amino acid sequence in the EBV antigen polypeptide. Immunogenic fragments which are not adjacent are separated from each other by at least one, two, three, four, five, ten or more amino acids that are not from the same EBV protein as the immunogenic fragments.

For example, in one embodiment, the polyvalent EBV antigen polypeptide comprises at least two, at least three, at least four, at least five, at least six, at least seven, at least eight, at least nine, or at least ten fragments of LMP1 (SEQ ID NO: 1), wherein the fragments of LMP1 are not adjacent to each other.

In another embodiment, the polyvalent EBV antigen polypeptide comprises at least two, at least three, at least four, at least five, at least six, at least seven, at least eight, at least nine, or at least ten fragments of LMP2 (SEQ ID NO: 6), wherein the fragments of LMP2 are not adjacent to each other.

In another embodiment, the polyvalent EBV antigen polypeptide comprises at least two, at least three, at least four, at least five, at least six, at least seven, at least eight, at least nine, or at least ten fragments of EBNA1 (SEQ ID NO: 11), wherein the fragments of EBNA1 are not adjacent to each other.

In another embodiment, the polyvalent EBV antigen polypeptide comprises at least two, at least three, at least four, at least five, at least six, at least seven, at least eight, at least nine, or at least ten fragments of EBNA3A (SEQ ID NO: 13), wherein the fragments of EBNA3A are not adjacent to each other.

In another embodiment, the polyvalent EBV antigen polypeptide comprises at least two, at least three, at least four, at least five, at least six, at least seven, at least eight, at least nine, or at least ten fragments of ZEBRA (SEQ ID NO: 21), wherein the fragments of ZEBRA are not adjacent to each other.

In one embodiment, the polyvalent EBV antigen polypeptide comprises:
- (a) a first and a second fragment of LMP1, wherein said first and second fragments of LMP1 are selected from the group consisting SEQ ID NOs: 2-5 and wherein said first and second fragments of LMP1 are not adjacent to each other in the polypeptide,
- (b) a first and a second fragment of LMP2, wherein said first and second fragments of LMP1 are selected from the group consisting SEQ ID NOs: 7-10 and wherein said first and second fragments of LMP2 are not adjacent to each other in the polypeptide,
- (c) a fragment of EBNA1 consisting of SEQ ID NO: 12, and
- (d) a first and a second fragment of EBNA3A, wherein said first and second fragments of EBNA3A are selected from the group consisting SEQ ID NOs: 14-20 and wherein said first and second fragments of EBNA3A are not adjacent to each other in the polypeptide.

Optionally, the polyvalent EBV antigen further comprises:
- (a) a first fragment of ZEBRA consisting of SEQ ID NO: 22, and
- (b) a second fragment of ZEBRA consisting of SEQ ID NO: 23;

wherein the first and second ZEBRA fragments are not adjacent to each other.

In one embodiment, the polyvalent EBV antigen polypeptide comprises:
- (a) a first fragment of LMP1 consisting of SEQ ID NO: 2,
- (b) a second fragment of LMP1 consisting of SEQ ID NO: 3,
- (c) a third fragment of LMP1 consisting of SEQ ID NO: 4,
- (d) a fourth fragment of LMP1 consisting of SEQ ID NO: 5,
- (e) a first fragment of LMP2 consisting of SEQ ID NO: 7,
- (f) a second fragment of LMP2 consisting of SEQ ID NO: 8,
- (g) a third fragment of LMP2 consisting of SEQ ID NO: 9,
- (h) a fourth fragment of LMP2 consisting of SEQ ID NO: 10,
- (i) a first fragment of EBNA1 consisting of SEQ ID NO: 12,
- (j) a first fragment of EBNA3A consisting of SEQ ID NO: 14,
- (k) a second fragment of EBNA3A consisting of SEQ ID NO: 15,
- (l) a third fragment of EBNA3A consisting of SEQ ID NO: 16,
- (m) a fourth fragment of EBNA3A consisting of SEQ ID NO: 17,
- (n) a fifth fragment of EBNA3A consisting of SEQ ID NO: 18,
- (o) a sixth fragment of EBNA3A consisting of SEQ ID NO: 19, and
- (p) a seventh fragment of EBNA3A consisting of SEQ ID NO: 20;

wherein the first, second, third and fourth LMP1 fragments are not adjacent to each other; the first, second, third and fourth LMP2 fragments are not adjacent to each other; and the first, second, third, fourth, fifth, sixth, and seventh EBNA3A fragments are not adjacent to each other. Optionally, the polyvalent EBV antigen further comprises:
- (a) a first fragment of ZEBRA consisting of SEQ ID NO: 22, and
- (b) a second fragment of ZEBRA consisting of SEQ ID NO: 23;

wherein the first and second ZEBRA fragments are not adjacent to each other.

To facilitate a clear description of the polypeptides and polynucleotides described herein, particular sequence components are referred to as a "first" polypeptide or polynucleotide sequence, a "second" polypeptide or polynucleotide sequence, etc. It is to be understood that the first, second, etc. sequences can appear in any desired order or orientation, and that no particular order or orientation is intended by the words "first", "second" etc.

In some embodiments, the polyvalent EBV antigen does not contain junctional neo-epitopes that map to human (i.e. self) proteins. An immunogenic junctional neo-epitope is an epitope that elicits an immune response to the junction of two heterologous protein sequences, wherein the epitope is not present in either of the heterologous protein sequences themselves. T cell responses to junctional neo-epitopes can be identified using methods known in the art, for example immunological assays using peptide pools covering all junctions to be used, as described in Example 4.

Figure 2:
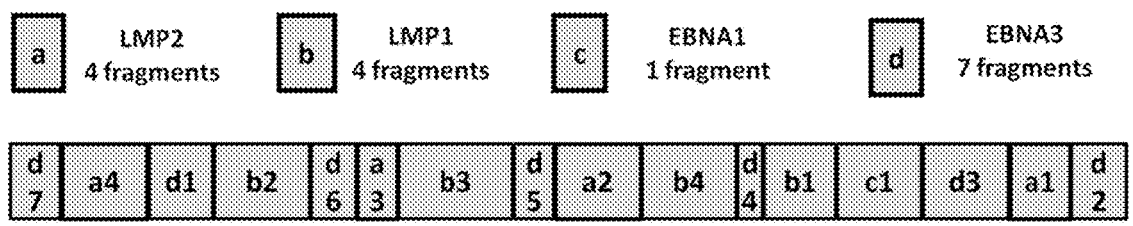
FIG. 2A-B: Schematic representation of polyvalent EBV antigen constructs. A) EBV latent antigen construct (EBV-L), comprising immunogenic fragments derived from LMP2 (identified as a1 to a4), LMP1 (identified as b1 to b4), EBNA1 (identified as c1) and EBNA3A (identified as d1 to d7). B) EBV latent+lytic antigen construct (EBV-LLy), comprising immunogenic fragments derived from LMP1, LMP2, EBNA1, EBNA3A (all identified as in FIG. 2A) and ZEBRA (identified as e1 to e2). Regions of the polyvalent antigens with the same letter prefix (i.e., a, b, c, d, e) are derived from the same EBV protein.
Figure 2:
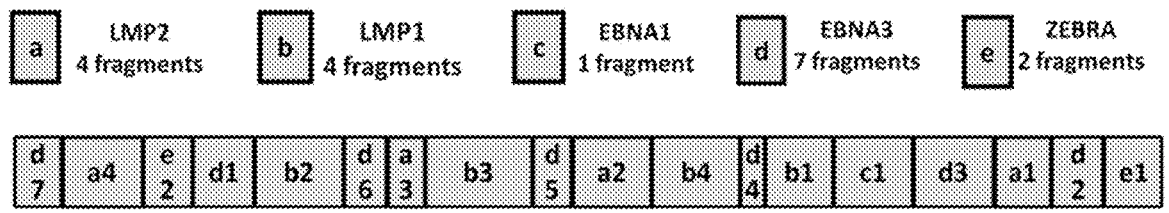
Figure 3:
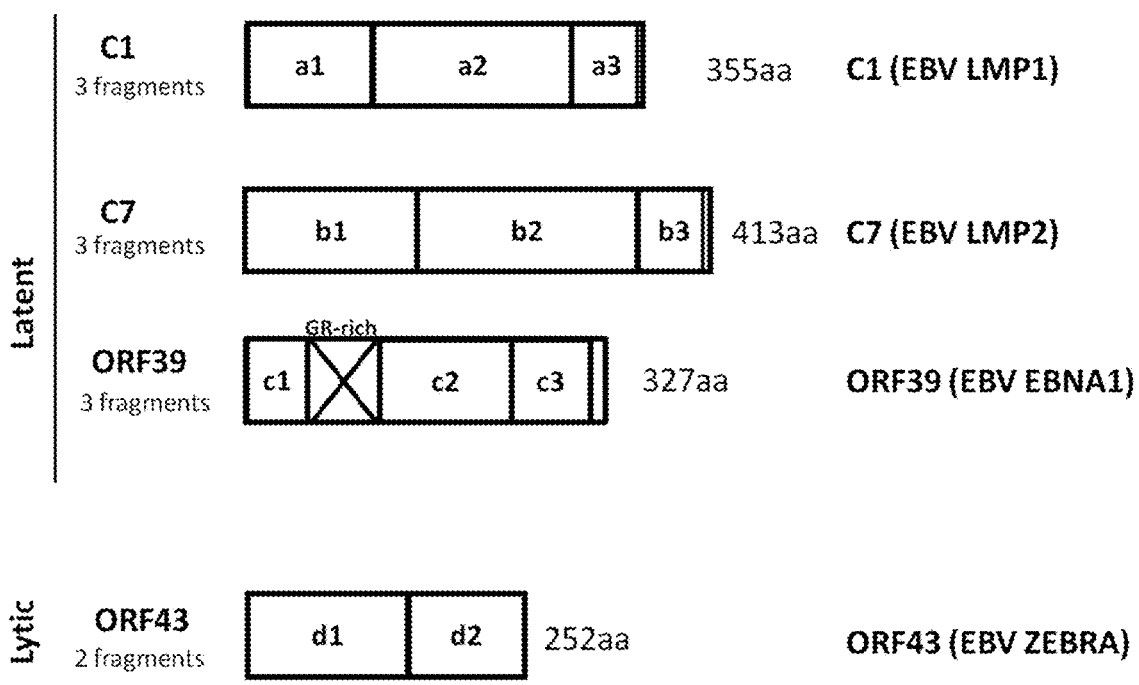
FIG. 3: Schematic representation of CalHV3 latent (C1, C7 and ORF39) and lytic (ORF43) proteins. Numbered regions indicate immunogenic fragments used to construct polyvalent CalHV3 antigen polypeptides. Alphanumeric identifiers (e.g., a1, a2, b1, b2) correspond to the fragments represented in polyvalent constructs shown in FIG. 4A-C. C1, C7, ORF39 and ORF43 antigens were selected because they are the putative marmoset (Callithrix jacchus) herpesvirus orthologs of EBV proteins LMP1, LMP2, EBNA1 and ZEBRA, respectively.

In one embodiment, the polyvalent EBV antigen is the "EBV-L" construct illustrated in FIG. 2A. In another embodiment, the polyvalent EBV antigen polypeptide is a polypeptide at least 80%, at least 85%, at least 90%, at least 95% or at least 99% identical to SEQ ID NO: 24.

In another embodiment, the polyvalent EBV antigen is the "EBV-LLy" construct illustrated in FIG. 2B. In another embodiment, the polyvalent EBV antigen polypeptide is a polypeptide at least 80%, at least 85%, at least 90%, at least 95% or at least 99% identical to SEQ ID NO: 26.

In preferred embodiments, an EBV antigen polypeptide of the invention contains at least one amino acid insertion, deletion and/or substitution as compared to a wild type EBV protein.

In another embodiment, the EBV antigen polypeptide is a polypeptide encoded by a polynucleotide described herein.

Polynucleotides

Polynucleotides and expression cassettes encoding EBV antigen polypeptides described herein are also provided. By "expression cassette" is meant the combination of a selected heterologous gene (a "transgene" encoding an EBV antigen polypeptide) and the other regulatory elements necessary to drive translation, transcription and/or expression of the gene product in a host cell.

The invention provides a polynucleotide encoding an EBV antigen polypeptide of the invention.

In one embodiment is provided a polynucleotide encoding a polypeptide at least 80%, at least 85%, at least 90%, at least 95% or at least 99% identical to SEQ ID NO: 24. In one embodiment, the polynucleotide is at least 80%, at least 85%, at least 90%, at least 95% or at least 99% identical to SEQ ID NO: 25.

In one embodiment is provided a polynucleotide encoding a polypeptide at least 80%, at least 85%, at least 90%, at least 95% or at least 99% identical to SEQ ID NO: 26. In one embodiment, the polynucleotide is at least 80%, at least 85%, at least 90%, at least 95% or at least 99% identical to SEQ ID NO: 27.

Suitably the polynucleotides of the invention are recombinant. Recombinant means that the polynucleotide is the product of at least one of cloning, restriction, recombination or ligation steps, or other procedures that result in a polynucleotide that is distinct from a polynucleotide found in nature. A recombinant virus is a virus comprising a recombinant polynucleotide. A recombinant vector is a vector comprising a recombinant polynucleotide. A recombinant virus includes progeny of the original recombinant virus. A "recombinant vector" includes replicates of the original recombinant vector. A "recombinant polynucleotide" includes replicates of the original recombinant polynucleotide. Recombinant polynucleotides of the invention contain at least one nucleic acid substitution as compared to the wild-type EBV genome.

In some embodiments, EBV antigen-encoding polynucleotides of the invention are operatively linked to one or more control elements in a manner that permits its transcription, translation and/or expression in a cell transfected or infected with the polynucleotide. As used herein, "operably linked" sequences include both expression control sequences that are contiguous with the gene of interest and expression control sequences that act in trans or at a distance to control the gene of interest. Thus, in one embodiment a polynucleotide is operatively linked to one or more sequences which direct expression of said polypeptide in a host cell. In some embodiments the expression control sequence is heterologous to the EBV antigen-encoding polynucleotide Expression control sequences include appropriate transcription initiation, termination, promoter and enhancer sequences; efficient RNA processing signals such as splicing and polyadenylation (poly A) signals including rabbit beta-globin polyA; sequences that stabilize cytoplasmic mRNA; sequences that enhance translation efficiency (e.g., Kozak consensus sequence); sequences that enhance protein stability; and when desired, sequences that enhance secretion of the encoded product. Among other sequences, chimeric introns may be used.

A "promoter" is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A great number of expression control sequences, including promoters which are internal, heterologous, native, constitutive, inducible and/or tissue-specific, are known in the art and may be utilized.

In one embodiment, the polynucleotide is operatively linked to a heterologous expression control sequence, such as a promoter. Typically, "heterologous" means derived from a genotypically distinct entity from that of the rest of the entity to which it is being compared. A heterologous nucleic acid sequence refers to any nucleic acid sequence that is not isolated from, derived from, or based upon a naturally occurring nucleic acid sequence of the adenoviral vector.

Examples of constitutive promoters include, without limitation, the TBG promoter, the retroviral Rous sarcoma virus LTR promoter (optionally with the enhancer), the cytomegalovirus (CMV) promoter (optionally with the CMV enhancer, see, e.g., Boshart et al, Cell, 41:521-530 (1985)), the CASI promoter (WO2012/115980), the SV40 promoter, the dihydrofolate reductase promoter, the β-actin promoter, the phosphoglycerol kinase (PGK) promoter, and the EF1a promoter (Invitrogen).

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. For example, inducible promoters include the zinc-inducible sheep metallothionine (MT) promoter and the dexamethasone (Dex)-inducible mouse mammary tumor virus (MMTV) promoter. Other inducible systems include the T7 polymerase promoter system; the ecdysone insect promoter, the tetracycline-repressible system and the tetracycline-inducible system. Other systems include the FK506 dimer, VP16 or p65 using castradiol, diphenol murislerone, the RU486-inducible system and the rapamycin-inducible system. The effectiveness of some inducible promoters increases over time. In such cases one can enhance the effectiveness of such systems by inserting multiple repressors in tandem, e.g., TetR linked to a TetR by an IRES.

In another embodiment, a native EBV promoter may be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

The transgene may be operably linked to a tissue-specific promoter. For instance, if expression in skeletal muscle is desired, a promoter active in muscle should be used. These include the promoters from genes encoding skeletal p-actin, myosin light chain 2A, dystrophin, muscle creatine kinase, as well as synthetic muscle promoters with activities higher than naturally occurring promoters. Examples of promoters that are tissue-specific are known for liver; hepatitis B virus core; alpha-fetoprotein, bone osteocalcin; bone sialoprotein, lymphocytes, immunoglobulin heavy chain; T cell receptor chain), neuronal such as neuron-specific enolase (NSE) promoter, neurofilament light-chain gene, and the neuron-specific vgf gene, among others.

Vectors

Vectors containing polynucleotides encoding EBV antigen constructs as described herein are also provided. Such vectors will be suitable for delivery to and expression in a host cell. Vectors can be in the form of a replicating or replication defective vector, such as a viral vector. Numerous viral vectors suitable for introducing immunogenic nucleic acids into a subject are known in the art, and include both DNA and RNA viruses. Examples of vectors suitable for encoding EBV antigens described herein include: adenovirus vectors (replicating or replication deficient), pox virus vectors, including vaccinia virus vectors, such as modified vaccinia Ankara virus (MVA), NYVAC, avipox vectors, canarypox (ALVAC) and fowl pox virus (FPV), Alphavirus vectors (such as Sindbis virus, Semliki Forest virus (SFV), Ross River virus, and Venezuelan equine encephalitis (VEE) virus) and chimeras and replicons thereof, herpes virus vectors (e.g., cytomegalovirus (CMV)-derived vectors), arena virus vectors, such as lymphocytic choriomeningitis virus (LCMV) vectors, measles virus vectors, vesicular stomatitis virus vectors, pseudorabies virus, adeno-associated virus, retrovirus, lentivirus, viral like particles, and many others.

In one embodiment, the vector is an adenovirus. The production and use of adenovirus vectors are well known to those of ordinary skill in the art. In the context of the immunogenic combinations disclosed here, examples of disclosure of the design, production and use of adenovirus vectors expressing vaccine antigens can be found in, e.g., in US published application No. 2014/0141042 (WO 2012/089833); U.S. Pat. No. 8,216,834 (WO 2005/071093); US published application No. US 2012/0027788 (WO 2010/086189); and US published application No. US 2005/0214323.

Typically, an adenoviral vector is designed such that the expression cassette is located in a nucleic acid molecule which contains other adenoviral sequences in the region native to a selected adenoviral gene. The expression cassette may be inserted into an existing gene region to disrupt the function of that region, if desired. Alternatively, the expression cassette may be inserted into the site of a partially or fully deleted adenoviral gene. For example, the expression cassette may be located in the site of a mutation, insertion or deletion which renders non-functional at least one gene of a genomic region selected from the group consisting of E1A, E1B, E2A, E2B, E3 and E4. The term "renders non-functional" means that a sufficient amount of the gene region is removed or otherwise disrupted, so that the gene region is no longer capable of producing functional products of gene expression. If desired, the entire gene region may be removed (and suitably replaced with the expression cassette). Suitably, E1 genes of adenovirus are deleted and replaced with an expression cassette consisting of a promoter of choice, a cDNA sequence of the gene of interest and a poly A signal, resulting in a replication defective recombinant virus.

Adenoviral vectors of use in the present invention may be derived from a range of mammalian hosts. Over 100 distinct serotypes of adenovirus have been isolated which infect various mammalian species, 51 of which are of human origin. Thus one or more of the adenoviral vectors may be derived from a human adenovirus. Examples of such human-derived adenoviruses are Ad1, Ad2, Ad4, Ad5, Ad6, Ad11, Ad24, Ad26, Ad34, Ad35, Ad48, particularly Ad5, Ad11 and Ad35. The human and nonhuman adenoviral serotypes have been categorized into six subgenera (A-F) based on a number of biological, chemical, immunological and structural criteria.

Although Ad5-based vectors have been used extensively in a number of gene therapy trials, there may be limitations on the use of Ad5 and other human group C adenoviral vectors due to preexisting immunity in the general population due to natural infection. Ad5 and other human group C members tend to be among the most seroprevalent serotypes. Immunity to existing vectors may develop as a result of exposure to the vector during treatment. These types of preexisting or developed immunity to seroprevalent vectors may limit the effectiveness of gene therapy or vaccination efforts. Alternative adenovirus serotypes, thus constitute very important targets in the pursuit of gene delivery systems capable of evading the host immune response.

One such area of alternative serotypes are those derived from non-human primates, especially adenoviruses isolated from chimpanzee, bonobos and gorillas. See U.S. Pat. No. 6,083,716 which describes the genome of two chimpanzee adenoviruses.

It has been shown that non-human simian adenoviral vectors induce strong immune responses to transgene products as efficiently as human adenoviral vectors (Fitzgerald et al. (2003) J. Immunol. 170:1416; Colloca et al. (2012) Science Translational Medicine 4:1-9; Roy et al. (2004) Virology 324: 361-372; Roy et al. (2010) J. of Gene Medicine 13:17-25).

Non-human simian adenoviruses can be isolated from the mesenteric lymph nodes or feces of the animals and can replicate in vitro in HEK 293 cells. Despite these similarities, nonhuman simian adenoviruses are phylogenetically and immunologically distinct from the more common human serotypes (Ad2 and Ad5).

Thus, in one embodiment one or more of the adenoviral vectors may be derived from a non-human primate adenovirus eg a chimpanzee adenovirus such as one selected from serotypes ChAd3, ChAd63, ChAd83, ChAd155, Pan5, Pan6, Pan 7 (also referred to as C7) and Pan9. Specifically, the virus may be a non-human adenovirus, such as a simian adenovirus and in particular a chimpanzee adenovirus such as ChAd155, Pan 5, 6, 7 or 9. Examples of such strains are described in US 20040241181 (WO03/000283) and are available from the American Type Culture Collection, 10801 University Boulevard, Manassas, Va. 20110-2209, and other sources. Desirable chimpanzee adenovirus strains include Pan 5 [ATCC VR-591], Pan 6 [ATCC VR-592], and Pan 7 [ATCC VR-593]. Alternatively, adenoviral vectors may be derived from nonhuman simian adenoviruses derived from bonobos, such as PanAd1, PanAd2 or PanAd3. Examples of such vectors described herein can be found for example in US 20110217332 (WO2005/071093), US 2012/0027788 (WO2010/086189) and WO2016/198621.

Use of nonhuman simian adenoviruses is thought to be advantageous over use of human adenovirus serotypes because of low and infrequent pre-existing immunity, in particular the lack of cross-neutralising antibodies, to adenoviruses in the target population. Cross-reaction of the chimpanzee adenoviruses with pre-existing neutralizing antibody responses is only present in 2% of the target population compared with 35% in the case of certain candidate human adenovirus vectors. Pan 6 is less closely related to Pan 5, 7 and 9.

The adenovirus of the invention may be replication defective. This means that it has a reduced ability to replicate in non-complementing cells, compared to the wild type virus. This may be brought about by mutating the virus e.g. by deleting a gene involved in replication, for example deletion of the E1a, E1b, E3 or E4 gene.

The adenoviral vectors in accordance with the present invention may be derived from replication defective adenovirus comprising a functional E1 deletion. Thus the adenoviral vectors according to the invention may be replication defective due to the absence of the ability to express adenoviral E1a and E1b, i.e., are functionally deleted in E1a and E1b. The recombinant adenoviruses may also bear functional deletions in other genes [see, e.g., US 20040241181 (WO 03/000283)] for example, deletions in E3 or E4 genes. The adenovirus delayed early gene E3 may be eliminated from the adenovirus sequence which forms part of the recombinant virus. The function of E3 is not necessary to the production of the recombinant adenovirus particle. Thus, it is unnecessary to replace the function of this gene product in order to package a recombinant adenovirus useful in the invention. In one particular embodiment the recombinant adenoviruses have functionally deleted E1 and E3 genes. The construction of such vectors is described in Roy et al., (2004) Human Gene Therapy 15:519-530.

Recombinant adenoviruses may also be constructed having a functional deletion of the E4 gene, although it may be desirable to retain the E4 ORF6 function. Adenovirus vectors according to the invention may also contain a deletion in the delayed early gene E2a. Deletions may also be made in any of the late genes L1 through to L5 of the adenovirus genome. Similarly deletions in the intermediate genes IX and IVa may be useful.

Other deletions may be made in the other structural or non-structural adenovirus genes. The above deletions may be used individually, i.e. an adenovirus sequence for use in the present invention may contain deletions of E1 only. Alternatively, deletions of entire genes or portions thereof effective to destroy their biological activity may be used in any combination. For example in one exemplary vector, the adenovirus sequences may have deletions of the E1 genes and the E4 gene, or of the E1, E2a and E3 genes, or of the E1 and E3 genes (such as functional deletions in E1a and E1b, and a deletion of at least part of E3), or of the E1, E2a and E4 genes, with or without deletion of E3 and so on. Such deletions may be partial or full deletions of these genes and may be used in combination with other mutations, such as temperature sensitive mutations to achieve a desired result. Adenoviral vectors of use in the present invention include PanAd3 (WO 2010/086189) and ChAd155 (WO 2016/198621).

In another embodiment, the viral vector is a pox virus vector. In a specific embodiment, the poxvirus vector is a vaccinia virus vector, such as a modified vaccinia Ankara virus (MVA) vector. (MVA) vector is replication-deficient in humans and other mammals. It was initially developed to improve the safety of smallpox vaccination by passage of Vaccinia virus over 570 times in chicken embryo fibroblast (CEF) cells, resulting in multiple, fully characterised deletions after which the virus was highly attenuated and replication-deficient in humans and other mammals. The replication defect occurs at a late stage of virion assembly such that viral and recombinant gene expression is unimpaired, making MVA an efficient single round expression vector incapable of causing infection in mammals.

MVA has subsequently been extensively used as a viral vector to induce antigen-specific immunity against transgenes, both in animal models and in humans. A description of MVA can be found in Mayr A, et al. "The smallpox vaccination strain MVA: marker, genetic structure, experience gained with the parenteral vaccination and behavior in organisms with a debilitated defense mechanism. "Abstammung, Eigenschaften und Verwendung des attenuierten Vaccinia-Stammes MVA." Zentralbl Bakteriol B. 1978 December; 167(5-6):375-90 and in Mayr, A., Hochstein-Mintzel, V. & Stickl, H. (1975). Infection 3, 6-14.

In one embodiment, MVA is derived from the virus seed batch 460 MG obtained from the 571st passage of Vaccinia Virus on CEF cells. In a further embodiment, MVA is derived or produced prior to 31 Dec. 1978 and is free of prion contamination.

MVA vectors and methods of production of such vectors are described, for example in U.S. Pat. No. 6,761,893 (WO02/042480); U.S. Pat. Nos. 7,964,395; 7,964,396; US published application no. US 2013/0183335 (WO2012/048817); and US Published Application No. 2015/0209421 (WO2014/019718). Each of the preceding is incorporated herein by reference for the teaching of suitable MVA vectors and methods.

In another embodiment, the viral vector is an Alphavirus vector, such as an alphavirus replicon or other self-replicating RNA vector. Exemplary alphavirus vectors and methods for producing and delivering them suitable for use in the context of the immunogenic combinations disclosed herein are described in, e.g., US20090104226 (WO2006078294); US20110300205 (WO2011005799); US20130195968 (WO 2012/006376); US20130177639 (WO2012006377); WO2013006838; and WO2013006842, each of which are incorporated herein for their disclosure of exemplary self-replicating RNA vectors suitable in the context of the disclosed immunogenic combinations.

Also provided is a method of producing a recombinant viral particle expressing an EBV antigen of the invention, comprising expressing a vector described herein in a host cell. Viral particles can be produced in any suitable cell line in which the viral vector is capable of replication.

Adenoviral vectors can be produced in any suitable cell line in which the virus is capable of replication. In particular, complementing cell lines which provide the factors missing from the viral vector that result in its impaired replication characteristics (such as E1 and/or E4) can be used. Without limitation, such a cell line may be HeLa [ATCC Accession No. CCL 2], A549 [ATCC Accession No. CCL 185], HEK 293, KB [CCL 17], Detroit [e.g., Detroit 510, CCL 72] and WI-38 [CCL 75] cells, among others. These cell lines are all available from the American Type Culture Collection, 10801 University Boulevard, Manassas, Va. 20110-2209. Other suitable parent cell lines may be obtained from other sources, such as PER.C6 cells, as represented by the cells deposited under ECACC no. 96022940 at the European Collection of Animal Cell Cultures (ECACC) at the Centre for Applied Microbiology and Research (CAMR, UK) or Her 96 cells (Crucell).

A particularly suitable complementation cell line is the Procell92 cell line. The Procell92 cell line is based on HEK 293 cells which express adenoviral E1 genes, transfected with the Tet repressor under control of the human phosphoglycerate kinase-1 (PGK) promoter, and the G418-resistance gene (Vitelli et al. PLOS One (2013) 8(e55435):1-9). Procell92.S is adapted for growth in suspension conditions and is also useful for producing adenoviral vectors expressing toxic proteins (www_okairos.com/e/inner-s.php?m=00084, last accessed 13 Apr. 2015).

Vaccinia vectors can be produced according to methods described in the art. For example, preparation and use of MVA vectors is described in Ourmanov et al., J. Virol. (2009) 83:5388-5400; and Martinon et al. Vaccine (2008) 26:532-545.

Compositions

EBV antigen polypeptides, polynucleotides and vectors described herein may be administered in immunogenic compositions. An immunogenic composition as described herein is a composition comprising one or more recombinant polypeptides, polynucleotides and/or vectors capable of inducing an immune response, for example a humoral (e.g., antibody) and/or cell-mediated (e.g., a cytotoxic T cell) response. following delivery to a mammal, suitably a human.

The immunogenic compositions disclosed herein typically contain one or more pharmaceutically acceptable carriers and/or excipients. Pharmaceutically acceptable carriers and excipients are well known and can be selected by those of skill in the art. The adjective "pharmaceutically acceptable" indicates that the referent is suitable for administration to a subject (e.g., a human or animal subject). Remington's Pharmaceutical Sciences, by E. W. Martin, Mack Publishing Co., Easton, Pa., 15th Edition (1975), describes compositions and formulations (including diluents) suitable for pharmaceutical delivery of therapeutic and/or prophylactic compositions, including immunogenic compositions.

For example, the carrier or excipient can favorably include a buffer. Optionally, the carrier or excipient also contains at least one component that stabilizes solubility and/or stability. Examples of solubilizing/stabilizing agents include detergents, for example, laurel sarcosine and/or tween. Alternative solubilizing/stabilizing agents include arginine, and glass forming polyols (such as sucrose, trehalose and the like). Numerous pharmaceutically acceptable carriers and/or pharmaceutically acceptable excipients are known in the art and are described, e.g., in Remington's Pharmaceutical Sciences, by E. W. Martin, Mack Publishing Co., Easton, Pa., 5th Edition (1975).

Accordingly, suitable excipients and carriers can be selected by those of skill in the art to produce a formulation suitable for delivery to a subject by a selected route of administration.

Suitable excipients include, without limitation: glycerol, Polyethylene glycol (PEG), Sorbitol, Trehalose, N-lauroyl-sarcosine sodium salt, L-proline, Non detergent sulfobetaine, Guanidine hydrochloride, Urea, Trimethylamine oxide, KCl, Ca2+, Mg2+, Mn2+, Zn2+ and other divalent cation related salts, Dithiothreitol, Dithioerytrol, and 13-mercaptoethanol. Other excipients can be detergents (including: Tween80, Tween20, Triton X-00, NP-40, Empigen BB, Octylglucoside, Lauroyl maltoside, Zwittergent 3-08, Zwittergent 3-0, Zwittergent 3-2, Zwittergent 3-4, Zwittergent 3-6, CHAPS, Sodium deoxycholate, Sodium dodecyl sulphate, Cetyltrimethylammonium bromide).

Optionally, an immunogenic composition of the invention may be formulated to contain other components, including, e.g., adjuvants, stabilizers, pH adjusters, preservatives and the like. Examples of suitable adjuvants are provided below under "Adjuvants."

Methods of Use

EBV antigen polypeptides, polynucleotides, vectors described herein may be used in the prevention and/or treatment of EBV infection and EBV-associated diseases, e.g., as a vaccine for induction of an immune response. As used herein, induction of an immune response refers to the ability of a protein to induce a T cell and/or a humoral immune response to the protein.

As used herein, induction of an immune response refers to the ability of a protein, also known as an "antigen" or "immunogen," to induce a T cell and/or a humoral immune response to the protein. For example, an immunogenic composition may induce a memory T and/or B cell population relative to an untreated subject following immunization with the composition, particularly in those embodiments where the composition comprises a nucleic acid comprising a sequence which encodes an EBV antigen polypeptide. In some embodiments, the subject is a vertebrate, such as a mammal e.g. a human or a veterinary mammal.

Immune responses can be measured by methods known in the art, including assays of the induction of proliferation or effector function of the particular lymphocyte type of interest, e.g., B cells, T cells, T cell lines, and T cell clones.

Thus in one embodiment is provided a method of inducing an immune response in a subject comprising administering a polynucleotide, a polypeptide, a vector or an immunogenic composition of the invention to the subject. In one embodiment, the subject is Epstein-Barr virus seronegative. A subject is "seronegative" if the subject has no serological evidence of past or current EBV infection. In another embodiment the subject is Epstein-Barr virus seropositive. A subject is "seropositive" if the subject has serological evidence of past or current EBV infection.

Also provided is a method of treating or preventing an EBV-associated disease in a subject, comprising administering a polynucleotide, a polypeptide, a vector or an immunogenic composition of the invention to the subject. In one embodiment, the EBV-associated disease is an EBV-associated malignancy or an EBV-associated autoimmune disease. EBV-associated diseases, include, for example, multiple sclerosis, rheumatoid arthritis and systemic lupus erythematosus.

Also provided are dosing regimens designed to maximize the immunogenicity of polynucleotides, polypeptides, vectors and immunogenic compositions of the invention. Thus, in one embodiment is provided a method of inducing an immune response in a subject comprising administering two or more doses of a polynucleotide, a polypeptide, a vector and/or an immunogenic composition of the invention to the subject. In certain embodiments the doses are separated by one, two, three, four, five, six, seven, eight, nine, ten, eleven, twelve or more weeks. In another embodiment the doses are separated by one, two, three, four, five, six, seven, eight, nine, ten, eleven, twelve or more months. Alternatively, doses may be separated by one, two, three, four, five, six, seven, eight, nine, ten, eleven, twelve or more years.

In one embodiment is provided a method of inducing an immune response in a subject comprising:
 (a) administering an adenovirus vector comprising a polynucleotide of the invention; and
 (b) administering a vaccinia virus vector comprising a polynucleotide of the invention;
wherein steps (a) and (b) are conducted in either order. In one embodiment the adenovirus vector is ChAd155. In another embodiment the vaccinia virus vector is MVA. In one embodiment, step (b) is carried out one, two, three, four, five, six, seven, eight, nine, ten, eleven, twelve or more weeks after step (a). In one embodiment, step (b) is carried out one, two, three, four, five, six, seven, eight, nine, ten, eleven, twelve or more months after step (a).

In one embodiment is provided a method of treating or preventing an EBV-associated disease in a subject comprising:
 (a) administering an adenovirus vector comprising a polynucleotide of the invention; and
 (b) administering a vaccinia virus vector comprising a polynucleotide of the invention;
wherein steps (a) and (b) are conducted in either order. In one embodiment the adenovirus vector is ChAd155. In another embodiment the vaccinia virus vector is MVA. In one embodiment, step (b) is carried out one, two, three, four, five, six, seven, eight, nine, ten, eleven, twelve or more weeks after step (a). In one embodiment, step (b) is carried out one, two, three, four, five, six, seven, eight, nine, ten, eleven, twelve or more months after step (a).

Also provided is the use of a polynucleotide, vector, polypeptide, or immunogenic composition of the invention in the manufacture of a medicament for the treatment or prophylaxis of a disease caused by Epstein-Barr Virus infection.

Adjuvants

An "adjuvant" as used herein refers to a composition that enhances the immune response to an immunogen. A composition according to the invention that comprises an adjuvant can be used as a vaccine, e.g. for human subjects. The adjuvant accelerates, prolongs and/or enhances the quality and/or strength of an immune response to an antigen/immunogen in comparison to the administration of the antigen alone, thus, reduces the quantity of antigen/immunogen necessary in any given vaccine, and/or the frequency of injection necessary in order to generate an adequate immune response to the antigen/immunogen of interest.

Examples of adjuvants that may be used in the context of the compositions of the invention include inorganic adjuvants (e.g. inorganic metal salts such as aluminum phosphate or aluminum hydroxide), gel-like precipitates of aluminum hydroxide (alum); AlPO$_4$; alhydrogel; bacterial products from the outer membrane of Gram-negative bacteria, in particular monophosphoryl lipid A (MPLA), lipopolysaccharides (LPS), muramyl dipeptides and derivatives thereof; Freund's incomplete adjuvant; liposomes, in particular neutral liposomes, liposomes containing the composition and optionally cytokines; AS01B, AS01E, AS02; non-ionic block copolymers; ISCOMATRIX adjuvant; unmethylated DNA comprising CpG dinucleotides (CpG motif), in particular CpG ODN with a phosphorothioate (PTO) backbone (CpG PTO ODN) or phosphodiester (PO) backbone (CpG PO ODN); synthetic lipopeptide derivatives, in particular Pam$_3$Cys; lipoarabinomannan; peptidoglycan; zymosan; heat shock proteins (HSP), in particular HSP 70; dsRNA and synthetic derivatives thereof, in particular Poly I:poly C; polycationic peptides, in particular poly-L-arginine; taxol; fibronectin; flagellin; imidazoquinoline; cytokines with adjuvant activity, in particular GM-CSF, interleukin- (IL-2, IL-6, IL-7, IL-18, type I and II interferons, in particular interferon-gamma, TNF-alpha; 25-dihydroxyvitamin D3 (calcitriol); and synthetic oligopeptides, in particular MHCII-presented peptides. Non-ionic block polymers containing polyoxyethylene (POE) and polyoxypropylene (POP), such as POE-POP-POE block copolymers may be used as an adjuvant.

Additional examples of adjuvants include inorganic adjuvants (e.g. inorganic metal salts such as aluminium phosphate or aluminium hydroxide), organic adjuvants (e.g. saponins, such as QS21, or squalene), oil-based adjuvants (e.g. Freund's complete adjuvant and Freund's incomplete adjuvant), cytokines (e.g. IL-1p, IL-2, IL-7, IL-12, IL-18, GM-CFS, and INF-γ) particulate adjuvants (e.g. immunostimulatory complexes (ISCOMS), liposomes, biodegradable microspheres, virosomes, bacterial adjuvants (e.g. monophosphoryl lipid A, such as 3-de-O-acylated monophosphoryl lipid A (3D-MPL), or muramyl peptides), synthetic adjuvants (e.g. monophosphoryl lipid A (MPL), in particular 3-de-O-acylated monophosphoryl lipid A (3D-MPL and muramyl peptide analogues, or synthetic lipid A, and synthetic polynucleotides adjuvants, e.g., polyarginine or polylysine.

Saponins are also suitable adjuvants, for example, the saponin Quil A, derived from the bark of the South American tree Quillaja *Saponaria* Molina, and fractions thereof. Purified fractions of Quil A are also known as immunostimulants, such as squalene, QS21, QS17 and QS7, a non-haemolytic fraction of Quil-A. Combinations of QS21 and polysorbate or cyclodextrin are also suitable. Another example of an adjuvant is an immunostimulatory oligonucleotide containing unmethylated cytosine-guanosine dinucleotide motifs present in DNA ("CpG"). CpG is known as an adjuvant when administered by both systemic and mucosal routes. When formulated into vaccines, it may be administered in free solution together with free antigen or covalently conjugated to an antigen or formulated with a carrier such as aluminium hydroxide.

Activation of specific receptors can stimulate an immune response. Such receptors are known to the skilled artisan and comprise, for example, cytokine receptors, in particular type I cytokine receptors, type II cytokine receptors, TNF receptors; and a vitamin D receptor acting as transcription factor; and the Toll-like receptors 1 (TLR1), TLR-2, TLR 3, TLR4, TLR5, TLR-6, TLR7, and TLR9. Agonists to such receptors have adjuvant activity, i.e., are immunostimulatory. Other suitable adjuvants include alkyl glucosaminide phosphates (AGPs) or pharmaceutically acceptable salts of AGPs. Some AGPs are TLR4 agonists, and some are TLR4 antagonists. An adjuvant of the composition of the present invention may be one or more Toll-like receptor agonists. In a more preferred embodiment, the adjuvant is a Toll-like receptor 4 agonist. In a particular preferred embodiment, the adjuvant is a Toll-like receptor 9 agonist.

Adjuvants such as those described above may be formulated together with carriers, such as liposomes, oil in water emulsions, and/or metallic salts (including aluminum salts such as aluminum hydroxide). For example, 3D-MPL may be formulated with aluminum hydroxide or oil in water emulsions; QS21 may be formulated with cholesterol containing liposomes, oil in water emulsions or alum; CpG may be formulated with alum or with other cationic carriers.

Combinations of adjuvants may be utilized in the present invention, in particular a combination of a monophosphoryl lipid A and a saponin derivative, more particularly the combination of QS21 and 3D-MPL or a composition where the QS21 is quenched in cholesterol-containing liposomes (DQ). Alternatively, a combination of CpG plus a saponin such as QS21 is an adjuvant suitable for use in the present invention, as is a potent adjuvant formulation involving QS21, 3D-MPL and tocopherol in an oil in water emulsion. Saponin adjuvants may be formulated in a liposome and combined with an immunostimulatory oligonucleotide. Thus, suitable adjuvant systems include, for example, a combination of monophosphoryl lipid A, preferably 3D-MPL, together with an aluminium salt. A further exemplary adjuvant comprises QS21 and/or MPL and/or CpG. QS21 may be quenched in cholesterol-containing liposomes.

The fusion of the MHC class II invariant chain (also known as CD74) to an antigen which is comprised by an expression system used for vaccination increases the immune response against said antigen, if it is administered with a viral vector, e.g. an adenovirus. Accordingly, in one embodiment of the invention, the immunogenic transgene may be co-expressed with invariant chain in a recombinant ChAd155 viral vector.

In another embodiment, the invention provides the use of the capsid of ChAd155 (optionally an intact or recombinant viral particle or an empty capsid is used) to induce an immunomodulatory response, or to enhance or adjuvant a cytotoxic T cell response to another active agent by delivering a ChAd155 capsid to a subject. The ChAd155 capsid can be delivered alone or in a combination regimen with an active agent to enhance the immune response thereto. Advantageously, the desired effect can be accomplished without infecting the host with an adenovirus.

Sequence Identity

Identity with respect to a sequence is defined herein as the percentage of amino acid residues in the candidate sequence that are identical with the reference amino acid sequence after aligning the sequences and introducing gaps, if necessary, to achieve the maximum percent sequence identity, and not considering any conservative substitutions as part of the sequence identity.

Sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences or along a pre-determined portion of one or both sequences). The programs provide a default opening penalty and a default gap penalty, and a scoring matrix such as PAM 250 (a standard scoring matrix can be used in conjunction with the computer program. For example, the percent identity can then be calculated as the total number of identical matches multiplied by 100 and then divided by the sum of the length of the longer sequence within the matched span and the number of gaps introduced into the shorter sequences in order to align the two sequences.

Where the present disclosure refers to a sequence by reference to a UniProt or Genbank accession code, the sequence referred to is the current version as of the filing date of the present application.

The skilled person will recognise that individual substitutions, deletions or additions to a protein which alters, adds or deletes a single amino acid or a small percentage of amino acids is an "immunogenic derivative" where the alteration(s) results in the substitution of an amino acid with a functionally similar amino acid or the substitution/deletion/addition of residues which do not substantially impact the immunogenic function.

Conservative substitution tables providing functionally similar amino acids are well known in the art. In general, such conservative substitutions will fall within one of the amino-acid groupings specified below, though in some circumstances other substitutions may be possible without substantially affecting the immunogenic properties of the antigen. The following eight groups each contain amino acids that are typically conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M).

Suitably such substitutions do not occur in the region of an epitope, and do not therefore have a significant impact on the immunogenic properties of the antigen.

Immunogenic derivatives may also include those wherein additional amino acids are inserted compared to the reference sequence. Suitably such insertions do not occur in the region of an epitope, and do not therefore have a significant impact on the immunogenic properties of the antigen. One example of insertions includes a short stretch of histidine residues (e.g. 2-6 residues) to aid expression and/or purification of the antigen in question.

Immunogenic derivatives include those wherein amino acids have been deleted compared to the reference sequence. Suitably such deletions do not occur in the region of an epitope, and do not therefore have a significant impact on the immunogenic properties of the antigen.

The skilled person will recognise that a particular immunogenic derivative may comprise substitutions, deletions and additions (or any combination thereof).

General

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. The term "plurality" refers to two or more. Additionally, numerical limitations given with respect to concentrations or levels of a substance, such as solution component concentrations or ratios thereof, and reaction conditions such as temperatures, pressures and cycle times are intended to be approximate. The term "about" used herein is intended to mean the amount ±10%.

The term "comprises" means "includes." Thus, unless the context requires otherwise, the word "comprises," and variations such as "comprise" and "comprising" will be understood to imply the inclusion of a stated compound or composition (e.g., nucleic acid, polypeptide, antigen) or step, or group of compounds or steps, but not to the exclusion of any other compounds, composition, steps, or groups thereof. The abbreviation, "e.g." is derived from the Latin exempli gratia, and is used herein to indicate a non-limiting example. Thus, the abbreviation "e.g." is synonymous with the term "for example."

The invention will be further described by reference to the following, non-limiting, examples and figures.

EXAMPLES

Example 1: Antigen Design a. EBV Antigen Design

Polyvalent Epstein-Barr Virus antigen constructs were rationally designed with the following design goals in mind:
1) to broadly target EBV antigens that are expressed in EBV-associated multiple sclerosis (EBV-MS) by including multiple latent stage antigens in the design, and optionally including lytic stage antigens;
2) to reduce the risk of oncogenesis and immune interference by exclusion of known problematic regions, fragmenting and shuffling EBV protein antigens in the polyvalent antigen construct;
3) to focus the induced immune response on EBV-specific T-cell activation by including T-cell epitopes in the polyvalent antigen constructs; and
4) to exclude the presence of unwanted anti-self neo-epitopes in the final antigen sequence.

Two polyvalent EBV antigen constructs meeting these criteria were designed. The first polyvalent antigen construct (EBV-L; FIG. 2A) includes immunogenic fragments of latent stage EBV proteins LMP1, LMP2, EBNA1 and EBNA3A. A second construct (EBV-LLy; FIG. 2B) contains the same latent antigen fragments as EBV-L, and also includes an immunogenic fragment of the EBV lytic protein ZEBRA. The EBV latent proteins selected for inclusion in the antigen constructs have been reported to be expressed by B cells in post-mortem brain tissue of multiple sclerosis patients (Serafini et al., J. Exp. Medicine (2007) 204(12): 2899; Serafini et al., J. Neuropathol. Exp. Neurol. (2010) 69(7):677. Inclusion of the lytic antigen ZEBRA, a key regulator of the EBV switch from latency to lytic phase, is aimed at controlling the reactivation of the virus and limiting further amplification and spread of EBV.

Full length EBV proteins have the potential to transform immune cells. Therefore, to improve the safety of the antigen constructs, problematic regions were excluded and only remaining fragments of the EBV proteins were selected for the construct designs. FIG. 1 illustrates the location of the selected immunogenic fragments in each of the EBV proteins. As illustrated in FIGS. 2A-B, the selected fragments were shuffled to produce a polyprotein comprising 16 (EBV-L) or 18 (EBV-LLy) immunogenic fragments, assembled so that fragments derived from the same EBV protein are not adjacent to each other.

Finally, to reduce the risk of unwanted junctional epitopes formed by joining two immunogenic fragments together, a bioinformatics screen was conducted to identify potential anti-self neoepitopes at the junctional areas of candidate antigen constructs. Briefly, sixteen amino acid-long peptides spanning the border (junction) region between each pair of two consecutive antigen fragments were extracted from the vaccine polypeptide sequence (8 amino acids from each antigen fragment). The length of 16 amino acids of the junction region guarantees that each 9mer sequence within the junction region contains amino acids from both antigens. For each 16mer junction peptide, all 9mer peptides were then compared with a collection of 9mer peptides representing the complete human proteome (generated from the NCBI RefSeq peptide database). In no case was a 9mer peptide from a junction region of the vaccine polypeptide sequence found to be present in a human protein.

b. CalHV3 Antigen Design

CalHV3 is a gamma herpesvirus isolated from common marmosets (Callithrix jacchus). Based on similarities in sequence and structure, viral reproduction cycle and pathogenesis, CalHV3 is considered to be the marmoset equivalent of human EBV. See, e.g., Cho et al., PNAS 98(3):1224-1229 (2001). CalHV3 is acquired early in life and is reported to be highly prevalent in natural as well as captive marmoset colonies.

Figure 4:
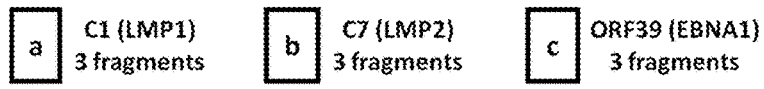
FIG. 4A-C: Schematic representation of polyvalent CalHV3 antigen constructs. A) CalHV3 latent antigen construct (CalHV3-L), comprising immunogenic fragments derived from C1, C7 and ORF39. B) CalHV3 latent+lytic antigen construct (CalHV3-LLy), comprising immunogenic fragments derived from C1, C7, ORF39 and ORF43. C) CalHV3-LLy construct from (B), fused to the marmoset MHC class II-associated invariant chain (Ii). Regions of the polyvalent antigens with the same letter prefix (i.e., a, b, c, d) are derived from the same CalHV3 protein.
Figure 4:
Figure 4:
Figure 4:
Figure 4:
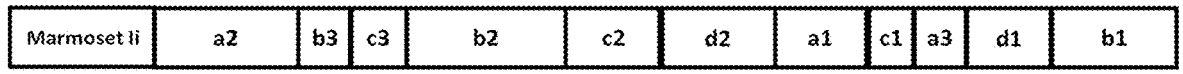

To evaluate the capacity of a similar vaccine to re-expand functional T cell responses to latent and lytic viral antigens in gamma-herpesvirus latently infected individuals in the marmoset model, orthologous CalHV3 antigen constructs were developed. Briefly, a CalHV3 latent antigen construct (CalHV3-L; illustrated in FIG. 4A) was constructed from immunogenic fragments of proteins C1 (SEQ ID NO: 28), C7 (SEQ ID NO: 32) and ORF39 (SEQ ID NO: 36), which are the CalHV3 orthologs of EBV LMP1, LMP2 and EBNA1, respectively. As in the EBV-L antigen construct, antigenic regions included in CalHV3-L construct were fragmented and shuffled so that fragments from the same CalHV3 protein are not adjacent to each other. The amino acid sequence of the final CalHV3-L antigen construct is shown in SEQ ID NO: 44 (encoded by the polynucleotide shown in SEQ ID NO: 45).

A CalHV3 Latent/Lytic antigen construct (CalHV3-LLy; illustrated in FIG. 4B) was also constructed. In addition to containing fragments of the latent proteins C1, C7 and ORF39, CalHV3-LLy also contains fragments of ORF43, the CalHV3 ortholog of the EBV ZEBRA protein. The amino acid sequence of the final CalHV3-LLy antigen construct is shown in SEQ ID NO: 46 (encoded by the polynucleotide shown in SEQ ID NO: 47).

Finally, a genetically-adjuvanted version of CalHV3-LLy (li-CalHV3-LLy) was constructed by fusing a marmoset MHC class II-associated invariant chain polypeptide (SEQ ID NO: 43) to the N-terminus of CalHV3-LLy. The amino acid sequence of the final li-CalHV3-LLy antigen construct is shown in SEQ ID NO: 48 (encoded by the polynucleotide shown in SEQ ID NO: 49).

Example 2: Vector Construction

Polynucleotides encoding EBV-L (SEQ ID NO: 25) and EBV-LLy (SEQ ID NO: 27) were cloned into plasmid pvjTetOhCMV-bghpolyA, containing a tetOhCMV promoter and bovine growth hormone poly-adenylation signal (BGH pA), according to methods described in WO2016/198621. The EBV-L and EBV-LLy expression cassettes were then transferred into a ChAd155 vector backbone by homologous recombination in E. coli BJ5183 competent cells to produce the pChAd155 (ΔE1, ΔE4_Ad5E4 orf6) TetO hCMV-EBV-L (and EBV-LLy) vectors. The nucleic acid sequence of vector pChAd155 (ΔE1, ΔE4_Ad5E4 orf6) TetO hCMV-EBV-L is shown in SEQ ID NO: 50. The antigen-encoding region is at nucleotides 1348-4806 of SEQ ID NO: 50. The nucleic acid sequence of vector pChAd155 (ΔE1, ΔE3, ΔE4_Ad5E4 orf6) TetO hCMV-EBV-LLy expression vector is shown in SEQ ID NO: 51. The antigen-encoding region is at nucleotides 1348-5157 of SEQ ID NO: 51. ChAd155-EBV vector construction was confirmed by transgene sequencing and restriction analysis. The same methods can be used to prepare EBV adenoviral vectors based on alternative modified ChAd155 backbones as described, for example, in WO2016/198621.

The same methods were followed to prepare vectors ChAd155-CalHV3-L, ChAd155-CalHV3-LLy, and ChAd155-li-CalHV3-LLy (encoding CalHV3 antigens CalHV3-L, CalHV3-LLy, and li-CalHV3-LLy, respectively). The nucleic acid sequence of vector pChAd155 (ΔE1, ΔE4_Ad5E4 orf6) TetO hCMV-CalHV3-L is shown in SEQ ID NO: 52 (antigen-encoding region at nucleotides 1348-4482). The nucleic acid sequence of vector pChAd155 (ΔE1, ΔE3, ΔE4_Ad5E4 orf6) TetO hCMV-CalHV3-LLy is shown in SEQ ID NO: 53 (antigen-encoding region at nucleotides 1348-5238). The nucleic acid sequence of vector pChAd155 (ΔE1, ΔE3, ΔE4_Ad5E4 orf6) TetO hCMV-li-CalHV3-LLy is shown in SEQ ID NO: 54 (antigen-encoding region at nucleotides 1348-5883).

MVA vectors encoding the EBV-LLy and CalHV3-LLy antigen constructs were also prepared, according to methods known in the art. See, e.g., Ourmanov et al., J. Virol. (2009) 83:5388-5400; and Martinon et al. Vaccine (2008) 26:532-545.

Example 3: Viral Particle Production

ChAd155_EBV-L and ChAD155_EBV-LLy vectors were linearized with the restriction endonuclease PmeI and transfected into a HEK293-derived cell line (Procell92.S), as described in Vitelli et al., PLOS One (2013) 8(e55435):1-9. These cells are genetically modified to constitutively express the TetO repressor in order to repress transgene expression during virus generation. Viral amplification was performed at small scale (shake flask) and ChAd155-EBV viral particles were purified on double CsCl gradient from 1 liter scale suspension culture. ChAd155-EBV viral particle titers were determined by QPCR targeting the tetOhCMV promoter. The same methods were followed to prepare viral particles from ChAd155-CalHV3-L, ChAd155-CalHV3-LLy, and ChAd155-li-CalHV3-LLy.

Recombinant MVA expressing the EBV-LLy and CalHV3-LLy antigen constructs were obtained using standard methods. Briefly, primary cell cultures of chicken embryo fibroblast (CEF) cells at a defined cell density were infected with MVA-EBV and MVA-CalHV3 viral seed at a defined multiplicity of infection. The MVA-EBV and MVA-CalHV3 virus harvest was purified by fractional gradient centrifugation.

Example 4: Immunogenicity of ChAd155-EBV and ChAd155-CalHV3 Antigens in Mice a. ChAd155-EBV The immunogenicity of ChAd155-EBV viral particles produced from vectors expressing latent or latent+lytic antigens was evaluated in mice using the experimental design shown in Table 1. Briefly, CB6F1 mice (6 per group) were administered a single dose ($10^6$, $10^7$ or $10^8$ viral particles, intramuscularly) of vectors ChAd155-EBV-L or ChAd155-EBV-LLy.

Three weeks after immunization, splenocytes were isolated and assayed for T-cell responses to EBV antigens according to a standard IFNγ ELISpot assay. Briefly, splenocytes from immunized animals were stimulated with overlapping 15mer peptides arranged in 5 pools, each covering the immunogenic fragments from each of the EBV proteins included in the vaccine (LMP1, LMP2, EBNA1, EBNA3A, ZEBRA; n=19 to 84 single peptides/pool). A sixth pool of 16mer peptides ($E_j$, n=18 peptides) covering each single junction between fragments, and DMSO (the peptide diluent) were also used as stimulants to monitor response to junctional epitopes and as negative control, respectively. T-cell activation was detected by enumerating IFNγ-secreting vaccine-elicited T cells by enzyme-linked immunoSpot (ELISPOT).

TABLE 1

| Group | Vector | n | dose (vp) |
|---|---|---|---|
| 1 | ChAd155 EBV-L | 6 | $10^8$ |
| 2 | ChAd155 EBV-L | 6 | $10^7$ |
| 3 | ChAd155 EBV-L | 6 | $10^6$ |
| 4 | ChAd155 EBV-LLy | 6 | $10^8$ |
| 5 | ChAd155 EBV-LLy | 6 | $10^7$ |
| 6 | ChAd155 EBV-LLy | 6 | $10^6$ |

Figure 5:
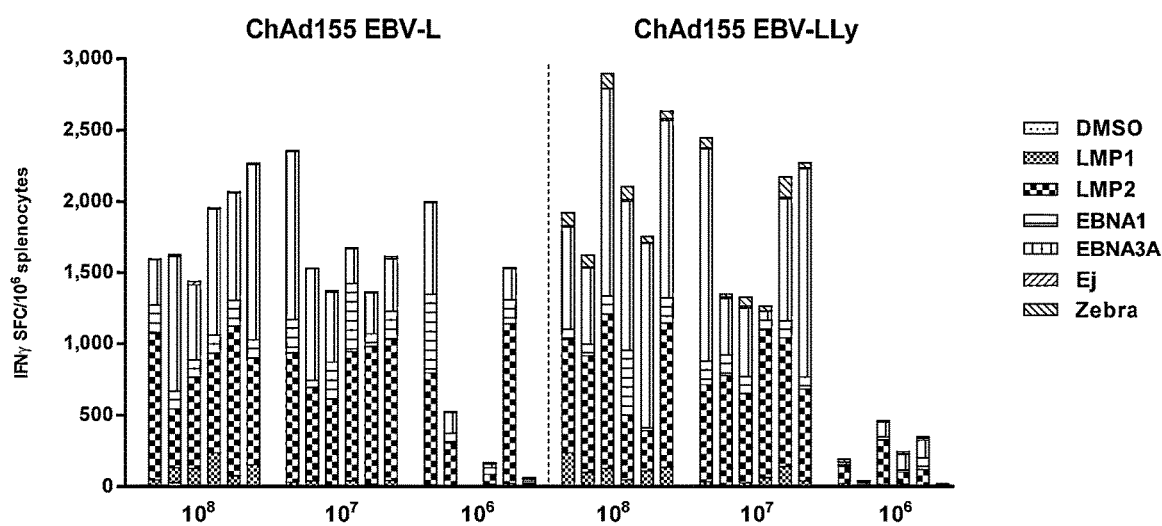
Figure 5:
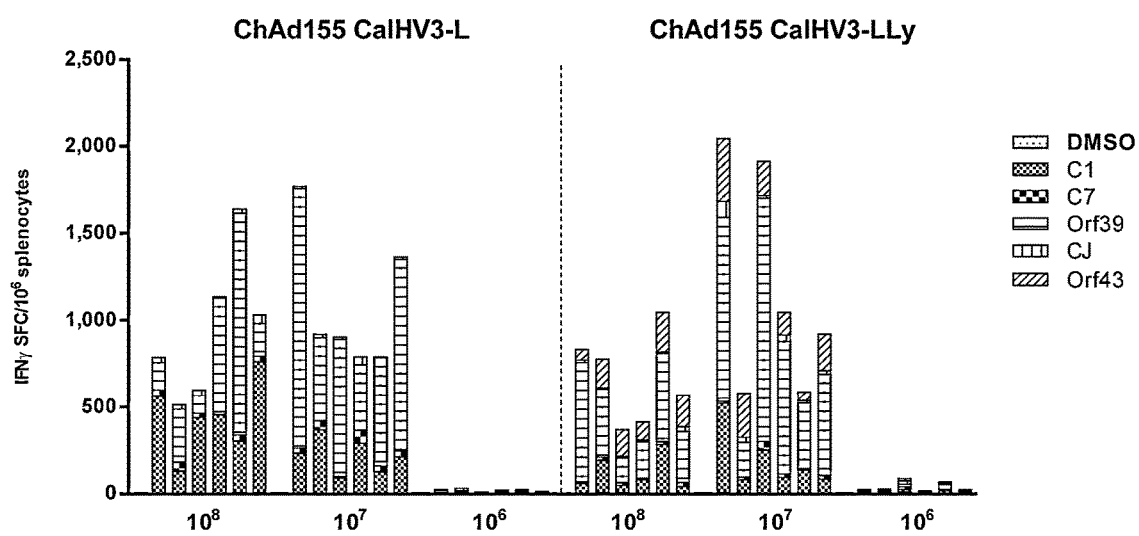

The results are shown in FIG. 5A. Both ChAd155-EBV-L and ChAd155-EBV-LLy elicited T-cells secreting IFNγ in vaccinated mice in a dose-dependent manner. T-cell responses were detected to each of the EBV latent antigens (LMP1, LMP2, EBNA1 and EBNA3A) in both EBV-L and EBV-LLy immunized mice. However, T-cell responses to the EBV lytic protein, ZEBRA, were only detected in EBV-LLy immunized mice. No responses were detected to the EBV junctional peptides (Ej) or to DMSO negative control.

The results indicate that viral particles produced from ChAd155-EBV-L and ChAd155-EBV-LLy vectors are capable of eliciting antigen specific T-cell responses to the immunogenic fragments contained within the antigen constructs. Furthermore, the primary immune response to EBV-L and EBV-LLy antigen constructs is not directed to junctional epitopes.

b. ChAd155-CalHV3

The immunogenicity of ChAd155-CalHV3 viral particles was assessed following the same methods described above for ChAd155-EBV viral particles. Antigen stimulation of splenocytes 3 weeks post vaccination was carried out with overlapping 15mer peptides arranged in 4 pools, each covering the immunogenic fragments included in the vaccine (C1, C7, ORF39, ORF43, n=58 to 96 single peptides/pool). A fifth pool of 16mer peptides ($C_j$, n=12 peptides) covering each single junction between fragments, and DMSO (the peptide diluent) were also used as stimulants to monitor response to junctional epitopes and as negative control, respectively. The experimental design is summarized in Table 2.

TABLE 2

| Group | Vector | n | dose (vp) |
|---|---|---|---|
| 1 | ChAd155 CalHV3-L | 6 | $10^8$ |
| 2 | ChAd155 CalHV3-L | 6 | $10^7$ |
| 3 | ChAd155 CalHV3-L | 6 | $10^6$ |
| 4 | ChAd155 CalHV3-LLy | 6 | $10^8$ |
| 5 | ChAd155 CalHV3-LLy | 6 | $10^7$ |
| 6 | ChAd155 CalHV3-LLy | 6 | $10^6$ |

The results are shown in FIG. 5B. Both ChAd155-CalHV3-L and ChAd155-CalHV3-LLy elicited T cells secreting IFNγ in vaccinated mice in a dose-dependent manner. T-cell responses to peptide pools covering CalHV3 latent antigens C1, C7 and ORF39 were detected in both CalHV3-L and CalHV3-LLy immunized mice. However, T-cell responses to the CalHV3 lytic protein, ORF43, were only detected in CalHV3-LLy immunized mice. No responses were detected to the CalHV3 junctional peptides (Cj) or to the negative control, DMSO.

The results indicate that viral particles produced from ChAd155-EBV-L and ChAd155-EBV-LLy vectors are capable of eliciting antigen specific T-cell responses to the immunogenic fragments contained within the antigen constructs. Furthermore, the primary immune response to CalHV3-L and CalHV3-LLy antigen constructs is not directed to junctional epitopes.

Example 5: Effect of Prime-Boost in Mice a. EBV-LLy Prime-Boost

The ability of a second dose of EBV-LLy antigen to boost the immune response of a first dose of EBV-LLy antigen was evaluated using the experimental design summarized in Table 3. Briefly, groups of CB6F1 mice (n=5/group) were immunized intramuscularly on day 0 with $5 \times 10^7$ viral particles of Chad155-EBV-LLy. On day 21 (week 3), Group 2 received a second immunization with $10^7$ plaque forming units (PFU) of MVA-EBV-LLy. Control mice received either no additional immunizations (Group 3: "no boost") or a boost immunization with an MVA vector encoding an EBV unrelated antigen (Group 1: MVA-unrelated).

TABLE 3

| Group | Prime (w0) | Boost (w3) | n | dose (vp or pfu) |
|---|---|---|---|---|
| 1 | ChAd155 EBV-LLy | MVA-unrelated | 5 | $10^7$ vp/$10^7$ pfu |
| 2 | ChAd155 EBV-LLy | MVA EBV-LLy | 5 | $10^7$ vp/$10^7$ pfu |
| 3 | ChAd155 EBV-LLy | no boost | 5 | $10^7$ vp |

Four weeks after the first immunization, splenocytes were isolated from the mice and antigen-specific T-cell responses were assessed using the methods described in Example 4.

Figure 6:
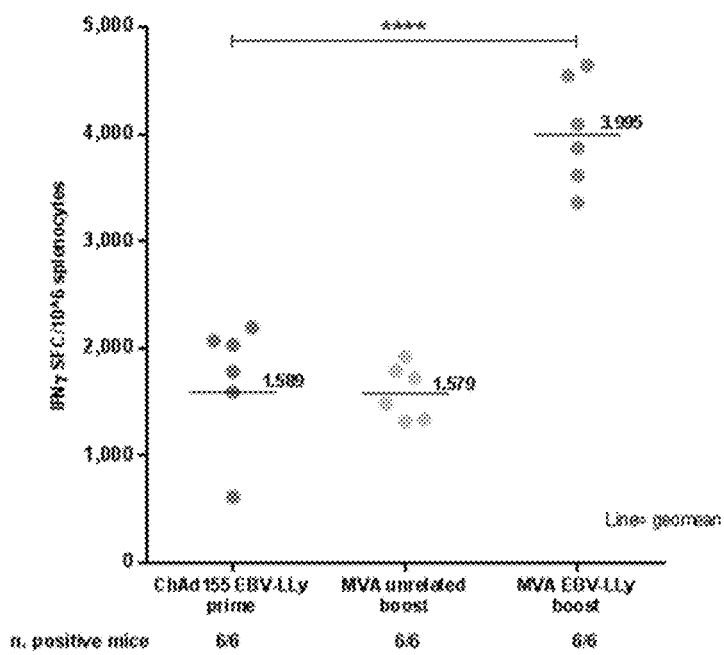
Figure 6:
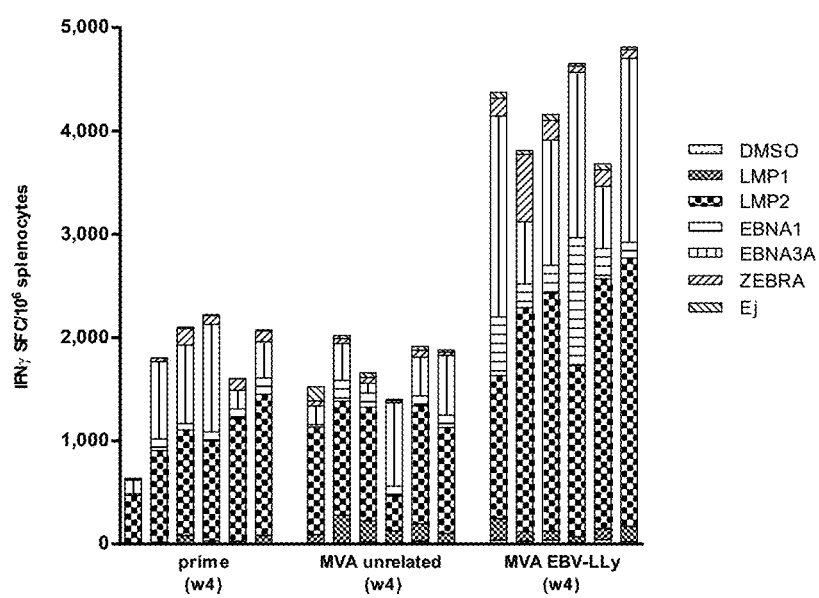

As shown in FIG. 6, immunization with ChAd155-EBV-LLy followed by a boost immunization with MVA-EBV- LLy produced a significant increase in EBV-specific interferon gamma release, as compared to unboosted mice or mice receiving a "boost" injection of an unrelated antigen. FIG. 6A presents the cumulative T-cell responses to all antigens (LMP1, LMP2, EBNA1, EBNA3A and ZEBRA), and FIG. 6B shows the responses to individual antigens.

b. CalHV3-LLy Prime-Boost

The ability to boost immune responses to CalHV3 antigens was assessed using the experimental design summarized in Table 4. Briefly, groups of CB6F1 mice (n=6/group) were immunized intramuscularly on day 0 with $5 \times 10^7$ viral particles of Chad155-CalHV3-LLy. On day 42 (week 6), Group 4 received a second immunization with same ChAd155-CalHV3-LLy antigen construct, while Group 3 received a boost immunization with MVA-CalHV3-LLy. Control mice received either no boost (Group 1) or a boost with an MVA encoding for a CalHV3-unrelated antigen (MVA-unrelated).

TABLE 4

| Group | Prime (w0) | Boost (w6) | n | dose (vp or pfu) |
|---|---|---|---|---|
| 1 | ChAd155 CalHV3-LLy | no boost | 6 | $5 \times 10^7$ vp |
| 2 | ChAd155 CalHV3-LLy | MVA-unrelated | 6 | $5 \times 10^7$ vp/$10^7$ pfu |
| 3 | ChAd155 CalHV3-LLy | MVA CalHV3-LLy | 6 | $5 \times 10^7$ vp/$10^7$ pfu |
| 4 | ChAd155 CalHV3-LLy | ChAd155 CalHV3-LLy | 6 | $5 \times 10^7$ vp/ $5 \times 10^7$ vp |

Seven weeks after the first immunization, splenocytes were isolated from the mice and antigen-specific T-cell responses were assessed using the methods described in Example 4.

Figure 7:
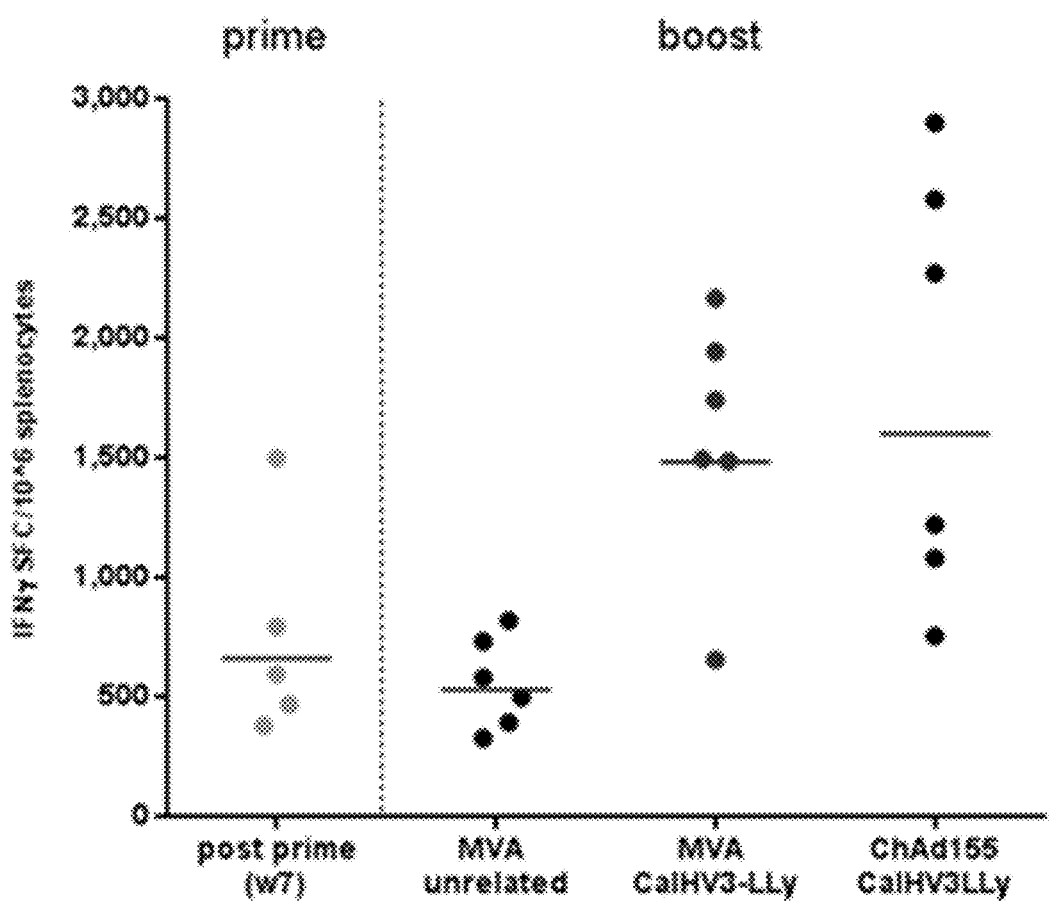

As shown in FIG. 7, immunization with ChAd155-CalHV3-LLy followed by a boost immunization with either the same antigen construct (ChAd155-CalHV3) or MVA-CalHV3-LLy produced a significant increase in CalHV3-specific interferon gamma release at week 7, as compared to unboosted mice or mice receiving a "boost" injection of an unrelated antigen.

These results demonstrate the ability to enhance the immune response to EBV and CalHV3 antigen constructs using prime-boost regimens.

Example 6: Invariant Chain-CalHV3-LLy Fusion Proteins

Fusing antigens to the major histocompatibility complex (MHC) class II-associated invariant chain (li) has been reported to enhance antigen-specific T-cell responses. See, e.g., Capone et al., Mol Ther. 2014 May; 22(5): 1039-1047. Therefore, the immunogenicity of viral particles expressing the marmoset invariant chain (li) fused to the N-terminus of the CalHV3-LLy antigen polypeptide was assessed in CB6F1 mice according to the study design outlined in Table 5. Antigen-specific T-cell responses were assessed using the IFNγ assays described in Example 4.

TABLE 5

| Group | Prime (w0) | n | dose (vp) |
|---|---|---|---|
| 1 | ChAd155 CalHV3-LLy | 6 | $5 \times 10^7$ vp |
| 2 | ChAd155 CalHV3-LLy | 6 | $5 \times 10^6$ vp |
| 3 | ChAd155 marmoset li CalHV3-LLy | 6 | $5 \times 10^7$ vp |
| 4 | ChAd155 marmoset li CalHV3-LLy | 6 | $5 \times 10^6$ vp |

Figure 8:
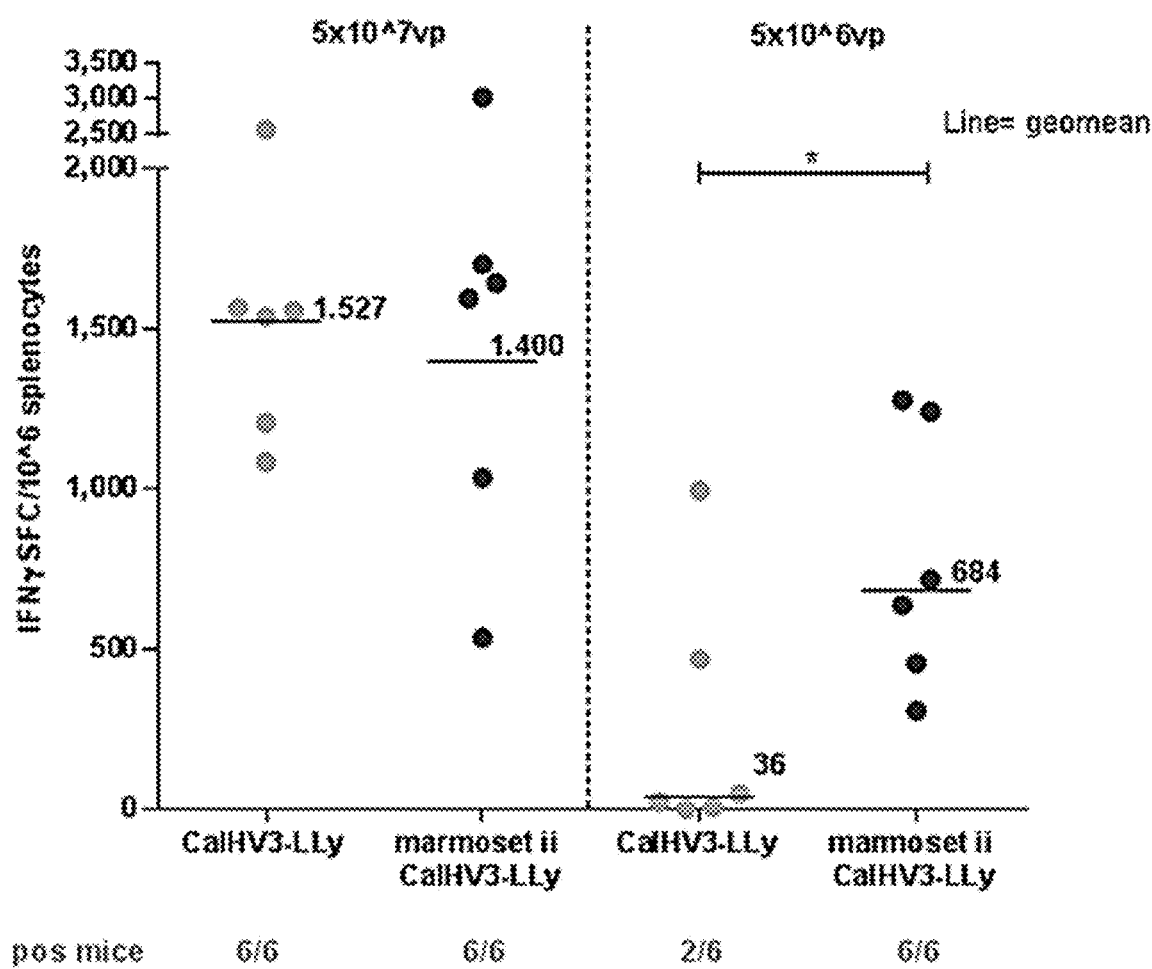
Figure 9:
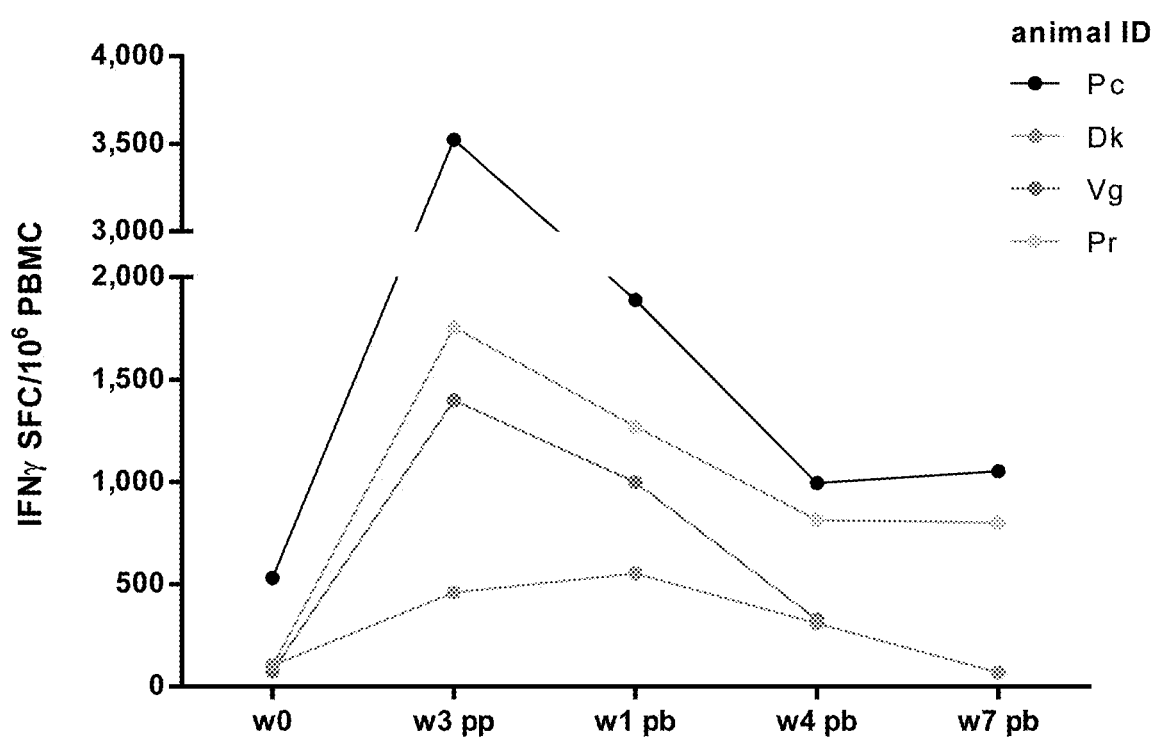
Figure 10:
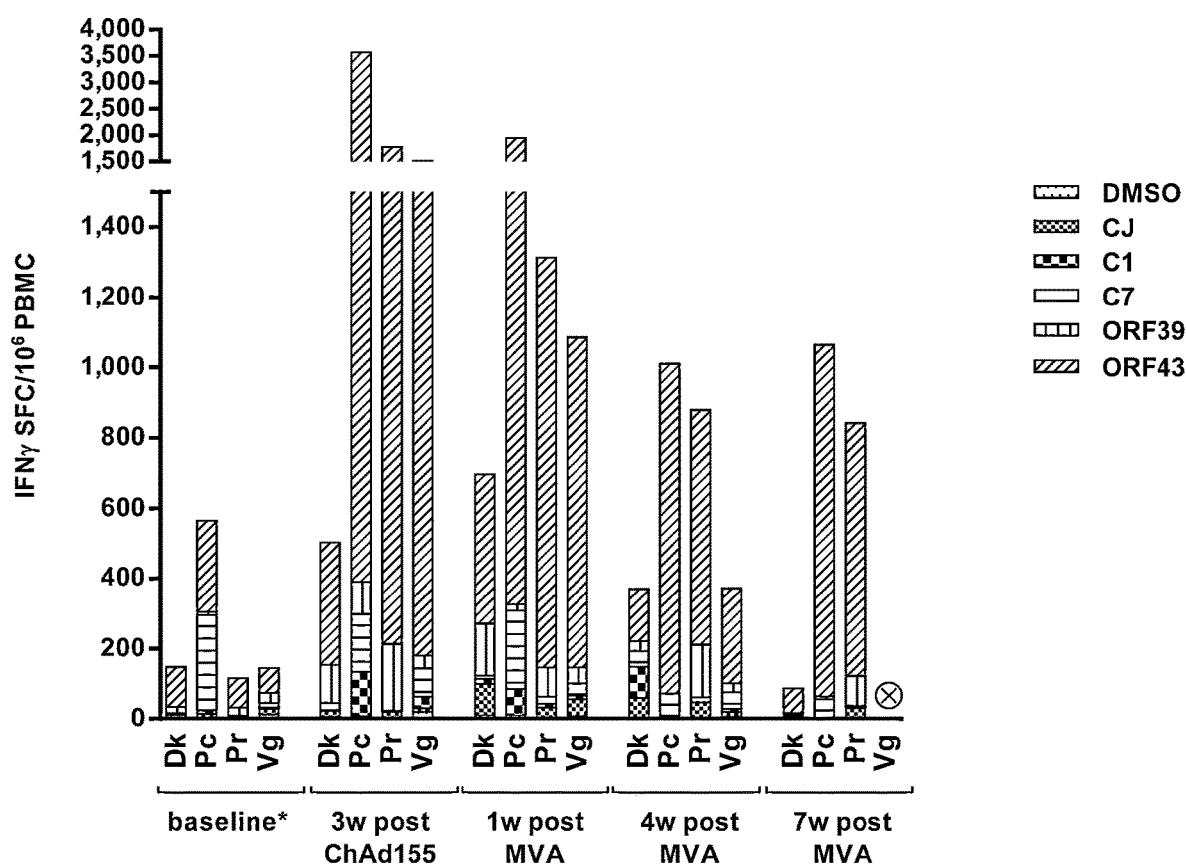

FIG. 8 summarizes cumulative T-cell responses to all CalHV3-LLy antigens (C1, C7, ORF39 and ORF43) observed two weeks after immunization. At the lower dose of antigen ($5 \times 10^6$ viral particles), ChAd155-li-CalHV3-LLy elicited significantly greater IFNγ release in immunized mice than ChAd155-CalHV3-LLy. No differences were observed at the higher antigen dose tested ($5 \times 10^7$ viral particles).

These results indicate that fusion of the CalHV3-LLy antigen polypeptide to an MHC class II-associated invariant chain polypeptide enhances the T-cell immune response to CalHV3 latent and lytic antigens.

Example 7: Immunogenicity of CalHV3 Antigens in Non-Human Primates

The immunogenicity of CalHV3 antigen constructs was evaluated in CalHV3 seropositive marmosets (Callithrix jacchus), a genus of New World primates. CalHV3 infection is known to be prevalent in marmosets. See, e.g., Cho et al., PNAS 98(3):1224-1229 (2001). Due to the structural and pathological similarities between CalHV3 and EBV, CalHV3-positive marmosets can serve as a valuable model of human EBV infection and pathology. Id.

Animals were immunized using a ChAd155 prime/MVA boost vaccination schedule. Briefly, a group composed of four adult animals (3 males and one female) received a prime immunization of ChAd155-CalHV3-LLy ($5\times10^{10}$ vp) on day 0 and a boost immunization of MVA-CalHV3-LLy ($2\times10^8$) on day 56 (week 8). Blood samples were drawn 2 weeks before prime injections, 3 weeks after prime injections, and 1, 4 and 7 weeks after boost injections. Antigen-specific T-cell responses in peripheral blood mononuclear cells (PBMCs) were assessed using the methods described in Example 4.

FIG. 9 shows cumulative T-cell responses in individual animals to all CalHV3-LLy antigens (C1, C7, ORF39 and ORF43) observed at baseline (w0); at three weeks post-prime (w3 pp); and at one, four and seven weeks post-boost (w1, w4, w7 pb). Prior to immunizations, animals exhibited baseline CalHV3-specific T-cell responses, consistent with the fact that the animals are virus carriers. Three weeks after ChAd155-CalHV3-LLy immunization, animals exhibited significant expansion of pre-existing CalHV3-specific T cell responses. T cell responses continued to be elevated 1 week post-boost with MVA-CalHV3-LLy, and contracted in the following 2 months, still remaining above baseline levels in most animals. As shown in FIG. 10, the enhanced T-cell responses to CalHV3-LLy was sustained and was polyspecific (i.e., to C1, C7, ORF39 and ORF43).

These results indicate that ChAd155 and MVA vectors encoding CalHV3-LLy antigens can efficiently re-expand and sustain pre-existing antigen-specific T-cell responses in CalHV3-positive marmosets, and that circulating T cells elicited by gamma herpesviruses are not functionally impaired or exhausted.

Example 8: Recognition of EBV Fragments Encoded by ChAd155 and MVA Latent+Lytic EBV Vaccines by Human PBMC To validate the selection of EBV latent (EBNA1, EBNA3A, LMP1 and LMP2) and lytic (ZEBRA) antigenic fragments included in the vaccine, T cell responses to the corresponding peptide pools were measured in otherwise healthy human EBV carriers.

Briefly, frozen peripheral blood mononuclear cells (PBMC) from 8 healthy human donors were thawed and assayed for T-cell responses to EBV antigens according to a standard IFNγ ELISpot assay. PBMC were plated in triplicates at 2×10⁵ cells/well and were stimulated overnight with overlapping 15-mer peptides arranged in 5 pools, each covering the immunogenic fragments from each of the EBV proteins included in the vaccine (LMP1, LMP2, EBNA1, EBNA3A, ZEBRA; n=19 to 84 single peptides/pool). Stimulation with DMSO (the peptide diluent) was used as negative control. T-cell activation was detected by enumerating IFNγ-secreting T cells by enzyme-linked immunoSpot (ELISPOT).

Figure 11:
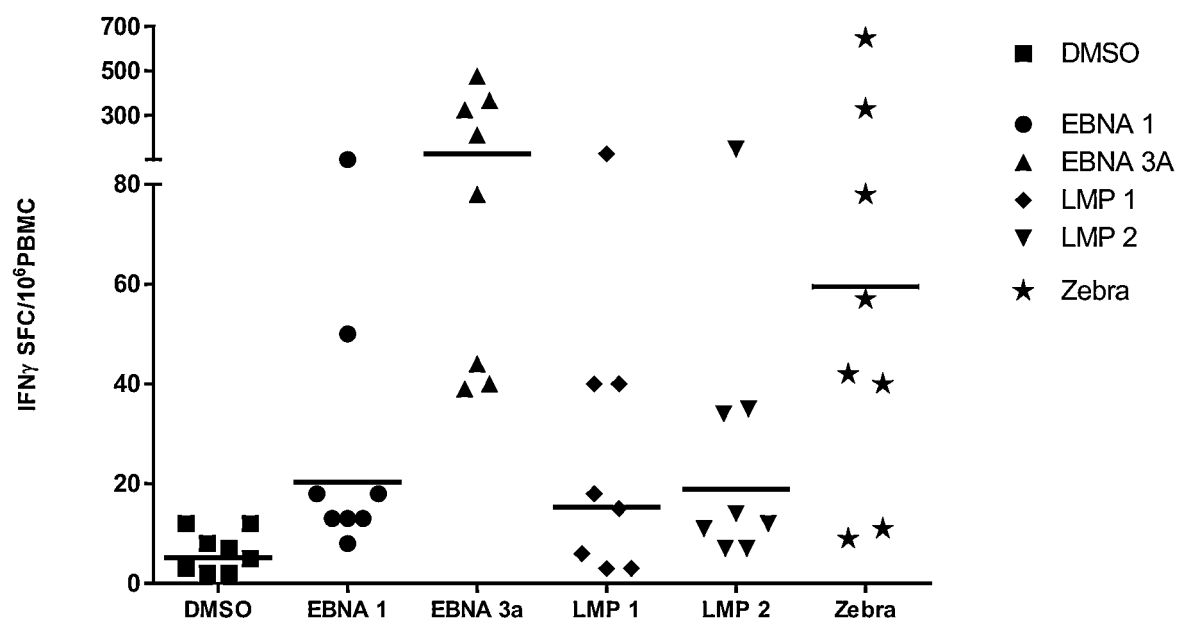

As shown in FIG. 11, the results indicate that antigen specific T-cell responses to the immunogenic fragments contained within the EBV Lly antigen constructs can be readily detected in healthy EBV carriers, with EBNA3A and ZEBRA being the most frequently recognized and eliciting the highest responses, consistent with previous reports (e.g., Taylor et al. Ann. Rev. Immunol. 33:787-821, 2015).

What is claimed is:

1. A polynucleotide encoding a polypeptide comprising:
   (a) at least one fragment of at least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of an LMP1 protein,
   (b) at least one fragment of at least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of an LMP2 protein,
   (c) at least one fragment of at least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of an EBNA1 protein, and
   (d) at least one fragment of at least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of an EBNA3A protein;
   wherein the polynucleotide is operatively linked to one or more sequences which direct expression of said polypeptide in a host cell;
   and wherein the polypeptide is at least 80%, at least 85%, at least 90%, at least 95% or at least 99% identical to SEQ ID NO: 24 or SEQ ID NO: 26.

2. The polynucleotide of claim 1, wherein the polypeptide further comprises at least one fragment of at least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of a ZEBRA protein.

3. The polynucleotide of claim 1, wherein the polypeptide comprises:
   (a) at least two fragments of at least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of the LMP1 protein,
   (b) at least two fragments of at least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of the LMP2 protein,
   (c) at least two fragments of at least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of the EBNA1 protein,
   (d) at least two fragments of at least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of the EBNA3A protein, or
   (e) at least two fragments of at least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of the ZEBRA protein.

4. The polynucleotide of claim 1, wherein the polypeptide comprises:
   (a) at least three fragments of at least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of the LMP1 protein,
   (b) at least three fragments of at least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of the LMP2 protein,
   (c) at least three fragments of at least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of the EBNA1 protein,
   (d) at least three fragments of at least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of the EBNA3 protein, or
   (e) at least three fragments of at least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of the ZEBRA protein.

5. The polynucleotide of claim 1, wherein the polypeptide comprises:
   (a) at least four fragments of at least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of the LMP1 protein,
   (b) at least four fragments of at least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of the LMP2 protein,
   (c) at least four fragments of at least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of the EBNA1 protein,
   (d) at least four fragments of at least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of the EBNA3A protein, or
   (e) at least four fragments of at least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of the ZEBRA protein.

6. The polynucleotide of claim 3, wherein the fragments of the LMP1 protein are not adjacent to each other; and wherein the polynucleotide is recombinant.

7. The polynucleotide of claim 3, wherein the fragments of the LMP2 protein are not adjacent to each other; and wherein the polynucleotide is recombinant.

8. The polynucleotide of claim 3, wherein the fragments of the EBNA1 protein are not adjacent to each other; and wherein the polynucleotide is recombinant.

9. The polynucleotide of claim 3, wherein the fragments of the EBNA3 protein are not adjacent to each other; and wherein the polynucleotide is recombinant.

10. The polynucleotide of claim 3, wherein the fragments of the ZEBRA protein are not adjacent to each other; and wherein the polynucleotide is recombinant.

11. The polynucleotide of claim 1, wherein the polypeptide comprises:
    (a) a first and a second fragment of LMP1, wherein said first and second fragments of LMP1 are selected from the group consisting of SEQ ID NOs: 2-5 and wherein said first and second fragments of LMP1 are not adjacent to each other in the polypeptide,
    (b) a first and a second fragment of LMP2, wherein said first and second fragments of LMP1 are selected from the group consisting of SEQ ID NOs: 7-10 and wherein said first and second fragments of LMP2 are not adjacent to each other in the polypeptide,
    (c) a fragment of EBNA1 consisting of SEQ ID NO: 12, and
    (d) a first and a second fragment of EBNA3A, wherein said first and second fragments of EBNA3A are selected from the group consisting of SEQ ID NOs: 14-20 and wherein said first and second fragments of EBNA3A are not adjacent to each other in the polypeptide.

12. The polynucleotide of claim 1, wherein the polypeptide comprises:
    (a) a first fragment of the LMP1 protein consisting of SEQ ID NO: 2,
    (b) a second fragment of the the LMP1 protein consisting of SEQ ID NO: 3,
    (c) a third fragment of the LMP1 protein consisting of SEQ ID NO: 4,
    (d) a fourth fragment of the LMP1 protein consisting of SEQ ID NO: 5,
    (e) a first fragment of the LMP2 protein consisting of SEQ ID NO: 7,
    (f) a second fragment of the LMP2 protein consisting of SEQ ID NO: 8, (g) a third fragment of the LMP2 protein consisting of SEQ ID NO: 9,
(h) a fourth fragment of the LMP2 protein consisting of SEQ ID NO: 10,
(i) a first fragment of the EBNA1 protein consisting of SEQ ID NO: 12,
(j) a first fragment of the EBNA3A protein consisting of SEQ ID NO: 14,
(k) a second fragment of the EBNA3A protein consisting of SEQ ID NO: 15,
(l) a third fragment of the EBNA3A protein consisting of SEQ ID NO: 16,
(m) a fourth fragment of the EBNA3A protein consisting of SEQ ID NO: 17,
(n) a fifth fragment of the EBNA3A protein consisting of SEQ ID NO: 18,
(o) a sixth fragment of the EBNA3A protein consisting of SEQ ID NO: 19, and
(p) a seventh fragment of the EBNA3A protein consisting of SEQ ID NO: 20;
wherein the first, second, third and fourth LMP1 fragments are not adjacent to each other;
wherein the first, second, third and fourth LMP2 fragments are not adjacent to each other;
wherein the first, second, third, fourth, fifth, sixth, and seventh EBNA3A fragments are not adjacent to each other; and wherein the polynucleotide is recombinant.

13. The polynucleotide of claim 11, wherein the polypeptide further comprises:
(a) a first fragment of the ZEBRA protein consisting of SEQ ID NO: 22, and
(b) a second fragment of the ZEBRA protein consisting of SEQ ID NO: 23;
wherein the first and second ZEBRA fragments are not adjacent to each other; and wherein the polynucleotide is recombinant.

14. The polynucleotide of claim 1, wherein the fragments are immunogenic fragments.

15. A vector comprising the polynucleotide of claim 1.

16. The vector of claim 15, wherein the vector is an adenovirus vector or a vaccinia virus vector.

17. The vector of claim 16, wherein the vector is a ChAd155-EBV-L expression vector comprising a nucleic acid sequence at least 90%, at least 95%, at least 96%, at least 97%, at least 98% or at least 99% identical to SEQ ID NO: 50.

18. The vector of claim 16, wherein the vector is a ChAd155-EBV-LLy expression vector comprising a nucleic acid sequence at least 90%, at least 95%, at least 96%, at least 97%, at least 98% or at least 99% identical to SEQ ID NO: 51.

* * * * *